United States Patent
Perkins et al.

(10) Patent No.: US 11,931,736 B2
(45) Date of Patent: *Mar. 19, 2024

(54) SYSTEMS AND METHODS FOR SERIAL FLOW EMULSION PROCESSES

(71) Applicant: Dropworks, Inc., Boulder, CO (US)

(72) Inventors: Christopher Michael Perkins, Boulder, CO (US); Matthew Ryan Dunn, Melrose, MA (US); Andrew Carl Larsen, Superior, CO (US); Donna Kelley, Louisville, CO (US); Michael Barich, Longmont, CO (US); Kristopher Holub, Boulder, CO (US); Pin Kao, Fremont, CA (US)

(73) Assignee: DROPWORKS, INC., Boulder, CO (US)

( * ) Notice: Subject to any disclaimer, the term of this patent is extended or adjusted under 35 U.S.C. 154(b) by 222 days.

This patent is subject to a terminal disclaimer.

(21) Appl. No.: 17/062,040

(22) Filed: Oct. 2, 2020

(65) Prior Publication Data

US 2021/0023557 A1   Jan. 28, 2021

Related U.S. Application Data

(63) Continuation of application No. 16/372,290, filed on Apr. 1, 2019, now Pat. No. 11,471,884.
(Continued)

(51) Int. Cl.
| | |
|---|---|
| *B01L 3/00* | (2006.01) |
| *B01F 23/41* | (2022.01) |
| *B01F 25/314* | (2022.01) |
| *C12Q 1/686* | (2018.01) |
| *G01N 15/14* | (2006.01) |

(Continued)

(52) U.S. Cl.
CPC ........ *B01L 3/502715* (2013.01); *B01F 23/41* (2022.01); *B01F 25/314* (2022.01); *B01L 3/502784* (2013.01); *C12Q 1/686* (2013.01); *G01N 15/1459* (2013.01); *G01N 21/62* (2013.01); *B01F 33/3021* (2022.01); *B01F 2101/16* (2022.01); *B01L 2200/0673* (2013.01); *B01L 2300/041* (2013.01);
(Continued)

(58) Field of Classification Search
CPC . B01L 2200/0673; B01L 7/52; B01F 13/0071
See application file for complete search history.

(56) References Cited

U.S. PATENT DOCUMENTS

| | | |
|---|---|---|
| 3,600,953 A | 8/1971 | Isreeli et al. |
| 6,296,771 B1 | 10/2001 | Miroslav |

(Continued)

FOREIGN PATENT DOCUMENTS

| | | |
|---|---|---|
| CN | 201714171 U | 1/2011 |
| CN | 202280305 U | 6/2012 |

(Continued)

OTHER PUBLICATIONS

Extended European Search Report and Written Opinion for EP 19782031.9 dated Mar. 23, 2022; 10 pages.
(Continued)

*Primary Examiner* — Jonathan M Hurst
(74) *Attorney, Agent, or Firm* — Storella & Witt, LLP

(57) ABSTRACT

Disclosed herein are systems and methods for serial flow emulsion processes. Systems and methods as described herein result in reduced cross-contamination.

30 Claims, 94 Drawing Sheets

Related U.S. Application Data

(60) Provisional application No. 62/651,619, filed on Apr. 2, 2018.

(51) Int. Cl.
*G01N 21/62* (2006.01)
*B01F 33/302* (2022.01)
*B01F 101/16* (2022.01)
*G01N 35/08* (2006.01)

(52) U.S. Cl.
CPC .............. *B01L 2300/0654* (2013.01); *B01L 2300/0829* (2013.01); *B01L 2300/0867* (2013.01); *G01N 35/08* (2013.01)

(56) References Cited

U.S. PATENT DOCUMENTS

| | | |
|---|---|---|
| 6,675,616 B1 | 1/2004 | Horton |
| 6,960,437 B2 | 11/2005 | Enzelberger et al. |
| 6,977,145 B2 | 12/2005 | Fouillet et al. |
| 7,129,091 B2 | 10/2006 | Ismagilov et al. |
| 7,268,167 B2 | 9/2007 | Higuchi et al. |
| 7,294,503 B2 | 11/2007 | Quake et al. |
| 7,622,076 B2 | 11/2009 | Davies et al. |
| 7,622,081 B2 | 11/2009 | Chou et al. |
| 7,655,570 B2 | 2/2010 | Kikuchi et al. |
| 7,767,706 B2 | 8/2010 | Phadke et al. |
| 7,772,287 B2 | 8/2010 | Higuchi et al. |
| RE41,780 E | 9/2010 | Anderson et al. |
| 8,067,159 B2 | 11/2011 | Brown et al. |
| RE43,365 E | 5/2012 | Anderson et al. |
| 8,273,573 B2 | 9/2012 | Ismagilov et al. |
| 8,278,071 B2 | 10/2012 | Brown et al. |
| 8,298,833 B2 | 10/2012 | Davies et al. |
| 8,304,193 B2 | 11/2012 | Ismagilov et al. |
| 8,329,407 B2 | 12/2012 | Ismagilov et al. |
| 8,399,198 B2 | 3/2013 | Hiddessen et al. |
| 8,633,015 B2 | 1/2014 | Ness et al. |
| 8,709,762 B2 | 4/2014 | Hindson |
| 8,730,479 B2 | 5/2014 | Ness et al. |
| 8,765,382 B2 | 7/2014 | Drmanac |
| 8,771,747 B2 | 7/2014 | O'Hagan et al. |
| 8,822,148 B2 | 9/2014 | Ismagliov et al. |
| 8,841,093 B2 | 9/2014 | Takahashi et al. |
| 8,871,444 B2 | 10/2014 | Griffiths et al. |
| 8,889,083 B2 | 11/2014 | Ismagilov et al. |
| 8,951,732 B2 | 2/2015 | Pollack et al. |
| 8,968,659 B2 | 3/2015 | Davies et al. |
| 9,012,390 B2 | 4/2015 | Holtze et al. |
| 9,029,083 B2 | 5/2015 | Griffiths et al. |
| RE45,539 E | 6/2015 | Anderson et al. |
| 9,074,242 B2 | 7/2015 | Larson et al. |
| 9,127,310 B2 | 9/2015 | Larson et al. |
| 9,132,394 B2 | 9/2015 | Makarewicz, Jr. et al. |
| 9,156,010 B2 | 10/2015 | Colston et al. |
| 9,216,392 B2 | 12/2015 | Hindson et al. |
| 9,222,115 B2 | 12/2015 | Marble et al. |
| 9,243,288 B2 | 1/2016 | Ness et al. |
| 9,248,417 B2 | 2/2016 | Hindson et al. |
| 9,273,308 B2 | 3/2016 | Link et al. |
| 9,347,059 B2 | 5/2016 | Saxonov |
| 9,364,803 B2 | 6/2016 | Yurkovetsky et al. |
| 9,366,632 B2 | 6/2016 | Link et al. |
| 9,441,266 B2 | 9/2016 | Larson et al. |
| 9,492,797 B2 | 11/2016 | Makarewicz et al. |
| 9,498,761 B2 | 11/2016 | Holtze et al. |
| RE46,322 E | 2/2017 | Anderson et al. |
| 9,562,837 B2 | 2/2017 | Link |
| 9,623,384 B2 | 4/2017 | Hindson et al. |
| 9,631,230 B2 | 4/2017 | Davies et al. |
| 9,731,293 B2 | 8/2017 | Terray et al. |
| 9,752,141 B2 | 9/2017 | Link et al. |
| 9,968,933 B2 | 5/2018 | Ismagilov et al. |
| 10,054,961 B2 | 8/2018 | Ismagilov et al. |
| RE47,080 E | 10/2018 | Anderson et al. |
| 10,357,771 B2 | 7/2019 | Bharadwaj et al. |
| 2002/0058332 A1 | 5/2002 | Quake et al. |
| 2002/0180963 A1 | 12/2002 | Chien et al. |
| 2003/0036206 A1 | 2/2003 | Chien et al. |
| 2004/0017981 A1 | 1/2004 | Jovanovich et al. |
| 2006/0097155 A1 | 5/2006 | Adachi et al. |
| 2008/0070311 A1 | 3/2008 | Li |
| 2008/0124726 A1 | 5/2008 | Monforte |
| 2010/0092973 A1 | 4/2010 | Davies et al. |
| 2010/0173394 A1 | 7/2010 | Colston, Jr. et al. |
| 2010/0297748 A1 | 11/2010 | Davies et al. |
| 2011/0053798 A1 | 3/2011 | Hindson et al. |
| 2011/0311978 A1 | 12/2011 | Makarewicz, Jr. et al. |
| 2012/0019033 A1 | 1/2012 | Kelly |
| 2012/0190033 A1 | 7/2012 | Ness et al. |
| 2012/0194805 A1 | 8/2012 | Ness et al. |
| 2013/0260447 A1 | 10/2013 | Link |
| 2014/0045712 A1 | 2/2014 | Link et al. |
| 2014/0193800 A1 | 7/2014 | Aguanno et al. |
| 2014/0200164 A1 | 7/2014 | Makarewicz, Jr. et al. |
| 2014/0202546 A1 | 7/2014 | Ismagilov et al. |
| 2015/0018236 A1 | 1/2015 | Green et al. |
| 2015/0065396 A1 | 3/2015 | Kiani et al. |
| 2016/0045914 A1 | 2/2016 | Abate et al. |
| 2016/0097087 A1 | 4/2016 | Wiyatno et al. |
| 2016/0123513 A1 | 5/2016 | Davies et al. |
| 2016/0177375 A1 | 6/2016 | Abate et al. |
| 2016/0194697 A1 | 7/2016 | Lee et al. |
| 2017/0144116 A1 | 5/2017 | Ness et al. |
| 2017/0216844 A1 | 8/2017 | Rodriguez et al. |
| 2019/0187043 A1 | 6/2019 | Wagner et al. |
| 2019/0195773 A1 | 6/2019 | Hart et al. |
| 2019/0291114 A1 | 9/2019 | Youngbull et al. |

FOREIGN PATENT DOCUMENTS

| | | | |
|---|---|---|---|
| CN | 105298239 A | | 2/2016 |
| CN | 205100689 U | | 3/2016 |
| EP | 1574586 A3 | | 12/2005 |
| EP | 1663497 A1 | | 6/2006 |
| EP | 2553472 A2 | | 2/2013 |
| EP | 1735458 B1 | | 7/2013 |
| EP | 2805769 A1 | | 11/2014 |
| JP | 2002295076 A | | 10/2002 |
| WO | 1984002000 A1 | | 5/1984 |
| WO | 2013165748 A1 | | 11/2013 |
| WO | 2014008381 A2 | | 1/2014 |
| WO | 2014201207 A2 | | 12/2014 |
| WO | 2017084250 A1 | | 5/2017 |
| WO | 2018098438 A1 | | 5/2018 |
| WO | PCTUS1925244 | | 4/2019 |

OTHER PUBLICATIONS

Intellectual Property Office of Singapore, Search Report dated Jan. 14, 2022 and Written Opinion dated Feb. 4, 2022 for Application No. 11202009478P, 10 pages.

Notification on Grant in Chinese Application No. 2019800370349 dated Jan. 19, 2022, 5 pages.

Office Action in Chinese Application No. 2019800370349 dated Aug. 23, 2021, 5 pages.

Qiao, Yuxin et al., "Fluorescence-Activated Droplet Sorting of Lipolytic Microorganisms Using a Compact Optical System," Lab Chip, 2018, 18, 190-196; doi:10.1039/c7lc0093c.

Rosenfeld, Liat et al., "Review and Analysis of Performance Metrics of Droplet Microfluidics Systems," Microfluid Nanofluid, (2014) 16:921-939; doi 10.1007/s10404-013-1310-x.

Schaerli, Yolanda, et al., "The Potential of Microfluidic Water-in-Oil Droplets in Experimental Biology," Molecular BioSystems, Dec. 2009, Doi: 10.1039/b907578J; https://www.researchgate.net/publication/40731206.

Sciambi, Adam et al., Accurate Microfluidic Sorting of Droplets at 30 zHz, Lab Chip, 2015, 15, 47-51; doi: 10.1039/c4lc01194e.

Shim, Jung-uk et al., "Ultrarapid Generation of Femtoliter Microfluidic Droplets for Single-Molecule-Counting Immunoassays," ACNANO, vol. 7, No. 7, pp. 5955-5964, 2013.

(56) References Cited

OTHER PUBLICATIONS

Sidore, A.M. et al., "Enhanced Sequencing Coverage With Digital Droplet Multiple Displacement Amplification," Nucleic Acids Research Advanced Access, 1, Dec. 23, 2015; doi: 10.1093/narlgkv1493.

Siedler, Solvej et al., "Development of a Bacterial Biosensor for Rapid Screening of Yeast p-Coumaric Acid Production," ACS Synthetic Biology, doi: 10.1021/acssynbio.7b00009.

Sjostrom, Staffan L. et al., "High-Throughput Screening For Industrial Enzyme Production Hosts by Droplet Microfluidics," Lab Chip, 2014, 14, 806-813; doi: 10.1039/c3lc51202a.

Terekhov, Stanislav et al., "Microfluidic Droplet Platform for Ultrahigh-Throughput Single-Cell Screening of Biodiversity," PNAS, vol. 114, No. 10, Mar. 7, 2017, pp. 2550-2555.

Theberge, Ashleigh B. et al., "Microdroplets in Microfluidics: An Evolving Platform for Discoveries in Chemistry and Biology," Angewandte Chemie, Angew. Chem. Int. Ed. 2010, 49, pp. 5846-5868; Doi: 10.1002/anie.200906653.

Thorsen, Todd Thesis, "Microfluidic Technologies for High-Throughput Screening Applications," California Institute of Technology, pp. 1-180, 2003.

Van Loo, B. et al., "High-Throughput, Lysis-free Screening for Sulfatase Activity Using *Escherichia coli* Autodisplay in Microdroplets," Institute for Evolution and Biodiversity, University of Munster, Germany; Department of Biochemistry, University of Cambridge, United Kingdom; Institute of Pharmaceutical and Medicinal Chemistry, University of Munster, Germany; Nov. 26, 2018; http://dx.doi.org/10.1101/479162.

Yu, Ziyi, et al., "Droplet-based Microfluidic Analysis and Screening of Single Plant Cells," PLoS One, 13(5):e20196810, pp. 1-15, May 3, 2018, https://doi.org/10.1371/journal.pone.0196810.

Zinchenko, A. et al., "One in a Million: Flow Cytometric Sorting of Single Cell-Lysate Assays in Monodisperse Picolitre Double Emulsion Droplets for Directed Evolution," Analytical Chemistry 2014, 86, pp. 2526-2533; dx.doi.org/10.1021/ac403585p.

U.S. Appl. No. 16/675,091, filed Nov. 5, 2016, Christopher Michael Perkins.

U.S. Appl. No. 16/733,206, filed Jan. 2, 2020, Christopher Michael Perkins.

Hatch, Andrew et al, "Continuous flow real-time PCR device using multi-channel fluorescence excitation and detection", the Royal Society of Chemistry 2013, 2013, 7 pages.

International Searching Authority—China, International Search Report and Written Opinion for PCT/CN2016/081795 with English Translation dated Aug. 9, 2016, 22 pages.

International Searching Authority—US, International Search Report and Written Opinion for PCT/US19/25244 dated Aug. 16, 2019, 16 pages.

International Searching Authority—US, International Search Report and Written Opinion for PCT/US2017/063293 dated Jan. 18, 2018, 14 pages.

Qvarnstrom et al. (2006) Multiplex Real-Time PCR Assay for Simultaneous Detection of *Acanthamoeba* spp. Balamuthia mandrillaris and Naegleria fowleri J. Clin. Microbiology 44:3589-3595; DOI 10.1128/JCM.00875-06.

Ray, Tathagata, "Lower Power, High Throughout Continuous Flow PCR Instruments for Environmental Applications", Dec. 1, 2013, Arizona State University, XP055439631, 181 pages.

Riche, et al., Flow invariant droplet formation for stable parallel microreactors, Nature Communications, (2016), 7:10780; DOI 10.1038/ncomms10780.

Abate, Adam R. et al., "Corrections and Editorial Expression of Concern," PNAS, vol. 107. No. 14, pp. 6550-6551; Apr. 6, 2010.

Autour, Alexis et al., "Ultrahigh-Throughput Improvement and Discovery of Enzymes Using Droplet-Based Microfluidic Screening," Micromachines 2017, 8, 128; doi: 10.3390/mi804128.

Ballen, Miguel Angel Tovar, Dissertation "Engineering Picoliter Droplets for Ultrahigh-Throughput Microbial Biotechnology," Submitted to the Council of the Faculty of Biological Sciences of the Friedrich Schiller University Jena; Feb. 8, 2018; pp. 1-195.

Baret, Jean-Christophe et al., "Fluorescence-Activated Droplet Sorting (FADS): Efficient Microfluidic Cell Sorting Based on Enzymatic Activity," Lab Chip, 2009, 9, pp. 1850-1858; Doi: 10.1039/b9902504a.

Beneyton, Thomas et al. "Droplet-based Microfluidic High-Throughput Screening of Heterologous Enzymes Secreted by the Yeast *Yarrowia lipolytica*," Microbial Cell Factories, (2017) 16:18; doi. 10.1186/s12934-017-0629-5.

Beneyton, Thomas et al., "CotA Laccase: High-Throughput Manipulation and Analysis of Recombinant Enzyme Libraries Expressed in *E. coli* Using Droplet-Based Microfluidics," Analyst, 2014, 139, 3314; doi: 10.1039/c4an00228h.

Beneyton, Thomas et al., "High-Throughput Screening of Filamentous Fungi Using Nanoliter-Range Droplet-Based Microfluidics," Scientific Reports, 6:27223; Doi: 10.1038/srep27223.

Caen, Oureil et al. "High-Throughput Multiplexed Fluorescence-Activated Droplets Sorting," Microsystems & Nanoengineering (2018) 4:33; Doi: 10.1038/s41378-018-0033-2.

Caen, Ouriel et al., "Microfluidics as a Strategic Player to Decipher Single-Cell Omics?," Trends in Biotechnology, vol. 35, No. 8, Aug. 2017, pp. 713-727; http://dx.doi.org/10.1016/j.tibtech.2017.05.004.

Cao, Zhenning et al., "Droplet Sorting Based on the No. of Encapsulated Partaicles Using a Solenoid Valve," Lab Chip, 2013, 13, 171; doi: 10.1039/c2lc40950j.

Chowdhury, et al., "Dendronized Fluorosurfactant for Highly Stable Water-In-Fluorinated Oil Emulsions With Minimal Inter-Droplet Transfer of Small Molecules," Nature Communications, (2019) 10:45-46; https://doi.org/10.1038/s41467-5.

Colin, Pierre-Yves et al., "Ultrahigh-Throughput Discovery of Promiscuous Enzymes by Picodroplet Functional Metagenomics," Nature Communications, 6:10008; doi: 10.1038/ncomms10008 ;2015.

Diefenbach, Xue W. et al., "Enabling Biocatalysis by High-Throughput Protein Engineering Using Droplet Microfluidics Coupled to Mass Spectrometry," ACS Omega 3, pp. 1498-1508; 2018; doi:10.1021/acsomega.7b01973.

Dolan, J.W. et al., "Injectors and Autossamplers," Troubleshooting LC Systems, Springer Science + Business Media New York 1989; pp. 235-289.

Dong, Michael W., "HPLC Instrumentation in Pharmaceutical Analysis: Status, Advances, and Trends," Elsevier Inc. Handbook of Pharmaceutical Analysis by HPLC, 2005, pp. 47-75.

Dressler, Oliver Thesis, "Active And Passive Control in High-Throughput Microfluidic Experimentation," ETH Zurich Research Collection, pp. 1-222, Feb. 26, 2018, https://doi.org/10.3929/ethz-b-000269520.

Eastburn, Dennis J. et al., "Picoinjection Enables Digital Detection of RNA With Droplet RT-PCR," Plos One 8(4):e62961; doi: 10.1371/journal.pone.0062961 ;2013.

Eastburn, Dennis J., et al., "Ultrahigh-Throughput Mammalian Single-Cell Reverse-Transcriptase Polymerase Chain Reaction in Microfluidic Drops," Anal. Chem. 2013, 85, pp. 8016-8021; dx.doi.org/10.1021/ac402057q.

Fischlechner, Martin et al., "Evolution of Enzyme Catalysts Caged in Biomimetic Gel-Shell Beads," Nature Chemistry, vol. 6, pp. 791-796; and pp. 1-33, Sep. 2014; Doi: 10.1038/nchem.1996.

Frenz, Lucas et al., "Reliable Microfluidic On-Chip Incubation of Droplets in Delay-Lines," The Royal Society of Chemistry, Lab Chip, 9, pp. 1344-1348, 2009; www.rsc.org/loc; Doi:10.1039/b816049j.

Girault, Mathias, et al., "An On-Chip Imaging Droplet-Sorting System: A Real-Time Shape Recognition Method to Screen Target Cells in Droplets With Single Cell Resolution," Scientific Reports, 7:40072, pp. 1-10; Doi: 10.1038/srep40072;2017.

Gruner, Philipp et al., "Controlling Molecular Transport in Minimal Emulsions," Nature Communications, 7:10392; doi:10.1038/ncomms10392 ;2016.

Gruner, Philipp, et al., "Stabilisers for Water-In-Fluorinated-Oil Dispersions: Key Properties for Microfluidic Applications," Current Opinion in Colloid & Interface Science 20 (2015) pp. 183-191; http://dx.doi.org/10.1016/j.cocis.2015.07.005.

Hammar, Petter et al., "Single-Cell Screening of Photosynthetic Growth and Lactate Production by Cyanobacteria," Biotechnol Biofuels, (2015) 8:198; Doi: 10.1186/s13068-015-380-2.

(56) References Cited

OTHER PUBLICATIONS

Hardiman, Elizabeth et al., "Directed Evolution of a Thermophilic β-glucosidase for Cellulosic Bioethanol Production," Appl. Biochem Biotechnol (2010) 161:301-302; Doi: 10.1007/s12010-009-8794-6.
Hatch, Andrew C. et al., "1-Million Droplet Array With Wide-Field Fluorescence Imaging for Digital PCR," Lab Chip, 2011, 11, 838; www.rsc.org/loc; Doi: 10.1039/cllc20561lg.
Hatch, Andrew C. et al., "Passive Droplet Sorting Using Viscoelastic Flow Focusing," Lab Chip, 2013, 13, 1308; doi: 10.1039/c2lc41160a.
Hori, Yutaka et al., "Cell-Free Extract Based Optimization of Biomolecular Circuits With Droplet Microfluidics," Lab Chip, 2017, doi: 10.1039/c7lc00552k.
Huang, Mingtao et al., "Microfluidic Screening and Whole Genome Sequencing Identifies Mutations Associated With Improved Protein Secretion by Yeast," PNAS, Aug. 10, 2015, pp. E4689-E4696; www.pnas.org/cgi/doi/10.1073/pnas.150646112.
International Search Report and Written Opinion for International Patent Application No. PCT/US2019/025244 dated Aug. 16, 2019 16 pages.
Kaminski, Tomasz S. et al., "Droplet Microfluidics For Microbiology: Techniques, Applications and Challenges," Lab Chip, 2016, 16, 2168; doi: 10.1039/c6lc00367b.
Kim, Hyon Soo, et al. "High-Throughput Droplet Microfluidics Screening Platform for Selecting Fast-Growing and High Lipid-Producing Microalgae From a Mutant Library," Plant Direct, pp. 1-13, 2017; wileyonlinelibrary.com/journal/pld3; doi: 10.1002/pld3.11.
Kim, Hyun Soo et al., "A Droplet Microfluidics Platform for Rapid Microalgal Growth and Oil Production Analysis," Biotechnology and Bioengineering, vol. 113, No. 8, Aug. 2016, pp. 1691-1701.
Kintses, Balint, et al., "Picoliter Cell Lysate Assays in Microfluidic Droplet Compartments for Directed Enzyme Evolution," Chemistry & Biology 19, pp. 1001-1009, Aug. 24, 2012; http://dx.doi.org/10.1016/j.chembiol.2012.06.009.
Krafft, Marie Pierre, et al., "Advanced Fluorocarbon-Based Systems for Oxygen and Drug Delivery, and Diagnosis," Advanced Drug Delivery Reviews, 47 (2001) pp. 209-228; Doi: 10.3109/10731199709118896.
Lan, Freeman et al., "Droplet Barcoding for Massively Parallel Single-Molecule Deep Sequencing," Nature Communications, 7:11784, doi: 10.1038/ncomms11784; www.nature.com/naturecommunications ;2016.
Levin, Itay et al., "Evolution in Microfluidic Droplet," Chemistry & Biology, 19, Aug. 24, 2012; http://dx.doi.org/10.1016/j.chembiol.2012.08.004.
Lim, Jiseok et al., "Ultra-High Throughput Detection of a Single Cell β-Galactosidase Activity in Droplets Using Micro-Optical Lens Array," Applied Physics Letters 103, 203704, pp. 1-4 (2013).
Lim, Shaun W. et al., "PCR-Activated Cell Sorting for Cultivation-Free Enrichment and Sequencing of Rare Microbes," PLoS One, Doi: 10.1371/journal.pone.0113549, pp. 1-16, Jan. 28, 2015.
Macconnell, Andrew B. et al., "The Poisson Statistics of Combinatorial Library Sampling Predict False Discovery Rates of Screening," ACS Combinatorial Science, Jul. 6, 2017; doi: 10.1021/acscombsci.7b00061.
Macosko, Evan Z. et al., "Highly Parallel Genome-Wide Expression Profiling of Individual Cells Using Nanoliter Droplets," Cell, 161, pp. 1202-1214; May 21, 2015; http://dx.doi.org/10.1016/j.cell.2015.05.002.
Mair, Philip et al., "Exploring Sequence Space in Search of Functional Enzymes Using Microfluidic Droplets," Current Opinion in Chemical Biology, 37:137-144, 2017; http://dx.doi.org/10.1016/j.cbpa.2017.02.018.
Mazutis, Linas et al., "Single-Cell Analysis and Sorting Using Droplet-Based Microfluidics," Nature Protocols, vol. 8, No. 5, pp. 870-891, 2013; doi: 10.1038/nprot.2013.046.
Meyer, Andreas et al., "Optimization of a Whole Cell Biocatalyst by Employing Genetically Encoded Product Sensors Inside Nanolitre Reactors," Nature Chemistry, vol. 7, Aug. 2015, pp. 673-678; Doi: 10.1038/nchem.2301.
Najah, Majdi et al., "Droplet-Based Microfluidics Platform for Ultra-High-Throughput Bioprospecting of Cellulolytic Microorganisms," Chemistry & Biology 21, pp. 1722-1732, Dec. 18, 2014; http://dx.doi.org/10.1016/j.chembiol.2014.10.020.
Nisisako, Takasi et al., "Formation of Droplets Using Branch Channels in a Microfluidic Circuit," SICE Aug. 2002. 5-7, 2002, Osaka; pp. 1262-1264.
Obexer, Richard et al., "Efficient Laboratory Evolution of Computationally Designed Enzymes With Low Starting Activities Using Fluorescence-Activated Droplet Sorting," Protein Engineering, Design & Selection, vol. 29, 9, pp. 355-366, 2016; doi: 10.1093/protein/gzw032.
Ostafe, Raluca et al.,, "A High-Throughput Cellulase Screening System Based on Droplet Microfluidics," Biomicrofluidics 8, 041102 (2014); http://dx.doi.org/10.1063/1.4886771.
Pekin, Deniz et al., "Quantitative and Sensitive Detection of Rare Mutations Using Droplet-Based Microfluidics," Lab Chip, 2011, 11, 2156; www.rsc.org/loc; Doi: 10.1039/cllc20128j.
Prakadan, Sangay M., et al., "Scaling by Shrinking: Empowering Single-Cell 'Omics' with Microfluidic Devices," Nature Reviews, Genetics; Macmillan Publishers Limited Part of Springer Nature, pp. 1-17, 2017; doi: 10.1038/nrg.2017.15.
China, First Office Action for Application No. 2022103546375, dated Feb. 11, 2023, 11 pages [Translation].
Lin Bingcheng et al. Illustrated Microfluidic Chip Laboratory ( 图解微流控芯片实 验室 ), Science Press, Sep. 2008, pp. 6-7) [Translation].
China, Decision of Rejection for Application No. 202210354637.5, dated Aug. 25, 2023, 10 pages [Translation].
Europe Patent Office, Office Action for EP 19782031.9 dated Oct. 16, 2023; 10 pages.

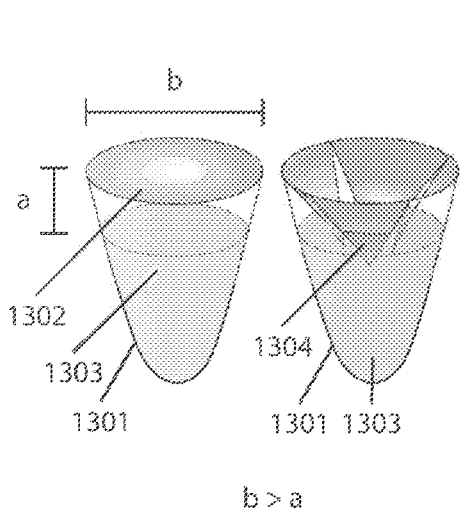
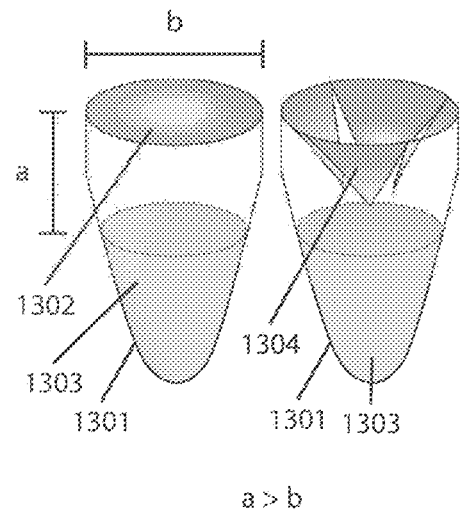
Figure 13A     Figure 13B

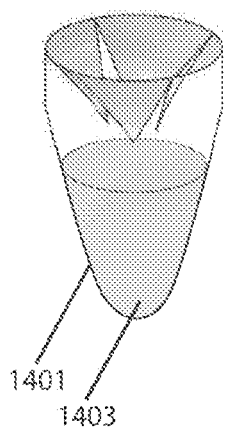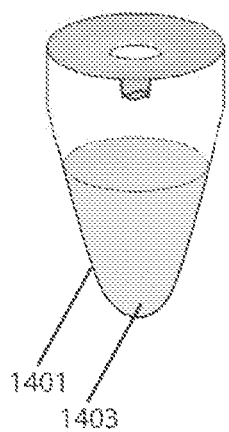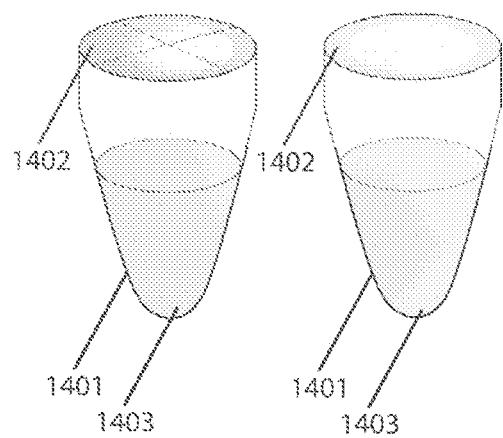
Figure 14A                Figure 14B

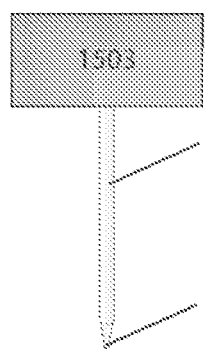 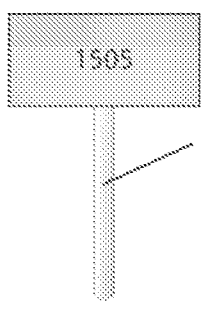 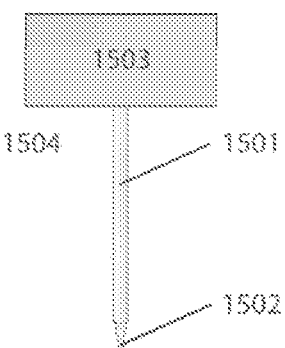 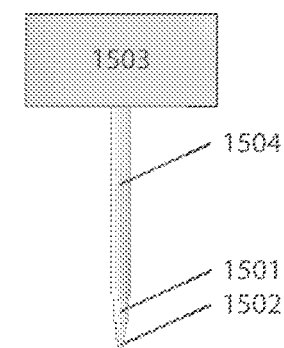
Figure 15A          Figure 15B          Figure 15C

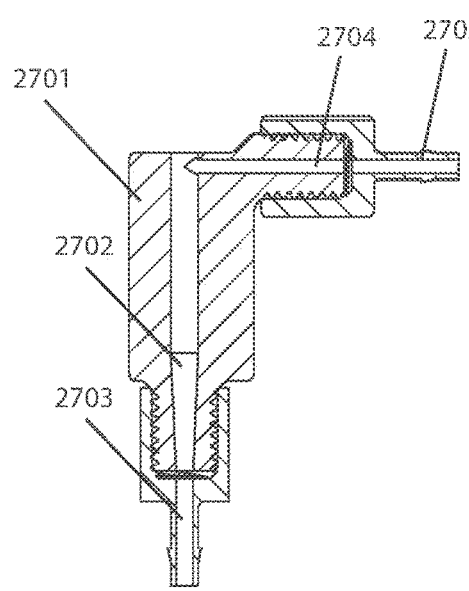
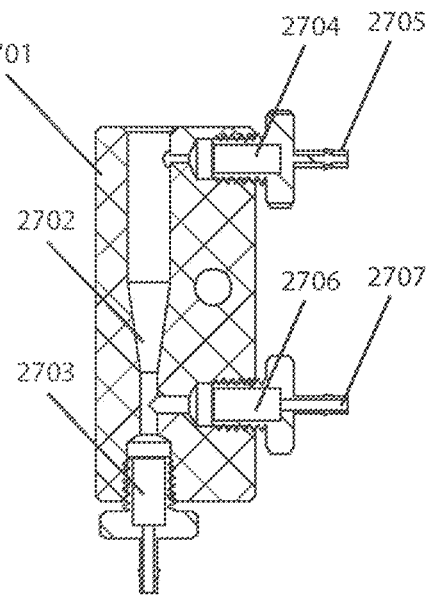
Figure 27A          Figure 27B
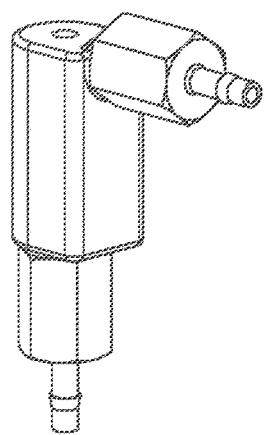
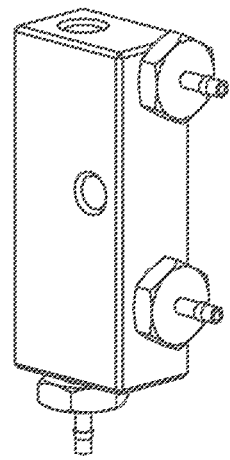
Figure 27C          Figure 27D

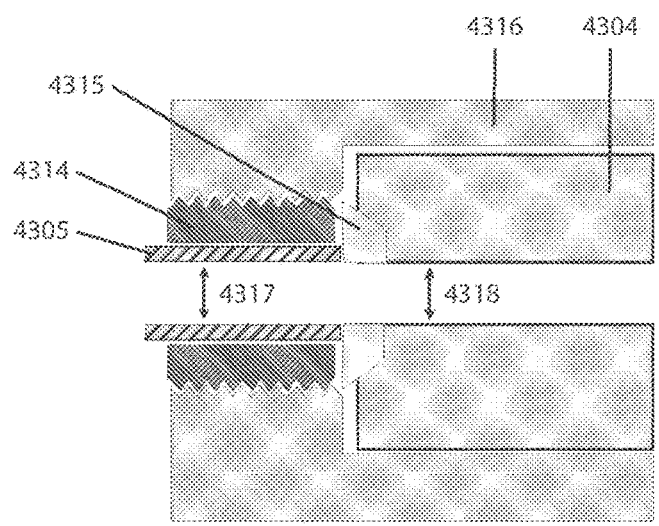
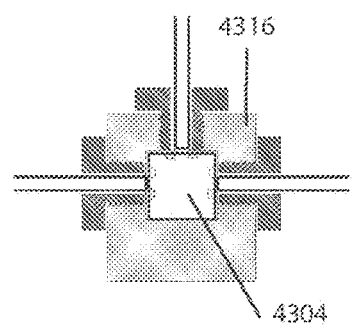
Figure 43A  Figure 43B
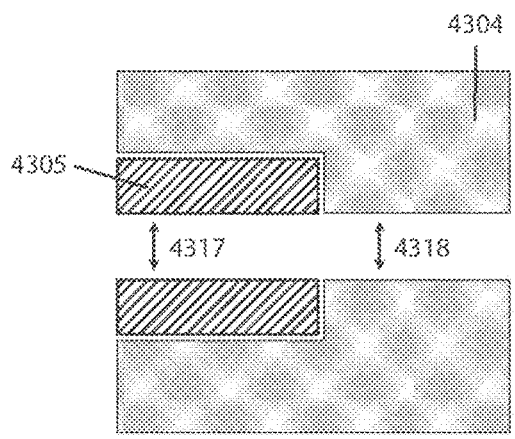
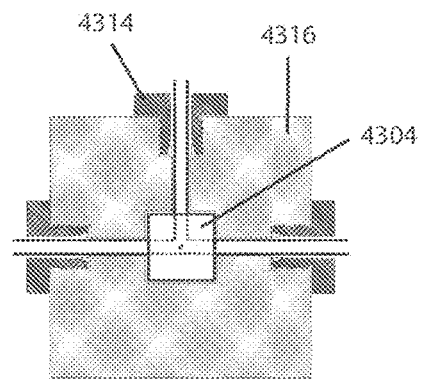
Figure 43C  Figure 43D

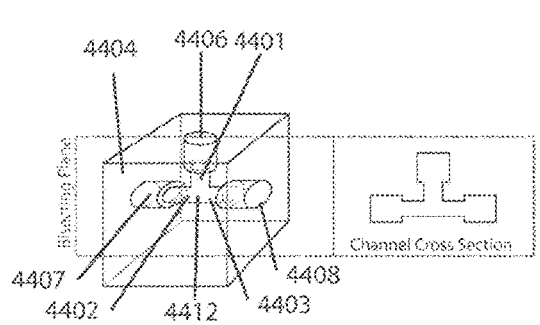
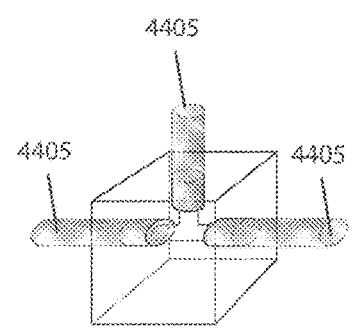
Figure 44A
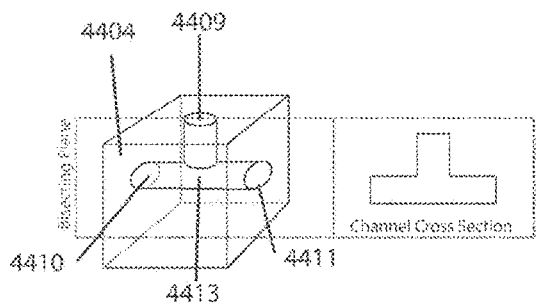
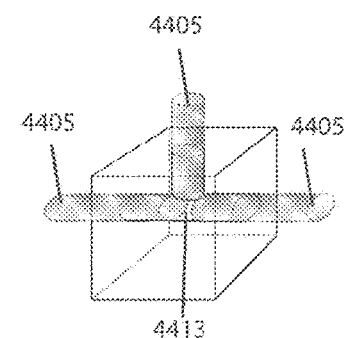
Figure 44B

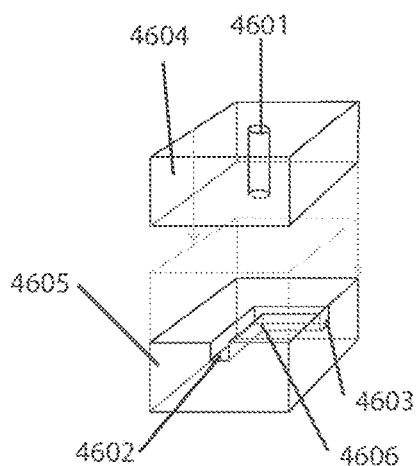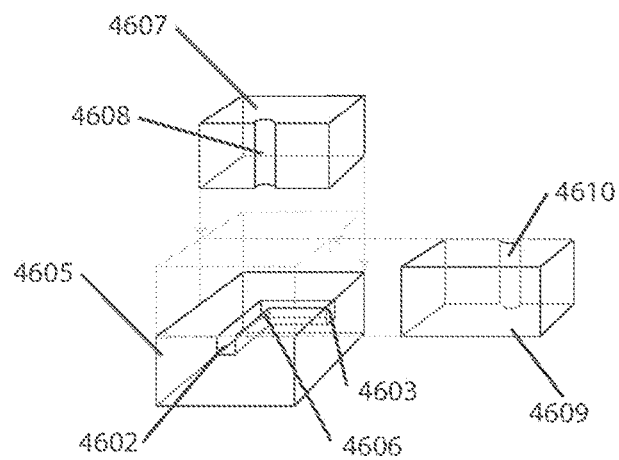
Figure 46A   Figure 46B

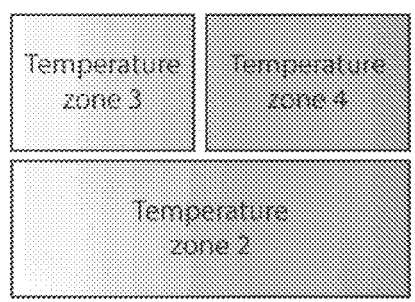
Two or more separate cylinders composed of many temperature zones
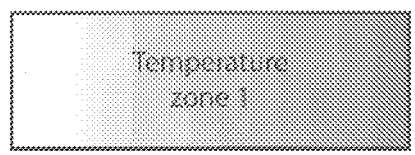
Figure 80

Increasing/decreasing temperature across a zone
within a PCR cycle

Increasing/decreasing temperature across a zone
between PCR cycles

Cylinder composed
of many fixed
temperature zones

SYSTEMS AND METHODS FOR SERIAL FLOW EMULSION PROCESSES

CROSS-REFERENCE

This application is a continuation of U.S. patent application Ser. No. 16/372,290, filed Apr. 1, 2019, which claims the benefit of U.S. Provisional Application No. 62/651,619, filed Apr. 2, 2018, which applications are incorporated herein by reference.

BACKGROUND

Serial flow emulsion systems processes have numerous applications in physical, chemical, and biological areas, and improvements in such systems and processes are useful. For example, the quantitation of nucleic acids is an indispensable technique in medical and biological applications. Methods for detecting and quantitating nucleic acids, such as emulsion-based digital nucleic acid amplification, including emulsion-based polymerase chain reaction (PCR), provide greater accuracy and convenience as compared to traditional nucleic acid amplification, such as traditional polymerase chain reaction (PCR) methods. Performing emulsion-based digital nucleic acid amplification in serial-flow, however, face problems with cross-contamination between individual volumes of the dispersed phase and/or the channel and/or tube containing the emulsion.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIGS. 13A and 13B shows a designs of seals to avoid sample contamination.
FIGS. 14A and 14B show sealing systems.
FIGS. 15A, 15B, and 15C show systems for aspirating samples and piercing seals.
FIGS. 27A and 27C show one system for cleaning a fluid aspirator.
FIGS. 27B and 27D show a second system for cleaning a fluid aspirator.
FIGS. 43A, 43B, 43C, and 43D show conduit, e.g., partitioner connections.
FIGS. 44A and 44B show different partitioner connections to tubing.
FIGS. 46A and 46B show different methods of manufacturing of partitioners.

FIG. 80 shows a discrete four temperature zone heater-reactor.

DETAILED DESCRIPTION

Figure 1:
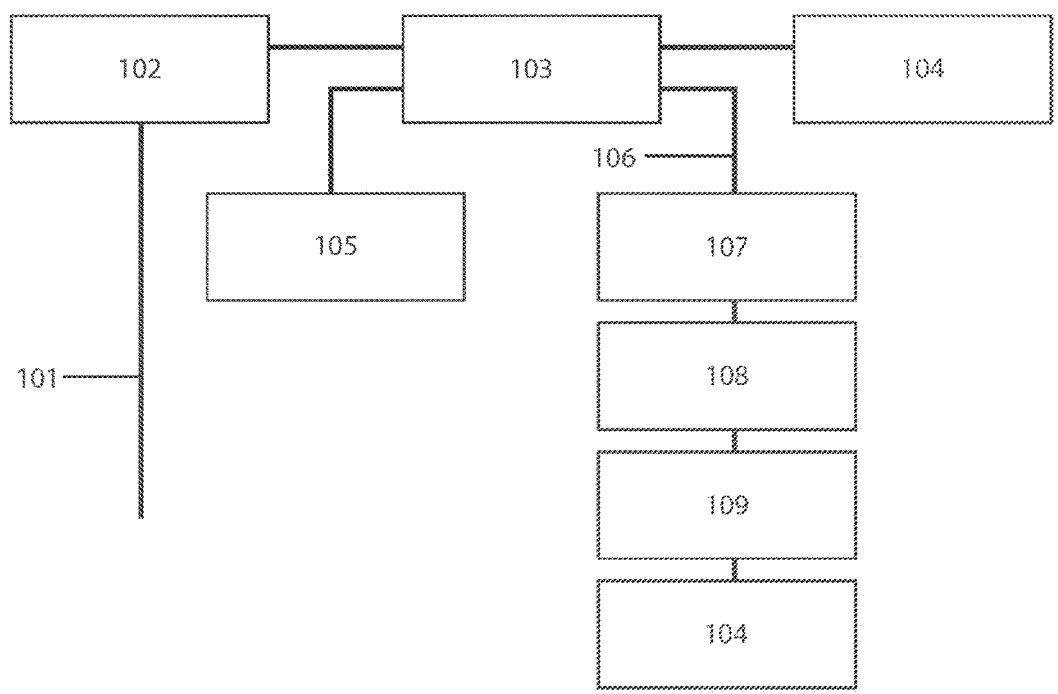
FIG. 1 shows an intake system with a waste.

I. Overview
II. Intake System
III. Injector
IV. Process System
  A. Partitioner
  B. Reactor
  C. Detector
V. Definitions
VI. Numbered Embodiments I. Overview Systems and methods provided herein relate to flowing emulsions.

In certain embodiments, provided herein are systems and methods comprising an intake system and a process system. An emulsion is formed and flows through the process system to be processed. The emulsion comprises partitions of a dispersed phase in a continuous phase; typically, the dispersed phase is supplied by the intake system, e.g., as a sample or portion of a sample that is taken up by the intake system, and continuous phase is supplied, at least in part, by the process system. In certain embodiments, the intake system and the process system are separate, e.g., at no time is there continuous flow between the intake system and the process system.

Systems and methods can include use of an injector, where the injector is positioned between the intake system and the process system, and the injector can be in fluid communication with the intake system, or in fluid communication with the process system, but not both simultaneously. A series of aliquots of dispersed phase, e.g., a series of aliquots from samples or portions of samples, can be flowed through the intake system into the injector, then each is injected separately into the process system. Methods can include flowing one or more of a purge fluid, a denaturing fluid, and/or a spacer fluid through the intake system, e.g., including the injector, such as methods as described herein, between flow of aliquots of dispersed phase, e.g., sample, through the intake system, e.g., including the injector, such as between injections of dispersed phase into the process system. The injector can be configured to inject a fixed volume from the intake system into the process system, for example, a volume of 0.1-200 uL, such as 0.1-100 uL, for example, 1-100 uL.

The process system can include a partitioner (also referred to as a droplet generator herein) for partitioning dispersed phase supplied by the intake system, e.g., a sample or portion of a sample comprising dispersed phase, into partitions in a continuous phase, e.g., forming an emulsion. Any suitable partitioner, such as partitioners described herein, may be used. The partitioner can have at least one inlet for dispersed phase, at least one inlet for continuous phase, and an outlet leading to the rest of the process system. In certain embodiments, the partitioner comprises a "reverse-y" partitioner, as described further herein. In certain embodiments, the partitioner is relatively insensitive to flow variations in the inlets, as described further herein. In certain embodiments, the partitioner comprises an inlet for dispersed phase and an inlet for continuous phase that comprise conduits that meet at an angle of 170-180 degrees, for example, at an angle of 180 degrees (co-axial), as described further herein. In certain embodiments, the partitioner can produce partitions of an average volume between 0.05 and 50 nL, such as between 0.1 and 10 nL.

The process system can further comprise a reactor for initiating or modulating a reaction in the partitions. The reactor can be any suitable reactor, such as reactors as described herein. In certain embodiments, the reactor comprises a thermal cycler, e.g., for performing polymerase chain reaction (PCR). In certain embodiments the reactor comprises a heating core maintained at a consistent temperature, e.g., for performing incubations. In certain embodiments, systems and methods include an intake system, a process system, an injector positioned between the intake system and the process system where the injector can be in fluid communication with the intake system, in fluid communication with the process system, but not both simultaneously, and a reactor, such as a reactor comprising a thermal cycler. Processes are generally described in terms of PCR herein, however, any suitable process may be conducted in the process system, including but not limited to sample processing applications including cell lysis, cell growth, ligation, digestions, nucleic acid assembly reactions, nucleic acid editing, nucleic acid modification, or sample analysis including the detection of nucleic acids, proteins, and microbial organisms using reactions include but are not limited to RNA transcription, hybridization chain reaction (HCR), nicking chain reaction, loop-mediated isothermal amplification (LAMP), strand displacement amplification (SDA), helicase-dependent amplification (HDA), nicking enzyme amplification reaction (NEAR), protein detection, protein melt temperature analysis, small molecule detection, microbial growth rate testing, antibiotic resistance testing, microbial small molecule production, molecule-molecule interaction studies. In certain embodiments systems and methods provide an intake system, an injector, where the injector is positioned between the intake system and the process system, and the injector can be in fluid communication with the intake system, or in fluid communication with the process system, but not both simultaneously, a partitioner, such as a partitioner described above or elsewhere herein, and a reactor. In certain embodiments, at least a portion of partitions formed by the partitioner comprise at least one nucleic acid and the reactor is a thermal cycler for performing PCR on the partitions.

The process system can comprise a detector for detecting one or more characteristics of partitions as they flow through the detector. The detector can be any suitable detector, such as a detector as described herein. Partitions flow through the detector in single file in a conduit that includes an interrogation region where, e.g. electromagnetic radiation from the flow through the interrogation region, such as electromagnetic radiation from a partition flowing through the interrogation region, is emitted to be detected by one or more detection elements. The detector can be configured so that electromagnetic radiation from partitions that is detected by the detection element all, or substantially all, comes from individual partitions as they flow through the interrogation region; that is, there is little or no overlap in detected electromagnetic radiation from one partition to another. 1) In certain embodiments, the detector comprises an optical restriction configured and positioned between the interrogation region and the detection element so that only a portion of electromagnetic radiation from the interrogation region that could otherwise be detected by the detection element is detected, for example, less than 10% of the electromagnetic radiation, such as less than 1%. In certain embodiments, systems and methods include an intake system, a process system, an injector positioned between the intake system and the process system where the injector can be in fluid communication with the intake system, in fluid communication with the process system, but not both simultaneously, where the process system comprises a detector comprising an optical restriction. In certain embodiments, systems and methods include a partitioner and a detector, where the detector comprises an optical restriction. 2) In certain embodiments, the region of the conduit in the interrogation region has a cross-sectional area that is equal to or less than the average spherical cross-sectional area of partitions flowing through the detector, such as less than 90% or less than 50%. In certain embodiments, systems and methods include an intake system, a process system, an injector positioned between the intake system and the process system where the injector can be in fluid communication with the intake system, in fluid communication with the process system, but not both simultaneously, where the process system comprises a detector comprising a conduit comprising an interrogation region where the region of the conduit in the interrogation region has a cross-sectional area that is equal to or less than the average spherical cross-sectional area of partitions flowing through the detector, such as less than 95%, or 90% or less than 50%. In certain embodiments, systems and methods include a partitioner and a detector, where the detector comprising a conduit comprising an interrogation region where the region of the conduit in the interrogation region has a cross-sectional area that is equal to or less than the average spherical cross-sectional area of partitions flowing through the detector, such as less than 90% or less than 50%. 3) In certain embodiments the detector comprises an excitation source, or a plurality of excitation sources, such as at least 2, 3, 4, or 5 excitation sources, for supplying electromagnetic radiation to the interrogation region, where the excitation source or sources comprise a lock-in amplification system. In such systems only a single detection element, e.g., photodetection element, such as a silicon photomultiplier, may be used, even with a plurality of excitation sources. In certain embodiments, systems and methods include an intake system, a process system, an injector positioned between the intake system and the process system where the injector can be in fluid communication with the intake system, in fluid communication with the process system, but not both simultaneously, where the process system comprises a detector and the detector comprises an excitation source, or a plurality of excitation sources, such as at least 2, 3, 4, or 5 excitation sources, for supplying electromagnetic radiation to the interrogation region, where the excitation source or sources comprise a lock-in amplification system; in certain embodiments, only a single detection element is used. 4) In certain embodiments the detector comprises a partition separation system that separates partitions before they reach the interrogation region, e.g., by adding continuous phase between partitions before they reach the interrogation region. In certain embodiments, systems and methods include an intake system, a process system, an injector positioned between the intake system and the process system where the injector can be in fluid communication with the intake system, in fluid communication with the process system, but not both simultaneously, where the process system comprises a detector that comprises a partition separation system that separates partitions before they reach the interrogation region, e.g., by adding continuous phase between partitions before they reach the interrogation region. 5) Systems and methods provided herein may also include one or more disengager, e.g., a system that removes continuous phase from an emulsion, for example, after a partitioner but prior to a reactor, or after a detector, or both, and, in certain embodiments, adds back some or all of the removed continuous phase to the process system, e.g., at a partition separation system. In certain embodiments, systems and methods include an intake system, a process system, an injector positioned between the intake system and the process system where the injector can be in fluid communication with the intake system, in fluid communication with the process system, but not both simultaneously, where the process system comprises one or more disengager, e.g., a system that removes continuous phase from an emulsion, for example, after a partitioner but prior to a reactor, or after a detector, or both, and, in certain embodiments, adds back some or all of the removed continuous phase to the process system, e.g., at a partition separation system. 6) In certain embodiments the conduit of the interrogation region is configured to have the same or substantially the same transmittance, e.g., for electromagnetic radiation from excitation sources that reaches the interrogation region and for electromagnetic radiation from the interrogation region that is detected by the detection element, around the circumference of the conduit; for example, the conduit can be a tube, such as a tube with a circular or substantially circular cross-section. Such a configuration can allow for, e.g., coplanar or substantially coplanar arrangement of a plurality of excitation sources, such as at least 2, 3, 4, or 5 excitation sources, and/or one or more detection elements, such as in a plane orthogonal or substantially orthogonal to an axis of flow of partitions in the interrogation region. In certain embodiments, systems and methods include an intake system, a process system, an injector positioned between the intake system and the process system where the injector can be in fluid communication with the intake system, in fluid communication with the process system, but not both simultaneously, where the process system comprises a detector comprising an interrogation region comprising a conduit, where the conduit of the interrogation region is configured to have the same or substantially the same transmittance, e.g., for electromagnetic radiation from excitation sources that reaches the interrogation region and for electromagnetic radiation from the interrogation region that is detected by the detection element, around the circumference of the conduit; for example, the conduit can be a tube, such as a tube with a circular or substantially circular cross-section. In certain embodiments, systems and methods provided herein include a detector with characteristics of at least one of 1), 2), 3), 4), 5) and 6). In certain embodiments, systems and methods provided herein include a detector with characteristics of at least two of 1), 2), 3), 4), 5) and 6). In certain embodiments, systems and methods provided herein include a detector with characteristics of at least three of 1), 2), 3), 4), 5) and 6). In certain embodiments, systems and methods provided herein include a detector with characteristics of at least four of 1), 2), 3), 4), 5) and 6). In certain embodiments, systems and methods provided herein include characteristics of at least five of 1), 2), 3), 4), 5) and 6). In certain embodiments, systems and methods provided herein include a detector with characteristics of all of 1), 2), 3), 4), 5) and 6). In certain embodiments, systems and methods provided herein include an intake system and a process system, wherein the intake system and the process system are never in fluid communication, and the process system comprises a detector with characteristics of at least one of 1), 2), 3), 4), 5) and 6). In certain embodiments, systems and methods provided herein include an intake system and a process system, wherein the intake system and the process system are never in fluid communication, and the process system comprises a detector with characteristics of at least two of 1), 2), 3), 4), 5) and 6). In certain embodiments, systems and methods provided herein include an intake system and a process system, wherein the intake system and the process system are never in fluid communication, and the process system comprises a detector with characteristics of at least three of 1), 2), 3), 4), 5) and 6). In certain embodiments, systems and methods provided herein include an intake system and a process system, wherein the intake system and the process system are never in fluid communication, and the process system comprises a detector with characteristics of at least four of 1), 2), 3), 4), 5) and 6). In certain embodiments, systems and methods provided herein include an intake system and a process system, wherein the intake system and the process system are never in fluid communication, and the process system comprises a detector with characteristics of at least five of 1), 2), 3), 4), 5) and 6). In certain embodiments, systems and methods provided herein include an intake system and a process system, wherein the intake system and the process system are never in fluid communication, and the process system comprises a detector with characteristics of all of 1), 2), 3), 4), 5) and 6).

Components of the systems are fluidly connected as appropriate and as described further herein. Generally, the intake side can comprises a continuous conduit between an intake tip and the injector; where the injector comprises a common conduit that is configured to be fluidly connected to the intake side at a first intake system conduit; it will also be fluidly connected to a second intake system conduit, e.g., leading to waste. This allows a dispersed phase, e.g., a sample, such as a sample in aqueous phase, to be transported into the common conduit of the injector and fill or partially fill the common conduit. The common conduit can have a fixed volume so that this volume can be injected into the process side. Surfaces of the intake conduit that come in contact with dispersed phase comprising a first fluid, transported by the intake system, e.g., with sample, such as sample in a aqueous phase, can have greater affinity for a second fluid that is passed through part or all of the conduit, such as a continuous phase, or such as a purge fluid or other fluid as described herein. In this way, e.g., residual sample can be displaced from the conduit through, e.g. a cleaning phase. In certain embodiments, the surfaces comprise a fluoropolymer and the second fluid comprises a fluorinated oil. Surfaces of the injector that come in contact with dispersed phase comprising a first fluid, transported by the intake system, e.g., with sample, such as sample in a aqueous phase, can have greater affinity for a second fluid that is passed through the injector, such as a continuous phase, or such as a purge fluid or other fluid as described herein. In certain embodiments, the surfaces comprise a fluoropolymer and the second fluid comprises a fluorinated oil. When the injector is positioned to be in fluid communication with the process side, there is typically a first process conduit positioned to be in fluid communication with the common conduit of the injector and a second process conduit in fluid communication with the common conduit, where the first process conduit transports a fluid, such as continuous phase, into the injector and displaces the dispersed phase, e.g., sample, such as sample in an aqueous phase, into the second process conduit where it is transported to the rest of the process system. The second process conduit is generally fluidly connected to further conduits in the system, so that dispersed phase transported in the intake side and through the injector flows in the conduits from the injector through the process system and eventually exits the system. At various points other conduits may join the main process conduit, for example, at a partitioner where, e.g., continuous phase is added to dispersed phase to produce an emulsion; in certain embodiments, a partition separation system may be used to, e.g., add continuous phase between partitions to separate the partitions prior to detection. In certain embodiments, flow through the conduit from at least a partitioner through the rest of the system is continuous; in certain embodiments, flow from the injector into the process system is discontinuous, e.g., there are times when the injector is disconnected from the process system and no flow occurs through the injector to the process system. Thus, e.g., introduction of dispersed phase, e.g., sample, into the system may be discontinuous. For example, a first aliquot of dispersed phase, e.g., comprising a first sample, may be introduced into the process system, then a second aliquot of dispersed phase, e.g., comprising a second sample, may be separately introduced into the process system, separated from the first sample. Surfaces of the process system conduit and other conduits and surfaces that come in contact with dispersed phase comprising a first fluid, transported by the intake system, e.g., with sample, such as sample in a aqueous phase, can have greater affinity for a second fluid that is passed through the conduit, such as a continuous phase. In certain embodiments, the surfaces comprise a fluoropolymer and the second fluid comprises a fluorinated oil. In certain embodiments, all or a substantial portion of surfaces of the system that come in contact with a first fluid, such as a dispersed phase, e.g., a sample such as an aqueous sample, from intake system through injector through process system, have greater affinity for a second fluid, e.g., a continuous phase, that is introduced into the system after the first fluid. In certain embodiments, at least 90, 95, 99, 99.5, 99.9, 99.95, or 99.99% of surfaces of the system have greater affinity for the second fluid than for the first fluid. In certain embodiments, surfaces comprise a fluoropolymer and the second fluid comprises a fluorinated oil.

Dimensions of conduits may be any suitable dimensions, as described herein. Exemplary dimensions for various components (given as diameters for a circular cross-section): aspiration tip/intake tip, 0.1-254 um, for example 1-254 um, such as 25-75 um; aspiration line/intake line, 10-3175 um, for example, 200-800 um, such as 200-300 um; common conduit of injector, 10-3100 um, for example, 250-750 um, such as 450-550 um; conduit from injector to partitioner, 100-2500 um, for example, 200-500 um, such as 200-300 um; inlet to partitioner, 10-2500 um, for example 100-500 um, such as 200-300 um; outlet from partitioner, 10-2500 um, for example 100-500 um, such as 200-300 um; reactor, 10-2500 um, for example 100-500 um, such as 200-300 um; interrogation region of detector, 10-250 um, for example 75-100 um, such as 80-100 um.

At certain points in the system, a first conduit may be connected to a second, different conduit. This can occur, e.g., at a junction between a conduit from the injector to a conduit in a partitioner, and/or between a conduit in a partitioner and a conduit leading to a reactor, and/or be a conduit leading from a reactor to a conduit in a partition separation system, and/or between a conduit leading from a partition separation system to a conduit in a detector, and/or between a conduit leading from a reactor to a conduit in a detector. Any or all of these connections represent points where a disruption of flow may occur. In certain embodiments provided herein, connections between a first conduit and a second, different, conduit, are configured to cause minimal or no disruption to flow. Such connections are described further herein.

In certain embodiments a dispersed phase is transported by an intake system from a container, e.g., a sample container, into the injector, and injected from the injector into the process system, where it moves through the process system, e.g., through a partitioner. The dispersed phase may be surrounded by continuous phase at least in the injector, and generally from the start of the intake system, so that when it is injected in the process system, it comprises dispersed phase in continuous phase. As the intake system transports a series of dispersed phase aliquots into the injector and ultimately into the process system, the aliquots each form a packet of dispersed phase in continuous phase (also referred to herein as a programmed emulsion) as they are introduced into the process system, i.e., a first emulsion. The packets (i.e., partitions in this first emulsion) may be any suitable volume, such as volumes described herein, such as 0.1-200 uL, or 0.1-100 uL, or 1-50 uL, or 5-50 uL. This volume may be a fixed volume from a fixed volume in the injector. Each packet can then be further divided into a plurality of partitions in continuous phase at a partitioner, e.g., each packet can be further divided into at least 100, 500, 1000, 5000, 10,000, 15,000, 20,000, 25,000, 30,000, 40,000, 50,000, or 100,000 partitions in continuous phase, i.e., further divided into a second emulsion, for example, partitions of any suitable volume in continuous phase, such as volumes described herein, for example, an average volume of 0.05-50 nL, such as 0.1-10 nL, for example, 0.1-1.0 nL. The plurality of partitions flow in a common conduit through the rest of the system; in certain cases, e.g., when a separation fluid is added prior to a detector, one or more branch conduits may intersect with the main conduit, e.g., for adding a separation fluid or removing a fluid.

In systems that include an intake side and a process side, where the intake side is used to take up a series of aliquots, e.g., sample and/or other material, from one or more containers, e.g., sample containers, and send them to the process side, problems with contamination, e.g., cross-contamination, can occur. As used herein, "cross-contamination" includes 1) sample-to-sample carryover; 2) within-sample alterations that affect processes occurring on the process side of the system (for example, coalescence of partitions within a sample); and 3) introduction of material into a sample from the environment, e.g., dust, materials from a user, and the like. In systems and methods provided herein, the same intake and process system can be used to process a series of samples, without the need either to replace portions of either intake or process system, or to use separate portions of intake or process system for separate samples, and still maintain very low levels of cross-contamination of samples, for example, an average of less than 20, 10, 5, 2, 1, 0.5, 0.2, 0.1, 0.05, 0.01, 0.05, or 0.01, or 0.005, or 0.001%. Thus, systems and methods provided herein can utilize the same components from sample to sample, e.g., the same intake line, the same injector, the same partitioner, the same reactor, and/or the same detection unit, with little or no cross-contamination of samples, for example, an average of less than 10, 5, 2, 1, 0.5, 0.2, 0.1, 0.05, 0.01, 0.05, 0.01, 0.005, or 0.001%. One suitable method for measuring cross-contamination is to introduce a first sample in the system that contains a high level of molecules of interest, e.g., a high level of a nucleic acid, such as DNA, perform normal cleaning routines, then introduce a second sample into the system that contains no molecules of interest, e.g., no nucleic acid such as DNA. Both samples are processed by the process system, e.g., undergo PCR in the case of a digital PCR system. If cross-contamination is zero, then partitions of the second sample will contain no molecules of interest from the first sample, e.g., no DNA molecules, and should be processed and detected so that no positive signals are received at the detector. Any partitions of the second sample that give a positive signal at the detector, such as a signal indicating nucleic acid amplification, indicates cross-contamination from the first sample to the second sample. For example, in a digital PCR system, if a first sample contains 50,000 molecules of DNA, and the second sample contains no DNA, all partition formed from the second sample should give a negative signal (no DNA amplification). If a single partition of the second sample gives a positive signal, it can be assumed that a molecule of DNA from the first sample has cross-contaminated the second sample, and the level of cross-contamination is 1/50,000, or 0.002%. If ten partitions of the second sample give a positive signal, it can be assumed that 10 molecules of DNA from the first sample has cross-contaminated the second sample, and the level of cross-contamination is 10/50,000, or 0.02%. For purposes of this type of assay, it is assumed that a positive signal in a partition of the second sample represents a single molecule of interest, e.g., a single DNA molecule, in the partition of the second sample.

a) Sample-to-sample carryover is one source of cross-contamination. That is, remnants of a first sample can carry over into a second, subsequent sample, and/or into further subsequent samples. In certain embodiments, such as in PCR systems, e.g., digital PCR systems, even a single molecule from a first sample, e.g., a single nucleic acid, if present in a second sample, can be, e.g., amplified and detected and give a false positive in the second sample. Other contaminants can also carry over from a first sample, e.g., materials that interfere with one or more processes that occur on the process side. In systems and methods provided herein, the same intake and process system can be used to process a series of samples, without the need either to replace portions of either intake or process system, or to use separate portions of intake or process system for separate samples, and still maintain very low levels of sample-to-sample carryover between samples. Thus, systems and methods provided herein can utilize the same components from sample to sample, e.g., the same intake line, the same injector, the same partitioner, the same reactor, and/or the same detection unit, with little or no sample-to-sample carryover between samples. For example, in certain embodiments, systems and methods are designed to flow a series of different samples through the components of the system where the same component, e.g., the same intake line, the same injector, the same partitioner, the same partition separator, and/or the same detector, is used for at least a first and a second different and consecutive samples (such as at least 2, 5, 10, 20, 50, 100, 200, 500, 1000, 5000, or 10,000 samples), and where the system is configured so sample-to-sample carryover from the first sample to the second sample is no more than 1%, or 0.1%, or 0.05%, or 0.01%, or 0.005%, or 0.001%, or 0.0005%, or 0.0001%, or 0.00001%, or 0.000001%. Sample to sample carryover can be measured as described above for cross-contamination.

b) Within-sample alterations that affect processes occurring on the process side of the system can include any such alteration. One alteration is coalescence of partitions within a sample (though coalescence between samples can also occur).

c) Introduction of environmental material. A third source of cross-contamination, as that term is used herein, includes introduction of material into a sample from the environment, e.g., dust, materials from a user, and the like. While some of these materials are neutral in terms of affecting the process side, others can have an effect. For example, particulate matter can clog one or more conduits. Particulate matter may also transit the system without introducing a clog but may be fluorescent in one or more channels generating false positive results in the data. Material from a user (e.g., from a sneeze or cough) can contain nucleic acids which can affect, e.g., results of PCR processes.

Cross-contamination can occur in a number of ways, and systems and methods provided herein can be designed to reduce or eliminate one or more of these.

1) Barriers. If a container comprising a volume of fluid to be placed into a process system, such as a container that contains a discrete volume of dispersed phase, e.g., a sample container, is used, where the container, e.g., sample container, is open, material from one container, e.g., sample container can potentially move to another, e.g., if the system is jostled or similar event, or exterior material, e.g., dust, dirt, materials from the user, or the like, can enter the container. In order to prevent this, in certain embodiments, systems and methods provided herein can include one or more barriers between a discrete volume of fluid to be subject to intake into a system, and the exterior environment, such as a seal over the top of the container in which the volume of fluid is situated, or a non-sample-fluid layered over the top, or both. In certain cases, a holder comprising a plurality of containers of fluid to be placed into the process system, such as a plurality of containers each of which contains a discrete volume of dispersed phase, e.g., a plurality of sample containers, such as a microtiter plate, is used, one or more barriers may be placed over the plurality of containers of fluid. Such barriers can also be useful in preventing evaporation of a portion of the sample, which can affect the accuracy of analysis of the sample. Another barrier includes filters integrated into the fluidic conduits delivering continuous phase or dispersed phase from the corresponding reservoirs. The filters are of an appropriate size to allow adequate flow rate of the material while maximizing the removal of debris. Another barrier can be a filter element that is positioned, e.g., at the intake end of an intake line. This can be as simple as a narrowing of the line at the end, to a dimension suitable to prevent uptake of undesired particulate matter.

2) Cleaning exterior of intake conduit. If the same intake conduit is used to provide first and second samples to an intake system, material from the first sample can adhere to the conduit and contaminate the second sample. Thus systems and methods provided herein include systems and methods to remove dispersed phase, e.g., sample, adhering to an intake conduit. The systems and methods can be automated.

3) Surfaces with greater affinity for one fluid than another. If sample comprises a fluid, e.g., a hydrophilic fluid such as water, then if one or more surfaces that come in contact with the sample as it moves through the system (e.g., both intake and process system) have equal or greater affinity for the fluid than for one or more other phases that come in contact with the surface (e.g., than for a continuous phase when the sample is partitioned into a plurality of partitions of dispersed phase in continuous phase), then part of the sample will tend to adhere to the surface, and can lag behind the rest of the sample, thus potentially coming in contact with, and contaminating, later samples. Thus systems and methods provided herein include systems and methods where surfaces that come in contact with a first fluid, e.g., dispersed phase, such as sample, and at least one other fluid, e.g., at least one other phase, such as continuous phase, have greater affinity for the second fluid than for the first fluid, e.g., have greater affinity for continuous phase than for dispersed phase. This can apply to the system as a whole, from intake side through process side, until processed sample are beyond a detection zone, and/or to individual parts of a system, such as intake line, injector, partitioner, reactor (e.g., thermal cycler), partition separation system (if used), and/or detector, as well as any connections between these. It will be appreciated that 100% of the surface in contact with the first fluid, e.g., dispersed phase, such as sample, does not have to have the requisite affinities, so long as sufficient surface has requisite affinities so that a desired level of cross-contamination, e.g., a desired maximum level, is achieved. Thus, in certain embodiments, at least 80, 90, 95, 98, 99, 99.5, 99.9, 99.95, 99.99, 99.995, or 99.999% of surfaces that come in contact with first fluid, e.g., fluid of a sample, have greater affinity for at least a second fluid that comes in contact with the surfaces, for example, have less affinity for fluid of a sample, than for at least one second fluid that comes in contact with the surface, such as continuous phase; this applies to the system as a whole and independently to each component of the system, e.g., intake line, injector, partitioner, reactor, partition separator, detector, and/or conduits and connections between components.

4) Cleaning intake system. Systems and methods can be designed to clean portions of an intake system that come in contact with dispersed phase, e.g., sample; in certain embodiments, this can be done while the intake system is isolated from a process system. For example, an intake system can be cleaned between samples so that no, or very little, of one sample is carried over by the intake system into the process system with a following sample or samples, while leaving the process system undisturbed. Thus, in a system where serial aliquots of dispersed phase, e.g., serial samples, are placed into the process system, in certain embodiments the intake system can be cleaned between aliquots of dispersed phase, e.g., between samples, without disturbing the process system. Thus, in certain embodiments, provided herein are continuous flow serial emulsion systems that comprise an intake system and a process system, where the intake system can be isolated from the process system, e.g., for cleaning, such as between intake of a series of aliquots of dispersed phase on the intake side, e.g., intake of samples. This can be accomplished in any suitable manner, such as described further herein.

In certain embodiments, an injector is positioned between the intake system and the process system, where the injector is configured to move between being in fluid communication with the intake system and not in fluid communication with the process system and being in fluid communication with the process system and not in fluid communication with the intake system, e.g., so that the intake system and the process system are never in continuous fluid communication. In the configuration in which the injector is in fluid communication with the process system and not in fluid communication with the intake system, the injector can transport a portion or all of dispersed phase, e.g., a sample, into the process side, for example a portion or all of dispersed phase, e.g., a sample, that is in a common conduit of the injector; while in the configuration in which the injector is in fluid communication with the intake system and not in fluid communication with the process system, the intake system, and the injector, can be cleaned between aliquots of dispersed phase, e.g., between samples. Cleaning can include one or more of purging and/or denaturing steps, and any other suitable steps, such as described more fully herein.

5) Spacer fluid. Where serial aliquots of dispersed phase, e.g., serial samples, are moved into a process system in a conduit as an emulsion in a continuous phase, axial dispersion may cause one aliquot, e.g., one sample, to overlap with another as they move through the system. One way to minimize or eliminate overlap of successive aliquots of dispersed phase, e.g., successive samples, is to place a spacer fluid between successive aliquots, e.g., samples, preferably a spacer fluid that is immiscible with dispersed phase in the aliquots, e.g., samples. Thus, in certain embodiments systems and methods provide for insertion of a spacer fluid between successive aliquots of dispersed phase, e.g., successive samples, that enter a process system. Such a spacer fluid may be provided, e.g., by an intake system, or other suitable system, before or after a partitioner; if before a partitioner, spacer fluid may be broken into a plurality of partitions but, in general, has a composition such that it reforms into a continuous plug. In embodiments where for example, in systems where an injector is positioned between an intake system and a process system, the injector and the intake system can, e.g., transport an aliquot of dispersed phase, e.g., sample, into the process system, then the injector and intake system can inject a spacer fluid into the process system. The injector and intake system can, optionally, be cleaned, for example, between the injection of an aliquot of dispersed phase, e.g., sample and injection of the spacer fluid.

6) Reduction of flow disturbances. Flow in the system, e.g., in conduits of the system, can be subject to disturbances that cause one aliquot of dispersed phase, e.g., one sample, to be held up in the system and potentially be available to contaminate one or more following aliquots of dispersed phase, e.g., one or more following samples. Disturbances in flow can also encourage coalescence of partitions. Typically, systems and methods provided herein are configured to cause laminar flow through conduits of the system.

Connections Disturbances to flow can occur at connections between components of the system, if a smooth transition is not made between a conduit on one side of the connection and a conduit on the other side of the connection. An exemplary disturbance may include the creation of microeddies at connections where a self is generated between two conduits of different cross-sectional diameters. These microeddies can lead to sample hold up leading to partition transiting between samples or introduce high shear force to partitions resulting in coalescence. Thus, in certain embodiments, connections between a first conduit and a second conduit, are configured in such a way as to not disturb flow, or minimally disturb flow, from one side to the other, for example, the connection can be made so that the cross-section of a first side of a connection matches a cross-section of a second side of the connection where the first and second sides are at a junction in the connection, and where second side is downstream of the first side, for example, matches within 80, 90, 95, 98, 99, 99.5, or 99.9% (e.g., cross-sections of first and second sides overlap to at least this degree), and/or where little or no space (gap) occurs in the connection, e.g., the connection comprises no gap, or a gap that is less than 20, 15, 10, 5, 2, 1, 0.5, 0.1, 0.01, 0.001, or 0.0001% the length of a characteristic dimension of the first conduit; for example, at a connection between a conduit of an injector and a conduit leading from the injector, and/or at a connection between a conduit (such as a conduit from the injector) and a conduit of a partitioner, and/or at a connection between a conduit of a partitioner and a conduit exiting the partitioner (such as a conduit leading to a reactor), and/or at a connection between a conduit (such as a conduit leading from a reactor) and a conduit of a partition separator, and/or at a connection between a conduit of a partition separator and a conduit exiting the partition separator (such as a conduit leading to a detector), and/or a connection between a conduit (such as a conduit from a partition separator, or from a reactor) and a conduit of a detector, and/or a connection between a conduit of a detector and an exit conduit from the detector (such as a conduit downstream from the detector).

Direction change Flow disturbance can also occur where a conduit changes direction. If the direction change is too abrupt, depending on flow rate and cross-sectional area of the conduit and the like, an area of turbulence or other disturbance will be created. Thus, in certain embodiments, the combination of flow rate, cross-sectional area, and radius of curvature of conduits in the system is such that shear forces in the conduit are minimized. It will be appreciated that in certain components, for example, in partitioners or partition separators, shear forces may deliberately be created, e.g., to create partitions, and such are not included in this flow description. In certain embodiments, fluidic velocity can be, e.g., 0.15 mm/s-858 mm/s, such as 1-50 mm/s or 5-10 mm/s.

7) Reducing buoyancy effects Buoyancy effects can also cause one aliquot of dispersed phase or portions thereof, to move in such a way as to overlap with a second aliquot of dispersed phase or portions thereof, e.g., when an aliquot of dispersed phase, such as a sample, is partitioned into a plurality of partitions and the partitions move through a conduit in a continuous phase, where the dispersed phase and continuous phase have properties such that one tends to be buoyant in the other, e.g., dispersed phase tends to rise in continuous phase, buoyancy effects in the conduit can cause uneven flow of partitions, so that partitions from one sample can overlap with those of another sample. These effects can be minimized if the conduit comprising the partitions is kept in a plane or nearly in a plane such that flow in the conduit is orthogonal to gravity, for example, within 45, 30, 20, 15, 10, 5, 4, 3, 2, or 1 degree of a plane orthogonal to gravity. In particular, in certain embodiments, at least 80, 90, 95, 96, 97, 98, or 99% of a portion of a conduit from the exit of a partitioner, or a conduit leading from the exit in the case where the exit is not orthogonal to gravity, to a separator for separating partitions for detection, or, if such a separator is not used, to a detector, is within 45, 30, 20, 15, 10, 5, 4, 3, 2, or 1 degree of a plane orthogonal to gravity as measured from the axis of flow through the conduit.

8) Surfactants Systems and methods provided herein can include the use of surfactants. Surfactants can stabilize individual partitions in continuous phase and can reduce coalescence of partitions. To stabilize emulsions against coalescence, surfactants are used to lower the interfacial tension and thus the Gibbs free energy, provide steric or electrostatic repulsion, increase film drainage time, or increase the surface elasticity. Emulsifiers mostly are amphiphilic molecules comprising groups soluble in each of the two phases. When present in a single solvent, either aqueous or oil, they form micellular structures. At the time of and for some period after, the micelles disperse and adsorb to an oil-water interface.

Surfactant added to the sampling side of the injector may prevent disruption of the dispersed phase packet after injection into the process side of the system before the dispersed phase packet is subdivided by the partitioner. Disruption of the dispersed phase packet prior to reaching the partitioner may result in sample hold up and possible cross-contamination as well as reduce the consistency of subdivide partition sizes generated by the partitioner. Surfactant may be introduced at one or more suitable points in the system, e.g., at the injector and/or the partitioner, etc. One benefit to injector introduction is to minimize contamination due to prevention of aqueous phase adsorption to the conduit as well as stabilizing the sample packet before it reaches the partitioner so it doesn't fragment and leave a part of the sample packet in the conduit. Surfactant can be added to any suitable concentration, such as 0.1-5%, 0.5-2%, or 0.5-1.5%, or 0.8-1.2%, expressed as w/v, in general in the continuous phase as it enters a partitioner. In certain embodiments, the surfactant comprises a fluorosurfactant; in certain embodiments the continuous phase comprises a fluorinated oil and a fluorosurfactant.

Thus, systems and methods for serial flow emulsion reactions may comprise use of a surfactant. The surfactant may stabilize droplets of dispersed phases or continuous phases such that droplets do not coalesce when in proximity. In some instances, the surfactant is a fluorocarbon, a hydrocarbon, or a silicone. In some instances, the surfactant is a fluorosurfactant.

A volume of surfactant used may vary. In some instances, the volume of surfactant depends on a volume of the dispersed phase. In some instances, the volume of the surfactant is a droplet of at least or about 0.001 nanoliter (nL), 0.002 nL, 0.003 nL, 0.004 nL, 0.005 nL, 0.006 nL, 0.007 nL, 0.008 nL, 0.009 nL, 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, or more than 5.0 nL. In some instances, the volume of the surfactant is in a range of about 0.01 nL to about 1.5 nL. In some instances, a volume of the surfactant is at least or about 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, or more than 5.0 nL. In some instances, the volume of the surfactant is in a range of about 0.1 nL to about 0.75 nL.

In certain embodiments, the emulsion, e.g. as it exits the partitioner, comprises surfactant at a level of less than 2, 1.7, 1.5, 1.4, 1.3, 1.2, 1.1, 1.0, 0.9, 0.8, 0.7, 0.6, 0.5, 0.3, or 0.1% and/or at least 1.7, 1.5, 1.4, 1.3, 1.2, 1.1, 1.0, 0.9, 0.8, 0.7, 0.6, 0.5, 0.3, 0.1 or 0.05%, such as 0.5-2.0%, for example 0.2-1.5%, in some instances 0.2-1.3%. In certain embodiments, dispersed phase, e.g. as it exits the partitioner, comprises surfactant at a level of less than 2, 1.7, 1.5, 1.4, 1.3, 1.2, 1.1, 1.0, 0.9, 0.8, 0.7, 0.6, 0.5, 0.3, or 0.1% and/or at least 1.7, 1.5, 1.4, 1.3, 1.2, 1.1, 1.0, 0.9, 0.8, 0.7, 0.6, 0.5, 0.3, 0.1 or 0.05%, such as 0.2-2.0%, for example 0.2-1.5%, in some instances 0.2-1.3%. However, other methods of expressing surfactant concentration, such as concentration in continuous phase entering a partitioner, may also be used, as described herein.

Surfactants and other components of dispersed phase, e.g., of an aqueous sample, as well as components of continuous phase, and other materials useful in systems and methods provided herein, are described further, below.

In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least one of 1) a barrier between a discrete volume of fluid to be subject to intake into a system to provide serial flow of emulsions, and the exterior environment, such as a seal over the top of the container in which the volume of fluid is situated; in certain cases a holder comprising a plurality of containers of fluid to be placed into the process system, such as a plurality of containers each of which contains a discrete volume of dispersed phase, e.g., a plurality of sample containers, such as a microtiter plate, and one or more barriers positioned over the plurality of containers of fluid; 2) a system or method to remove dispersed phase, e.g., sample, adhering to an exterior surface of an intake conduit; 3) surfaces that come in contact with a first fluid, e.g., dispersed phase, such as sample, and at least one other fluid, e.g., at least one other phase, such as continuous phase, having greater affinity for the second fluid than for the first fluid, e.g., having greater affinity for continuous phase than for dispersed phase, e.g., at least 80, 90, 95, 98, 99, 99.5, 99.9, 99.95, 99.99, 99.995, or 99.999% of surfaces that come in contact with first fluid have greater affinity for at least a second fluid that comes in contact with the surfaces, for example, have greater affinity for continuous phase than for dispersed phase, e.g., sample; 4) an intake system for providing aliquots of dispersed phase, e.g., samples, to a process system, where the intake system can be cleaned between aliquots of dispersed phase, e.g., between samples, without disturbing the process system; for example, where an injector is positioned between the intake system and the process system, where the injector is configured to move between being in fluid communication with the intake system and not in fluid communication with the process system and being in fluid communication with the process system and not in fluid communication with the intake system, but not both simultaneously, e.g., so that the intake system and the process system are never in continuous fluid communication and, in the configuration in which the injector is in fluid communication with the process system and not in fluid communication with the intake system, the injector can transport a portion or all of dispersed phase, e.g., a sample, into the process side, for example a portion or all of dispersed phase, e.g., a sample, that is in an injection chamber (common conduit) of the injector; while in the configuration in which the injector is in fluid communication with the intake system and not in fluid communication with the process system, the intake system, and the injector, can be cleaned between aliquots of dispersed phase, e.g., between samples; 5) systems and methods that provide for insertion of a spacer fluid between successive aliquots of dispersed phase, e.g., successive samples, that enter a process system; 6) connections between a first conduit and a second conduit, where the first and second conduits are different, are configured in such a way as to not disturb flow, or minimally disturb flow, from one side to the other, for example, the connection can be made so that the cross-section of a first side of a connection matches a cross-section of a second side of the connection where the first and second sides are at a junction in the connection, and where second side is downstream of the first side, for example, matches within 80, 90, 95, 98, 99, 99.5, or 99.9% (e.g., cross-sections of first and second sides overlap to at least this degree), and/or where little or no space (gap) occurs in the connection, e.g., the connection comprises no gap, or a gap that is less than 20, 15, 10, 5, 2, 1, 0.5, 0.1, 0.01, 0.001, or 0.0001% the length of a characteristic dimension of the first conduit; for example, at a connection between a conduit of an injector and a conduit leading from the injector, and/or at a connection between a conduit (such as a conduit from the injector) and a conduit of a partitioner, and/or at a connection between a conduit of a partitioner and a conduit exiting the partitioner (such as a conduit leading to a reactor), and/or at a connection between a conduit (such as a conduit leading from a reactor) and a conduit of a partition separator, and/or at a connection between a conduit of a partition separator and a conduit exiting the partition separator (such as a conduit leading to a detector), and/or a connection between a conduit (such as a conduit from a partition separator, or from a reactor) and a conduit of a detector, and/or a connection between a conduit of a detector and an exit conduit from the detector (such as a conduit downstream from the detector); 7) a combination of flow rate, cross-sectional area, and radius of curvature of conduits in the system is such that flow in the conduits is laminar or substantially laminar, 8) at least 80, 90, 95, 96, 97, 98, or 99% of a portion of a conduit from an exit of a partitioner, or a conduit leading from the exit in a case where the exit is not orthogonal to gravity, to a separator for separating partitions for detection, or, if such a separator is not used, to a detector, is within 45, 30, 20, 15, 10, 5, 4, 3, 2, or 1 degree of a plane orthogonal to gravity as measured from the axis of flow through the conduit; and/or 9) surfactants, such as one or more surfactants as described herein, e.g., at a level in a continuous phase flowing into an inlet of partitioner of between 0.5 and 2%, or between 0.5 and 1.5%, or between 0.8 and 1.2%. The systems and methods can provide a level of cross contamination that is less than 20, 10, 5, 2, 1, 0.5, 0.2, 0.1, 0.05, 0.01, 0.05, 0.01, or 0.005%. Any or all of the preceding can be accomplished in a system or method that utilizes the same components from sample to sample, e.g., the same intake line, the same injector, the same partitioner, the same reactor, and/or the same detection unit. For example, in certain embodiments, systems and methods are designed to flow a series of different samples through the components of the system where the same component, e.g., the same intake line, the same injector, the same partitioner, the same partition separator, and/or the same detector, is used for at least a first and a second different and consecutive samples (such as at least 2, 5, 10, 20, 50, 100, 200, 500, 1000, 5000, or 10,000 samples). In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least two of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least three of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least four of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least five of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least six of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least seven of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include at least eight of 1)-9), above. In certain embodiments, provided herein are systems and methods of serial flow of emulsion, for example systems and methods comprising an intake system and a process system, such as described more fully herein, that, when used to process a series of samples, have levels of cross-contamination between samples of less than 0.1%, for example, less than 0.01%, such as less than 0.005%. Thus, in certain embodiments, provided herein are systems and methods of serial flow of emulsion, for example systems and methods comprising an intake system and a process system, that can include all of 1)-9), above.

Sample processing. Sample processing applications including cell lysis, cell growth, ligation, digestions, nucleic acid assembly reactions, nucleic acid editing, nucleic acid modification, or sample analysis including the detection of nucleic acids, proteins, and microbial organisms using reactions include but are not limited to RNA transcription, hybridization chain reaction (HCR), nicking chain reaction, loop-mediated isothermal amplification (LAMP), strand displacement amplification (SDA), helicase-dependent amplification (HDA), nicking enzyme amplification reaction (NEAR), nucleic acid melt temperature analysis, protein detection, protein melt temperature analysis, small molecule detection, microbial growth rate testing, antibiotic resistance testing, microbial small molecule production, molecule-molecule interaction studies. These reactions may occur at one more fixed temperature also known as isothermal reactions or may undergo temperature cycling to promote reaction progress. Many reactions can be combined in the same partitions For example the quantification of mRNA and protein from the same sample, or the same cell, can generate biologically relevant information only available when the reactions are contained within the same partition.

RNA transcription reactions are isothermal reactions carried out by RNA polymerase enzymes. The polymerases bind to DNA sequences bearing promoter sequences to initiate the production of RNA in a template directed reaction. Monitoring the production of RNA allows this reaction to be used for the detection of the DNA sequences bearing particular promoters.

In an example of an RNA transcription reaction the aqueous reaction phase would be prepared to consist of appropriate buffer, for instance Tris-HCl pH 8.5, nucleotide triphosphates, magnesium chloride, sodium chloride, dithiothreitol, reporter system, for example an RNA binding dye, fluorescent nucleotide triphosphate derivative, or a hybridization probe like a molecular beacon, and an RNA polymerase. The aqueous reaction phase is combined with an aqueous sample to be tested for the presence of particular DNA sequences. The combined sample is then ready for injection into the process stream of the instrument. After injection the sample is partitioned so that sample partitions can be incubate at a fixed temperature, for instance 37 C, for fixed period of time, for example 1 min, 5 min, 15 min, 30 min, 45 min, 1 hr, 2 hr, 4 hr, 8 hr. The intensity of the reporter system in the partition is then interrogated in order to identify the presence of the DNA sequences of interest.

HCR is an isothermal nucleic acid detection method that utilizes a series of metastable hairpins that upon binding to a target nucleic acid exponentially unfold. In HCR, a target nucleic acid is added to mixture of two or more metastable hairpin molecules. Upon binding the target nucleic acid sequence, the first of said hairpins opens exposing a region complementary to the second of said hairpins. This process, in turn, exposes a single-stranded region identical to the first of said hairpins. The resulting chain reaction leads to the formation of a nicked double helix that grows until the hairpin supply is exhausted. HCR is capable of detecting both DNA and RNA molecules.

LAMP is an isothermal nucleic acid amplification reaction that employs either two or three sets of primers and a polymerase with high strand displacement activity in addition to a replication activity. Typically, 4 different primers are used to identify 6 distinct regions on the target gene, which adds highly to the specificity. An additional pair of "loop primers" can further accelerate the reaction. Due to the specific nature of the action of these primers, the amount of DNA produced in LAMP is considerably higher than PCR based amplification. LAMP is capable of detecting both DNA and RNA molecules.

SDA is an isothermal DNA amplification reaction that relies on a strand-displacing DNA polymerase, typically Bst DNA Polymerase, Large Fragment or Klenow Fragment (3'-5' exo-), to initiate at nicks created by a strand-limited restriction endonuclease or nicking enzyme at a site contained in a primer. The nicking site is regenerated with each polymerase displacement step, resulting in exponential amplification. SDA is capable of detecting both DNA and RNA molecules.

HDA employs the double-stranded DNA unwinding activity of a helicase to separate strands, enabling primer annealing and extension by a strand-displacing DNA polymerase. Since an enzyme replaces the denaturing step used in traditional PCR, HDA reactions proceed at a single temperature and result in logarithmic amplification of the target DNA.

NEAR employs a strand-displacing DNA polymerase initiating at a nick created by a nicking enzyme, rapidly producing many short nucleic acids from the target sequence. This process is extremely rapid and sensitive, enabling detection of small target amounts in minutes. The nicking enzyme and polymerase are precisely matched to function at the same temperature removing the need for thermal cycling. NEAR is capable of detecting both DNA and RNA molecules.

An exemplary NEAR reaction is, prepare aqueous phase consisting of appropriate buffer like tris pH 8.5, deoxynucleotide triphosphates, magnesium chloride, sodium chloride, BSA, a suitable nicking enzyme described below, and a suitable polymerase described below. Combine aqueous phase with nucleic acid to be tested. Inject sample into process side. Partition sample. Incubate sample at desired temperature for polymerase and nickase function for fixed period of time, for example 1 min, 5 min, 15 min, 30 min, 45 min, 1 hr, 2 hr, 4 hr, 8 hr. Analyze DNA production with suitable reporter including DNA binding dyes, fluorescent nucleotide triphosphate derivatives, hybridization probes like molecular beacons. Nicking specific hybridization probes may be used. Nicking probes might look like a fluorophore and quencher linked to a oligonucleotide between 5-20 nt apart with a nickase recognition sequence internal to the oligonucleotide. In this example the probe binds to single stranded DNA produced by the polymerase, upon complementation, the probe generates a double stranded nicking site recognizable by the nicking enzyme. Upon nicking the probe, the oligo is cleaved separating the fluorophore and quencher allowing for the production of a detectable signal. Quantify the amount of fluorescence with the detector assembly.

RT-PCR is a method of RNA detection that relies on first converting the RNA to its complementary DNA form called cDNA and then amplifying the cDNA by PCR.

An exemplary RT-PCR reaction is, prepare aqueous phase consisting of appropriate buffer like tris pH 8.5, deoxynucleotide triphosphates, magnesium chloride, sodium chloride, BSA, a suitable reverse transcriptase described below, and a suitable polymerase described below, primers, and detection reagents. Combine aqueous phase with nucleic acid to be tested. Inject sample into process side. Partition sample. Incubate sample at desired temperature for polymerase function for fixed period of time, for example 1 min, 5 min, 15 min, 30 min, 45 min, 1 hr, 2 hr, 4 hr, 8 hr. Thermal cycle the reaction. Analyze DNA production with suitable reporter including DNA binding dyes, fluorescent deoxynucleotide triphosphate derivatives, hydrolysis probes like taq man probes. Quantify the amount of fluorescence with the detector assembly.

Polymerases useful in the methods described herein are capable of catalyzing the incorporation of nucleotides to extend a 3' hydroxyl terminus of an oligonucleotide bound to a target nucleic acid molecule. Such polymerases include those capable of amplification and/or strand displacement. The polymerase may bear or lack 5'-3' exonuclease activity. In other embodiments, a polymerase also has reverse transcriptase activity (e.g., Bst (large fragment), Therminator, Therminator II). Exemplary polymerases include but are not limited to BST (large fragment), DNA polymerase I (*E. coli*), DNA polymerase I, Large (Klenow) fragment, Klenow fragment (3'-5' exo-), T4 DNA polymerase, T7 DNA polymerase, Deep VentR. (exo-) DNA Polymerase, Deep VentR DNA Polymerase, DyNAzyme, High-Fidelity DNA Polymerase, Therminator, Therminator II DNA Polymerase, AmpliTherm DNA Polymerase, Taq DNA polymerase, Tth DNA polymerase, Tfl DNA polymerase, Tgo DNA polymerase, SP6 DNA polymerase, Thr DNA polymerase. The following non-limiting examples of Reverse Transcriptases (RT) can be used in the reactions of the present method to improve performance when detecting an RNA sequence: OmniScript, SensiScript, MonsterScript, Transcriptor, HIV RT, SuperScript III, ThermoScript, Thermo-X, ImProm II. The following non-limited examples of RNA polymerases include but are not limited to T3, T7, SP6, *E. coli* RNA pol, RNA pol II, and mtRNA pol.

A nicking enzyme binds double-stranded DNA and cleaves one strand of a double-stranded duplex. The nicking enzyme may cleave either upstream or downstream of the binding site or nicking enzyme recognition site. In exemplary embodiments, the reaction comprises the use of a nicking enzyme that cleaves or nicks downstream of the binding site such that the product sequence does not contain the nicking site. Using an enzyme that cleaves downstream of the binding site allows the polymerase to more easily extend without having to displace the nicking enzyme. Ideally, the nicking enzyme is functional under the same reaction conditions as the polymerase. Exemplary nicking include, but are not limited to, Nt.BspQI(NEB), Nb.BbvCI (NEB), Nb.BsmI(NEB), Nb.BsrDI(NEB), Nb.BtsI(NEB), Nt.AlwI(NEB), Nt.BbvCI(NEB), Nt.BstNBI(NEB), Nt.CviPII(NEB), Nb.Bpu10I(Fermantas), and Nt.Bpu10I(Fermentas).

Fluorogenic substrates, a nonfluorescence material that when acted upon by an enzyme converts to a fluorescent state, may be used to identify the presence of a particular protein with a partition. Fluorogenic substrates have been developed for the detection and characterization of a wide array of enzyme classes.

An example of small molecule detection includes the detection of bacterial endotoxin using a factor C assay. Gram negative bacterial endotoxin is a biological pyrogen that causes fever when introduced intravenously. The endotoxin, also known as lipopolysaccharide (LPS), is found in the outer membrane of Gram-negative bacteria. During Gramnegative sepsis, endotoxin stimulates host macrophages to release inflammatory cytokines. However, excessive inflammation causes multiple organ failure and death. Endotoxins, which are ubiquitous pathogenic molecules, are a bane to the pharmaceutical industry and healthcare community. Thus early and sensitive detection of endotoxin is crucial to prevent endotoxaemia. The gold standard for LPS detection is the limulus amebocyte lysate (LAL) test and has been widely used for ~30 years for the detection of endotoxin in the quality assurance of injectable drugs and medical devices. The LAL constitutes a cascade of serine proteases which are triggered by trace levels of endotoxin, culminating in a gel clot at the end of the reaction. The Factor C, which normally exists as a zymogen, is the primer of this coagulation cascade. In vivo, Factor C is the perfect biosensor, which alerts the horseshoe crab of the presence of a Gram-negative invader. The hemostatic end-point entraps the invader, killing it and limiting further infection. However, as an in vitro endotoxin detection tool, variations in the sensitivity and specificity of LAL to endotoxin, and the dwindling supply of horseshoe crabs are posing increasing challenges to the biotechnology industry. Therefore, methods for the miniaturization and digitization of said assay has the potential to lower the need for LAL as well as increase its sensitivity.

Microbial growth studies using various metabolic sources may be performed. Bacteria may be encapsulated in droplets with a specific medium source at a single occupancy. The bacteria are incubated at a constant temperature and then measured after a fixed period of time. Those bacteria capable of metabolizing the medium constituents will have a higher fitness and growth rate than bacteria incapable of metabolizing said medium. Antibiotic susceptibility studies may be performed in a similar way. In these cases, bacteria may be encapsulated in the presence and absence of specific antibiotics. Those bacteria susceptible and those resistant will demonstrate slower or higher growth rates respectively. In these cases, bacteria may be monitored using droplet imaging and image processing, cell-specific stains and either fluorescence or absorption measurements, or be genetically modified to produce datable reporter phenotypes including but not limited to fluorescent or colored proteins, reporter enzymes, etc.

Other specific examples include but are not limited to environmental DNA analysis, forensic sample analysis, agricultural sample analysis including GMO and pathogen detection, detection of RNA and DNA methylation patterns, detection of DNA damage, copy number variation, gene rearrangement analysis, splicing variants, DNA and RNA structural rearrangements, SNP detection, antibody testing and/or identification, next generation sequencing library absolute quantification, viral load quantification, telomere length testing, protein:nucleic acid correlations, gene editing efficiency, enzyme quantification.

Materials Used in Systems and Methods Provided Herein.

Dyes (fluorescent molecules). In certain embodiments, a fluorescent moiety, such as a molecule may be used (fluorophores). Any suitable fluorescent moiety may be used. Examples of dyes include Eva Green, SYBR green I, SYBR green II, SYBR gold, ethidium bromide, methylene blue, Pyronin Y, DAPI, acridine orange, Blue View or phycoerythrin. A wide variety of reactive fluorescent probes can also be used. The fluorophore can be an aromatic or heteroaromatic compound. The fluorophore can be, for example, a pyrene, anthracene, naphthalene, acridine, stilbene, benzoxaazole, indole, benzindole, oxazole, thiazole, benzothiazole, canine, carbocyanine, salicylate, anthranilate, xanthenes dye, coumarin. Exemplary xanthene dyes include, e.g., fluorescein and rhodamine dyes. Fluorescein and rhodamine dyes include, but are not limited to 6-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N; N'-tetramethyl-6-carboxyrhodamine (TAMRA), 6-carboxy-X-rhodamine (ROX). Suitable fluorescent probes also include the naphthylamine dyes that have an amino group in the alpha or beta position. For example, naphthylamino compounds include 1-dimethylaminonaphthyl-5-sulfonate, 1-anilino-8-naphthalene sulfonate and 2-p-toluidinyl-6-naphthalene sulfonate, 5-(2'-aminoethyl)aminonaphthalene-1-sulfonic acid (EDANS). Exemplary coumarins include, e.g., 3-phenyl-7-isocyanatocoumarin; acridines, such as 9-isothiocyanatoacridine and acridine orange; N-(p-(2-benzoxazolyl)phenyl) maleimide; cyanines, such as, e.g., indodicarbocyanine 3 (Cy3), indodicarbocyanine 5 (Cy5), indodicarbocyanine 5.5 (Cy5.5), 3-(-carboxy-pentyl)-3'-ethyl-5,5'-dimethyloxacarbocyanine (CyA); 1H, 5H, 11H, 15H-Xantheno[2,3,4-ij:5,6,7-i'j']diquinolizin-18-ium, 9-[2 (or 4)-[[[6-(2,5-dioxo-1-pyrrolidinyl)oxy]-6-oxohexyl]amino]sulfonyl]-4 (or 2)-sulfophenyl]-2,3,6,7,12,13,16,17-octahydro-inner salt (TR or Texas Red); or BODIPY™ dyes Methods to reduce partition coalescence include the use of fluorinated oils, surfactants in either the continuous or discontinuous phase, using defined conduit cross-sectional areas, limiting any abrupt changes in conduit cross-sectional area, maintaining partition fluidic velocities within a defined range within the conduits of the system, grounding the system to eliminate significant voltage potentials, including dissipation of static charges, limiting the aggregation of partitions that can occur due to buoyant forces.

Surfactants demonstrate utility in both the injector and process sides of the system. On the injector side, surfactants may stabilize dispersed phase packets upon injector into the process side. This will prevent disruption of the dispersed phase packet prior to reaching the partitoner. Disruption of the dispersed phase prior to partitioning may result in sample hold up leading to cross-contamination, and/or will result in higher variance is subdivided partition size upon partitioning at the partitioner.

In one embodiment, a single surfactant type is present in both injection and process streams. In a second embodiment, a single surfactant is present only in the process stream. In a third embodiment two different surfactant types are used in the partitioner and injector streams but the surfactants are at the same concentration. In a fourth embodiment the relative concentrations of surfactants between the two streams is different. In a fifth embodiment one or more surfactant types are used in the injection stream and one or more surfactant type is used in the process stream.

In certain embodiments, a fluorinated oil is used, e.g., as continuous phase and/or for other fluid components as described further herein. Fluorinated oils may comprise (3-ethoxy-1,1,1,2,3,4,4,5,5,6,6,6-dodecafluoro-2-trifluoromethyle-hexane), methyl nonafluorobutyl ether, methyl nonafluoroisobutyl ether, ethyl nonafluoroisobutyl ether, ethyl nonofluorobutul ether, (pentane, 1,1,1,2,2,3,4,5,5,5-decafluoro-3-methoxy-4-(trifluoromethyl-)), isopropyl alcohol, (1,2-trans-dicholorethylene), (butane,1,1,1,2,2,3,3,4,4-nonafluoro-4-methoxy-), (1,1,1,2,2,4,5,5,5-nonafluoro-4-(trifluoromethyl)-3-pentanone), (furan,2,3,3,4,4-pentafluorotetrahydro-5-methoxy-2,5-bis[1,2,2,2-tetrafluoro-1-(trifluoromethyl)ethyl]-), perfluoro compounds comprising between 5 and 18 carbon atoms, polychlorotrifluoroethylene, (2,2,2-trifluoroethanol), Novec 8200™, Novec 71DE™, Novec 7100™, Novec 7200DL™, Novec 7300DL™, Novec 71IPA™, Novec 72FL™, Novec 7500™, Novec 71DA™, Novec 7100DL™, Novec 7000™, Novec 7200™, Novec 7300™, Novec 72DA™, Novec 72DE™, Novec 649™, Novec 73DE™, Novec 7700™, Novec 612™, FC-40™, FC-43™, FC-70™, FC-72™, FC-770™, FC-3283™, FC-3284™, PF-5056™, PF5058™, Halocarbon 0.8™, Halocarbon 1.8™, Halocarbon 4.2™, Halocarbon 6.3™, Halocarbon 27™, Halocarbon 56™, Halocarbon 95™, Halocarbon 200™, Halocarbon 400™, Halocarbon 700™, Halocarbon 1000N™, Uniflor 4622R™, Uniflor 8172™, Uniflor 8472CP™, Uniflor 8512S™, Uniflor 8731™, Uniflor 8917™, Uniflor 8951™, TRIFLUNOX 3005™, TRIFLUNOX 3007™, TRIFLUNOX 3015™, TRIFLUNOX 3032™, TRIFLUNOX 3068™, TRIFLUNOX 3150™, TRIFLUNOX 3220™, or TRIFLUNOX 3460™.

Components as described herein may comprise a surfactant; e.g., in certain embodiments a surfactant is in a continuous phase, but it will be appreciated that surfactant can be added to the system at any suitable point and in any suitable fluid. In certain embodiments, a surfactant is a fluorinated surfactant. In certain embodiments, fluorosurfactants comprise an oligoethylene glycol, TRIS, or polyethylene glycol moiety. In certain embodiments, fluorosurfactants comprise a fluorocarbon and/or chlorofluorocarbon moiety. In some embodiments, fluorosurfactants have head and tail moieties linked by ether, amide, or carbamide bonds. In a preferred embodiment, fluorosurfactants have a polyethylene glycol moiety linked to a fluorocarbon moiety through a carbamide, ether, or amide bond. Fluorinated surfactants include but are not limited to Picosurf-1, Ran FS-008, FC-4430, FC-4432, FC-4434.

In certain embodiments, a fluorinated oil is used with a fluorosurfactant.

In certain embodiments, the fluorinated oil comprises (3-ethoxy-1,1,1,2,3,4,4,5,5,6,6,6-dodecafluoro-2-trifluoromethyle-hexane), (furan,2,3,3,4,4-pentafluorotetrahydro-5-methoxy-2,5-bis[1,2,2,2-tetrafluoro-1-(trifluoromethyl) ethyl]-), and/or perfluoro compounds comprising between 5 and 18 carbon atoms and the fluorosurfactant comprises a polyethylene moiety linked to a fluorocarbon moiety with a carbamide, amide, or ether bond. Fluorosurfactant can have a concentration between 0.01% w/v to 5% w/v in the fluorinated oil. In certain embodiments, fluorosurfactant concentration ranges from 0.5% to 2% w/v, such as 0.5-1.5%. In general herein, surfactant concentrations are expressed as a percentage of surfactant in continuous phase, e.g., the percentage of surfactant in the continuous phase as it is flowed into a partitioner to produce partitions of dispersed phase.

A dispersed phase, e.g., an aqueous phase may contain one or more buffering components included in but not limited to the following list: 1,3-Bis[tris(hydroxymethyl)-methylamino]propane (Bis-Tris-Propane), 1,4-Piperazinediethanesulfonic acid (PIPES), 2-(Cyclohexylamino)ethanesulfonic acid (CHES), 2-(N-Morpholino)ethanesulfonic acid (YMS), 2-[(2-Hydroxy-1,1-bis[hydroxymethyl]ethyl) amino]ethanesulfonic acid (TES), 2-Amino-2-methyl-1-propanol (AMP), 2-Amino-2-methyl-1,3-propanediol (AMPD), 2-Aminoethanesulfonic acid (AES), 2,2-Bis(hydroxymethyl)-2,2',2''-nitrilotriethanol (Bis-Tris), 3-([1,1-Dimethyl-2-hydroxyethyl]amino)-2-hydroxypropanesulfonic acid (AMPSO), 3-(Cyclohexylamino)-1-propanesulfonic acid (CAPS), 3-(Cyclohexylamino)-2-hydroxy-1-propanesulfonic acid (CAPSO), 3-(N-Morpholino)propanesulfonic acid (MOPS), 3-(N-Morpholinyl)-2-hydroxypropanesulfonic acid (MOPSO), 3-(N-tris[Hydroxymethyl]methylamino)-2-hydroxypropanesulfonic acid (TAPSO), 3-(N,N-Bis[2-hydroxyethyl]amino)-2-hydroxypropanesulfonic acid (DIPSO), 4-(2-Hydroxyethyl)-1-piperazinepropanesulfonic acid (EPPS), 4-(2-Hydroxyethyl)piperazine-1-ethanesulfonic acid (HEPES), 4-(Cyclohexylamino)-1-butanesulfonic acid (CABS), 4-(N-Morpholino)butanesulfonic acid (MOBS), Acetic acid, Ammonia, Boric acid, Cacodylic acid, Carbonate-Bicarbonate, Carbonic acid, Citrate-dextrose, Citrate-phosphate-dextrose, Citric acid, Diglycine, Dimethylarsinic acid, Ethanolaminie, Ethylenediaminetetraacetic acid (EDTA), Ethylene glycol-bis(β-aminoethyl ether)-N,N, N',N'-tetraacetic acid (EGTA), Formic acid, Glycine, Glycylglycine, Hydroxyacetic acid, Imidazole, Lactic acid, Malic acid, Maleic acid, N-(2-Acetamido)-2-aminoethanesulfonic acid, N-(Carbamoylmethyl)-2-aminoethanesulfonic acid (ACES), N-(2-Acetamido)-2-iminodiacetic acid (ADA), N-(2-Hydroxyethyl)piperazine-N'-(4-butanesulfonic acid) (HEPBS), N-(2-Hydroxyethyl)-piperazine-N'-(2-hydroxypropanesulfonic acid) (HEPPSO), N-[Tris(hydroxymethyl)methyl]glycine (Tricine), N-tris (Hydroxymethyl)methyl-3-aminopropanesulfonic acid (TAPS), N,N-Bis(2-hydroxyethyl)-2-aminoethanesulfonic acid (BES), N,N-Bis(2-hydroxyethyl)glycine (Bicine), Phosphoric acid, Piperazine-1,4-bis(2-hydroxypropanesulfonic acid) (POPSO), Pyrophosphoric acid, Succinic acid, Tetraboric acid, Tricinie, Triethylammonium acetate, Triethylammonium bicarbonate, Triethylammonium phosphate, Triethanolamine (TEA), Tris-acetate, Tris-acetate-EDTA, Tris-borate, Tris-borate-EDTA, Tris-EDTA, Tris-Glycine, Tris-Tricine, tris(hydroxymethyl)aminomethan (Tris).

A dispersed phase, e.g., an aqueous phase may contain one or more protease inhibitor included in but not limited by the following list that may target aspartic, cysteine, metallo-, serine, threonine, and trypsin proteases: Alpha-2-Macroglobulin, Antipain, Aprotinin, Benzamidine, Bestatin, Calpain inhibitor I and II, Chymostatin, E-64, Ethylene glycol-bis(β-aminoethyl ether)-N,N,N',N'-tetraacetic acid (EGTA), Ethylenediaminetetraacetic acid (EDTA), Leupeptin (N-acetyl-L-leucyl-L-leucyl-L-argininal), Pefabloc SC, Pepstatin, Phenylmethylsulfonyl fluoride (PMSF), Tosyl phenylalanyl chloromethyl ketone (TLCK), Trypsin inhibitors.

A dispersed phase, e.g., an aqueous phase may contain one or more antimicrobial agent included in but not limited by the following list: Actinomycin D, Ampicillin, Anhydrotetracycline, Apramycin, Asinomycin, Azidothymidine, Azithromycin, Blasticidin, Bleocin, Carbenicillin, Cefazolin, Cefotaxime, Cefoxitin, Ceftazidime, Ceftriaxone, Cefuroxime, Cetrimide, Chloramphenicol, Ciprofloxacin, Clindamycin, Cotrimoxazole, Coumermycin, Cycloheximide, Cycloserine, Erthromycin, Erythromycin, Fungizone, Geneticin, Gentamycin, Hygromycin, Kanamycin, Kasugamycin, Levofloxacin, Linezolid, Mycophenolic Acid, Nafcillin, Nalidixic Acid, Neomycin, Novobiocin, Nystatin, Oxacillin, Oxolinic Acid, Penicillin, Pipemidic Acid, Polymyxin B, Puromycin, Rifampcin, Sodium azide, Spectinomycin, Streptomycin, Tetracycline, Thimerosal, Thiostrepton, Ticarcillin, Tobramycin, Triclosan, Vancomycin, Zeocin.

A dispersed phase, e.g. an aqueous phase may contain one or more crowding agent included in but not limited by the following list: 1,2-propanediol, Carboxymethyl cellulose, Ethylene glycol, Glycerol, PEG 200, PEG300, PEG 400, PEG 600, PEG 1000, PEG 1300, PEG 1600, PEG 1450, PEG 1500, PEG 2000, PEG 3000, PEG 2050, PEG 3350, PEG 4000, PEG 4600, PEG 6000, PEG 8000, PEG 10000, PEG 12000, PEG 20000, PEG 35000, PEG 40000, PEG 108000, PEG 218000, PEG 510000, PEG 90M, Polysucrose, Polyvinyl alcohol, Polyvinylpyroolidone, Propylene glycol.

A dispersed phase, e.g., an aqueous phase may contain one or more detergent included in but not limited by the following list: 1-Octanesulfonic acid, 1-Oleoyl-rac-glycerol, 2-Cyclohexylethyl β-D-maltoside, 3-(1-Pyridinio)-1-propanesulfonate, 3-(4-tert-Butyl-1-pyridinio)-1-propanesulfonate, 3-(Benzyldimethylammonio)propanesulfonate, 3-(Decyldimethylammonio)-propane-sulfonate inner salt zwitterionic detergent, 3-(N,N-Dimethylmyristylammonio) propanesulfonate, 3-(N,N-Dimethyloctadecylammonio)propanesulfonate, 3-(N,N-Dimethyloctylammonio)propanesulfonate inner salt, 3-(N,N-Dimethylpalmitylammonio) propanesulfonate, 3-[N,N-Dimethyl(3-palmitoylaminopropyl)ammonio]-propanesulfonate, 4-Dodecylbenzenesulfonic acid, 4-Nonylphenyl-polyethylene glycol, 5-Cyclohexylpentyl β-D-maltoside, 6-Cyclohexylhexyl β-D-maltoside, Alkyltrimethylammonium bromide, Amprolium hydrochloride, APO-10, APO-12, ASB-14, ASB-16, ASB-C80, Benzalkonium chloride, Benzethonium chloride, Benzethonium hydroxide, Benzyldimethyldodecylammonium chloride, Benzyldimethylhexadecylammonium chloride, Benzyldodecyldimethylammonium bromide, Bile salts, BRIJ® 35 Detergent, Brij® 58, Brij® L23, Brij® L4, Brij® O10, BRIJ® O20, $C_{12}E_8$, C7BzO, Caprolyl sulfobetaine, Cetylpyridinium chloride, CHAPS, CHAPSO, Chenodeoxycholic acid, Cholic acid, Cremophor EL®, DDMAB, Decaethylene glycol mono-dodecyl ether, Decyl β-D-glucopyranoside, Decyl β-D-maltopyranoside, Decyl-β-D-1-thiomaltopyranoside, Decyl-β-D-maltoside, Deoxycholic acid, DGEA, Dicyclohexyl sulfosuccinate, Diethylene glycol, diethylene glycol octadecyl ether, Digitonin, Digitoxigenin, Dihexadecyl phosphate, Dihexyl sulfosuccinate, Dimethyldioctadecylammonium bromide, Dimethylethylammoniumpropane sulfonate, Docusate sodium, Dodecylethyldimethylammonium bromide, Dodecyltrimethylammonium bromide, ELUGENT™ Detergent, EMPIGEN® BB Detergent, Ethanesulfonic acid, Ethylene glycol monododecyl ether, Ethylene glycol monohexadecyl ether, Ethylene glycol monohexyl ether, Ethylhexadecyldimethylammonium bromide, FC-4430, FC-4432, FC-4434, Genapol® C-100, Genapol® X-080, Genapol® X-100, Girard's reagent T, Glucopone 600 CS, Glycocholic acid, HECAMEG®, Hexadecyl(2-hydroxyethyl)dimethylammonium dihydrogen phosphate, Hexadecylpyridinium bromide, Hexadecylpyridinium chloride, Hexadecyltrimethylammonium bromide, Hexadecyltrimethylammonium chloride, Hexadecyltrimethylammonium p-toluenesulfonate, Hexaethylene glycol monododecyl ether, Hexaethylene glycol monohexadecyl ether, Hexaethylene glycol monotetradecyl ether, Hexyl β-D-glucopyranoside, IGEPAL® CA-630, IGEPAL® CA-720, Imbentin AGS/35, Isopropyl 0-D-1-thiogalactopyranoside, Kolliphor® EL, L-α-Lysophosphatidylcholine, Lithium 3,5-diiodosalicylate, Lithium dodecyl sulfate, Lugol, Lutrol® OP 2000, Luviquat™ FC 370, Luviquat™ FC 550, Luviquat™ HOLD, Luviquat™ Mono LS, Methoxypolyethylene glycol 350, Methyl 6-O—(N-heptylcarbamoyl)-α-D-glucopyranoside, Methylbenzethonium chloride, Miltefosine, Myristyltrimethylammonium bromide, N-Decanoyl-N-methylglucamine, N-Decanoylsucrose, N-Decyl-β-D-maltopyranoside, N-Dodecanoylsucrose, N-Dodecyl β-D-glucopyranoside, N-Dodecyl β-D-maltoside, N-Dodecyl-N,N-dimethyl-3-ammonio-1-propanesulfonate, N-Dodecyl-β-D-glucopyranoside, N-Dodecyl-β-D-maltoside, N-Heptyl β-D-glucopyranoside, N-Heptyl β-D-thioglucopyranoside, N-Hexadecyl β-D-maltoside, N-Lauroyl-L-alanine, N-Lauroylsarcosine, N-Nonanoyl-N-methylglucamine, N-Nonyl-β-D-glucopyranoside, N-Octanoyl-N-methylglucamine≥97%, N-Octanoylsucrose, N-Octyl β-D-maltoside, N-Octyl-β-D-glucopyranoside, N-Octyl-β-D-thioglucopyranoside, N,N-Bis[3-(D-gluconamido)propyl]deoxycholamide, N,N-Dimethyldecylamine N-oxide, N,N-Dimethyldodecylamine N-oxide, NDSB 211, NDSB-195, NDSB-201, NDSB-256, Niaproof® 4, Nonaethylene glycol monododecyl ether, Nonidet™ P 40, Nonyl β-D-glucopyranoside, Nonyl β-D-maltoside, Nonyl-β-D-1-thiomaltoside, Nonylphenyl-polyethyleneglycol acetate, O-(Decylphosphoryl)choline, Octaethylene glycol monodecyl ether, Octaethylene glycol monododecyl ether, Octaethylene glycol monohexadecyl ether, Octaethylene glycol monooctadecyl ether, Octyl β-D-1-thioglucopyranoside, Octyl β-D-glucopyranoside, Octyl-α/β-glucoside, Octyl-β-D-glucopyranoside, Pentaethylene glycol monodecyl ether, Pentaethylene glycol monododecyl ether, Pentaethylene glycol monohexyl ether, Pentaethylene glycol monooctyl ether, Pluronic® F-127, Pluronic® F-68, Poloxamer 188, Poloxamer 407, Poly(maleic anhydride-alt-1-decene), 3-(dimethylamino)-1-propylamine, Poly(maleic anhydride-alt-1-tetradecene), 3-(dimethylamino)-1-propylamine, Polyoxyethylene (10) tridecyl ether, Polyoxyethylene (20) sorbitan monolaurate, Polyoxyethylene (40) stearate, Polysorbate 20, Polysorbate 60, Polysorbate 80, Saponin, SB 3-10, SB 3-14, Sodium 1-butanesulfonate, Sodium 1-decanesulfonate, Sodium 1-heptanesulfonate, Sodium 1-hexanesulfonate, Sodium 1-nonanesulfonate, Sodium 1-octanesulfonate, Sodium 1-pentanesulfonate, Sodium 1-propanesulfonate, Sodium 2-ethylhexyl sulfate, Sodium 2,3-dimercaptopropanesulfonate, Sodium chenodeoxycholate, Sodium choleate, Sodium cholesteryl sulfate, Sodium deoxycholate, Sodium dodecyl sulfate, Sodium glycochenodeoxycholate, Sodium glycocholate hydrate, Sodium glycodeoxycholate, Sodium hexanesulfonate, Sodium octanoate, Sodium octyl sulfate, Sodium pentanesulfonate, Sodium taurochenodeoxycholate, Sodium taurocholate hydrate, Sodium taurodeoxycholate hydrate, Sodium taurohyodeoxycholate hydrate, Sodium taurolithocholate, Sodium tauroursodeoxycholate, SODOSIL™ RM 003, SODOSIL™ RM 01, Span® 20, Span® 60, Span® 65, Span® 80, Span® 85, Sucrose monodecanoate, Sucrose monolaurate, Surfactin, Synperonic® F 108, Synperonic® PE P105, Synperonic® PE/P84, Taurocholic acid, Taurolithocholic acid 3-sulfate, Teepol™ 610 S, TERGITOL™ MIN FOAM, TERGITOL™ TMN 10, TERGITOL™ TMN 6, TERGITOL™ Type 15-S-5, TERGITOL™ Type 15-S-7, TERGITOL™ Type 15-S-9, TERGITOL™ Type NP-10, TERGITOL™ Type NP-9, Tetradecyl-β-D-maltoside, Tetraethylene glycol monododecyl ether, Tetraethylene glycol monooctadecyl ether, Tetraethylene glycol monooctyl ether, Tetraglycol, Tetraheptylammonium bromide, Tetrakis(decyl)ammonium bromide, Tetramethylammonium hydroxide, Thesit®, Tri-C8-10-alkylmethylammonium chloride, Tridecyl β-D-maltoside, Tridodecylmethylammonium chloride, Triethylene glycol monodecyl, Triethylene glycol monomethyl ether, Triton™ N-57, Triton™ N-60, Triton™ QS-15, Triton™ X-100, Triton™ X-102, Triton™ X-114, Triton™ X-114, Triton™ X-165, Triton™ X-305, Triton™ X-405, Triton™ X-45, Turkey red oil, Tween® 20, Tween® 40, Tween® 60, Tween® 65, Tween® 80, Tween® 85, Tyloxapol, Undecyl β-D-maltoside, Ursodeoxycholic acid, ZWITTERGENT® 3-08, ZWITTERGENT® 3-10, ZWITTERGENT® 3-12, ZWITTERGENT® 3-14, ZWITTERGENT® 3-16.

A dispersed phase, e.g., an aqueous phase, may comprise one or more nucleotide or derivatives of said nucleotides included in but not limited by the following list: 5-Fluoroorotic Acid (5-FOA), Adenine, Adenosine, Adenosine diphosphate, Adenosine monophosphate, Adenosine triphosphate, Cytidine, Cytidine diphosphate, Cytidine monophosphate, Cytidine triphosphate, Cytosine, Deoxyadenosine, Deoxyadenosine diphosphate, Deoxyadenosine monophosphate, Deoxyadenosine triphosphate, Deoxycytidine, Deoxycytidine diphosphate, Deoxycytidine monophosphate, Deoxycytidine triphosphate, Deoxyguanosine, Deoxyguanosine diphosphate, Deoxyguanosine monophosphate, Deoxyguanosine triphosphate, Guanine, Guanosine, Guanosine diphosphate, Guanosine monophosphate, Guanosine triphosphate, Hypoxanthine, Inositol, Thymidine, Thymidine diphosphate, Thymidine monophosphate, Thymidine triphosphate, Thymine, Uracil, Uridine, Uridine diphosphate, Uridine monophosphate, Uridine triphosphate.

A dispersed phase, e.g., an aqueous phase may comprise water and/or one or more amino acids, amino acid derivatives, peptides, polypeptides, proteins/enzymes, co-factors, vitamins, salts, detergents, and/or buffers.

Some preferred dispersed phase, e.g., aqueous phase formulations do not comprise ionic detergents. Preferred dispersed phase fluids comprise non-ionic detergents at concentrations lower than 5%, less than 0.5% is preferred, 0.1% is even more preferred. Glycerol concentrations<20%, less than 10% preferred, <5% even more preferred. Total salt concentration below 3 M, <1 M preferred. Total buffer concentration higher than 5 mM, higher than 10 mM preferred. An exemplary aqueous formulation for PCR may look like but is not limited to 20 mM Tris-HCl, 2.5 mM MgCl2, 50 mM KCl, 0.06% IGEPAL® CA-630 (NP-40), 0.05% Tween® 20, 25 mM NH4Cl, 200 uM each dNTP (dATP, dTTP/dUTP, dCTP, dGTP), (pH 8.9 @ 25° C.). This reaction would include a suitable polymerase listed in the list herein.

Dispersed phase, e.g., aqueous phase formulations include any suitable reporter reagent as known by someone skilled in the art. See, e.g., "Dyes," above.

Partitions will demonstrate stability in a flow rate regime where the shear forces traveling through the system conduits are not larger than the interfacial tension stabilizing the partition surface. Acceptable shear forces may occur at partition velocities between 1 mm/sec and 75 mm/sec, with preferred partition velocities between 4 mm/sec and 53 mm/sec Fluoropolymers. In certain embodiments, one or more surfaces of components described herein, or, in some cases, entire components (e.g., partitioners, etc.) may comprise a fluoropolymer. In these embodiments, any suitable fluoropolymer may be used. Exemplary fluoropolymers include polytetrafluoromethylene (PTFE), chlorotrifluoroethylene (CTFE), polyvinylidene difluoride (PVDF), perfluoroalkoxy polymer (PFA), fluorinated ethylene-propylene (FEP), polychlorotrifluoroethylene (PCTFE), polyethylenetetrafluoroethylene (ETFE), ECTFE (polyethylenechlorotrifluoroethylene), FFPM/FFKM (Perfluorinated Elastomer [Perfluoroelastomer]), FPM/FKM (Fluorocarbon [Chlorotrifluoroethylenevinylidene fluoride]), FEPM (Fluoroelastomer [Tetrafluoroethylene-Propylene]), PFPE (Perfluoropolyether), PFFS (Perfluorosulfonic acid) or any combination thereof.

Thus, systems and methods as described herein may provide for accurate quantification or detection of biological material in a sample. In some instances, systems and methods result in reduced contamination. In certain further embodiments, reduction in contamination may be measured by a frequency of amplification in droplets not comprising biological material (e.g. DNA or RNA) and/or droplets comprising biological material (e.g., DNA or RNA) from a sample other than the sample being analyzed. For example, reduction in contamination is measured in droplets generated from the dispersed phase comprising purging fluid or separation fluid. In some instances, the frequency of amplification is at most or about 5%, 10%, 15%, 20%, 25%, 30%, 35%, 40%, 45%, 50%, 55%, 60%, 70%, or 75%. In some instances, the frequency of amplification is in a range of about 5% to about 75%, about 10% to about 70%, about 15% to about 65%, about 20% to about 60%, or about 25% to about 50%. Reduction in a contamination may be measured by a rate of false amplification. In some instances, the rate of false amplification is at least or about 1:300, 1:400, 1:500, 1:600, 1:700, 1:800, 1:900, 1:1000, 1:1250, 1:1500, 1:2000, 1:2500, 1:3000, 1:4000, 1:5000, 1:6000, 1:7000, 1:8000, 1:9000, 1:10000, 1:12000, 1:15000, 1:20000, 1:25000, 1:30000, 1:40000, 1:50000, 1:60000, 1:70000, 1:80000, 1:90000, 1:100000, 1:125000, 1:150000, 1:200000, 1:300000, 1:400000, 1:500000, 1:600000, 1:700000, 1:800000, 1:900000, 1:1000000. In some instances, the rate of false amplification is at most 1:300, 1:400, 1:500, 1:600, 1:700, 1:800, 1:900, 1:1000, 1:1250, 1:1500, 1:2000, 1:2500, 1:3000, 1:4000, 1:5000, 1:6000, 1:7000, 1:8000, 1:9000, 1:10000, 1:12000, 1:15000, 1:20000, 1:25000, 1:30000, 1:40000, 1:50000, 1:60000, 1:70000, 1:80000, 1:90000, 1:100000, 1:125000, 1:150000, 1:200000, 1:300000, 1:400000, 1:500000, 1:600000, 1:700000, 1:800000, 1:900000, 1:1000000.

Serial flow emulsion reactions such as quantification and detection of nucleic acids or proteins are useful biological techniques. Traditional methods for quantification of samples, for example quantitative polymerase chain reaction, require a number of amplifications to reach a threshold fluorescence intensity such that target nucleic acids in the sample may be detected. Digital reaction assays (e.g. digital PCR) are not dependent on the number of amplification and/or reaction cycles to determine the initial sample amount, eliminating the reliance on uncertain exponential data to quantify target nucleic acids and providing absolute quantification. Further serial flow emulsion reactions allow for on-demand analysis and require less material.

Generally, digital assays require dividing a sample into partitions. In the serial flow emulsion reactions discussed herein, these partitions are droplets. In a serial flow emulsion reaction system, samples to be assayed may be in the dispersed phase of the emulsion. These samples may injected serially (i.e. one-by-one) into the continuous phase of the emulsion and flowed through the steps necessary to partition, react, and detect the results of the reaction in the samples. Such a system may lead to cross-contamination between samples. For example, individual volumes of dispersed phase in the continuous phase can have a tendency to coalesce. When partitioned droplets coalesce into larger droplets, the validity of the digital assay may be compromised. As another example, axial dispersion of flowing partitioned droplets can cause droplets formed from a first sample to become interspersed with droplets formed from a second sample. Such interspersion can cause the results of the digital assay for both samples to be invalid. The axial dispersion can occur when individual sample injections are not temporally or spatially separated enough in the channel or tube containing the emulsion. The axial dispersion can also occur when dead zones exist in the flow of emulsion, causing droplets formed from a first sample to have a long enough residence time in the system that they become interspersed with droplets formed from a second sample. As another example, volumes of dispersed phase in the emulsion corresponding to a first sample and a second sample can coalesce if they contact each other prior to partitioning. Finally, cross-contamination may also result when all or part of a dispersed phase volume strongly interacts with a surface of the channel or tube containing the emulsion, leading to long residence times and possible incorporation of all or part of the dispersed phase volume by a subsequent sample or samples, leading to a compromised validity of assays on the subsequent sample or samples.

Provided herein are systems and methods for conducting reactions in serial flow of dispersed phase volumes of an emulsion, wherein cross-contamination is minimized. In some instances, cross-contamination occurs as a result of incorporation of all or part of an individual dispersed phase volumes with one or more other dispersed phase volumes. Such cross-contamination can result in invalid assay results, undesired reaction results or products, or incomplete separation or partitioning of elements in the emulsion (e.g. single cells). In some instances, the reactions of interest are assays to quantify a biological compound comprising individual dispersed phase volumes that represent separate biological samples and/or reagents required to detect and/or quantify the desired compound or compounds in the sample. In some instances, the assay is a digital assay. In some instances, the digital assay is a digital PCR assay to quantify one or more nucleic acids in the samples. Further systems and methods as provided herein may detect individual droplets accurately. Accurate detection of individual droplets may occur by the reduction of cross-contamination in the system. Reduction of cross-contamination may occur through prevention of wetting of system surfaces by volumes of dispersed phase, droplets becoming stuck on surfaces of the system or slowed by dead-zones in system flow, decontamination of surfaces that have been exposed to biological or chemical samples, separation of individual droplets with a fluid, separation of groups of droplets in a fluid originally produced from distinct reaction mixtures, samples, or assay mixtures, or detection of an individual droplets in serial flow. Further described herein are systems and methods that allow for reaction multiplexing using spatial and temporal techniques, where multiplexing refers to conducting multiple reactions or assays on the same volume of reaction mixture, sample, or assay mixture. Systems and methods as described herein may not require plugs for achieving desired reaction results, accurate assays, or accurate detection of individual droplets. Systems and methods described herein may allow reactions in serially flowing dispersed phase volumes of an emulsion to be conducted without the requirement that those volumes have substantially the same cross section as the tube or channel containing the emulsion.

Described herein are systems and methods for serial flow emulsion reactions. In some instances, the systems comprise a sampling device, an injector, a reactor, and a detector. In some instances, the sampling device pulls in either reaction mixtures or samples to be assayed. In some instances, the reaction mixtures or samples to be assayed are in a dispersed phase. In some instances, the dispersed phase comprising reaction mixtures or samples to be assayed are referred to as a first dispersed phase. The samples may be pulled in through a tube or a channel comprising a material with low affinity or surface energy for the first dispersed phase and a higher affinity or surface energy for the continuous phase of the emulsion. The first dispersed phase may comprise an aqueous phase solution of water, PCR mastermix (buffers, salts, dNTPs), primers, probes, and nucleic acid molecules (e.g. DNA or RNA). In some instances, the first dispersed phase comprises a solution of reactants, markers, and protein. In some instances, the first dispersed phase comprises a chemical species or a nanoparticulate of a chemical species for chemical synthesis.

Described herein are methods and systems for serial flow emulsion reactions, wherein the serial flow emulsion reactions may be performed on a sample comprising at least one nucleic acid. In some instances, the sample comprises multiple nucleic acids. Exemplary nucleic acids include, but are not limited to, coding or non-coding regions of a gene or gene fragment, intergenic DNA, exons, introns, messenger RNA (mRNA), transfer RNA, ribosomal RNA, short interfering RNA (siRNA), short-hairpin RNA (shRNA), microRNA (miRNA), small nucleolar RNA, ribozymes, complementary DNA (cDNA), DNA molecules produced synthetically or by amplification, genomic DNA, recombinant polynucleotides, branched polynucleotides, plasmids, vectors, isolated DNA of any sequence, or isolated RNA of any sequence. In some instances, the sample comprises DNA. In some instances, the sample comprises RNA.

Samples as described herein may further comprise one or more reagents for performing a reaction. In some instances, the reaction is a nucleic acid amplification reaction. For example, the nucleic acid amplification reaction is polymerase chain reaction (PCR). Non-limiting amplification reactions include, but are not limited to, PCR, quantitative polymerase chain reaction (qPCR), self-sustained sequence replication, transcriptional amplification system, Q-Beta Replicase, or rolling circle replication. In some instances, PCR comprises digital PCR in droplets. Exemplary reagents for a nucleic acid amplification reaction include, but are not limited to, enzymes (e.g. polymerase, transcriptase), buffers, dNTPs, primers, or probes. In some instances, the sample comprises an intercalating dye, probes, or molecular beacons.

In some instances, the first dispersed phase comprises oils. In some instances, the first dispersed phase is dispersed phase in an oil-in-water emulsion. In some instances, the dispersed phases combine with a continuous or semi-continuous flow of a continuous phase to form a flowing emulsion. An "emulsion" may be referred to as a two-phase mixture of a dispersed phase in a continuous phase. In some instances, the continuous phase is hydrophobic. In some instances, the continuous phase comprises a hydrophobic oil. In some instances, the hydrophobic oil is a fluorinated oil. In some instances, the continuous phase is hydrophilic. In some instances, surfaces of the injector or one or more channels are fluorinated. In some instances, the surfaces of the injector or one or more channels are hydrophilic.

II. Intake System

Systems and methods provided herein can include an intake system and a process system, where the intake system and process system are configured so that they are not in continuous fluid connection, but a dispersed phase, e.g., a sample, taken up by the intake system from a suitable dispersed phase container, e.g., sample container, or series of dispersed phase containers, e.g., sample containers, can be moved from the intake system to the process system. This can be accomplished in any suitable manner. In certain embodiments, an injector serves as an interface between the intake system, also referred to herein as a sampler, autosampler, or similar wording, and the process system, where the injector can cycle between a configuration that is in fluid communication with the intake system and a configuration that is fluid communication with the process system. The injector can be configured to have additional configurations, e.g., configurations that allow cleaning of one or more parts of the intake system and injector. In certain embodiments, the injector comprises common conduit (also referred to herein as an injection chamber, or injection loop) where the common conduit can be in fluid communication with the intake system or in fluid communication with the process system, but cannot simultaneously be in fluid communication with both. Thus, the intake system and/or the injector can be treated between injections of dispersed phase, e.g., between samples, in order to reduce or eliminate and/or render non-reactive, traces of dispersed phase, e.g., sample, between rounds of intake of dispersed phase, e.g., sample. It will be appreciated that "intake system" can include the injector when the system is configured to be fluidly connected to the injector, as will be clear from context in the following description Thus, systems and methods as described herein for serial flow emulsion reactions comprise a sampling device, or sampler, also referred to as an intake system herein. In some instances, the sampling device is used to introduce one or more samples into systems as described herein.

Described herein are systems and methods for serial flow emulsion reactions comprise use of a sampling device, wherein the sampling device comprises a staging container (e.g., sample container, or plurality of sample containers). The staging container may be a microwell plate, a strip of PCR tubes, or a single PCR tube. In some instances, the microwell plate has at least or about 24 wells, 48 wells, 96 wells, or 384 wells. In some instances, the microwell plate has at least or about 12 wells, 24 wells, 36 wells, 48 wells, 60 wells, 72 wells, 96 wells, 108 wells, 120 wells, 240 wells, 384 wells, 768 wells, 1536 wells, or more than 1536 wells. In some instances, the fluid injector selects a specific sample from the staging container by physically moving an intake portion of the fluid injector to a geometric position of the staging container that contains the specific sample. In some instances, the fluid injector selects a specific sample from the staging container by changing the state of a multiport valve in fluid communication with at least two geometric zones of the staging container containing a distinct sample within each geometric zone.

In some instances, each well of the staging container comprises at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL. In some instances, each well of the staging container comprise at least 10 uL, 20 uL, 50 uL, 100 uL, 200 uL, or more than 200 uL.

Cleaning routines. The intake system can include an intake line, also referred to herein as an intake channel, intake conduit, aspiration conduit, or similar wording for moving sample from a sample container to an injector, and the portions of the injector that are exposed to sample, for example, a common conduit. The intake line can undergo a cleaning cycle between samples.

The purpose of a cleaning cycle on the intake system is to: 1) Purge any contaminant, such as detectable (before or after amplification) material, from the intake section of the system; 2) Render any material not purged from the system undetectable; and/or 3) Inject a spacer fluid in between each of the samples so that the partitions from one sample do not intermingle with the partitions from the other sample. In practice, this can include of a variety of sequences. These can include one or more of purge, denature, and/or space. Possible sequences include: purge only; denature and purge; purge and space; denature, purge, and space.

In certain embodiments, an aliquot of a first fluid, such as dispersed phase, e.g., a sample, is transported from a container via an intake line to an injection chamber (common conduit) in an injector (generally considered part of the intake line when the system is configured to allow a fluid connection between the injector and the intake system) is injected from the injector into the process side. A certain portion of the first fluid is moved from the intake line to the process side in this step, e.g., at least 60, 70, 80, 90, 95, 99, or 99.5% of the first fluid. In certain embodiments, at least a second fluid is moved through part of all of the intake line, such as a purge fluid, denaturing fluid, spacer fluid or any other suitable fluid as described herein. After this step, at least 60, 70, 80, 90, 95, 99, or 99.5% of any remaining first fluid in the intake line is removed. In certain embodiments, a third fluid is moved through part of all of the intake line, such as a purge fluid, denaturing fluid, spacer fluid, or any other suitable fluid as described herein. After this step, at least 60, 70, 80, 90, 95, 99, or 99.5% of any remaining first fluid in the intake line is removed. Any suitable number of such steps can be performed, where after each step at least 60, 70, 80, 90, 95, 99, or 99.5% of any remaining first fluid in the intake line is removed.

Purging can be done by effusion or by a mixture of effusion and preferential chemical compatibility. In certain embodiments, suction is created at the intake point to pull material into an intake line. The intake line can be any suitable intake line, for example, a tube or a needle. The intake line, e.g., tube can be made of fluoropolymer (e.g. PTFE, CTFE), polymer (e.g. nylon, polyethylene, etc.), metal (e.g. stainless steel, aluminum, etc.), or any other suitable material. In certain embodiments, surfaces of the intake line that come in contact with sample have greater affinity for one or more purge, denaturing, and/or spacer fluids (or other fluids, e.g., dead-volume fluids as described below) than for sample, e.g., sample in an aqueous phase.

In the course of sampling, the intake line can retain contaminating material, including detectable or amplifiable material from the sample (e.g. DNA, RNA, cDNA, proteins, etc.), or any other material that could affect one or more operations on the process side in such a way as to alter or potentially alter a process operation in such a way as to materially affect results from the process, e.g., results from one or more other samples. This material may be suspended or solvated in aqueous phase (e.g. as part of a sample or aqueous residue from a sample), and/or it may be physically or chemically bound to the surface of the tube. If this material is incorporated into a subsequent sample injection into the process portion of the system, it could provide false or biased results. For PCR-based reactions, even a single molecule of amplifiable material can be detected, so it is important to either remove all or substantially all such material between samples or to completely denature any material that is remaining. By denature, it is meant that the material is incapable of or substantially unlikely to be involved in processes on the process side, e.g., reactions; in the case of PCR, this includes incapable or substantially unlikely either be amplified or detected or both.

The purpose of purging is to force material that does not contain contaminating material, such as detectable or potentially detectable material, through the intake system, displacing any contaminating material, such as detectable or potentially detectable material, from the intake system so that it does not get injected into the process portion of the system. In one basic element, the purging fluid comprises water. However, the purging fluid can also comprise other materials, e.g. fluorinated or perfluorinated oils, silicone oils, organic oils, mineral oils, acids/bases, detergents, combinations thereof, or any other suitable material.

To improve the efficacy of purging, the purging fluid can comprise a fluid that has a higher affinity for the material of construction of the surface of the intake line, than water, water soluble-compounds, or detectable/potentially-detectable material. In these cases, the higher affinity of the purging fluid acts to displace any sample fluid or residual contaminating material, e.g., detectable/potentially detectable material, from the intake line so that it will not be incorporated into a subsequent sample. In certain embodiments, the surface of the intake line comprises a fluoropolymer and the purging fluid comprises a fluorinated oil. The purging fluid can also comprise a hydrophobic material if the surface of the intake line is comprised of hydrophobic material. Alternatively, when the sample comprises a hydrophobic material, the purging fluid could comprise a hydrophilic material and the intake line could comprise a hydrophilic material. A purging step may comprise flowing more than one purging fluid through the intake line, such as at least two, three, or four purging fluids.

The purpose of denaturing is to chemically or physically alter any contaminating material, such as detectable or potentially detectable (e.g. detectable after an amplification reaction) material, so that it is no longer contaminating, e.g., no longer detectable or potentially detectable. By following a sample intake step with a denaturing fluid, residual contaminating material, e.g., detectable or potentially detectable material, may not cross-contaminate future samples. Denaturing agents can include any suitable agent or combination of agents, depending on the nature of the sample, e.g., acids/bases, peroxides, bleach, DNA modifying enzymes, intercalating agents, and the like. In certain embodiments where the sample comprises nucleic acids, e.g., nucleic acids to be amplified by PCR, the denaturing fluid may be any fluid that may prevent the nucleic acid molecule from being amplified. In some instances, the decontamination fluid comprises an aqueous solution comprising, e.g., azides, hypochlorite, e.g., sodium hypochlorite, mineral acids such as phosphoric acid, strongly alkaline solutions, e.g., sodium hydroxide, peroxides, RNAse, or DNAse, or a combination thereof. In some instances, the denaturing fluid comprises at least or about 0.5%, 1.0%, 1.5%, 2.0%, 4.0%, 6.0%, 8.0%, 10%, 12%, 14%, 16%, 18%, 20%, 24%, 28%, 32%, 34%, 36%, 40%, 44%, 50%, 60%, 70%, 80%, 90%, or more than 90% of azides, hypochlorite, e.g., sodium hypochlorite, mineral acids such as phosphoric acid, strongly alkaline solutions, e.g., sodium hydroxide, peroxides, RNAse, or DNAse, or a combination thereof.

Thus, in the case of nucleic acids, the denaturing (decontamination) fluid for use in the sampling device as described herein may comprise at least one chemical component that changes the chemical and/or physical composition of nucleic acids such that they can no longer undergo a reaction. In some instances, the reaction is polymerase chain reaction (PCR). In some instances, the wetted surfaces of the fluid injector and/or injection device are exposed to the at least one chemical component. In some instances, any cross-contamination from previous injected nucleic acid molecules is reduced or eliminated. In some instances, the denaturing (decontamination) fluid comprises water. In some instances, the decontamination fluid comprises at least one chemical component from the group consisting of sodium hypochlorite, phosphoric acid, sodium hydroxide, RNAse, or DNAse. In some instances, a concentration of the at least one chemical component is at least or about 0.5%, 1.0%, 1.5%, 2.0%, 4.0%, 6.0%, 8.0%, 10%, 12%, 14%, 16%, 18%, 20%, 24%, 28%, 32%, 34%, 36%, 40%, 44%, 50%, 60%, 70%, 80%, 90%, or more than 90%.

The purpose of a spacing fluid, also referred to as spacer fluid, separation fluid, and similar terms herein, is to provide a break between samples so that partitions from one sample flowing through the system are not interspersed with partitions from a second sample. In certain embodiments, the spacing fluid comprises water and does not comprise detectable or potentially detectable material. In certain embodiments, the spacing fluid may or may not comprise a surfactant to stabilize partitions comprising water flowing in a hydrophobic continuous phase; suitable surfactants can be, e.g., as described herein. In certain embodiments, the spacing fluid comprises an oil, such as silicone oil, organic oil, mineral oil, or a combination thereof, for example, mineral oil. In certain embodiments the spacing fluid comprises a material that is substantially immiscible with the sample and with the continuous phase; in certain embodiments the spacing fluid comprises a material that has a greater affinity for the surface of one or more conduits in the intake system or process system than do one or more of the samples. The physical size of the spacing fluid volume prevents partitions from a first sample injected at a first time into the process portion of the system from becoming interspersed with partitions from a second sample injected at a second time subsequent to the first time; even though it is expected some axial dispersion of partitions will occur, the scale of the dispersion will not be as large as the linear size of the volume of spacing fluid injected, so no partitions will intersperse. Additionally, since the spacing plugs are exceptionally large so that they consume the entire or substantially the entire cross-sectional diameter of flow conduit on the process side, partitions have a limited probability of transiting. While simply using an aqueous spacing fluid can work, problems may arise if partitions become trapped in regions of flow moving slower than the bulk flow (e.g. dead zones, eddies, and the like). Additionally, in regions of flow where there is a change in the vertical position of the partitions, relative differences in partition velocity as a function of size due to buoyancy can cause axial dispersion to be more severe. For these reasons, using a spacing fluid comprising a material immiscible with water is advantageous. If that material has a higher affinity for the material comprising the flow conduit, it can displace and force partitions in slow moving zones to move through the system. Similarly, if the material has a high viscosity the material will tend to exhibit a low deformation rate acting as a strong physical front that may displace materials from the conduit walls and prevent partition transit.

The order in which sample materials are added can be important to prevent cross-contamination in this system. The intake and process sections of the system can be separated by an injector. The injector is an element of the system that allows independent intake and then processing of fixed samples from that intake. In certain systems and methods provided herein, a "common conduit" approach (described elsewhere) is used—this allows separation of the intake and the process sections of the system by physically moving an inline section (the "common conduit") of tubing from the intake section to be inline with the process section. In certain embodiments, the surface of the common conduit comprises a material that has a higher affinity for the continuous phase of the emulsion to be created in the process side of the system. Thus, when said continuous phase is added to the common conduit, it will preferentially displace any dispersed phase from the system. This can be important to cleaning the system to prevent cross-contamination. In certain embodiments, the common conduit surface comprises a hydrophobic material, the continuous phase comprises a hydrophobic component, and the dispersed phase of the emulsion comprises a hydrophilic component.

Purge only: A sample is pulled into the intake section of the system and at least partially fills the injector's common conduit. The injector moves the common conduit to be in fluid communication with the process section of the system and the sample exits the common conduit towards, e.g. the partitioner. When the elements of the injector that contacted the sample are realigned with the intake section of the system, an aliquot of purge fluid is pulled into the system. The aliquot is large enough so as to completely displace any residual sample fluid that may contain contaminating material from the common conduit and intake system, such as detectable or potentially detectable material. Two or more aliquots may be sampled of two or more different purge fluids. In certain embodiments, the purge fluid comprises a material with a greater affinity for the conduit surface than does the material to be sampled, so as to displace any residual sample material from the common conduit and the intake system. In certain embodiments, a first purge fluid comprising water may be added to the system, displacing residual sample to injector waste. A second purge fluid comprising a hydrophobic material with higher affinity for the conduit surface than water may then be sampled, displacing any residual water and preparing the system for a new sample. In certain embodiments the second purge fluid comprises an oil, such as a fluorinated oil.

Denature and purge: This is the same as purge only, except an additional step or series of steps is added where denaturing fluid is pulled into the system ahead of the purge fluid or fluids. For example, a sample may be pulled into the common conduit of the injector, which is then positioned to be in fluid communication with the process system and the sample displaced by at least one continuous phase. The common conduit is then positioned to be in fluid communication with the intake system, and an aqueous solution comprising bleach is flowed through the common conduit so as to render nucleic acid in the intake system unable to be amplified, followed by a fluorinated oil to displace the aqueous solution comprising bleach from the common conduit and intake system.

Purge and space: This is the same as purge only, except in between sequences of sample injections, a spacing fluid is injected into the process system. A typical sequence can be, e.g., starting with an injector filled with purge fluid: Sample intake into injector, inject into process system, purge fluid(s) intake into injector, reject to waste, spacing fluid intake into injector, inject into process system, purge fluid(s) intake into injector, reject to waste.

Denature, purge, and space: This is the same as "Purge and space", except a denaturing fluid is injected ahead of the purging fluid in at least one part of the sequence. Such a sequence can be, e.g., starting with an injector filled with purge fluid: Sample intake into injector, inject into process system, denaturing fluid intake into injector, reject to waste, purge fluid(s) intake into injector, reject to waste, spacing fluid intake into injector, inject into process system, purge fluid(s) intake into injector, reject to waste. An alternate sequence can be, e.g.: Sample intake into injector, inject into process system, denaturing fluid intake into injector, reject to waste, purge fluid(s) intake into injector, reject to waste, spacing fluid intake into injector, inject into process system, denaturing fluid into injector, reject to waste, purge fluid(s) intake into injector, reject to waste.

If the inlet region of the intake line comprises a filtering element to reject or partially reject particulate matter above a certain size (generally, above some fraction of a critical dimension of the smallest element of the microfluidic system), then a "blowback" step may be added to any of the steps in the sampling sequence. In such a step, fluid flow may be reversed so as to, e.g., dislodge particulate material from the surface of the inlet region of the intake channel. This blowback step can be added after intake of either the denaturing or the purge fluid, but it can be added to any step in the process. The fluid rejected can be rejected into a waste receptacle. Preferably, the fluid rejected will be of low value.

In certain embodiments, the denature, purge and space fluids are injected using the sampling nozzle and are passed to either into the process section of the system (in the case of the spacing fluid) or to waste (in the case of purge and denature fluids). In certain embodiment the denature, purge and/or space fluids are pulled from fluid reservoirs (such as bottles, bags, and the like) and are passed in the reverse direction through the injector and sampling nozzle disposing into the now empty sample container, such as sample well, or into a separate container or well designated for waste.

It may be necessary to rinse the outside of the sample nozzle to remove any adsorbed or otherwise adhering liquids. This is especially problematic when working with viscous agents. The rinse may be done in any suitable manner, such as by wiping, dipping in a lower viscosity solution, or by rinsing the tip with continuous phase using an external stream of continuous phase.

Thus, in certain embodiments, sampling device may comprise a staging container, a pump, a decontamination fluid reservoir, a purge reservoir, and a sampler intake. The staging container may hold at least one sample to be analyzed on the instrument. The pump may provide the motive force required to move the sample fluid from the staging container to the injector. The decontamination fluid reservoir may comprise fluid for decontaminating the system between injections of samples from one or more staging containers. The purge reservoir may comprise a dispersed phase for separating each sample in the reaction flow pathway. The fluid injector may transfer sample, decontamination fluid, or the dispersed phase from the staging container to the injector. A controller may control the sequence and timing of events during sample loading and injection.

Thus, provided herein are systems and methods for serial flow emulsion reactions, wherein the sampling device introduces one or more samples and one or more dispersed phases in sequence. At the start of the sequence, an internal volume of the fluid injector (also referred to as an intake system, sampler, and other similar terms herein) may comprise decontamination (denaturing) fluid, second dispersed phase, aqueous solution not comprising nucleic acid, denatured nucleic acid, or combinations thereof. The fluid injector may select a sample from the staging device. The controller may activate the pump and may control the pump rate and activated time such that a first controlled volume of sample is loaded by the fluid injector into the injection device (also referred to herein as injector). Once complete, the controller may stop the pump and may direct the fluid injector to inject the decontamination fluid from the decontamination fluid reservoir into the injection device. The controller may start the pump and may control the pump rate and activated time such that a second controlled volume of decontamination fluid may loaded by the fluid injector into the injection device. Once complete, the controller may stop the pump and may direct the injector to inject the second dispersed phase from the purge fluid reservoir into the injector. The controller may start the pump and may control the pump rate and activated time so that a second controlled volume of separation and/or purge fluid may be loaded by the fluid injector into the injection device. Once complete, the controller may stop the pump and the system may ready to load another sample from the staging container.

In some instances, the sequence is varied. At the start of the sequence, the internal volume of the fluid injector may comprise decontamination fluid, second dispersed phase, aqueous solution not comprising nucleic acid, denatured nucleic acid, or combinations thereof. The fluid injector may select a sample from the staging device. The controller may activate the pump and may control the pump rate and activated time so that a first controlled volume of sample is loaded by the fluid injector into the injection device. Once complete, the controller may stop the pump and may direct the fluid injector to inject the second dispersed phase from the purge fluid reservoir into the injection device. The controller may start the pump and may control the pump rate and activated time so that a second controlled volume of decontamination fluid may be loaded by the fluid injector into the injection device. In some instances, decontamination fluid and first dispersed phase are prevented from intermingling. Once complete, the controller may stop the pump and may direct the fluid injector to inject the second dispersed phase from the purge fluid reservoir into the injection device. The controller may start the pump and may control the pump rate and activated time so that a second controlled volume of decontamination fluid is loaded by the fluid injector into the injection device. Once complete, the controller may stop the pump and the system may be ready to load another sample from the staging container. In some instances, the controller stops the pump and directs the fluid injector to inject the second dispersed phase from the purge fluid reservoir into the injection device. In some instances, the controller again the pump and controls the pump rate and activated time so that a second controlled volume of decontamination fluid is loaded by the fluid injector into the injection device before loading another sample from the staging container.

Dead volume fluid. Because the intake channel is of finite size and comprises a pathway to the injector, the total volume of the system will of necessity be larger than the volume injected in the injector. If the volume of the intake channel significantly exceeds the volume of the material to be sampled or a desired volume of any of the cleaning reagents, it may be desirable to add a sampling step or steps of a "dead volume fluid." This fluid occupies the dead volume of the system outside (or even partially comprising) the volume of the common conduit of the injector. In one embodiment, the dead volume fluid is air. Using air as the dead volume has the advantage of being free and of unlimited supply, and the interface of air with sample is easily detectable (see below); on the other hand, it is compressible, so is more difficult to meter into the system to ensure accurate loading of the injector. However, since the air-fluid interface is easily detectable using common methods, including but not limited to ultrasonic or optical methods, detectors may be used to ensure the placement of the sample into the common conduit. These detectors may provide additional functionality such as sample loading verification in the case of limited/no sample injection as well as a means for quantifying the volume of sample loaded into the common conduit. This may be derived since the flow rate and tube dimensions are fixed and therefore injected volume is a function of transit time of the sample through the air detector.

The dead volume fluid can comprise a material in the continuous phase of the emulsion to be created in the process portion of the system. For example, the dead volume fluid can be a fluorinated oil, a silicone oil, a hydrocarbon oil, an organic oil, or an aqueous fluid; in certain embodiments the dead volume fluid comprises a fluorinated oil. More than one dead volume fluid may be used in the system. See, e.g., "parfait" systems and methods, described below.

Dead volume fluid may be added to the intake line in any suitable manner. In certain embodiments, dead volume fluid is contained in an onboard reservoir that is accessible by the sampling head of the intake channel. After pulling sample from a sample container into the intake channel, the sampling head is repositioned so that the intake channel can pull the at least one dead volume fluid into the intake channel from the common reservoir. While this approach is simple, it risks contaminating the dead volume fluid with contaminating material, such as detectable or potentially detectable material, from previous sample containers sampled and additionally requires regular refilling. In certain embodiments, this can be prevented by having a plurality of dead volume fluid reservoirs; in the limiting case, there is one dead volume fluid reservoir for each sample container, which eliminates the potential for cross-contamination. In this embodiment, dead-volume fluid could be provided in a pre-filled consumable (e.g. a sealed microtiter plate) or a user-filled consumable and placed in a position accessible to the sampling head. Alternatively or additionally, there can be a set of fillable and cleanable reservoirs on the system that are filled from a central dead fluid reservoir. These reservoirs can be filled using a gravity feed, a pump system, or any suitable means to achieve fluid flow. In some cases, all of the dead volume fluid dispensed is pulled into the intake channel. In other cases, only a portion of the dead volume fluid is pulled into the intake channel, and the balance is removed through a drain in the dead volume fluid reservoir. A variety of configurations can be envisioned for valves, pumps, and drains to achieve this approach.

In certain embodiments, dead volume fluid may be dispensed into reservoirs through a channel attached to the sampling head. This may be the same channel as the intake channel or a separate channel; embodiments of these approaches are described further below. In some cases, a reservoir or reservoirs are filled with dead volume fluid between each intake of sample. For example, there can be a dedicated dead volume container; after pulling sample from the at least one sample container (e.g. a well of a microtiter plate), the dispensing channel of the sampling head can be positioned into the dead volume fluid reservoir and dead volume fluid can be pulled into the reservoir. Any suitable method of generating a driving force may be used, e.g., the use of peristaltic or syringe pumps to create a negative pressure environment. In another example, the well of the microtiter plate that contained the sample can be used as the dead volume reservoir. After pulling sample into the intake portion of the system, a second channel can be positioned over the well and dead volume fluid may be dispensed through that channel. The first channel may then be positioned over the well and dead volume fluid pulled in immediately behind the sample. In another example, the dead volume fluid is dispensed into wells in a microtiter plate that may be used a finite number of times before disposal, but are distinct from the wells that held the original sample.

In another embodiment, the dead volume fluid may be supplied through a branch channel to the intake channel but ahead of the injector. In such an embodiment, a three-way valve or similar device can select between the sample intake channel and the dead volume fluid channel as inlets to the injector. After intake of sample (potentially followed by air) and positioning of that sample in or substantially in the injector, the valve position can be changed so that intake of further fluid comes from the dead volume fluid reservoir.

In certain embodiments, the reservoir holding the dead volume fluid is the sample container itself (e.g. a well in a microtiter plate), and the dead volume fluid is separated from the immiscible sample fluid by gravity, electromagnetic force, or any other suitable force. In certain embodiments, the dead volume fluid and the sample fluid have different mass densities and gravity allows the dead volume fluid to settle out from the sample fluid. In certain embodiments, the dead volume fluid has a lower mass density than the sample fluid and floats on top of the dead volume fluid. The intake channel is inserted into a position of the sample fluid and intake started. As fluid is drawn into the intake channel, the level of the top of the fluid in the sample container falls until a transition is made to intake of the dead volume fluid due to complete injection of the sample fluid originally at a vertical position at or above the vertical position of the inlet of the intake channel. In this way, sample fluid and dead volume fluid can be added without repositioning the intake channel outlet or introducing air. In certain embodiments, the sample fluid may have either a lower gravimetric density or a higher gravimetric density as the dead volume fluid (but not the same), so that one of the fluids rests on top of the other fluid when settled under a gravitational force. The intake channel inlet is positioned so that it is located within or substantially within the sample fluid; a first volume of sample fluid is pulled into the intake channel; the intake channel inlet is next positioned so that it is located in or substantially in the dead volume fluid; a second volume of dead volume fluid is pulled into the intake channel. In this way, dead volume fluid can be injected immediately after sample fluid.

In the above set of embodiments, dead volume fluid can be added to the sample container containing sample fluid in any suitable manner. For example, the system user can prepare the fluids in the sample container externally to the system, e.g., the user can pipette sample fluid and dead volume fluid together into a well of a microtiter plate by hand. Alternatively or additionally, a liquid handling robot can perform the pipetting of either or both fluids. The fluids can be added in either order. In another example, the dead volume fluid can be dispensed by the system into the sample container, either through a channel distinct from the intake channel or through the intake channel itself. In the former instance, dead volume fluid can be driven from a dead volume fluid reservoir by an appropriate driving force through the supply channel and into the sample container. In the latter instance, dead volume fluid can be driven in the reverse direction of flow as sample intake through the intake channel by utilizing a valving arrangement either ahead of or behind the injector.

In these embodiments, separation of the fluid by gravity is important for proper functioning of the system. While the immiscibility of the dead volume fluid and the sample fluid will tend to make distinct phase separation of the system a stable equilibrium point, metastable states could exist where portions of one phase are suspended in the other phase. Agitating the two-phase system may be beneficial to phase separation. The velocity of the second fluid added may create enough turbulence to agitate the fluid and be sufficient to drive separation. In certain embodiments, mechanical force may be used to agitate the fluid and drive separation; this can be any suitable force, e.g., vibration, centrifugation, ultrasonic waves, or other methods that agitate the fluids in the internal mixture. In certain embodiments, the inlet of the intake channel may be moved vertically, horizontally, or a combination of these motions so as to mechanically stir or agitate the fluids inside the sample container and encourage phase separation.

More than one dead volume fluid may be used in the system. In some embodiments, a first dead volume fluid is a spacer fluid and a second dead volume fluid is a continuous phase or air. The common conduit of the injector is partially filled with sample then partially filled with the first dead volume fluid; the balance of the intake system is partially or fully filled with the second dead volume fluid. Taking this approach allows simultaneous injection of a sample fluid and a subsequent spacer fluid into the process system. In other embodiments, the system uses at least two dead volume fluids, where one of the dead volume fluids comprises air. Air and at least one additional dead volume fluid may be added to the intake system in any order and any number of aliquots. In an embodiment, air is added following intake of a sample fluid, followed by a second dead volume fluid, followed again by air. In certain embodiments, the second dead volume fluid comprises an oil, a fluorinated oil, a hydrocarbon oil, an organic oil, or a silicone oil.

Figure 84:
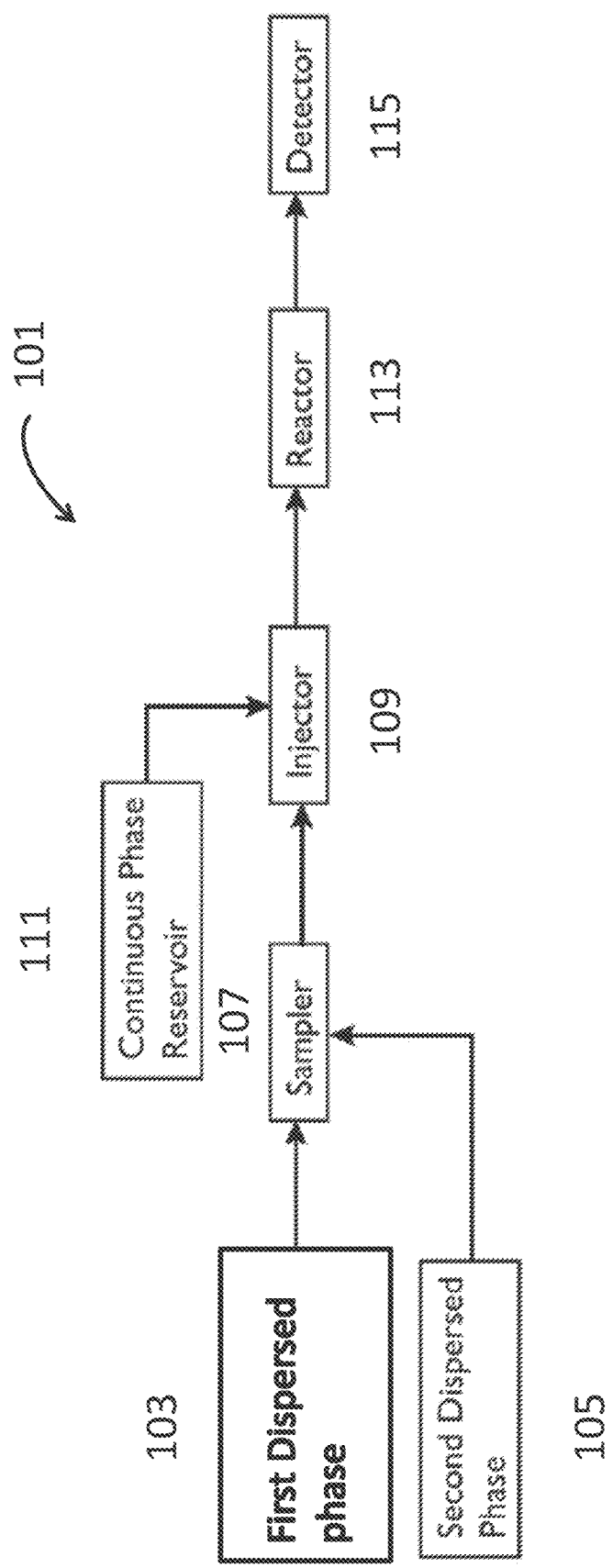
FIG. 84 shows a system diagram comprising a first dispersed phase, a second dispersed phase, a sampling device ("sampler"), a continuous phase reservoir, an injector, a reactor, and a detector.

Thus, systems and methods provided herein may include an exemplary system such as illustrated in FIG. 84. The system 101 comprises a first dispersed phase 103 comprising samples, for example comprising a nucleic acid molecule and/or reagents for performing a nucleic acid amplification reaction, and a second dispersed phase 105 comprising a fluid to prevent or eliminate cross-contamination. It will be appreciated that, in some instances, "dispersed phase," as that term is used herein, may include materials that are moved into a sampler and/or injector, such as sample, purge fluid, decontamination (e.g., denaturing) fluid, and the like; in some instances such substances do not form an emulsion in a continuous phase. Usage of the term is clear from context. In some instances, the first dispersed phase comprises a reaction mixture or reaction fluid. In some instances, the fluid is a decontamination fluid (also referred to as a denaturing fluid herein), a purge fluid, separation fluid (also referred to as spacer fluid herein), or a combination thereof. The decontamination fluid may be a fluid that prevents a reaction from occurring. The purge fluid may be any fluid that displaces any residual volume of the first dispersed system. In some instances, the purge fluid does not affect, interfere, or confound any measurement detected by the detector. The separation fluid (also referred to as "spacer fluid" herein) may be a fluid that acts as a physical buffer between two subsequent injections of a first dispersed phase. In some instances, the fluid is injected alternately with the first dispersed phase. The first dispersed phase 103 comprising samples and a second dispersed phase 105 pass to a sampling device ("sampler") 107 and then an injector 109. The sampling device may function to choose, transport, and/or potentially meter volumes of the various dispersed phases. The injector may insert or introduce a volume of dispersed phase into the continuous phase to form a volume of dispersed phase in the flowing emulsion. A continuous phase from a continuous phase reservoir 111 may be added to the injector 109. From the injector 109, the first dispersed phase 103 comprising samples and a second dispersed phase 105 pass to a reactor 113 and a detector 115. The reactor may cause a reaction on the various volumes of first dispersed phase, for example, through heat, light, or acoustic energy.

Samples as described herein may be in volumes of one or more dispersed phases. In some instances, a dispersed phase is aqueous. In some instances, a dispersed phase comprises more than about 51% (by mass or by molar concentration) of water. In some instances, a dispersed phase comprises at least or about 10%, 20%, 30%, 40%, 50%, 60%, 70%, 80%, 90%, 95%, or more than 95% water. In some instances, the reagent or target molecule is encapsulated within an aqueous fluid. In some instances, the encapsulated reagent or target molecule is mixed with an immiscible fluid to form an emulsion. In some instances, the emulsion is a single emulsion, a double emulsion, or a rod-like emulsion. In some instances, the immiscible fluid is oil. Exemplary oils are fluorinated oils, silicone oils, hydrocarbon oils, or mineral oils. In some cases, the immiscible fluid comprises oil and one or more surfactants; surfactant can be any suitable surfactant in any suitable concentration, for example, as described herein. In some instances, a ratio of a volume of the droplet (partition) to the immiscible fluid (continuous phase) is at least or about 1:20, 1:15, 1:10, 1:5, or 1:1. In some instances, the ratio of the volume of the droplet to the immiscible fluid is about 1:10. In some instances, the ratio of the volume of the droplet to the immiscible fluid is about 1:1, for example, 0.5:1 to 1.5:1. Sometimes a reagent or target molecule (e.g. DNA or RNA) is encapsulated in droplets of dispersed phases.

Figure 85:
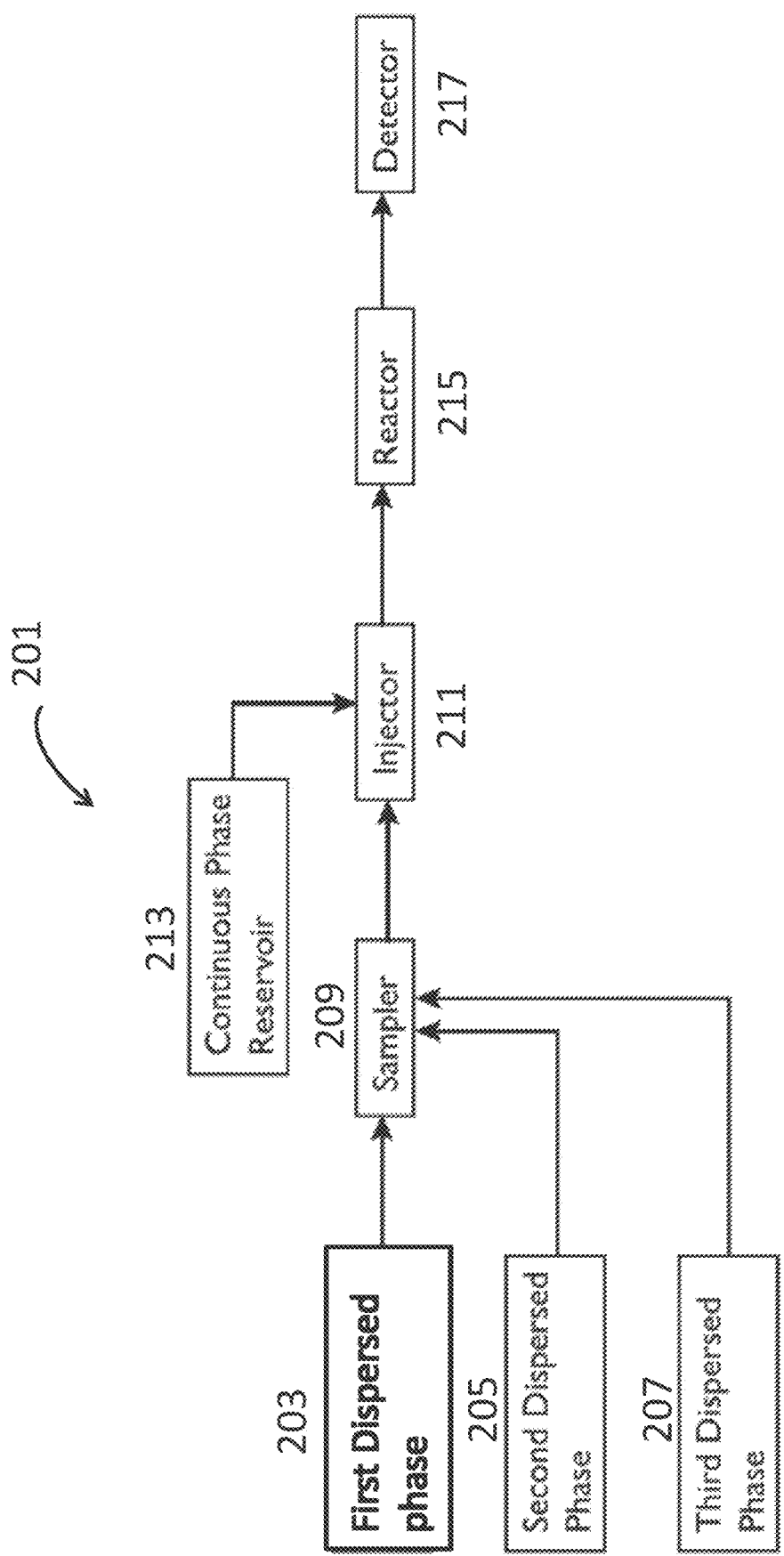
FIG. 85 shows a system diagram comprising a first dispersed phase, a second dispersed phase, a third dispersed phase, a sampling device ("sampler"), a continuous phase reservoir, an injector, a reactor, and a detector.

Systems and methods as described herein may comprise a plurality of dispersed phases. FIG. 85 shows a system 201 comprising three dispersed phases. A first dispersed phase 203 comprises a sample, for example comprising a nucleic acid molecule and/or reagents for performing a nucleic acid amplification reaction. The first dispersed phase 203 is sampled and injected and a portion may be rejected to waste. A second dispersed phase 205 comprises a decontamination fluid. The second dispersed phase 205 is sampled but not injected. The decontamination fluid may be any fluid that may prevent the nucleic acid molecule from being amplified when the sample comprises nucleic acid. In some instances, the decontamination fluid comprises sodium hypochlorite, phosphoric acid, sodium hydroxide, RNAse, or DNAse, or a combination thereof. The third dispersed phase 207 comprises a separation (spacer) fluid. The third dispersed phase may provide a buffer between the first dispersed phase and the second dispersed phase. The third dispersed phase may be sampled and injected and a portion may be rejected to waste. In some instances, the third dispersed phase comprises water. In some instances, the third dispersed phase comprises an immiscible fluid. The first dispersed phase 203 comprising samples, a second dispersed phase 205, and a third dispersed phase 207 pass to a sampling device ("sampler") 209 and then an injector 211. A continuous phase from a continuous phase reservoir 213 may be added to the injector 211. From the injector 211, the first dispersed phase 203 comprising samples, a second dispersed phase 205, and a third dispersed phase 207 pass to a reactor 215 and a detector 217.

Figure 86:
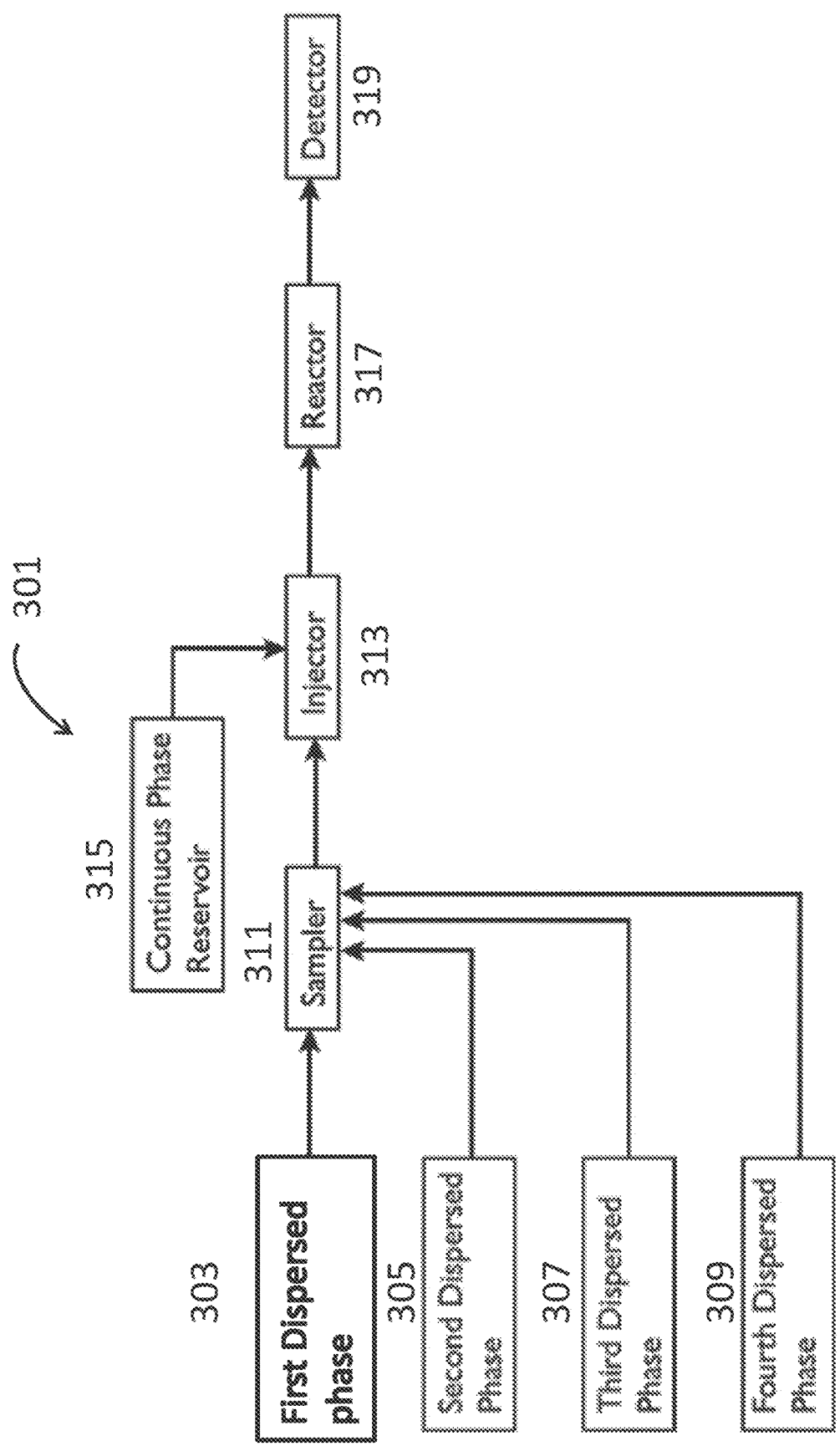
FIG. 86 shows a system diagram comprising a first dispersed phase, a second dispersed phase, a third dispersed phase, a fourth dispersed phase a sampling device ("sampler"), a continuous phase reservoir, an injector, a reactor, and a detector.

FIG. 86 shows a system 301 comprising four dispersed phases. A first dispersed phase 303 comprises a sample, for example, comprising a nucleic acid molecule and/or reagents for performing a nucleic acid amplification reaction. A second dispersed phase 305 comprises a decontamination fluid. In some instances, the second dispersed phase is injected. In some instances, the second dispersed phase is sampled but not injected. A third dispersed phase 307 comprises a separation fluid. A fourth dispersed phase comprises a purge fluid 309. The separation fluid may be immiscible with the first, second, or third dispersed phase. In some instances, the separation fluid is injected following the purge fluid. In some instances, the separation fluid is injected following the second dispersed phase. In some instances, the separation fluid is injected following the second dispersed phase and following the third dispersed phase. In some instances, the separation fluid is injected prior to the injection of the first dispersed phase. The separation fluid may be injected in interspersed amounts. The first dispersed phase 303 comprising samples, a second dispersed phase 305, a third dispersed phase 307, and a fourth dispersed phase 309 pass to a sampling device ("sampler") 309 and then an injector 313. A continuous phase from a continuous phase reservoir 315 may be added to the injector 313. From the injector 313, first dispersed phase 303 comprising samples, a second dispersed phase 305, a third dispersed phase 307, and a fourth dispersed phase 309 pass to a reactor 317 and a detector 319.

Separation (spacer) fluids as used in systems and method as described herein may be used between dispersed phases. In some instances, the separation fluid is immiscible with the dispersed phases. In some instances, the separation fluid does not form a plug in a channel or tube. In some instances, the separation fluid comprises a size that does not fill a cross section of the channel or the tube. In some instances, the separation fluid comprises a flat velocity profile. In some instances, the separation fluid has a greater affinity or surface energy for a surface of the channel or the tube than a dispersed phase. In some instances, the separation fluid has a lower affinity for a surface of the channel or the tube than a dispersed phase. In some instances, the separation fluid comprises an oil. In some instances, a movement of the separation fluid is in laminar flow. In some instances, the velocity front is curved.

Systems and methods as described herein may comprise a plurality of dispersed phases, wherein each dispersed phase of the plurality of dispersed phases is immiscible with another dispersed phase. In some instances, the dispersed phase is miscible with another dispersed phase. In some instances, due to the immiscibility of each of the dispersed phases, serial injection of the plurality of dispersed phases does not result in cross-contamination.

A volume of the dispersed phase may be at least or about 0.001 nanoliter (nL), 0.002 nL, 0.003 nL, 0.004 nL, 0.005 nL, 0.006 nL, 0.007 nL, 0.008 nL, 0.009 nL, 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL. In some instances, the volume of the dispersed phase comprises at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL. In some instances, volumes of the dispersed phase injected is at least or about 0.001 nanoliter (nL), 0.002 nL, 0.003 nL, 0.004 nL, 0.005 nL, 0.006 nL, 0.007 nL, 0.008 nL, 0.009 nL, 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL. In some instances, dispersed phase is injected into the process system (such as sample and/or spacer fluid); volumes of the dispersed phase injected are in a range of about 0.1 uL to 100 uL, or 0.5 uL to 1000 uL, or 1 uL-200 uL, or 1 uL-100 uL, or 1 uL-70 uL, or 1 uL to 50 uL, or 5 uL-200 uL, or 10 uL-200 uL, or 10 uL-100 uL, such as 0.1 uL to 100 uL, for example 0.5 uL to 80 ul, such as 1 uL to 40 uL. In some instances, volumes of the dispersed phase injected is at least or about at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL. Systems and methods described herein for serial flow emulsion reactions may comprise volumes of dispersed phases that are further partitioned into droplets. In some instances, the dispersed phase comprises sample assays or discrete reactions. In some instances, volumes of dispersed phases are separated. In some instances, droplets (partitions) of the dispersed phases are separated. In some instances, volumes of dispersed phase partitions (e.g. droplets), e.g., after dispersed phase, such as a sample, has moved through a partitioner, is at least or about 0.001 nanoliter (nL), 0.002 nL, 0.003 nL, 0.004 nL, 0.005 nL, 0.006 nL, 0.007 nL, 0.008 nL, 0.009 nL, 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL. In some instances, volumes of dispersed phase partitions comprises at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL. In some instances, volumes of dispersed phase partitions are in a range of about 10 pL to about 2 nL.

Provided herein, in some embodiments, are a series of sampler intake immersion stations for decontamination and/or purging of the fluid sampler intake. The sampler intake immersion stations may comprise a well, a valve, a reservoir of decontamination fluid, separation fluid, or purging fluid, a controller, and a flow pathway between the reservoir of decontamination fluid and/or separation fluid and/or purging fluid and the well. The sampler intake may enter a well and causes a valve to be partially or wholly opened for partially filling the well with decontamination fluid or purging fluid. The decontamination or purging fluid may contact both an outer portion of the sampler intake and an inner portion of the sampler intake. A controller may cause the injector to inject a portion of the decontamination fluid or purging fluid into the fluid pathway between the sampler intake and the injector. In some instances, the well is an open container for the contained fluid. In some instances, the well has a cover that comprises an access port so that contaminating elements may not enter the well but the sampler intake may have access. In some instances, the controller causes the sampler intake to draw a portion of the decontamination fluid or purging fluid into the injection device. An amount decontamination fluid or purging fluid that may be injected may comprise at least or about 0.001 nanoliter (nL), 0.002 nL, 0.003 nL, 0.004 nL, 0.005 nL, 0.006 nL, 0.007 nL, 0.008 nL, 0.009 nL, 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL. In some instances, the amount of decontamination fluid or purging fluid that is drawn comprises at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL. After drawing a volume of the decontamination fluid, separation fluid, or purging fluid into the injector, the controller may cause the sampler intake to stop drawing decontamination fluid, separation fluid, or purging fluid into the pathway between the sampler intake and the injector. In some instances, the controller causes the injector to stop injecting decontamination fluid or purging fluid to a waste channel or a flow pathway. The injector may leave the reservoir, which causes the valve to be closed. In some instances, the well comprises a volume of decontamination fluid and/or purging fluid. In some instances, the well comprises at least or about 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL. In some instances, the reservoir comprises at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL. In some instances, the well further comprises a drain to allow at least some of the decontamination fluid and/or purging fluid to leave the well. In some instances, the drain further comprises a valve that opens when the fluid injector is not in the valve and closes when the fluid injector is in the valve. In some instances, the decontamination fluid comprises water. In some instances, the decontamination fluid comprises sodium hypochlorite, phosphoric acid, sodium hydroxide, RNAse, or DNAase. In some instances, the decontamination fluid comprises at least or about 0.5%, 1.0%, 1.5%, 2.0%, 4.0%, 6.0%, 8.0%, 10%, 12%, 14%, 16%, 18%, 20%, 24%, 28%, 32%, 34%, 36%, 40%, 44%, 50%, 60%, 70%, 80%, 90%, or more than 90% of sodium hypochlorite, phosphoric acid, sodium hydroxide, RNAse, or DNAse, or a combination thereof Thus, a sampling device for use in systems and methods described herein may comprise a first dispersed phase reservoir, a second dispersed phase reservoir, a valve to select between the two reservoirs, and a tube connecting the various reservoirs to the valve and the valve to the injector. In some instances, a filter is added in between the first dispersed phase reservoir and the valve or between the valve and the injector. The pump may be placed either upstream of the injector inlet or downstream on an injector waste line. In some instances, the pump is placed downstream on an injector waste line. The valve may allow the first dispersed phase to fill the injector and then switches to only allow second dispersed phase to fill the injector. In some instances, the sampling device comprises a reservoir of dispersed phases comprising decontamination fluid, purge fluid, or separation fluid that is configured to quickly disconnect. In some instances, the sampling device comprises a valve that is configured to be flushed with second dispersed phase. Multiple reservoirs of dispersed phases comprising samples or assays and/or dispersed phases comprising decontamination fluid, purge fluid, or separation fluid may be used.

Multiple dispersed phases may be introduced into the system. In some instances, the dispersed phase is different from a dispersed phase comprising sample. In some instances, the multiple dispersed phases are provided from a common reservoir that is sampled after each dispersed phase comprising sample is injected. The reservoirs may be open containers of the multiple dispersed phases. The reservoirs may be fitted with a cover with a central poppet valve. In some instances, when the sampling tube and/or lance contacts the poppet, the valve depresses and provides access to the contents of the reservoir. In some instances, the sampling tube and/or lance are immersed in the reservoir. If the fluid is decontamination fluid, both the exterior and interior surfaces of the lance/sampling tube may be decontaminated. The reservoir may have a cover, a central poppet valve, an external reservoir, and a tube connecting the reservoir and external reservoir. When depressed, the central poppet valve may provide access to the contents of the reservoir and opens a pathway that releases a fixed volume of fluid from the external reservoir into the reservoir. The external reservoir may continuously replenish the reservoir at each injection. Because the central poppet valve may isolate the external reservoir and the reservoir when closed, the central poppet valve may allow for the external reservoir to be exchanged and/or refilled in between injections.

In some instances, the sampling system and the reservoir system are used in conjunction. In some instances, the central poppet is depressed as the lance is actuated downward. In some instances, the vertical stop rests on a top surface of the reservoir cover and the first spring allows for the central tube to continue to move generally downward into the reservoir. In some instances, when fully extended, both the exterior and interior surfaces of the lance and the sampling tube are immersed in the reservoir fluid at least to the level at which they are immersed when sampling first dispersed phase. In some instances, the sampling system pulls the reservoir fluid into the sampling tube with the pump and then the sampling system retracts first the tube then the lance.

Barriers

In the system, samples may have small volumes (<1 mL, often <50 uL) and are placed into a set of containers (also referred to herein as a staging component, or similar wording) (e.g. wells of a microtiter plate) that is sampled over time (in some cases over 30 min, up to over 6 hr or more). Such a small volume will be susceptible to evaporation. Thus, sealing these with a vapor barrier can prevent such evaporation and allow as much of the sample to be tested as possible while reducing errors in concentration measurements. Additionally, foreign material in the ambient environment surrounding the containers can be prevented from entering the containers and potentially contaminating the sample if a barrier is in place.

One such vapor barrier can be a film placed over the top of each sample container. In certain embodiments, this barrier comprises an adhesive film. The film can, e.g., cover more than one of the sample containers. In certain embodiments, the film covers all of the sample containers of a set of sample containers, e.g., a microtiter plate. Any suitable material may be used for the seal; potential materials of construction are a metal film, such as a film comprising aluminum, steel, copper, or any other metal, a polymer film, such as a film comprising polyethylene, acrylic, acrylonitrile butandiene styrene, bioplastics, cellophane, cellulose acetate, fluorinated polymers (PTFE, PVDF, ECTFE, FEP, PFA), nylon, polyamide acetal, polybutylene terephthalate, polycarbonate, polyester, polyetheretherketone, polyethersulfone, polyetherimide, polyethylene, polyimide, polyamide imide, polymethylpentene, polyolefins, polypropylene, polysulfone, polyphenylene sulfide, polyvinyl chloride, thermoplastic polyurethane], an elastomeric film, such as a film comprising silicone, rubber, hexafluoropropylene, ethylene propylene diene terpolymer, vinylidene fluoride, tetrafluoroethylene, vinylidene fluoride, hexafluoropropylene, perfluoromethylvinylether, acrylonitrile, polydimethylsiloxane, fluorosilicone, polyisoprene, polyisobutylene, polychloroprene, fluoroelastomers, polyurethane, epichlorohydrin, perfluoroelastomer, polysulfide, polytetrafluoroethylene, styrene butadiene, tetrafluoroethylene, ethylene acrylic, or any combination thereof. Unlike in typical real-time PCR machines (that also use a film to cover the sample containers and prevent evaporation), the film does not need to be either transparent or temperature stable above 44° C. The film may be placed over the container or containers by any suitable method, e.g., by hand, by roller, or by using a thermal plate sealer. Important to this method can be a system to pierce the seal prior to sampling. Any suitable system and method may be used; exemplary systems and methods are described herein. The film may be pre-perforated so as to break repeatably at the same position without fracturing into pieces smaller than the effective inlet size of the inlet region of the intake channel. The film may instead comprise a resealable polymer material, so that after sampling, the system can again prevent evaporation and/or contamination. This is useful should it be desirable to measure a single sample multiple times. An added advantage of such an approach is that it provides a "wiping" surface to remove fluids and/or solid materials adhering to the sampling tip, reducing the amount of sample material that may remain on the tip and helping to prevent cross-contamination.

Thus, the dispersed phase reservoir (set of containers) comprising a reaction sample may comprise a seal to reduce or prevent evaporation or to reduce or prevent contamination. In some instances, the seal adheres to a top surface of the first dispersed phase reservoir. In some instances, the seal is broken or removed without contaminating the contents of the first dispersed phase reservoir. In some instances, the seal is resistant to temperatures above about 20° C. to about 40° C. In some instances, the seal is not resistant to temperatures above about 20° C. to about 40° C. In some instances, the seal is transparent. In some instances, the seal is not transparent. In some instances, the seal is opaque. In some instances, a reservoir aspect ratio is chosen such that a material comprising the seal will not contact the surface of the fluid contents of the first dispersed phase reservoir when broken. In some instances, the seal comprises material of sufficient strength such that the seal will not fragment when broken or torn. The seal may comprise an adhesive tape or film. In some instances, the seal comprises a metal with an adhesive on one side of the seal. In some instances, the seal comprises a polymer material. Exemplary polymer materials include, but are not limited to, polyethylene, high density polyethylene, low density polyethylene, polypropylene, or combinations thereof.

Figures as described below illustrate a sampler intake, wherein the sampler intake comprises a sharp, hard tube (the "lance") for breaking through the seal and a sampling tube. In some instances, a knife, a needle, or any pointed device that forms a wedge at the surface of the seal and ruptures the seal is used. The sampling tube may be substantially concentric with the lance and resides inside the lance. The lance assembly may be mounted using a double spring comprising a first spring and a second spring for compliance and a vertical stop. As the lance is actuated toward the seal, the lance may push through the seal until the vertical stop contacts the surface of the staging container (e.g. a microwell plate, or a PCR strip or tube, or an element of a component designed to hold such a plate, PCR strip, or PCR tube). The vertical stop may prevent the lance from moving further, but the first spring allows for the sampling tube to continue traveling outward within the lance. The inlet of the sample tube is actuated until it reaches a position in the contents of the first dispersed phase reservoir. In some instances, the sampling tube continues to move until it contacts a bottom of the first dispersed phase reservoir. In some instances, the second spring allows the sampling tube to continue to move in the direction of first dispersed phase reservoir. In some instances, the second spring allows the sampler intake to self-position in the bottom of the tube. In some instances, the first and second spring provide x-y compliance as well as z-compliance.

The sampling system may prevent contamination of the inner sampling tube by the seal because the sampling tube is substantially contained within the lance as the lance breaks the seal. In some instances, the lance pushes the seal material such that the seal material is prevented from contacting the tube surface. In some instances, the sampling tube is attached to the lance. Once sample has been drawn out of the first dispersed phase reservoir or any dispersed phase reservoir, the sampling tube may be retracted inside the lance and the assembly retracted by reversing the initial steps.

Another such vapor barrier is a layer of fluid comprising a fluid of lower density than the fluid to be sampled. In certain embodiments, this fluid has a lower vapor pressure than the fluid to be sampled, although if a large enough volume of it is used, it can have a similar or higher vapor pressure than the sample fluid. A metric is that the combination of vapor pressure and volume added is such that the entire vapor barrier does not evaporate in the elapsed time before the fluid would be sampled. An advantage of this approach is that the vapor barrier fluid does not need to be pierced or broken by the sampling head; not only does this reduce the possibility of pieces of the vapor barrier seal being incorporated into the fluid being sampled, but it allows the fluid being sampled to "reseal" once the sampling head leaves the well. If the vapor barrier fluid has a higher viscosity than the fluid being sampled and/or a higher affinity for a material comprising the surface of the sampling head than does the fluid being sampled, the vapor barrier can act to "wipe" the sampling head clean of the fluid being sampled, leaving it in the container (e.g. a microtiter plate well). This helps in preventing cross-contamination. In certain embodiments, the vapor barrier fluid is added by the user before placing the sample containers into the area that can be accessed by the sampling head (i.e. in the instrument). In certain embodiments, the instrument is configured to dispense vapor barrier fluid into the sample containers after the user places it into the area that can be accessed by the sampling head. This fluid can be dispensed through the same channel that sample fluid is pulled into the system, or it can be dispensed through at least one separate channel, for example as described above for the system dispensing the dead volume fluid.

In certain embodiments, both a film seal and a vapor barrier fluid are used. In such an embodiment, the contents of a sample container comprise a sample fluid and the sample container is sealed by the film seal. The container is then positioned in the instrument and, at a subsequent time, is pierced by the sampling head. The instrument can then add vapor barrier fluid through a discrete channel. Such an approach eliminates the need for the user to handle the vapor barrier fluid, but reduces the amount of sample fluid that evaporates before the system can add vapor barrier fluid.

In certain embodiments, the vapor barrier fluid and the dead volume fluid are both simultaneously in the sample container (e.g. a well in a microtiter plate). As described above, these can be added by the system or by the user (by hand or by a liquid handling robot), or any combination of these.

This embodiment is referred to here as the "parfait" approach, as the different phases (e.g., sample fluid, dead volume fluid, and vapor barrier fluid) arrange themselves into a vertically striated system with clear phase boundaries. In a parfait, the vapor barrier fluid naturally has the lowest mass density; the mass densities of the sample and the dead volume fluid can be either greater or lower, respectively, from the other (but not the same). In some instances, the dead volume fluid and the vapor barrier fluid have the same composition. Parfait embodiments are described in more detail in the Figure descriptions, below.

Thus, a sampling device may be used for sampling from a well in a sealed plate. The sampling device may comprise a lance, sampling tube, first spring, positive stop, second spring, actuation mechanism, and motor. The sampling device may interface with a sample that is sealed using a seal. The sampling device may be positioned vertically above the sample container. The actuation mechanism may translate rotational motion of the motor into linear vertical motion of the lance, sampling tube first spring, second spring, and positive stop. To sample the contents of the sample container, the motor and actuation mechanism together may begin to move the lance, sampling tube, first spring, second spring, and positive stop toward the outer surface of the seal on the sample container. Upon contact with the seal, the lance may pierce the seal and forces the seal material out of the path of the sampling tube so that the outside of the sampling tube does not contact the portion of the seal material that was not exposed to the interior of the sample container. The motor and actuation mechanism may continue to move the assembly downward until the positive stop contacts a top surface of the sample container or a holder for the sample container. The positive stop may restrict further movement of the lance and first spring. Continued linear actuation of the motor and actuation mechanism may cause the sampling tube to move downward within the lance. The sampling tube may continue to move downward until the actuation mechanism encounters a second stop condition. In some instances, the stop condition is a total elapsed time for motor actuation at a given set of rotational rates. In some instances, the stop condition is a limit switch triggered by the vertical position of a portion of the assembly. In some instances, the limit switch comprises an optical interrupter, a mechanical switch, a magnetic switch, or a combination thereof. In some instances, the stop condition is an increase in motor current caused by an increase in resistance to motion caused by the sampling tube contacting the bottom of the sample container. In some instances, the motor is a stepper motor or a servo motor. In some instances, the stop condition is the achievement of a minimum number of steps. In some instances, the stop condition is set such that the vertical position of the assembly and the bottom of the sample container will interfere so as to ensure that the sampling tube is at the bottom of the sample container. In some instances, a negative pressure is created in a downstream portion of the sample tube so that a volume of fluid is pulled from the sample container into the sampling tube. In some instances, negative pressure is generated using a pump. In some instances, negative pressure is generated using a peristaltic pump.

The second spring for use in sampling devices as described herein may provide compliance. In some instances, compliance allows for no significant impact to the motor or actuation mechanism if the stop condition is encountered after the vertical positions of the sampling tube and the bottom of the sample container. In some instances, the second spring allows for flexible vertical or horizontal positioning.

Dispensing

In embodiments where at least one of the vapor barrier fluid and the dead volume fluid may be added by the instrument, the sampling head may carry elements that allow for this dispensing. In certain embodiments, the intake channel itself allows for dispensing of the vapor barrier fluid, the dead volume fluid, or both. As an example, the sampling system may comprise the intake channel, the injector, a reversible pump, a selector valve, a waste channel, and a reservoir of either dead volume fluid or vapor barrier fluid. When dispensing fluid, the selector valve is positioned so as to connect the reservoir through the injector to the intake channel. The pump provides motive force so as to dispense fluid from the reservoir through the inlet end of the intake channel (effectively making it an outlet). When sampling, the selector valve is positioned so as to connect the intake channel through the injector to the waste channel. When sampling, the pump provides motive force to pull fluid from the sample container through the inlet of the intake channel, through the injector, and to waste. In certain embodiments, the pump is a peristaltic pump and is inline with the injector and sampling valve. In another embodiment, the system further comprises a syringe pump, a service loop, and a second selector valve, and dispensing or injecting first involves pulling fluid into the service loop of the syringe pump, followed by pushing fluid out of the service loop of the syringe pump. In further embodiments, the system comprises yet another selector valve and a second reservoir of fluid (whichever fluid was not already included).

In certain embodiments, the dispensing channel is distinct from the intake channel. In certain embodiments, this channel is physically attached to the intake channel, so that positioning the intake channel of the injector effectively positions the dispensing channel. Doing so saves the need for an independent positioning mechanism. In certain embodiments, the dispensing channel has its own mechanism for positioning. In embodiments where the dispensing channel is distinct, dispensing of the fluid can be achieved by any suitable method. In certain embodiments, the system comprises a pump, the dispensing channel, and a reservoir of either dead volume fluid or vapor barrier fluid. Dispensing is achieved by actuating the pump to drive fluid through the outlet of the dispensing channel. In certain embodiments, the system comprises a selector valve and a second reservoir, and selection of fluids can be achieved by positioning the selector valve to connect one of the reservoirs to the outlet of the dispensing channel. Any suitable pump may be used, such as a peristaltic pump, diaphragm pump, syringe pump, and the like. In certain embodiments, the pump is a diaphragm pump. In certain embodiments, the pump is a syringe pump and the system comprises a second selector valve and a service loop, where fluid is first pulled into the service loop before dispensing it via the syringe pump.

In some embodiments, the sample container is not sealed before fluids are dispensed by the system into it. In other embodiments, there is a seal on the sample container, and the system first breaks the seal before dispensing fluids into the system.

Tips

The systems and methods of bringing sample into the system can be important. The inlet region of the intake channel of the sample head must be able to reliably convey sample fluid, dead volume fluid, or potentially vapor barrier fluid into the system, and/or other fluid. Because the system comprises microfluidic channels, it is important that particulate matter that could partially or completely obstruct microfluidic channels be rejected from the intake channel. It is not always possible to control the composition of the fluids to be drawn into the intake channel (especially in the case of sample fluid, which is provided by a user), and so systems and methods to prevent intake of problematic particulate matter are important. Additionally, in systems that have film-based seals over the sample container, methods to puncture or pierce that seal without contaminating the sample or introducing problematic particulate matter can be provided. Finally, the materials of construction of the elements of the sampling head that come into contact with the working fluids of the system can be such that they do not promote (and preferably, they hinder) cross-contamination in the system.

In certain embodiments, the inlet portion of the intake channel is simply a tube. Any suitable material of construction can be used. Exemplary materials of construction include polymers, fluoropolymers, glass, stainless steel, carbon steel, aluminum, titanium, or a combination thereof, or other suitable materials. In the case that a material of the tube comprises a material that has a substantial affinity for the fluid to be sampled or contaminating material such as detectable (or potentially detectable) material, the tube can have a coating or lining that comprises a material that does not have a substantial affinity for aqueous phase or contaminating material such as detectable (or potentially detectable) materials. In certain embodiments the surface comprises a material that has a greater affinity for hydrophobic or fluorophilic substances. In an example, the coating is a fluoropolymer. Rejection of problematic particulate material can be achieved by choosing a major channel dimension that is smaller than the smallest representative dimension of the particulate material to be rejected. For example, if the tube has a circular cross section, its diameter should be chosen so that it is smaller than a representative diameter of the particulate matter to be rejected. Such a tube can have a circular, oval, square, or any other suitable cross section. In an example, the tube is a continuous fluoropolymer tube that changes diameter between the inlet region and the injector so that particulate rejection can be achieved but flow is not overly restricted. Representative diameters in the inlet region are typically in the range 40 microns to 200 microns and in the region beyond the inlet region are typically in the range 50 microns to 5 mm. In another example, the tube is the interior of a stiff metal or polymer needle. The needle surfaces can be coated with a polymer, fluoropolymer or the like to prevent adherence of aqueous phase or detectable (or potentially detectable) material. The needle diameter may vary across its length, but at the inlet end it should be small enough to reject unwanted particulate matter. In some examples, the inlet end diameter ranges between 40 microns and 110 microns. In certain embodiments, the needle is removable and replaceable, so that should it become clogged, it can be replaced without replacing the system.

In certain embodiments, the inlet end of the intake channel comprises a micromachined channel, a representative dimension of which is small enough that the smallest unwanted particulate material cannot pass into the intake channel. In an example, the micromachined channel comprises a hole in a substrate, and the substrate can be connected to a tube or channel comprising the proximate portion of the intake channel. In examples, the substrate may be disconnected and replaced to allow for maintenance (e.g. if the micromachined channel becomes fouled or contaminated). The micromachined channel can be made of any suitable material, e.g., the same materials as described for the tube above. Micromachining may be done by any suitable operation, including drilling, milling, and/or laser drilling. In certain embodiments, the inlet end of the intake channel may be formed by a method comprising heating a polymer tube, applying a tensile force to the tube so as to reduce the cross-sectional area of the tube in a region, and cutting a tube in the region to form the inlet end of the intake channel. In certain embodiments, the inlet end of the intake channel may be formed by a method comprising inserting a mandrel of a desired cross-sectional area or profile into the internal volume of a polymer tube, applying a compressive force to the polymer tube so as to reduce the cross-sectional area of the tube in a region around the mandrel to that of (or nearly of) the mandrel, and cutting the tube in the region. In certain embodiments, the method additionally comprises heating the tube.

In certain embodiments, the inlet end of the intake channel comprises a bundle of tubes meeting at a common junction. Each of the tubes in the bundle has a characteristic dimension, e.g., diameter that is smaller than a characteristic dimension, e.g., diameter, required to reject problematic particulate material from the system. Beyond the junction, the intake channel of the instrument comprises the common channel that joins all the tubes in the bundle.

Thus, in some instances systems and methods of the invention provide a filter. The filter may be used to remove particulate matter that may block a flow in the injection device, droplet generator, microfluidic channel, PCR reactor, or detection device. In some instances, particulate matter is a result of variation in a composition of biological samples, incomplete digestion and/or lysis of cellular components during sample preparation, introduction of foreign material due to user error or laboratory environmental conditions, variances in manufacturing tolerances, and/or cleanliness, in the individual components comprising the sampling device, or any other source. In some instances, the filter comprises a single channel of a first dimension of lower value than a second dimension of the particulate matter. The first dimension may be of a dimension such that particulate matter comprising the second dimension is prevented from being blocked by the filter. In some instances, the first dimension is a hydraulic diameter, a cross-sectional area, or a circular diameter. In some instances, the second dimension is a Feret's Diameter, a Martin's diameter, an aspect ratio, projected area diameter, or dynamic diameter.

In some instances, the single channel comprises a polymer tube. In some instances, the polymer tube comprises a portion of its length where a tube diameter has been constricted. For example, the tube diameter is constricted by applying a tensile force along the tube. In some instances, the tube diameter is constricted by heating the tube and applying a tensile force along the tube. In some instances, a ratio of the smallest tube diameter to the bulk tube diameter is at least or about 0.2:1, 0.25:1, 0.5:1, 0.7:1 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, 5:1, 5.25:1, 5.5:1, 5.75:1, or 6:1. The ratio of the smallest tube diameter to the bulk tube diameter is a ratio as to prevent pinching or mechanical failure of the tube. In some instances, a ratio of the tube length in the constricted section to the total tube length is at least or about 0.2:1, 0.25:1, 0.5:1, 0.7:1 0.75:1, 1:1, 1.25:1, 1.5:1, 1.75:1, 2:1, 2.25:1, 2.5:1, 2.75:1, 3:1, 3.25:1, 3.5:1, 3.75:1, 4:1, 4.25:1, 4.5:1, 4.75:1, 5:1, 5.25:1, 5.5:1, 5.75:1, or 6:1.

The single channel may comprise one or more tubes of varying sizes. For example, the single channel may comprise a tube of a first size measure having a restriction comprising a second, smaller size measure placed at some point along the tube. In some instances, the first size is a hydraulic or circular diameter. In some instances, the second size measure is a hydraulic or circular diameter. The restriction may be held in the system by a housing. In some instances, a volume of fluid in the housing prevents fluid holdup. In some instances, a shape of the restriction is rectangular, tubular, oblong, circular, round, oval. In some instances, a shape of the restriction is circular. In some instances, a shape of the restriction is rectangular.

Thus, in some instances, a filter is used in the systems and methods as described herein. In such an arrangement, a cross-sectional area of the polymer input tubing is reduced such that the cross-sectional area is smaller than particulate matter that is blocked from entering. In some instances, the cross-sectional area of the input tubing, e.g., polymer input tubing is at least or about 1 to 100 um. In some instances, a microfluidic chip with a channel that has a reduced cross-sectional area is used. The channel of the microfluidic chip may be constructed by passing the channel through a constriction with an increase gain in size. In some instances, such a construction results in a filter that is compact and easy to place in-line.

In some instances, multiple channels are used to restrict particulate matter from entering. The multiple channels may comprise a first dimension smaller than a second dimension of the particulate matter. In some instances, the first dimension blocks particulate matter. In some instances, the first dimension allows fluid to pass. In some instances, a filter comprising porous material having pores of a first dimension is used to allow fluid to pass but block particulate matter. In some instances, a sampling tube is a lumen designed to reject particulate matter before it enters the system. In some instances, a chip-based system where a central channel branches to multiple channels for restricting particulate matter that then rejoin a main channel is used.

In certain embodiments, the inlet end of the intake channel has sufficient stiffness to pierce a film seal, as described above. In operation, the inlet end of the intake channel is positioned over the seal, force is applied to push the tip through the seal, and the tip then continues to travel into the sample. In some embodiments, the tip stops moving after piercing the seal, and then dispenses a fluid, such as a dead volume fluid, vapor barrier fluid, or both, into the sample container (e.g. a well in a microtiter plate). In certain embodiments, the sampling head comprises a separate device for piercing a film seal. Any suitable device may be used, such as a needle, a lancet, a lance, or any other appropriate means for piercing a seal.

Injector positioning. For a variety of reasons, it can be important to know to some practical extent the composition of the materials in the injector chamber, i.e., common conduit. First, it is desired to maximize the amount of sample that enters the process system. If the sample is not fully in the common conduit, then some amount of sample will be rejected when the injector is positioned to inject the sample, e.g., when the injector rotates. Second, it is important to prevent air from entering the process system. At the conditions of operation of the process system, air is a compressible gas. It may expand and/or contract in a reactor that employs heating or cooling, e.g., a thermal cycler, which causes periodicity in flow in the system, which affects, e.g., PCR timing. Additionally, it provides fluidic capacitance, which affects partition generation.

Thus, it is advantageous to be able to determine when 1) sample is in the injector chamber (common conduit) and/or 2) when air may be in the injector chamber (common conduit). Various systems and methods to achieve these objectives are described here. One set of ways to determine whether sample is in the injector is to use optical properties of the fluids in the injection system to determine which fluids are being added. In certain embodiments, at least one optical property of the sample fluid is sufficiently different from the at least one optical property of the dead volume fluid and/or vapor barrier fluid that, in quantifying the optical property, the sample fluid may be distinguished from the other fluids in the system. A detector capable of quantifying the optical property may be placed at a first distance upstream of the injector, and the optical property may be measured at this point. The volume of the intake channel between the injector chamber (common conduit) and the measurement point is a known function of the first distance, and the volume of the intake chamber (common conduit) is known. At the point in time that sample fluid is first indicated by a change in the measurement of the optical property, the system may draw a specific additional volume into the system related to the sum of the volume of the injector chamber (common conduit) and the volume of intake channel between the measurement point and the injector chamber (common conduit). In the case that the sample is of a smaller volume than the injector chamber (common conduit) and the user desires to contain the entire sample in the injector chamber (common conduit), this volume will be at least as large as the sum of the volume of the sample fluid and the volume of the intake line between the measurement point and the injector chamber (common conduit). In the case that the user desires to inject only sample fluid into the process side of the system and the volume of the sample fluid is larger than the volume of the injector chamber (common conduit), the drawn volume will be at least as large as the sum of the volumes of the injector chamber (common conduit) and the intake channel between the measurement point and the injector chamber (common conduit). In the case that the user wishes to avoid the injection of a fluid upstream ("trailing") of the sample fluid, the drawn volume will be less than the sum of the volumes of the sample fluid and the intake channel between the measurement point and the injector chamber (common conduit).

In certain embodiments, the optical property of the fluids is a refractive index and the change in fluids is detected by a change in the exit angle of a electromagnetic radiation source passing through the intake channel. Any suitable electromagnetic radiation source may be used, such as a light-emitting diode (LED), a laser, an incandescent light, or any combination thereof. In certain embodiments, the optical property is an absorbance or a scattering albedo in a wavelength range and the change in fluids is detected by the change in the intensity of electromagnetic radiation absorbed or scattered from the sample fluid (the electromagnetic radiation could either be detected in a transmissive or reflective setup). In certain embodiments, the wavelength range is in the infrared spectrum.

In certain embodiments, at least one of the fluids comprises a component that emits electromagnetic radiation in a first wavelength range when excited by a electromagnetic radiation source in a second wavelength range. In this case, the detector comprises a electromagnetic radiation source and a photodetection element. Changes in the emitted intensity of electromagnetic radiation from the intake channel, when excited, indicate changes in the fluids passing through the sample. In an example, the sample fluid comprises at least one excitable component (these could be the same or different as the fluorescent molecules used to detect PCR products), and the dead volume fluid or vapor barrier fluid do not comprise the at least one excitable component. When the intensity of electromagnetic radiation detected in the wavelength range of emission for the at least one excitable component increases above a minimum value, the presence of the sample fluid in the intake channel at the point of measurement is established. Likewise, when the intensity of electromagnetic radiation decreases below the minimum value, the absence of the sample fluid in the intake channel at the point of measurement is established. In other examples, the at least one excitable molecule may be in the dead volume fluid or in the vapor barrier fluid (or both), and the absence of an intensity above the minimum value indicates presence of the fluids (preferably the sample fluid) that do not contain the at least one excitable component. In an embodiment, the at least one excitable component comprises a fluorescent molecule, e.g., as described herein. In another embodiment, at least one excitable component comprises a phosphor or a quantum dot.

In certain embodiments, more than one of the fluids contain at least one excitable component, for example at least one pair of excitable components whose emissive wavelength ranges do not substantially overlap. In this embodiment, specific fluids in the system may be identified by the wavelength of electromagnetic radiation emitted by the fluid under irradiation by at least one electromagnetic radiation source. This is especially valuable if the volume of sample in the sample container is unknown, as the start and end of a sample may be demarcated as it passes by the measurement point by measuring the electromagnetic radiation intensity at the relevant wavelengths. An example of this in a PCR system is to put an oil soluble dye into the vapor barrier fluid, or whatever fluid is trailing the sample fluid, and using a water soluble dye (or the PCR probes themselves) in the sample fluid to detect the sample. A minimum intensity at a first wavelength is detected, indicating the start of a sample, and a minimum intensity at a second wavelength is detected, indicating the start of the trailing fluid.

In certain embodiments, more than one of the fluids contain at least one excitable component, where at least one first fluid contains at least one excitable component with an emissive wavelength range that substantially overlaps with the emissive wavelength range of at least one excitable component in at least one second fluid. In this embodiment, specific fluids in the system may be identified by the intensity of the signal at the emissive wavelength range of the component(s) with common emissive wavelength ranges. For this to be successful, the quantified emitted intensity from each fluid for a given excitation intensity should be different so that the two fluids may be distinguished.

Examples of methods to accept a variable volume of sample into the injector and/or to detect/prevent injection of air into the system follows. In a first example, there is only sample fluid in the sample fluid container. Prior to sample fluid intake, the intake channel between the inlet end of the intake channel and the outlet of the injector channel does not contain sample fluid (it may contain dead volume fluid, vapor barrier fluid, air, or anything else). A pump on the intake channel draws sample fluid from the sample fluid container into the intake fluid channel until the detector measures a value sufficient to indicate the front edge of the sample fluid. A controller directs the pump to continue to draw sample fluid into the system until the front edge of the sample fluid is a known volume beyond the outlet of the injector chamber (common conduit). If the controller has not detected a change in the quantity of the optical property sufficient to indicate a change from the sample fluid to air at the measurement point, the sample fluid may be injected. If the controller has detected a change in the quantity of the optical property sufficient to indicate a change from the sample fluid to air at the measurement point but the volume of fluid drawn into the system after that point in time is less than the volume of the intake channel between the measurement point and the injector channel plus the known volume beyond the injector channel the sample was drawn to, the sample may be injected without injecting air. If the controller has detected a change in the quantity of the optical property sufficient to indicate a change from the sample fluid to air at the measurement point and the volume of fluid drawn into the system after that point in time is greater than or equal to the volume of the intake channel between the measurement point and the injector channel, then the sample fluid drawn was of insufficient volume to fill the injector chamber (common conduit) and the sample fluid can be rejected without injecting it into the process side of the system, thus preventing, e.g., entry of air into the process side.

In a second example, there is both sample fluid and dead volume fluid in the sample container, and the sample fluid has a lower mass density than the dead volume fluid. The inlet of the intake channel is positioned so that it is substantially in the dead volume fluid, and the pump is actuated so that dead volume fluid begins to fill the intake channel. When the level of the fluid in the sample container decreases so that the interface between the sample fluid and the dead volume fluid is at the same height as the inlet of the intake channel, sample fluid will begin to follow the dead volume fluid into the intake channel. When the detector measures a change in a quantifiable property (e.g., in a electromagnetic radiation intensity) that indicates an interface between the dead volume fluid and the sample fluid, the pump then continues to draw a volume of fluid equal to the sum of the volume of the intake channel between the detector and the injector, the internal volume of the injector chamber (common conduit), and any desired overfill of the injector. If the detector has not subsequently indicated a phase interface between the sample fluid and either air or dead volume fluid, or if the detector has subsequently indicated a phase interface between the sample fluid and either air or the dead volume fluid but the additional volume drawn into the intake channel after this detection of a phase interface is less than the volume of the intake channel between the detector and the injector inlet, then no air has been included in the injector chamber (common conduit) and the sample may be injected into the process side of the system. Otherwise, the sample can be rejected.

In a third example, there is sample fluid, dead volume fluid, and a third immiscible fluid (which may be a vapor barrier fluid or may simply be a fluid designed to separate aliquots of sample injected into the process side of the system, e.g., spacer fluid) in the sample container. The inlet end of the intake channel is positioned so that it is in or substantially in the dead volume fluid. The pump is then actuated, causing dead volume fluid to be drawn into the intake channel. When the level of the fluid in the sample container decreases so that the interface between the sample fluid and the dead volume fluid is at the same height as the inlet of the intake channel, sample fluid will begin to follow the dead volume fluid into the intake channel. Once the sample fluid is completely drawn into the system, the third immiscible fluid begins to be drawn into the system. Similar to above, once the detector registers an interface between the sample fluid and the dead volume fluid, the pump continues to draw fluid into the system. If a second phase interface is not detected before the injector chamber (common conduit) is completely filled with fluid, then the injector can inject the sample into the system, and the injection will solely be sample. If a second phase interface is detected before the injector chamber (common conduit) is completely filled with fluid, the pump can continue to draw fluid in a quantity equal to the volume of the intake channel between the detector and the inlet of the injector. In this way, the intake channel will be filled with a mixture of sample fluid and the third immiscible fluid.

Cleaning Stations and Routines An important aspect of certain embodiments of systems and methods provided herein is the ability to use the intake channel for multiple sample injections without cross-contaminating the process side of the system. This allows for the use of higher quality components (e.g. tighter tolerances, machined, not injection molded, etc.) in the systems, because the cost of those components will be amortized over many sample fluid injections, as well as removing the requirement that a removable or disposable consumable element be incorporated into the system, which may produce poorer results due to the requirement that a user make/break connections (which can lead to channel misalignment, sharp interfaces, or air bubbles, all of which can impact droplet formation and stability) and that the disposable be low-cost (which leads to lower tolerance requirements, impacting quality and consistency of droplet formation). Multiple aspects provided herein aid in preventing cross-contamination. One such set of aspects are systems and methods for cleaning the intake side of the system between injections into the process side of the system.

In some embodiments, the surfaces of the channels in the intake system comprise materials that have a higher affinity for a cleaning fluid than for the sample fluid, allowing the cleaning fluid to displace the sample fluid when the cleaning fluid flows through the intake channel. "Cleaning fluid," as that term is used herein, includes any fluid that is moved through an intake system, e.g., an intake system including an injector, to remove and/or render inactive any sample or other contaminant in an intake pathway; exemplary cleaning fluids include purge fluids and denaturing fluids, as well as, in some cases, dead volume fluids and/or vapor barrier fluids, as well as any other fluids that can move through the intake side, e.g., without being moved into the process side, as described herein. By substantially displacing all of the sample fluid in at least the injector chamber (common conduit), and, in some cases, the entire intake channel, the cleaning fluid may prevent injection of sample fluid from previous samples when working with new sample fluid. In some embodiments, multiple cleaning fluids are used. The cleaning fluids may be immiscible with the sample fluid or miscible with the sample fluid, but in general, at least one of the cleaning fluids is immiscible with the sample fluid.

Systems and methods are described here to introduce the at least one cleaning fluid into the intake channel. In certain embodiments, the at least one cleaning fluid is supplied in a separate container from the sample container. In order to access the cleaning fluid, the inlet end of the intake channel is positioned so that it is substantially in the cleaning fluid in the at least one cleaning fluid container and a pump is actuated so that the cleaning fluid is drawn into the intake channel. In embodiments where there are multiple cleaning fluids, each cleaning fluid may be supplied in a separate cleaning fluid container, and the cleaning fluids are sequentially drawn into the system by positioning the inlet end of the intake channel so that it is substantially in each of the cleaning fluids in the order in which cleaning fluids are to be drawn into the system and the pump actuated for a given volume or time in each cleaning fluid. In some embodiments, air may be drawn into the intake channel by the (at least one) pump in between at least one of the cleaning fluids and the sample fluid or between at least two of the individual cleaning fluids. In a further embodiment, air is added between all of the fluid aspirations into the system. Air may be accessed by positioning the inlet end of the intake channel so that it is no longer substantially within a liquid volume.

The cleaning fluid containers may take any suitable form. In certain embodiments, at least one of the cleaning fluid containers is a disposable container. For example, at least one of the cleaning fluid containers could be a well of a microtiter plate, a PCR tube, a strip of PCR tubes, a conical-bottom tube, an injection molded polymer container meant to be disposed of after a set number of uses, or the like. In this embodiment, at least one of the cleaning fluid containers may be initially sealed by a polymer or metal film or closed by a cap to make it easier to supply to end users. In the case that it is sealed by a film, the system will have the capability of breaking the film (as described above).

In certain embodiments, at least one of the cleaning fluid containers is a fixed reservoir on the instrument over which the inlet end of the intake channel may be positioned. As an example, at least one cleaning fluid container may be an open tray filled with the cleaning fluid. As another example the cleaning fluid container may be a partially closed container with an access port for the inlet end of the intake channel. The access port may have a door or reversible seal to close off the cleaning fluid container when the inlet end of the intake channel is not positioned inside. In an example, the door may simply be mounted on a spring-loaded hinge that may be pushed open by the sampling head (comprised of the inlet end of the intake channel) and that would automatically close as the sampling head disengages. In another example, the door can be a spring loaded poppet or similar device that opens when depressed by the sampling head, but closes when the sampling head is withdrawn.

Cleaning fluid may be provided to the cleaning fluid containers in a variety of ways. In certain embodiments, the user manually adds a volume of cleaning fluid to the cleaning fluid reservoir sufficient to process at least one sample fluid volume in the system prior to operating the system. In certain embodiments, at least one cleaning fluid container is supplied with cleaning fluid through a cleaning fluid supply channel from a cleaning fluid reservoir that may be filled or interchanged by the user. In certain embodiments, the cleaning fluid flows from the cleaning fluid reservoir into the cleaning fluid container by gravity. In one example, the cleaning fluid reservoir is completely emptied upon loading by gravity into the cleaning fluid container (in this example, the cleaning fluid reservoir provides a convenient means for loading the cleaning fluid container). In another example, the cleaning fluid container has a smaller operating volume than the operating volume of the cleaning fluid reservoir and the system comprises a mechanism to control dispensing of cleaning fluids into the cleaning fluid reservoir. As one example, the cleaning fluid reservoir may be closed to the ambient atmosphere and of fixed overall volume so that, as the cleaning reservoir empties of fluid, the level of fluid in the cleaning fluid container is controlled by a balance of ambient atmospheric pressure on the surface of the cleaning fluid in the cleaning fluid container and the sum hydrostatic head of the cleaning fluid in the cleaning fluid reservoir and any air pressure in the cleaning fluid reservoir. In another example, a valve controls dispensing of the cleaning fluid from the cleaning fluid reservoir into the cleaning fluid container. This valve can be controlled by a controller on the system, opening the valve after at least one cleaning fluid intake cycles so as to dispense a set volume of fluid into the cleaning fluid reservoir. This set volume of fluid can be measured in any suitable manner, e.g., by the hydrostatic pressure in the cleaning fluid container or a level sensor in the cleaning fluid container, such as a float valve, capacitance level, or the like, by opening the valve for a set amount of time correlated to a calibrated flow rate in the channel connecting the cleaning fluid reservoir to the cleaning fluid container, by measuring a flow rate in the channel connecting the cleaning fluid reservoir to the cleaning fluid container and integrating that flow rate over time so as to determine when the set volume as been dispensed, by measuring a change in level in the cleaning fluid reservoir indicating when a set volume has been dispensed, or any other suitable manner. In another example, the valve system is constructed so as to only allow a set volume of fluid into the cleaning fluid container each time the valve is actuated. In this example, each time the valve is actuated, a priming chamber is filled with cleaning fluid. On the subsequent actuation, the priming chamber is dispensed into the cleaning fluid container.

In certain embodiments, the cleaning fluid is contained in the sample container. Due to differences in mass density and miscibility, the cleaning fluid forms a separate layer in the fluid "parfait" and may be loaded into the intake channel by changing the level of the inlet end of the intake channel so that it is substantially in the cleaning fluid layer, by drawing fluid into the inlet end of the intake channel so that the level of the interface of the cleaning fluid with the fluid into which the inlet end of the intake channel was originally positioned falls to be a level with the inlet end of the intake channel, or both. In certain embodiments, a cleaning fluid is also the dead volume fluid, the vapor barrier fluid, or both. Cleaning fluids may be added to the system in this approach in the same way as for the "parfait" approaches described above.

In certain embodiments, at least one cleaning fluid container comprises at least one cleaning fluid supply line and one cleaning fluid drain. At least one cleaning fluid is supplied through the at least one cleaning fluid supply line (they may have separate or common supply lines) into the cleaning fluid container. Cleaning fluid may be added to the inlet end of the intake channel in all the methods and sequences described above, or any other suitable method and sequence. Upon completion, the cleaning fluid may be drained out of the at least one drain line (the drain can go to an onboard waste container, an external waste storage container, or an external waste drain). In certain embodiments, a valve controls when the drain is open. In certain embodiments, the drain line comprises a pump for actively moving waste from the cleaning fluid container to its final destination.

In certain embodiment, the at least one cleaning fluid line is positioned so that a jet of fluid exits at least one cleaning fluid line and impinges on the intake channel so that it may wash or substantially wash any contaminating material, such as detectable or potentially detectable components, off of the intake channel and into the cleaning fluid reservoir. In certain embodiments, the at least one cleaning fluid line is positioned so that the outlet of the fluid line is submerged in the cleaning fluid in the cleaning fluid container, and driving at least one of the cleaning fluids through the cleaning fluid line induces vorticity in the fluid in the cleaning fluid container that aids in washing contaminating material, such as detectable or potentially detectable material off of the intake channel.

In certain embodiments, cleaning fluid is provided to the system through the intake channel by employing reverse flow. In these embodiments, the intake channel comprises, e.g., an inlet end, an injector, a pump, a selector valve, and a supply of at least one cleaning fluid. After injection of an aliquot of sample fluid in the injector and re-positioning the injector so that the injector chamber (common conduit) that contained the aliquot of sample fluid is once again realigned with the intake channel, the selector valve is positioned so that the supply of at least one cleaning fluid, the pump, the injector, and the inlet end of the intake channel are all aligned. A force is generated by the pump to drive flow of cleaning fluid from the cleaning fluid container, through the injector, and out the inlet end of the intake channel. In certain embodiments, at least one cleaning fluid has a higher affinity for a surface material of the intake channel than the sample fluid, so the cleaning fluid displaces the sample fluid from the intake channel and drives all or substantially all of the sample fluid out of the inlet end of the intake channel. The cleaning fluid may be driven into any of the cleaning fluid containers described above.

Figure 5A:
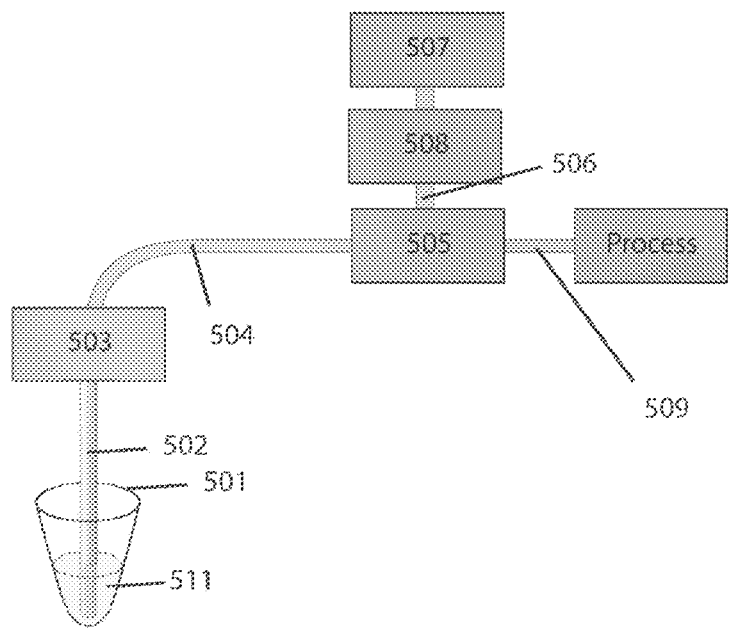
"
FIGS. 5A and 5B shows a system for cleaning an intake conduit.
Figure 5B:
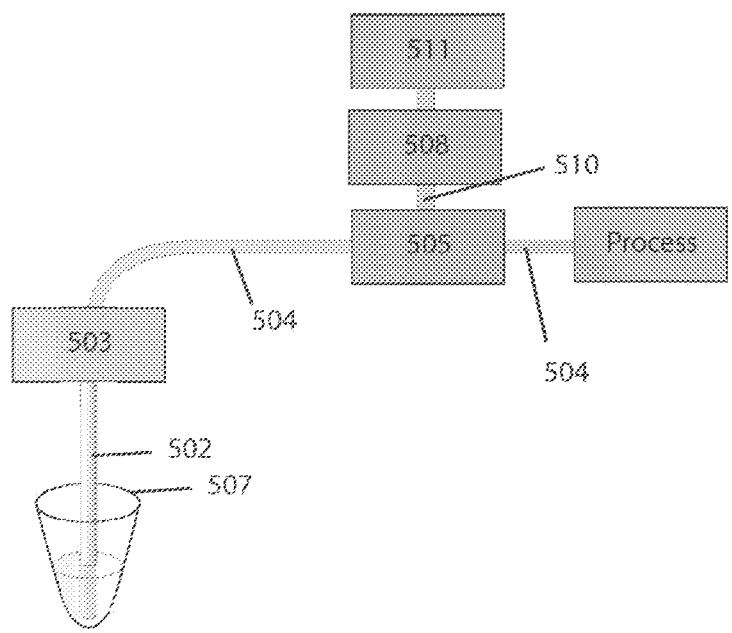

FIGS. 5A and 5B—System for cleaning an intake conduit FIG. 5 shows a system for cleaning an intake conduit. The system comprises at least one cleaning fluid container 501, an aspiration conduit 502 (also referred to as an "intake conduit," "intake line," and similar wording, herein), and a sampler assembly 503. The cleaning fluid container comprises at least one cleaning fluid. In certain embodiments, at least one of the cleaning fluids has a higher affinity for the surface of the aspiration conduit 502 than do dispersed phases in the system, allowing it to displace dispersed phases within in the aspiration conduit 502. In certain embodiments, the at least one cleaning fluid comprises an oil and the surface of the aspiration conduit 502 comprises a hydrophobic material. In certain embodiments, the at least one cleaning fluid comprises water and the surface of the aspiration conduit 502 comprises a hydrophilic material. In certain embodiments, the cleaning fluid comprises a fluorinated oil and the surface of aspiration conduit 502 comprises a fluorinated polymer. In certain embodiments, at least one of the cleaning fluids comprises a denaturing fluid, such as a denaturing fluid comprising water and a component capable of rendering a detectable or potentially detectable component undetectable. In certain embodiments, the detectable component is a nucleic acid and the denaturing component comprises any suitable denaturing fluid as described herein for nucleic acids. In certain embodiments, at least one of the cleaning fluids comprises a dilution fluid to reduce the concentration of detectable or potentially detectable component. A "dilution fluid" is a purge fluid that is miscible with at least one dispersed phase fluid. In certain embodiments, the dilution fluid comprises water. In certain embodiments, the dilution fluid comprises an oil. In certain embodiments, the cleaning fluid comprises a separation (spacer) fluid that is immiscible with at least one continuous phase and at least one dispersed phase. The separation fluid separates volumes of at least one dispersed phase fluid from each other when dispersed in the at least one continuous phase fluid. In certain embodiments, the aspiration conduit 502 comprises a tube. In certain embodiments, the aspiration conduit comprises a polymer tube, such as a fluoropolymer tube. The cleaning fluid container may be any suitable container. In certain embodiments, the at least one cleaning fluid container 501 comprises a well of a microtiter plate, a test tube, a well, a cuvette, or a tray.

The sampler assembly positions the aspiration conduit 502 into the cleaning fluid container 501. In certain embodiments, this positioning comprises moving the aspiration conduit 502 down or up into the cleaning fluid container 501. In certain embodiments, this positioning comprises moving the cleaning fluid container 501 down or up into the sample container. In some embodiments, this positioning comprises moving the aspiration conduit 502 in a plane normal or substantially normal to the central axis of the aspiration conduit 502 so as to position it to allow it to enter the cleaning fluid container 501. In some embodiments, this positioning comprises moving the cleaning fluid container 501 in a plane normal or substantially normal to the central axis of the aspiration conduit so as it position the cleaning fluid container 501 to allow the aspiration conduit 502 to enter the cleaning fluid container.

The system additionally comprises an injection conduit 504, an injector/valve assembly 505, a waste conduit 506, a waste 507, a motive force source 508, and an analysis conduit 509. The injection conduit 504 is in fluid communication with the aspiration conduit 502 and with the injector/valve assembly 505. The injector/valve assembly comprises a conduit that may exist in at least two states. In a first state, the conduit is in fluid communication with the injection conduit 504 and the waste conduit 506. In a second state, the conduit is in fluid communication with the analysis conduit 509. The conduit is in at most one of these states at any time.

In certain embodiments, such as shown in FIG. 5A, a method for cleaning the system to avoid cross-contamination between volumes of at least one dispersed phase comprises positioning the aspiration conduit 502 in the cleaning fluid container 501 such that the inlet of the aspiration conduit 502 is submerged in the cleaning fluid. The injector/valve assembly conduit is positioned such that the injection conduit 504 and the waste conduit 506 are in fluid communication. The motive force source 508 is actuated so as to create a suction to draw cleaning solution into the aspiration conduit 502 through the injector conduit 504 to the waste conduit 506 and into the waste container 507. In certain embodiments, at least one cleaning fluid has a higher affinity for a material comprising the internal surfaces of the aspiration conduit 502, the injector conduit 504, and the injector/valve assembly 505 than for any dispersed phase in the system, allowing the at least one cleaning fluid to displace dispersed phase from the surfaces of the conduits and into the waste container 507. In some embodiments, a plurality of cleaning solutions and/or cleaning solution containers is used, where the final cleaning solution aspirated in the method has a higher affinity for a material comprising the internal surfaces of the aspiration conduit 502, the injector conduit 504, and the injector/valve assembly 505 so as to displace dispersed phase from the surfaces of the conduits and into the waste container 507 and avoid cross contamination. The motive force source 508 may be positioned at any point in the system so as to create a suction in the aspiration conduit 502. In some embodiments, the motive force source 508 is positioned between the injector/valve assembly 505 and the waste container 507 so that the wetted surfaces of the motive force source 508 do not contact fluid that would enter the analysis conduit 509 when the injector/valve is positioned so as to place its conduit in fluid communication with the analysis conduit 509. In some embodiments, the motive force source 508 is a pump. In further embodiments, the pump is a peristaltic pump, a diaphragm pump, a centrifugal pump, a syringe pump, a positive displacement pump, or a reciprocating pump.

In certain embodiments, such as shown in FIG. 5B, the system comprises a purge/clean conduit 510 and at least one purge/clean fluid reservoir 511. The injector/valve assembly 505 comprises a conduit that may exist in at least two states. In a first state, the conduit is in fluid communication with the injection conduit 504 and the purge/clean conduit 510. In a second state, the conduit is in fluid communication with the analysis conduit 509. The conduit may be in at most one state at any time.

A method for cleaning the system so that volumes of at least one dispersed phase are not cross-contaminated comprises positioning the aspiration conduit 502 with the autosampler assembly 503 so that fluid leaving the aspiration conduit will deposit in the cleaning fluid container 507, positioning the injector/valve assembly conduit such that the injection conduit 504 is in fluid communication with the purge/clean conduit 510, actuating the motive force source 508 so as to drive fluid from the purge/clean reservoir 511 through the purge/clean conduit 510, the injector/valve assembly conduit 504, the aspiration conduit 502, and into the cleaning fluid container 507. In some embodiments, at least one cleaning fluid has a higher affinity for a material comprising the internal surfaces of the aspiration conduit 502, the injector conduit 504, the injector/valve assembly 505, and the purge/clean conduit 510 than for any dispersed phase, allowing the at least one cleaning fluid to displace dispersed phase from the surfaces of the conduits and into the at least one cleaning fluid container 507. In certain embodiments, a plurality of cleaning solutions and/or cleaning solution containers is used, where the final cleaning solution aspirated in the method has a higher affinity for a material comprising the internal surfaces of the aspiration conduit 502, the injector conduit 504, the injector/valve assembly 505, and the purge/clean conduit 510 so as to displace dispersed phase from the surfaces of the conduits and into the cleaning fluid container 507 and avoid cross contamination between volumes of the at least one dispersed phase.

In certain embodiments, the cleaning fluid container 507 comprises a drain such that cleaning fluids deposited in the cleaning fluid container 507 through the aspiration conduit 502 may periodically or continuously be removed through an outlet to a waste. In other embodiments, the at least one cleaning fluid container 507 does not comprise a drain, and the system comprises an aspiration device for periodically or continuously removing cleaning fluids deposited in the at least one cleaning fluid container 507 through the aspiration conduit 502. In other embodiments, the cleaning fluid container 507 does not comprise a drain, and the at least one cleaning fluid container 507 is disposable so that cleaning fluids deposited in the at least one cleaning fluid container 507 may be disposed of by disposing of the at least one cleaning fluid container 507.

Figure 6A:
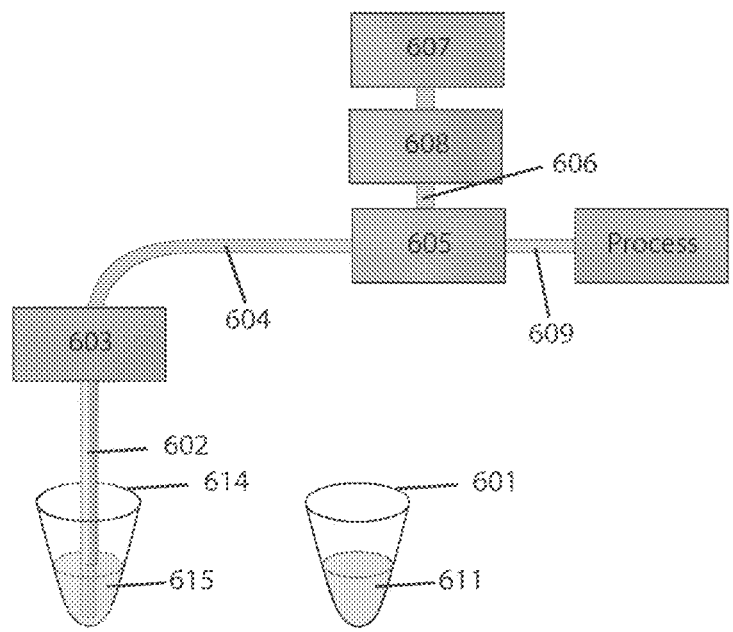
FIGS. 6A and 6B shows a system for sampling and cleaning an intake conduit.
Figure 6B:
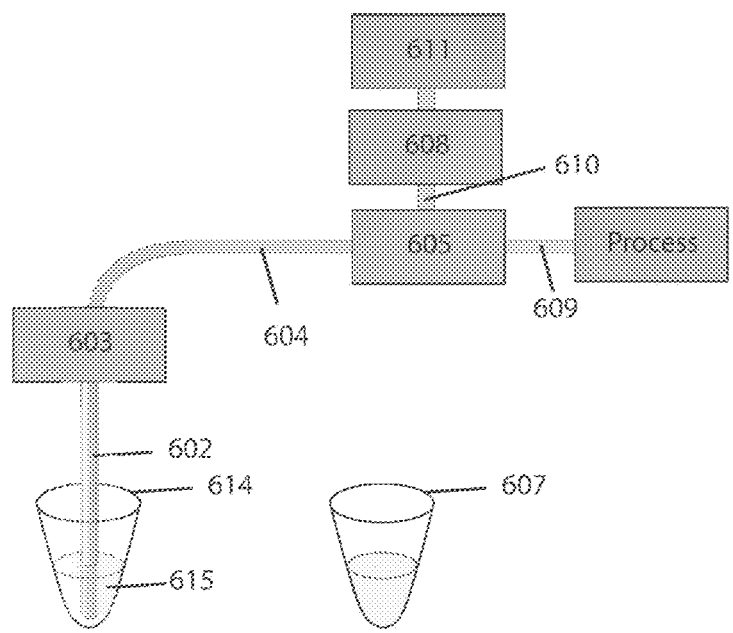

FIGS. 6A and 6B shows further embodiments for both intaking a first volume of a dispersed phase and subsequently cleaning the intake system so that other volumes of dispersed phase are not cross-contaminated by the first volume of dispersed phase. The system additionally comprises a dispersed phase container 614, and the autosampler assembly 603 is capable of causing components comprising the system to be positioned such that the aspiration tip 602 may aspirate fluids from the dispersed phase container 614 or aspirate fluids from or dispense fluids into the cleaning fluid container 601. The dispersed phase container may contain at least one dispersed phase. In certain embodiments, the dispersed phase comprises a biological or chemical sample, a biological or chemical reaction mixture, a biological or chemical assay, or a chemical or biochemical reagent. In certain embodiments, the dispersed phase comprises a nucleic acid, PCR reagents, reporter molecules, a protein, an antibody, a salt, glycerol, a surfactant, or combinations thereof. A method using the system of FIG. 6A comprises positioning components comprising the system such that the aspiration tip 602 may aspirate a volume of a dispersed phase in the dispersed phase container 614, positioning the injector/valve assembly 605 conduit such that the injection conduit 604 is in fluid communication with the waste conduit 606, actuating the motive force source 608 so that a first volume of dispersed phase fluid is aspirated and at least partially fills the volume of the injector/valve assembly 605 conduit, positioning the injector/valve assembly 605 conduit so that it is in fluid communication with the analysis conduit 609, actuating the analysis fluid source 615 so that a substantial first fraction of the dispersed phase fluid in the injector/valve assembly 605 conduit is displaced into the analysis conduit, positioning the injector/valve 605 conduit such that it is in fluid communication with the injector conduit 604 and the waste conduit 606, positioning components comprising the system such that the aspiration conduit 602 may aspirate a volume of at least one cleaning fluid from the at least one cleaning fluid reservoir 601, actuating the motive force source 608 to aspirate a volume of at least one cleaning fluid such that the at least one cleaning fluid passes through the aspiration conduit 602, the injection conduit 604, the waste conduit 606, and into the waste reservoir 607, such that a substantial second fraction of any volume, e.g., any residual volume, of at least one dispersed phase is displaced from the aspiration conduit 602, the injection conduit 604, and the injector/valve assembly 605 conduit and into the waste conduit 606 or the waste reservoir 607 and cross-contamination of subsequent volumes of dispersed phase fluid are cross-contaminated by the first volume of dispersed phase fluid. In certain embodiments, the first fraction is greater than 70%, greater than 80%, greater than 90%, greater than 95%, greater than 99%, greater than 99.9%, greater than 99.99%, greater than 99.999%, or greater than 99.9999%. In certain embodiments, the second fraction is greater than 70%, greater than 80%, greater than 90%, greater than 95%, greater than 99%, greater than 99.9%, greater than 99.99%, greater than 99.999%, or greater than 99.9999%. In certain embodiments, a plurality of cleaning fluids may be aspirated from a plurality of cleaning fluid containers. In certain embodiments, a first cleaning fluid is aspirated from a first cleaning fluid container 601 and a second cleaning fluid is aspirated from a second cleaning fluid container. This may be extended to three, four, or any other suitable number of more pairs of cleaning fluids and cleaning fluid reservoirs. In certain embodiments, more than one cleaning fluid is aspirated from a single cleaning fluid container. In a further embodiment, a first cleaning fluid has a gravimetric density that differs from at least one other cleaning fluid, and the cleaning fluids are contained in the same cleaning fluid container. Aspiration of different cleaning fluids is achieved by adjusting components comprising the system such that the tip of the aspiration conduit 602 may aspirate fluid of the respective cleaning fluid, aspirating fluid so that the interface between two cleaning fluids drops such that the tip of the aspiration conduit 602 shifts from aspirating a first cleaning fluid to a second cleaning fluid, or some combination thereof.

In certain embodiments, the injector/valve assembly 605 comprises a first conduit and a second conduit. The first conduit may exist in at least two states. In the first state, the first conduit is positioned such that the injection conduit 604 is in fluid communication with the waste conduit 606. In the second state, the first conduit is positioned such that the first conduit is in fluid communication with the analysis conduit 609. The second conduit may exist in at least two states. In the first state, the second conduit is positioned such that the injection conduit 604 is in fluid communication with the waste conduit 606. In the second state, the second conduit is positioned such that the second conduit is in fluid communication with the analysis conduit 609. The first and second conduit may each exist in at most one of their respective first and second states at any time. Additionally, if the first conduit is in the first state, the second conduit is not in the first state; if the first conduit is in the second state, the second conduit is not in the second state; if the second conduit is in the first state, the first conduit is not in the first state; if the second conduit is in the second state, the first conduit is not in the second state. The first conduit may be in the first state while the second conduit is in the second state; the first conduit may be in the second state while the second conduit is in the first state; the second conduit may be in the first state while the first conduit is in the second state; and the second conduit may be in the second state while the first conduit is in the first state. In some embodiments, the conduits may not be in either the first state or the second state for a finite time. In further embodiments, the conduits are not in any state for a finite time while transitioning between states.

A method using the system of FIG. 6A where the injector/valve assembly 605 comprises at least two conduits where, when the first conduit is in the first state, the second conduit is in the second state, and when the second conduit is in the first state, the first conduit is in the second state, comprises positioning components of the system such that the aspiration tip 602 may aspirate a volume of a dispersed phase in the dispersed phase container 614, positioning the injector/valve assembly 605 first conduit such that the injection conduit 604 is in fluid communication with the waste conduit 606, actuating the motive force source 608 so that a first volume of dispersed phase fluid is aspirated and at least partially fills the volume of the injector/valve assembly 605 first conduit and positioning the injector/valve assembly 605 first conduit so that it is in fluid communication with the analysis conduit 609. The method further comprises actuating the analysis fluid source 615 so that a substantial first fraction of the dispersed phase fluid in the injector/valve assembly 605 first conduit is displaced into the analysis conduit (process side conduit) and simultaneously positioning components comprising the system such that the aspiration conduit (tip) 602 may aspirate a volume of at least one cleaning fluid from the at least one cleaning fluid reservoir 601, actuating the motive force source 608 to aspirate a volume of at least one cleaning fluid such that the at least one cleaning fluid passes through the aspiration conduit 602, the injection conduit 604, the waste conduit 606, and into the waste reservoir 607, such that a substantial second fraction of any volume, e.g., any residual volume, of at least one dispersed phase is displaced from the aspiration conduit 602, the injection conduit 604, and the injector/valve assembly 605 second conduit and into the waste conduit 606 or the waste reservoir 607 and cross-contamination of subsequent volumes of dispersed phase fluid are cross-contaminated by the first volume of dispersed phase fluid. The method further comprises positioning the first conduit of the injector/valve assembly 605 such that the injection conduit 605 and the waste conduit 606 are in fluid communication, positioning components of the system such that the aspiration conduit 602 is may aspirate at least one cleaning fluid from at least one cleaning fluid reservoir, actuating the motive force source 608 such that at least one volume of at least one cleaning fluid is aspirated into the aspiration conduit 602, through the injection conduit 604 and injector/valve assembly 605 first conduit and into the waste conduit 606 or waste reservoir 607 such that a substantial third fraction of any remaining volume of dispersed phase is displaced from the aspiration conduit 602, injection conduit 604 and injector/valve assembly 605 first conduit, reducing the potential for cross-contamination between the first volume of dispersed phase and other volumes of dispersed phase. In certain embodiments, the first fraction is greater than 70%, greater than 80%, greater than 90%, greater than 95%, greater than 99%, greater than 99.9%, greater than 99.99%, greater than 99.999%, or greater than 99.9999%. In certain embodiments, the second fraction is greater than 70%, greater than 80%, greater than 90%, greater than 95%, greater than 99%, greater than 99.9%, greater than 99.99%, greater than 99.999%, or greater than 99.9999%. In certain embodiments, the third fraction is greater than 70%, greater than 80%, greater than 90%, greater than 95%, greater than 99%, greater than 99.9%, greater than 99.99%, greater than 99.999%, or greater than 99.9999%. In certain embodiments, a plurality of cleaning fluids may be aspirated from a plurality of cleaning fluid containers. In certain embodiments, a first cleaning fluid is aspirated from a first cleaning fluid container 601 and a second cleaning fluid is aspirated from a second cleaning fluid container. This may be extended to three, four, or any suitable number of more pairs of cleaning fluids and cleaning fluid reservoirs. In other embodiments, more than one cleaning fluid is aspirated from a single cleaning fluid container. In a further embodiment, a first cleaning fluid has a gravimetric density that differs from at least one other cleaning fluid, and the cleaning fluids are contained in the same cleaning fluid container. Aspiration of different cleaning fluids is achieved by adjusting components comprising the system such that the tip of the aspiration conduit 602 may aspirate fluid of the respective cleaning fluid, aspirating fluid so that the interface between two cleaning fluids drops such that the tip of the aspiration conduit 602 shifts from aspirating a first cleaning fluid to a second cleaning fluid, or some combination thereof.

In embodiments of certain methods, air may be aspirated before or after volumes of dispersed phase or cleaning fluids. This may be helpful when the volume of the aspiration conduit 602, the injection conduit 604, and one of the injector/valve assembly 605 conduits exceeds the volume of dispersed phase, at least one cleaning fluid, or any combination thereof, available to be aspirated. In some further embodiments, the system comprises a sensor to detect the boundaries between air and volumes of dispersed phase or at least one cleaning fluid or both.

A method using the system of FIG. 6B comprises positioning components of the system such that the aspiration tip 602 may aspirate a volume of a dispersed phase in the dispersed phase container 614, positioning the injector/valve assembly 605 conduit such that the injection conduit 604 is in fluid communication with the purge/clean conduit 610, actuating the motive force source 608 so that a first volume of dispersed phase fluid is aspirated and at least partially fills the volume of the injector/valve assembly 605 conduit, positioning the injector/valve assembly 605 conduit so that it is in fluid communication with the analysis conduit 609, actuating the analysis fluid source 615 so that a first fraction of the dispersed phase fluid in the injector/valve assembly 605 conduit is displaced into the analysis conduit, positioning the injector/valve 605 conduit such that it is in fluid communication with the injector conduit 604 and the waste conduit 606, positioning components comprising the system such that the aspiration conduit 602 may dispense a volume of at least one cleaning fluid into the least one cleaning fluid container 611, actuating the motive force source 608 to flow a volume of at least one cleaning fluid from the purge/clean reservoir such that the at least one cleaning fluid passes through the purge/clean conduit 610, the injection conduit 604, the aspiration conduit 602, and into the cleaning fluid container 607, such that a second fraction of any volume of at least one dispersed phase is displaced from the aspiration conduit 602, the injection conduit 604, and the injector/valve assembly 605 conduit and into the cleaning fluid container 607 and subsequent volumes of dispersed phase fluid are not cross-contaminated by the first volume of dispersed phase fluid. In certain embodiments, the first fraction is greater than 70%, greater than 80%, greater than 90%, greater than 95%, greater than 99%, greater than 99.9%, greater than 99.99%, greater than 99.999%, or greater than 99.9999%. In certain embodiments, the second fraction is greater than 70%, greater than 80%, greater than 90%, greater than 95%, greater than 99%, greater than 99.9%, greater than 99.99%, greater than 99.999%, or greater than 99.9999%. In certain embodiments, a plurality of cleaning fluids may be flowed from a plurality of purge/clean reservoirs. In some embodiments, a first cleaning fluid may be flowed from a first purge/clean reservoir, and a second cleaning fluid may subsequently be flowed from a second purge/clean reservoir. This may extend to any suitable additional number of purge/clean reservoirs.

A method using the system of FIG. 6B where the injector/valve assembly 605 comprises at least two conduits where, when the first conduit is in the first state, the second conduit is in the second state, and when the second conduit is in the first state, the first conduit is in the second state, comprises positioning components comprising the system such that the aspiration tip 602 may aspirate a volume of a dispersed phase in the dispersed phase container 614, positioning the injector/valve assembly 605 first conduit such that the injection conduit 604 is in fluid communication with the purge/clean conduit 610, actuating the motive force source 608 so that a first volume of dispersed phase fluid is aspirated and at least partially fills the volume of the injector/valve assembly 605 first conduit and positioning the injector/valve assembly 605 first conduit so that it is in fluid communication with the analysis conduit 609. The method further comprises actuating the analysis fluid source 615 so that a first fraction of the dispersed phase fluid in the injector/valve assembly 605 first conduit is displaced into the analysis conduit and simultaneously positioning components of the system such that the aspiration conduit 602 may dispense a volume of at least one cleaning fluid into the at least one cleaning fluid reservoir 601, actuating the motive force source 608 to flow a volume of at least one cleaning fluid such that the at least one cleaning fluid passes through the purge/clean conduit 610, the injection conduit 604, the aspiration conduit 602, and into the cleaning fluid container 601, such that a second fraction of any volume of at least one dispersed phase is displaced from the aspiration conduit 602, the injection conduit 604, and the injector/valve assembly 605 second conduit and into the cleaning fluid container 601 and cross-contamination of subsequent volumes of dispersed phase fluid by the first volume of dispersed phase fluid is reduced or eliminated. The method further comprises positioning the first conduit of the injector/valve assembly 605 such that the injection conduit 604 and the purge/clean conduit 610 are in fluid communication, positioning components comprising the system such that the aspiration conduit 602 may dispense at least one cleaning fluid into at least one cleaning fluid reservoir, actuating the motive force source 608 such that at least one volume of at least one cleaning fluid is flowed into the purge/clean conduit 606, through the injection conduit 604 and injector/valve assembly 605 first conduit and into the cleaning fluid reservoir 601 such that a third fraction of any remaining volume of dispersed phase is displaced from the aspiration conduit 602, injection conduit 604 and injector/valve assembly 605 first conduit, reducing the potential for cross-contamination between the first volume of dispersed phase and other volumes of dispersed phase. In certain embodiments, the first fraction is greater than 70%, greater than 80%, greater than 90%, greater than 95%, greater than 99%, greater than 99.9%, greater than 99.99%, greater than 99.999%, or greater than 99.9999%. In some embodiments, the second fraction is greater than 70%, greater than 80%, greater than 90%, greater than 95%, greater than 99%, greater than 99.9%, greater than 99.99%, greater than 99.999%, or greater than 99.9999%. In some embodiments, the third fraction is greater than 70%, greater than 80%, greater than 90%, greater than 95%, greater than 99%, greater than 99.9%, greater than 99.99%, greater than 99.999%, or greater than 99.9999%. In some embodiments, a plurality of cleaning fluids may be aspirated from a plurality of cleaning fluid containers. In some embodiments, a first cleaning fluid is aspirated from a first cleaning fluid container 601 and a second cleaning fluid is aspirated from a second cleaning fluid container. This may be extended to three, four, or arbitrarily more pairs of cleaning fluids and cleaning fluid reservoirs.

Figure 7:
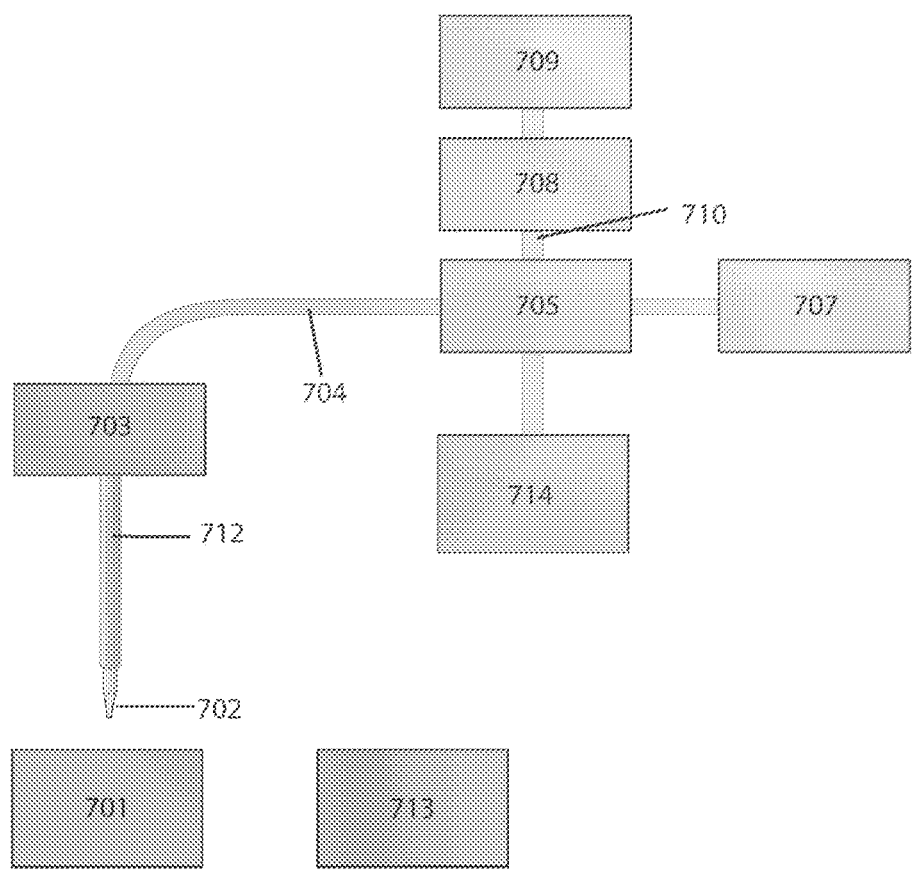
FIG. 7 shows a system for injecting a sample comprising a waste station.

FIG. 7—System for injecting a sample comprising a waste station FIG. 7 shows a further embodiment of the systems shown in FIG. 6B. The system further comprises a washing conduit 712 and the autosampler assembly 703 comprises a source of washing fluid in fluid communication with the washing conduit 712 and a second motive force source to drive the washing fluid through the washing conduit 712. The washing conduit 712 is positioned so that the inner surface of the washing conduit 712 substantially surrounds at least part of the outer surface of the aspiration conduit 701 but terminates at a vertical position above a tip of the aspiration conduit 701. An embodiment of a method of preventing cross-contamination using the system of FIG. 7 comprises positioning the aspiration conduit 702 with the autosampler assembly 703 such that fluids leaving the aspiration conduit and the washing conduit 712 deposit in the at least one cleaning fluid container 701, positioning the injector/valve assembly 705 conduit such that the injection conduit 704 is in fluid communication with the purge/clean conduit 706, actuating the motive force source 708 to move at least one cleaning fluid from the purge/clean reservoir 709 through the purge clean conduit 708, the injection conduit 704, and the aspiration conduit 702 so that the cleaning fluids are deposited in the at least one cleaning fluid container 701. The second motive force source is actuated to drive the washing fluid through the washing fluid conduit 712 and displace volumes of the at least one dispersed phase from the outer surface of the aspiration conduit 702 and into the cleaning fluid container 701. In some embodiments, the washing fluid has a higher affinity for the outer surface of the aspiration conduit 702 than the at least one dispersed phase so that the washing fluid may preferentially drive the at least one dispersed phase from the outer surface of the aspiration conduit 702. In some embodiments, the washing fluid comprises a component that is hydrophobic, the outer surface of the aspiration conduit 702 comprises a component that is hydrophobic, and the at least one dispersed phase comprises water. In an embodiment, the washing fluid is an oil and the outer surface of the aspiration conduit 702 comprises a polymer. In a preferred embodiment, the washing fluid is a fluorinated oil and the outer surface of the aspiration tube comprises a fluorinated polymer. In other embodiments, the washing fluid comprises a component that is hydrophilic, the outer surface of the aspiration tube 702 comprises a component that is hydrophilic, and the at least one dispersed phase comprises a component that is hydrophobic.

In some embodiments, the method additionally comprises flowing washing through the washing fluid conduit 712 and into the cleaning fluid container 701, re-positioning the aspiration tube 702 such that a tip of the aspiration tube 702 is vertically above the surface of at least one cleaning fluid in the cleaning fluid container 701, and then terminating flow of the washing fluid conduit 712 into the cleaning fluid container 701 such that the washing fluid continues to flow until the tip of the aspiration tube 702 is no longer in fluid communication with at least one cleaning fluid.

A method of sampling and cleaning an intake system at least one dispersed phase from at least one dispersed phase container using the system of FIG. 7 comprises positioning components comprising the system such that the aspiration tip 702 may aspirate a volume of a dispersed phase in the dispersed phase container 713, positioning the injector/valve assembly 705 conduit such that the injection conduit 704 is in fluid communication with the purge/clean conduit 710, actuating the motive force source 708 so that a first volume of dispersed phase fluid is aspirated and at least partially fills the volume of the injector/valve assembly 705 conduit, positioning the injector/valve assembly 705 conduit so that it is in fluid communication with the analysis conduit 707, actuating the analysis fluid source 715 so that a substantial first fraction of the dispersed phase fluid in the injector/valve assembly 705 conduit is displaced into the analysis conduit, positioning the injector/valve 705 conduit such that it is in fluid communication with the injector conduit 704 and the waste conduit 706, positioning components comprising the system such that the aspiration conduit 702 may dispense a volume of at least one cleaning fluid into the least one cleaning fluid container 701, actuating the motive force source 708 to flow a volume of at least one cleaning fluid from the purge/clean reservoir such that the at least one cleaning fluid passes through the purge/clean conduit 710, the injection conduit 704, the aspiration conduit 706, and into the cleaning fluid container 701, such that a substantial second fraction of any volume of at least one dispersed phase is displaced from the aspiration conduit 702, the injection conduit 704, and the injector/valve assembly 705 conduit and into the cleaning fluid container 701, flowing a washing fluid through the washing fluid 712 and into the cleaning fluid container 701 such that the washing fluid displaces dispersed phase fluid on the outer surface of the aspiration conduit 702 and into the cleaning fluid container 701 and cross-contamination of subsequent volumes of dispersed phase fluid are cross-contaminated by the first volume of dispersed phase fluid. In some embodiments, the first fraction is greater than 70%, greater than 80%, greater than 90%, greater than 95%, greater than 99%, greater than 99.9%, greater than 99.99%, greater than 99.999%, or greater than 99.9999%. In some embodiments, the second fraction is greater than 70%, greater than 80%, greater than 90%, greater than 95%, greater than 99%, greater than 99.9%, greater than 99.99%, greater than 99.999%, or greater than 99.9999%. In some embodiments, a plurality of cleaning fluids may be flowed from a plurality of purge/clean reservoirs. In some embodiments, a first cleaning fluid may be flowed from a first purge/clean reservoir, and a second cleaning fluid may subsequently be flowed from a second purge/clean reservoirs. This may arbitrarily extend to any number of purge/clean reservoirs. Methods that use an injector/valve assembly 705 comprising at least two conduits and a system additionally comprising the washing conduit 712 are analogous to methods not additionally comprising the washing conduit 712, additionally comprising a step flowing washing fluid through the washing conduit 712 and into the cleaning fluid container 701 such that the washing fluid displaces dispersed phase fluid from the outer surface of the aspiration tube 702.

Figure 8A:
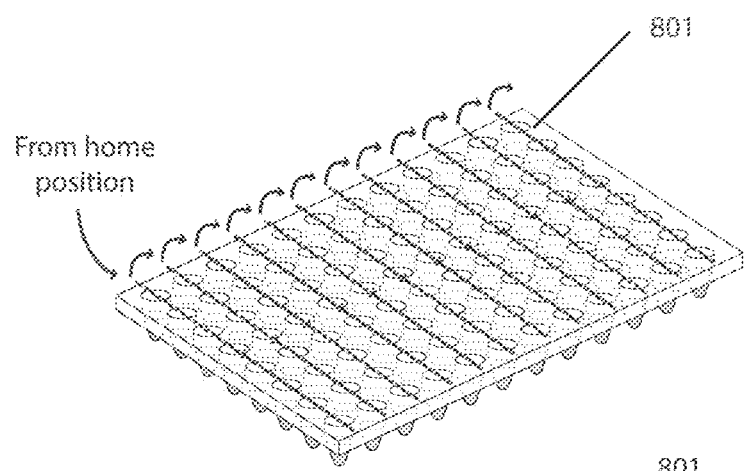
FIGS. 8A and 8B show patterns for sampling to avoid cross-contamination.
Figure 8B:
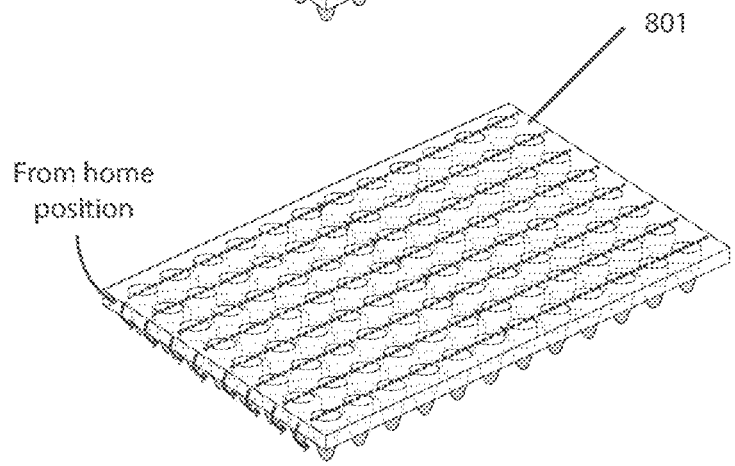

FIGS. 8A—Patterns for sampling to avoid cross-contamination FIGS. 8A and 8B show a system for containing dispersed phase volumes (e.g., samples) and methods for avoiding carryover and cross-contamination when aspirating consecutive volumes of dispersed phase. The system comprises a set of dispersed phase containers 801 comprising at least two dispersed phase containers which may contain at least one dispersed phase. When aspirating dispersed phase volumes, a tip of an aspiration conduit is submerged in at least one dispersed phase volume in a first dispersed phase container. The tip of the aspiration conduit is subsequently submerged in a second volume of dispersed phase in a second dispersed phase container. In certain embodiments, the tip of the aspiration conduit may be cleaned in between submerging the tip of the aspiration conduit in the first dispersed phase volume and submerging the tip of the aspiration conduit in the second dispersed phase volume, where the cleaning occurs at a site remote from the first and second dispersed phase containers. A method for avoiding carryover of a first dispersed phase fluid from a first dispersed phase fluid container to a second dispersed phase fluid in a second dispersed phase fluid container where an aspiration tip is cleaned at a location remote from both the first dispersed phase fluid container and the second dispersed phase fluid container comprises aspirating the first dispersed phase from the first dispersed phase container, moving to the remote location for tip cleaning where the movement does not traverse any position where the aspiration conduit tip is vertically positioned above the second dispersed phase container, cleaning the aspiration conduit tip in the remote location, and positioning the aspiration conduit tip so that it is vertically positioned above the second dispersed phase container such that, in positioning, the aspiration conduit tip only traverses positions where the tip of the aspiration conduit is above a dispersed phase container if the aspiration tip has already been submerged in a dispersed phase in that dispersed phase container. In certain embodiments, the dispersed phase containers are wells of a microtiter plate and the set 801 is a microtiter plate. Any suitable microtiter plate may be used; in certain embodiments, the microtiter plate is a 24-well plate, a 48-well plate, a 96-well plate, a 384-well plate, or a 1536-well plate. FIGS. 8A and B show sequential orders of aspirating wells in a microtiter plate such that, when positioning to aspirate a volume of dispersed phase from a dispersed phase container, the tip of the aspiration conduit only ever traverses positions where it is vertically above another dispersed phase container if it has already been submerged in dispersed phase fluid in the dispersed phase container.

Figure 9A:
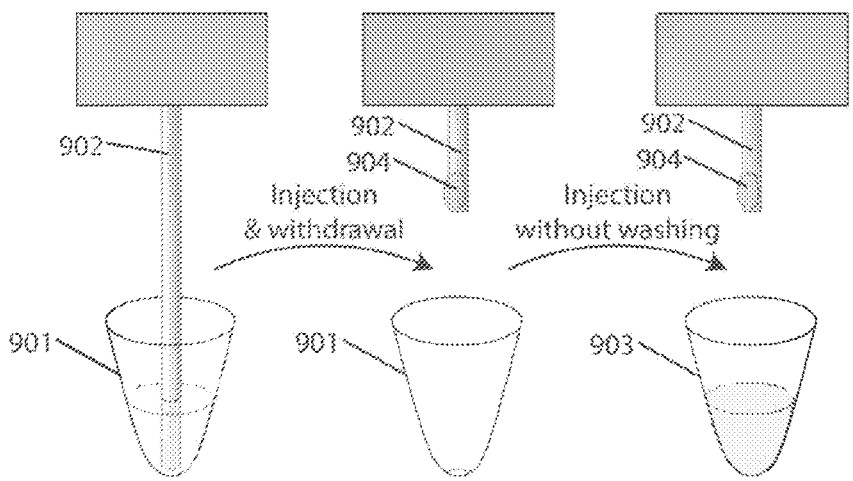
FIGS. 9A and 9B show examples of aspirating a fluid.
Figure 9B:
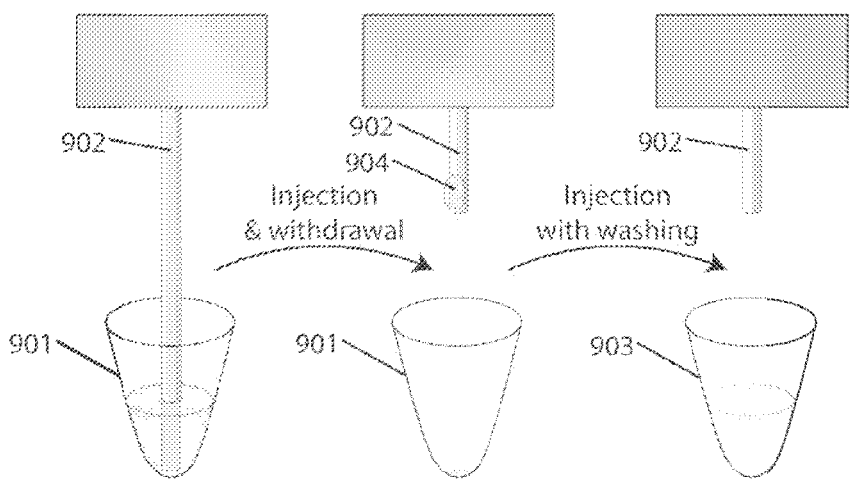

FIGS. 9A and 9B—Examples of aspirating a fluid FIGS. 9A and 9B show examples of aspirating a fluid from a system comprising a fluid container 901 and an aspiration conduit 902 comprising a tip. The internal volume of the fluid container 901 comprises at least one first fluid. When the tip is submerged in the at least one first fluid, both the inner and outer surfaces of the aspiration conduit 902 are exposed to the at least one fluid. After aspiration of some or all of the fluid, a portion of the first fluid may remain on the outer surface of the aspiration conduit 902. The system comprises a second fluid container 903, and subsequent aspiration of the fluid in the second fluid without washing the outer surface of the aspiration conduit 902 (as in FIG. 9A) may result in cross-contamination of the second fluid by the first fluid. Instead, if the outer surface of the aspiration conduit 902 is washed (as in FIG. 9B) such that a portion of any of the first fluid remaining on the outer surface of the aspiration conduit 902 is removed, and the potential for cross-contamination of the second fluid by the at least one first fluid is reduced. In some embodiments, the portion of first fluid that is removed is greater than 70%, greater than 80%, greater than 90%, greater than 95%, greater than 98%, greater than 99%, greater than 99.9%, greater than 99.99%, or greater than 99.999% of the at least one first fluid originally on the outer surface of the aspiration conduit 902. In certain embodiments, at least one washing fluid is used to wash the aspiration conduit, where the washing fluid has a higher affinity for a material comprising the outer surface of the aspiration conduit 902 than does the at least one first fluid. In certain embodiments, the outer surface of the aspiration conduit comprises a hydrophobic polymer, the at least one first fluid comprises water, and the washing fluid comprises a hydrophobic component. In certain embodiments, the surface of the aspiration conduit comprises a fluoropolymer, the at least one first fluid comprises water, and the washing fluid comprises a fluorinated oil.

Figure 10A:
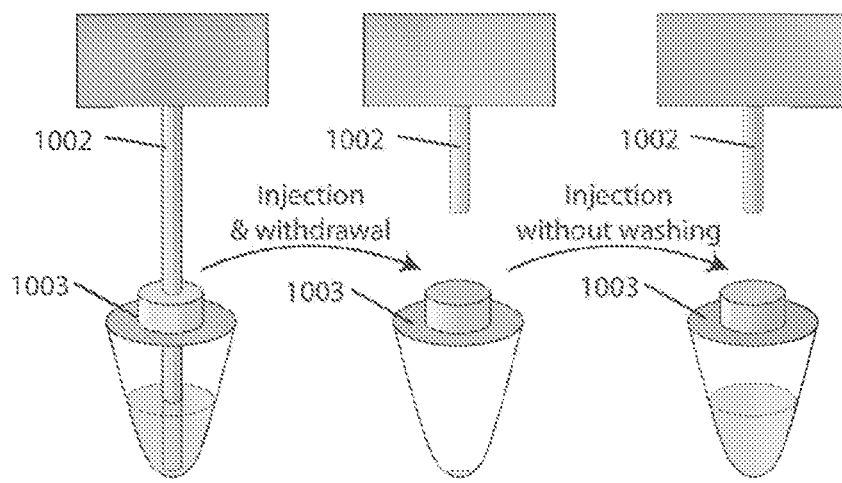
FIGS. 10A and 10B show examples of injecting a sample from a sample container with a cover.
Figure 10B:
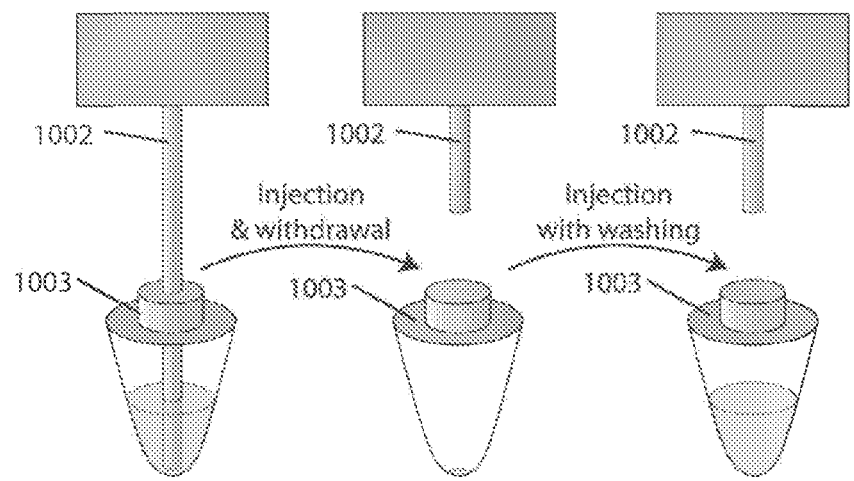

FIGS. 10A and 10B—Examples of injecting a sample from a sample container with a cover FIGS. 10A and 10B show systems for aspirating fluids from sample containers where a cover prevents carryover of one sample into another. The system comprises a first fluid container whose volume comprises at least one first fluid; a cover 1003; and an aspiration conduit 1002 where the aspiration conduit 1002 may pass through the cover in such a way that a substantial portion of the at least one first fluid is removed from the outer surface of the aspiration conduit 1002 as it passes outside of the first fluid container. In certain embodiments, the cover 1003 is a polymer seal. In certain embodiments, the cover 1003 is a silicone seal, and the aspiration conduit 1002 is capable of pushing through the silicone seal, where the silicone seal wipes the outer surface of the aspiration conduit 1002 to remove the first fluid. In some embodiments, the portion of the at least one first fluid removed from the aspiration conduit is greater than 70%, greater than 80%, greater than 90%, greater than 95%, greater than 98%, greater than 99%, greater than 99.9%, greater than 99.99%, or greater than 99.999% of the first fluid that remains on the aspiration conduit after it samples the first fluid.

Figures 4A, 4B, 4C, 4D:
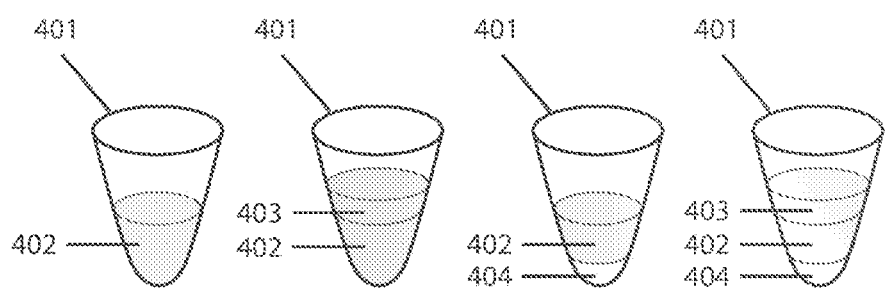
FIGS. 4A, 4B, 4C and 4D show fluid "parfait.

FIGS. 4A, 4B, 4C, and 4D—Layered fluids in sample containers FIG. 4 shows multiple systems for providing dispersed phase fluids and/or cleaning fluids to the system, where the fluids share a common container and are separated by, e.g., differences in mass density (e.g., parfait). The system comprises a fluid container 401 and at least one fluid 402. In FIG. 4A, the system only comprises a first fluid 402. In FIG. 4B, the system additionally comprises a second fluid 403 that is different from the first fluid and that has a lower mass density than the first fluid 402. The first and second fluids may independently be, e.g., continuous or dispersed phase fluids in the system. FIG. 4C shows where the system comprises two fluids, but that it comprises a third fluid 404 that has a lower mass density than the fluid 402. FIG. 4D shows a system that comprises three different fluids: a first fluid 402, a second fluid 403, and a third fluid 404. By deliberate choice of the fluids, dispersed phase fluids and cleaning fluids may be sequentially added to the system.

In certain embodiments, the first fluid 402 is a first dispersed phase fluid that comprises, e.g., an analyte or other component to be passed to a process system for processing, the second fluid 403 is a second dispersed phase fluid immiscible with the first dispersed phase, and the third fluid 404 is a continuous phase fluid. Layering the second fluid 403 on top of the first fluid 402 prevents the first fluid 402 from evaporating until the second fluid 403 has substantially evaporated or has been removed. Layering the third fluid 404 under the first fluid 402 raises the vertical position of the first fluid 402, reducing the difficulty of aspirating most or all of the first fluid 402 from the bottom of the fluid container 402. In certain embodiments, the second fluid 403 is also a spacer fluid to separate distinct volumes of first fluid aspirated into an aspiration conduit. In certain embodiments, the third fluid 404 is a purge fluid to displace volumes of first fluid from an aspiration and intake system, reducing the possibility of cross-contamination between distinct volumes of first fluid.

In certain embodiments, a single position of a tip of an aspiration conduit allows for aspirating a sequence of fluids. For example, positioning a tip of an aspiration conduit such that it is submerged in the third fluid 404 and then beginning aspiration will first draw third fluid 404 into the aspiration conduit, vertically lowering the interface between the third fluid 404 and the first fluid 402 until the aspiration tip is submerged in the first fluid 402. Further aspiration aspirates first fluid 402 into the aspiration conduit, vertically lowering the interface between the first fluid 402 and the second fluid 403 until the aspiration tip is submerged in the second fluid 403. Further aspiration aspirates second fluid into the aspiration conduit. In certain embodiments, systems and methods include sequentially positioning a tip of an aspiration conduit such that it is sequentially submerged in at least two fluids allows for the sequential ordering of aspiration of the at least two fluids.

Figure 11A:
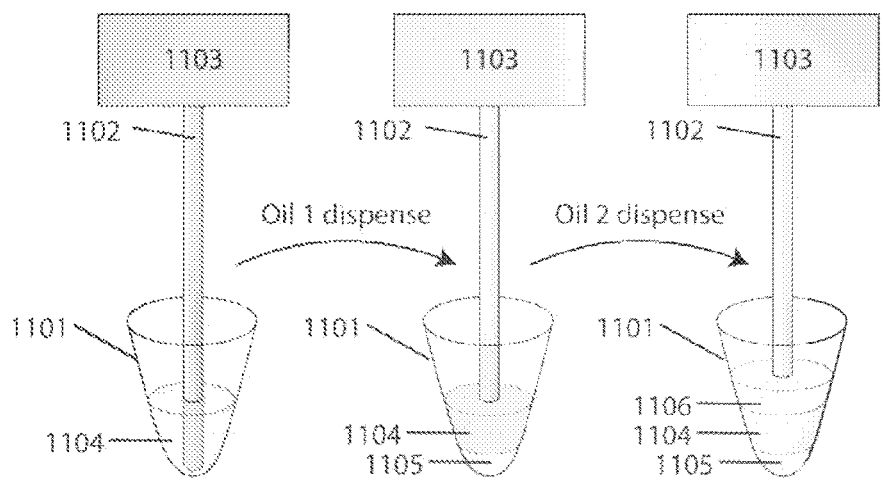
FIGS. 11A and 11B show systems and methods for creating layered fluids in sample containers.
Figure 11B:
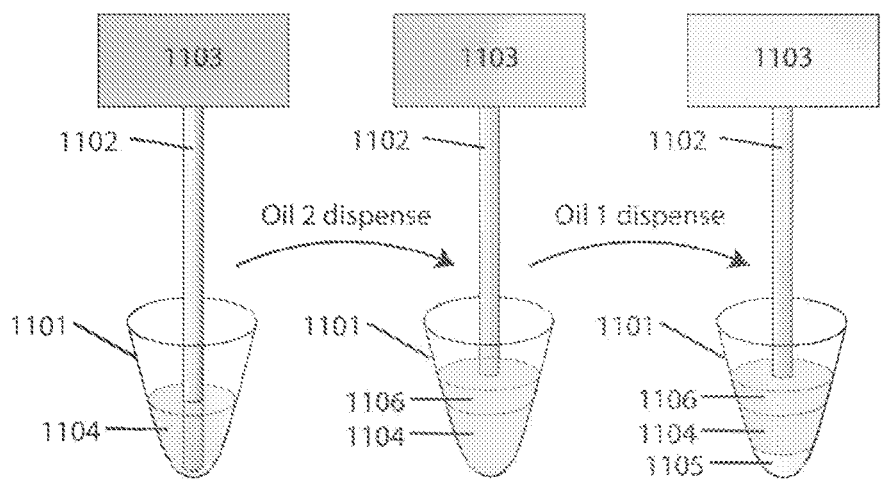

FIGS. 11A and 11B—Systems and methods for creating layered fluids in sample containers FIG. 11 shows systems and methods for dispensing fluids to create the vertically layered fluids (parfait) shown in FIG. 4. The system comprises a fluid container 1101, an aspiration conduit 1102, a fluid source 1102, and a first fluid 1104. In a method shown in FIG. 11A, the aspiration conduit 1102 is positioned so that a tip of the aspiration conduit 1102 is submerged in the first fluid 1104. A second fluid 1105 with a mass density greater than the mass density of the first fluid 1104 is provided by the fluid source 1103, flowed through the aspiration conduit 1102 through the tip of the aspiration conduit 1102 and into the fluid container 1101, where it settles to the bottom of the fluid container 1101. A third fluid 1106 with a mass density less than the mass density of the first fluid is provided by the fluid source 1103, flowed through the aspiration conduit 1102 and through the tip of the aspiration conduit 1102 and into the fluid container 1101, where it floats to the top of the first fluid 1104.

In a method shown in FIG. 11B, the aspiration conduit 1102 is positioned so that a tip of the aspiration conduit 1102 is submerged in the first fluid 1104. The third fluid 1106 is first provided by the fluid source 1103, flowed through the aspiration conduit 1102 through the tip of the aspiration conduit 1102 and into the fluid container 1101, where it floats to the top of the fluid container 1101. The second fluid 1105 is provided by the fluid source 1103, flowed through the aspiration conduit 1102 and through the tip of the aspiration conduit 1102 and into the fluid container 1101, where it settles to the bottom of the fluid container 1101.

In certain embodiments, the rate of volumetric flow through the aspiration conduit 1102 of the second fluid 1105 and third fluid 1106 is limited so that well-defined interfaces are maintained between the first, second, and third fluids. In preferred embodiments, the rate of volumetric flow is less than 1000 mL/min, less than 100 mL/min, or less than 10 mL/min.

In certain embodiments, the fluid source comprises a first reservoir for the second fluid 1105, a second reservoir for the third fluid 1106, at least one fluid selection valve, and a motive force source. The at least one fluid selection valve causes one or neither (but not both) of the second fluid 1105 or third fluid 1106 to flow when a motive force is provided by the motive force source. In some embodiments, the motive force source is a pump.

Figure 12:
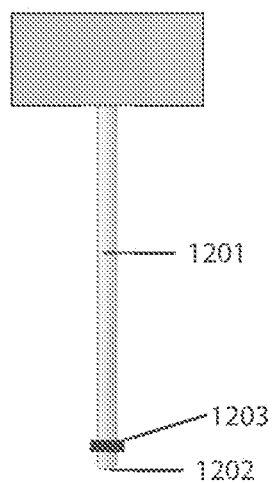
FIG. 12 shows a system for sensing the level of a fluid with a sampling inlet.

FIG. 12—System for sensing the level of a fluid with a sampling inlet. In certain embodiments of the systems and methods provided herein, it is desirable to determine when a tip of an aspiration conduit is submerged in a fluid volume. In certain embodiments, this is to ensure aspiration of sufficient volume, to avoid aspirating more than a maximum volume of air, or to ensure a fluid container contains a minimum volume of fluid before aspirating. The system shown in FIG. 12 comprises an aspiration conduit 1201 and an aspiration tip 1202 that comprises a fluid sensing device 1203. A signal from the fluid sensing device 1204 indicates whether the aspiration tip 1202 is submerged in a fluid. The fluid sensing device may be any suitable device; in certain embodiments, the fluid sensing device is an electrical resistance sensor, an electrical capacitance sensor, a thermal conductivity sensor, a heat capacity sensor, a nuclear or particulate radiation sensor, or a temperature sensor, or a combination thereof.

FIGS. 13A and 13B—Design of seal to avoid sample contamination In certain embodiments of the systems and methods provided herein, fluid containers are sealed so as to avoid evaporation of fluid contents or environmental contamination or both. In order to aspirate the fluid contents, the seal must be broken and an aspiration conduit inserted into the fluid contents volume. In FIG. 13, a sealed fluid container system comprises a fluid container 1301, a seal 1302, and fluid contents 1303. The system comprises a distance a from the inner surface of the seal 1302 to the top surface of the fluid contents and a maximum seal chord b. Because the outer surface of the seal 1302 is exposed to the ambient environment, environmental contaminants may accumulate on the outer surface of the seal 1302 before the seal 1302 is broken and the fluid contents aspirated. If the distance a is less than or equal to a multiple of the distance b, breakage of the seal 1302 may result in a seal fragment 1304 being submerged in the fluid contents 1303, potentially contaminating the fluid contents 1303 with environmental contaminants from the outer surface of the seal 1302 (FIG. 13A). If the distance a is greater than a multiple of the distance b, breakage of the seal 1302 will not result in a seal fragment 1304 being submerged in the fluid contents (FIG. 13B). At a minimum, the multiple must be 0.5. In such an embodiment, the seal must be perfectly broken such that no seal fragment 1304 has a longer segment than any other seal fragment. In preferred embodiments, the multiple is greater than 1, which guarantees that no seal fragment 1304 will be submerged in the fluid contents 1303.

FIGS. 14A and 14B—Sealing systems FIG. 14 shows systems for seals and breaking seals. The system in FIG. 14 comprises a fluid container 1401, a seal 1402 where the seal has been perforated to require a reduced breaking force and fluid contents 1403. Because the seal has been perforated to require a reduced breaking force, an aspiration conduit requires lower rigidity to break the seal than when there is no perforation (FIGS. 14A and 14B) In embodiments where the seal does not comprise a perforation, the system may additionally comprise a seal breaker distinct from an aspiration conduit to provide the force and rigidity required to break the seal.

FIGS. 15A, 15B, and 15C—Systems for aspirating samples and piercing seals FIG. 15 shows various systems for aspirating samples and piercing seals. The system in FIG. 15A comprises an aspiration conduit 1501 that comprises a tip 1502 and a piercing/aspiration assembly 1503. The aspiration tip 1502 is sufficiently rigid to pierce a fluid container seal used in the system, and the piercing aspiration assembly 1503 allows for vertical actuation of the assembly and creation of suction at the tip 1502 so as to aspirate fluids into the aspiration conduit 1501. The system in FIG. 15B comprises an aspiration conduit 1501 that comprises a tip 1502, where the tip 1502 is not sufficiently rigid or mechanically robust to pierce a fluid container seal used in the system. The system additionally comprises an aspiration assembly 1503 that allows for vertical actuation of the tip 1502 and creation of suction at the tip 1502 to aspirate fluids into the aspiration conduit 1501, a piercing tip 1504 and piercing assembly 1505, where the piercing assembly 1505 allows for vertical actuation of the piercing tip 1504 and creation of the force required to pierce a seal in the system. In an embodiment of a method to employ the system in FIG. 15B, the piercing tip 1504 is positioned above a seal in the system and actuated downward by the piercing assembly 1505 to break the seal. Once the seal is broke, the piercing assembly 1505 actuates the piercing tip 1504 upward, and the tip 1502 is positioned above the fluid container. The tip 1502 is positioned by the aspiration assembly 1503 downward into the fluid container and fluid is aspirated by the aspiration assembly 1503 into the aspiration conduit 1501. When aspiration is complete, the tip 1502 is actuated upward by the aspiration assembly 1503.

In certain embodiments, the piercing tip 1504 has a round, star, square, conical, serrated, pyramidal, or rectangular cross section. In certain embodiments, the piercing tip 1504 comprises a metal, a polymer, or a glass, or a combination thereof. In certain embodiments, the surface of the piercing tip 1504 has a higher affinity for at least one continuous phase in the system than for any dispersed phase in the system. In certain embodiments, the piercing tip comprises a fluoropolymer. In certain embodiments, the tip comprises a fluoropolymer.

The system in FIG. 15C comprises an aspiration conduit 1501 comprising a tip 1502, a piercing tip 1503 where the piercing tip substantially surrounds a portion of the aspiration conduit 1501, and an aspiration/piercing assembly 1504 that allows for independent vertical motion of the tip 1502 and piercing tip 1503 as well as generation of suction at the tip 1502 to drive aspiration of fluids into the aspiration conduit 1501. A method for breaking a seal and aspirating a fluid from a fluid container comprises positioning the tip 1502 above a seal of a fluid container, actuating the piercing tip 1503 downward so that it pierces the seal but so that it does not become submerged in fluid contents of the fluid container, actuating the tip 1502 downward so that it becomes submerged in fluid contents of the fluid container, and generating suction at the tip 1502 so as to aspirate part or all of the fluid contents into the aspiration conduit 1501. In certain embodiments, the piercing tip 1503 has a round cross-section, and the piercing tip 1503 and the tip 1502 are co-axial or substantially co-axial.

Figure 16:
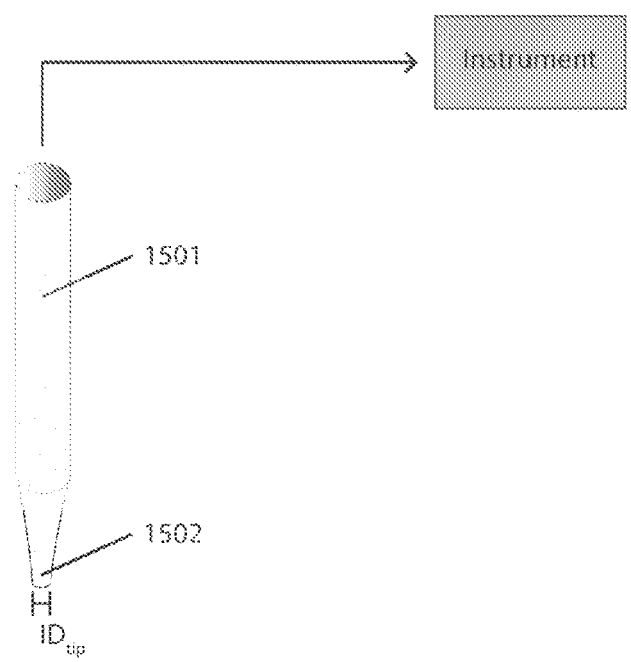
FIG. 16 shows design of aspiration tip for filtration.

FIG. 16—Design of an aspiration tip for filtration FIG. 16 shows an aspiration tip system for avoiding aspiration of particulate material that is oversized into the system. Particulate material with a large characteristic dimension may occlude fluid conduits in the system. The system comprises an aspiration conduit 1501 with a tip 1502, such that the tip 1502 has a smaller cross-sectional area than other portions of the aspiration conduit 1501. The tip 1502 has a major dimension a. To avoid aspiration of problematic particulate material, the major dimension a is chosen such that it is a fraction of the characteristic dimension of the smallest conduit in the present system. In certain embodiments, the major dimension is a diameter, a hydraulic diameter, or other suitable dimension. In certain embodiments, the major characteristic dimension is a diameter, a hydraulic diameter, or other suitable dimension. In some embodiments, a is less than 95%, less than 90%, less than 85%, less than 80%, less than 70%, less than 50%, less than 35% or less than 20% of the characteristic dimension of the smallest conduit in the present system. In an example, the smallest conduit is a rectangular channel with a minor axis that is 75 um, and a is a circular diameter chosen to be 50 um or less.

In certain embodiments, the aspiration conduit 1501 comprises a tube comprising a polymer. In a certain embodiments, the tip is manufactured by heating the aspiration conduit 1501 and applying a tensile force to the aspiration conduit 1501 such that a portion of the length of the aspiration conduit 1501 has a reduced cross-sectional area and subsequently cutting the aspiration conduit 1501 in the region of reduced cross-sectional area so as to create the tip 1501. In certain embodiments, the tip is manufactured by inserting a mandrel of fixed diameter into the internal volume of the aspiration conduit 1501, applying a compressive force to the aspiration conduit 1501 so as to reduce the cross-sectional area in a region of the aspiration conduit 1501 where the cross-sectional area is the same as the mandrel in at least part of the region, removing the mandrel, and cutting the aspiration conduit 1501 to create a tip 1502. In certain embodiments, the tip is manufactured by applying a compressive force to the aspiration conduit 1501 until the cross-sectional area of a portion of the aspiration conduit 1501 is zero, cutting the aspiration conduit 1501 in the region of zero cross-sectional area, and creating a hole in the face of the aspiration conduit 150-1 where the aspiration conduit is cut to form a tip, where the hole provides fluidic communication between the tip 1502 and the balance of the internal volume of the aspiration conduit 1502. In certain embodiments, the holes are created by drilling, application of coherent electromagnetic radiation, or wire EDM. In certain embodiments, the tip 1502 is manufactured by creating holes in a sheet comprising a polymer material and welding the sheet to the end of the aspiration conduit 1501.

In certain embodiments, the tip 1502 comprises a hypodermic needle. In certain embodiments, the surface of the needle comprises a material that has a higher affinity for at least one continuous phase than any dispersed phase in the system.

Figures 17A, 17B:
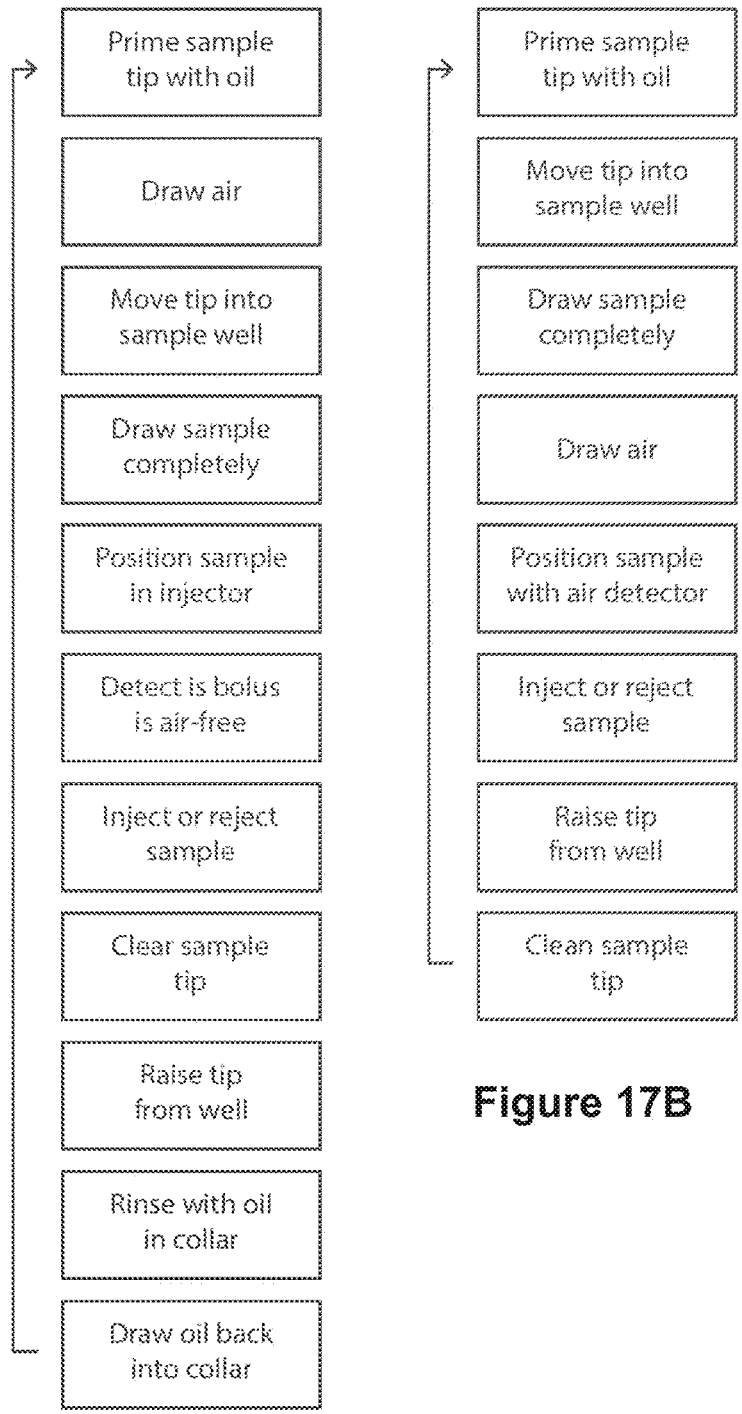
FIGS. 17A and 17B shows methods for aspirating a fluid.

FIGS. 17A and 17B—Methods for aspirating a fluid FIG. 17 shows methods for aspirating a sample in an intake system and transferring the sample to a process system using an injector so that air is not injected into the system. In an embodiment shown on the left of in FIG. 17A, a volume of sample drawn into the injector is checked to determine whether the volume of sample comprises air. The detection method may measure an optical, ultrasonic, thermal, or other appropriate quantity of the contents comprising the internal volume of the intake conduit, as described elsewhere herein. If the volume of sample does not comprise air, it may be transferred to the process system by positioning the injector such that the common conduit is in fluid communication with the process system. If the volume of sample comprises air, the sample may be rejected without transfer to the process system. In some embodiments, the sample is re-sampled to attempt to sample it without air. In other embodiments, intake of the sample is only attempted once. In some embodiments, the aspiration tip is cleaned with an outside wash collar to remove contaminants from the outer wall of the tip and/or blownback/injected with cleaning fluids internally to remove contaminants from the inner wall of the tip, as described elsewhere herein. The embodiment shown in FIG. 17B is similar, but does not check whether the volume of sample comprises air.

Figure 18:
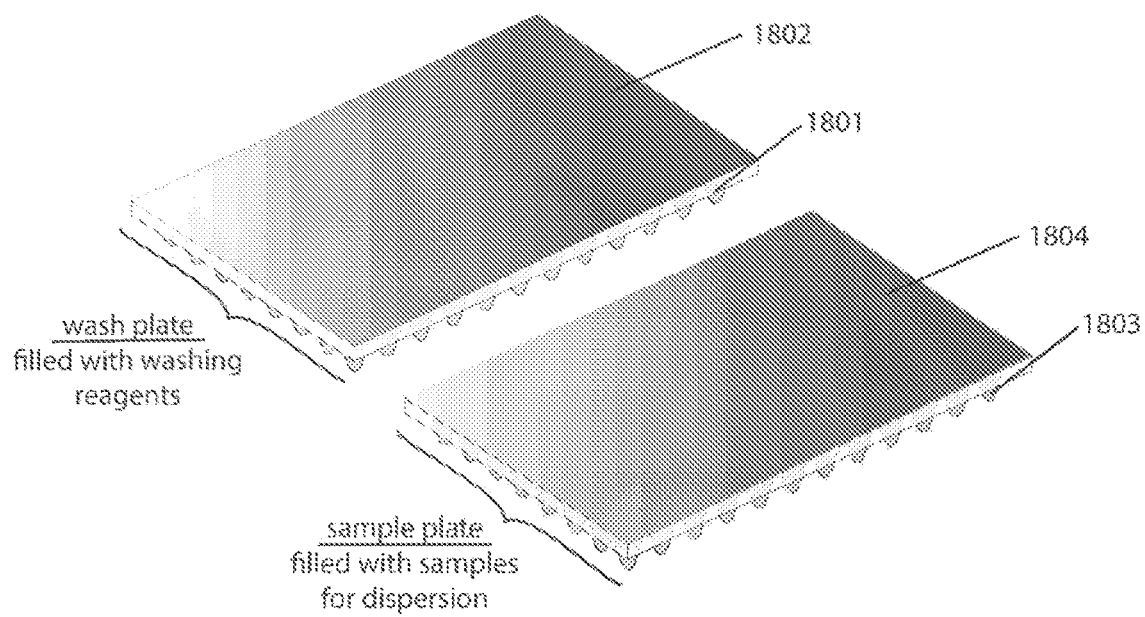
FIG. 18 shows systems for supplying sample fluids and cleaning.

FIG. 18—Systems for supplying sample fluids and cleaning fluids FIG. 18 shows a system for supplying both cleaning fluids and sample fluids to be aspirated. The system comprises a first set of fluid containers 1801 with a first seal 1802 and a second set of fluid containers 1803 with a second seal 1804. The first set of fluid containers comprise dispersed phase fluids for processing in the present system, and the second set of fluid containers comprise cleaning fluids for processing in the present system. In an embodiment shown in FIG. 18, the first set of fluid containers 1801 and the second set of fluid containers 1803 are microtiter plates. Microtiter plates can be any suitable size. In certain embodiments, the plates are independently 24-well, 48-well, 96-well, 384-well, or 1536-well microtiter plates.

Figure 19:
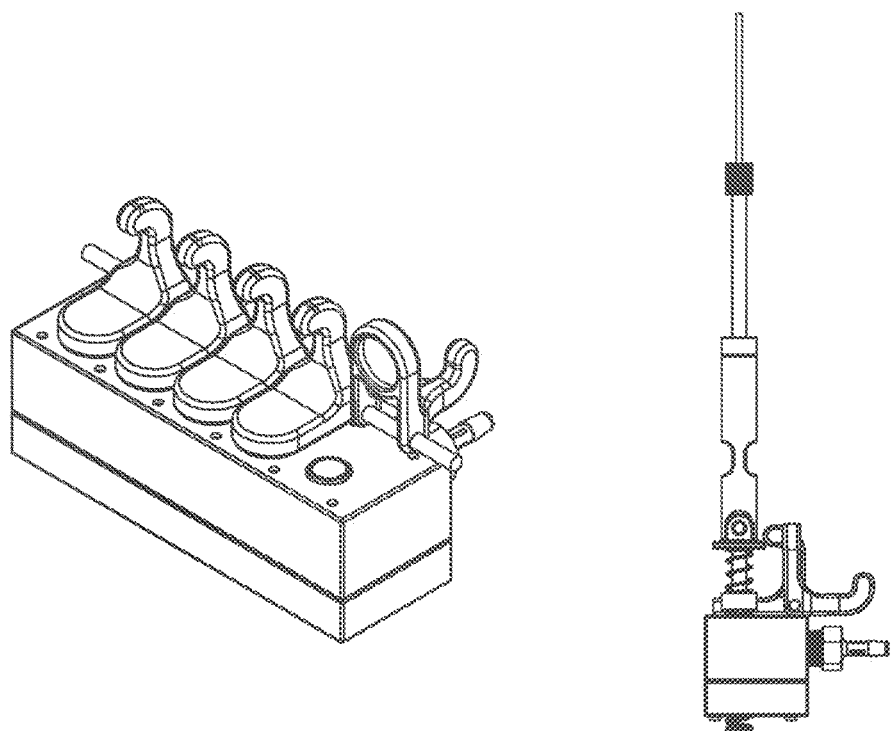
FIG. 19 shows systems for supplying sample fluids and cleaning.
Figure 20:
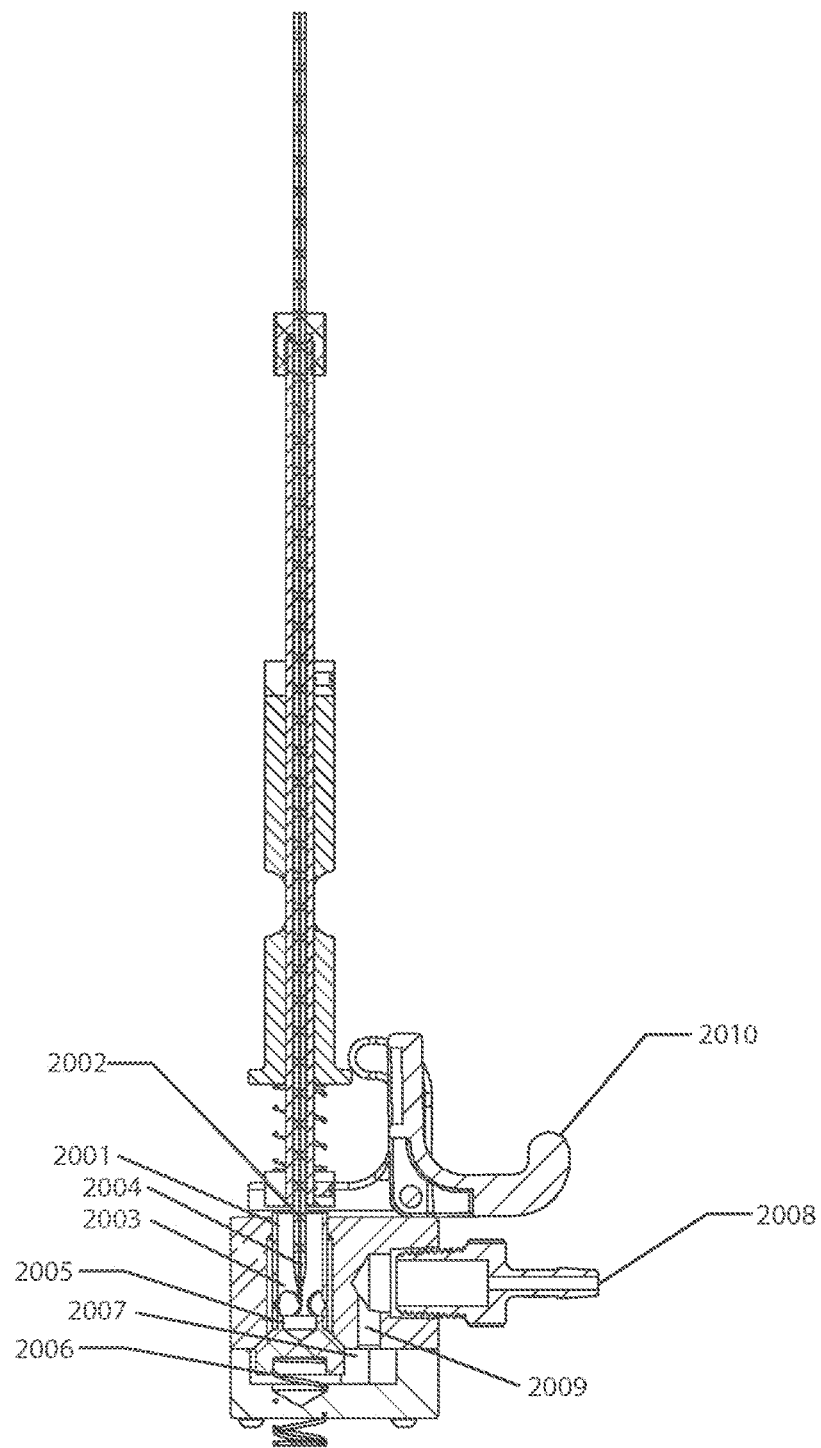
FIG. 20 shows a self-filling system for applying cleaning fluids.

FIG. 19—System for supplying cleaning fluids and FIG. 20—Self-filling system for supplying cleaning fluids FIGS. 19 and 20 show a system for providing cleaning fluids in the present system. The system comprises at least one cleaning fluid reservoir 2001 that comprises a port 2002 and an internal volume 2003. An aspiration tip 2004 is positioned into the cleaning fluid reservoir 2001 through the port 2002, where it pushes on a surface 2005 and compresses a spring 2006 that opens a valve 2007, allowing cleaning fluid to pass through a cleaning fluid inlet 2008 into a cleaning fluid conduit 2009. The cleaning fluid inlet 2008 is vertically positioned such that the volume of cleaning fluid allowed to pass into the cleaning fluid reservoir 2001 is limited to that volume at which the vertical position of the surface of the cleaning fluid in the cleaning fluid reservoir 2001 is equal to the vertical position of the cleaning fluid inlet 2008. In certain embodiments, a first volume of cleaning fluid may be aspirated while the valve 2007 is open, allowing additional cleaning fluid to flow through the cleaning fluid inlet 2008. In certain embodiments, the first volume is zero. The aspiration tip 2004 is positioned vertically such that the valve closes, and a portion of the cleaning fluid is aspirated into the aspiration tip 2004. In certain embodiments, all of the cleaning fluid in the cleaning fluid reservoir 2001 is aspirated into the aspiration tip 2004. In certain embodiments, the valve is actuated by direct pressure of the end of the aspiration tip 2004 on the surface 2005. In other embodiments, the valve is actuated by pressure of an attachment to the outer wall of the aspiration tip 2004 on the surface 2005. In certain embodiments, the system additionally comprises a cover 2010 that may cover the cleaning fluid reservoir 2001 when it is not occupied by the aspiration tip 2004, reducing the possibility for environmental contamination. In certain embodiments, the cover 2010 is automatically actuated. In certain embodiments, the system additionally comprises at least one reservoir of cleaning fluids vertically positioned above and in fluid communication with the cleaning fluid inlet 2008.

Figure 89:
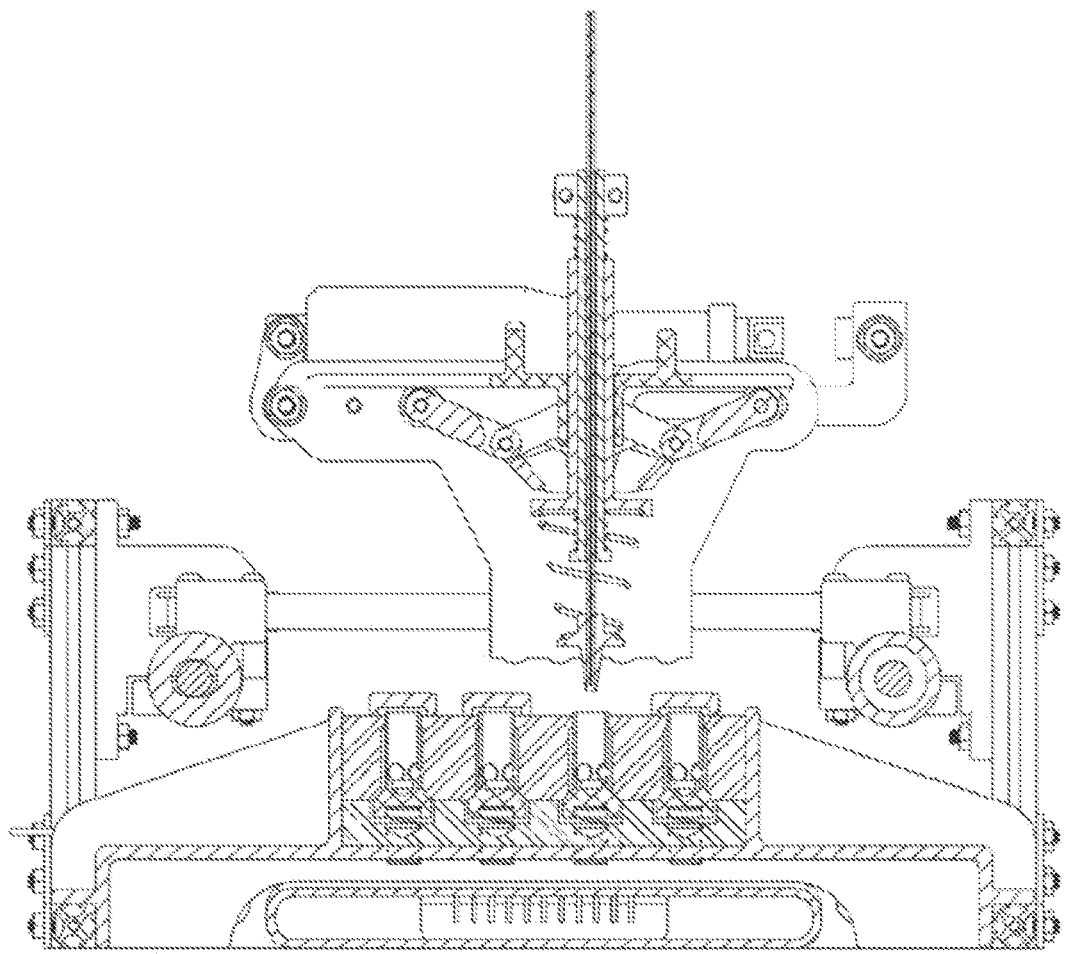
FIG. 89 shows a sampler intake comprising a sharp, hard tube for breaking through a seal and a sampling tube.

The sampling system may be positioned by mounting the carriage on a position actuator. See e.g. FIG. 89. In some instances, the carriage is linearly positioned over a single dispersed phase reservoir comprising sample (e.g. a PCR tube) or a linear array of single dispersed phase reservoirs comprising sample (e.g. a PCR strip). The reservoirs of additional dispersed phases may be positioned in the same linear array. The carriage may be moved back and forth and positioned over the dispersed phase to be injected. The sampling system may be actuated such that the sampling tube contacts the bottom of the dispersed phase reservoir for injection. The linear motion may be achieved using a lead screw/lead nut combination. In some instances, the sampling system comprises physical stops, stop sensors, limit switches, or other stopping mechanisms. In some instances, the sampling system runs in an open loop. In some instances, a belt and pulley system or a linear actuator is used.

In some instances, the carriage comprises two degrees of positioning freedom. The reservoirs of dispersed phase may comprise sample are arranged in a two-dimensional array (e.g. a microwell plate), and the reservoirs of additional dispersed phases are positioned so that the sampling system samples the additional dispersed phases in between sampling the dispersed phase comprising sample. The positioning may be achieved by a pair of lead screws/lead nuts, a belt and pulley system, or a linear actuator. Exemplary belt and pulley systems include, but are not limited to, H-bot pulley, direct belt drive, or Core XY pulley. In some instances, the sampling device comprises a filter.

Figure 21:
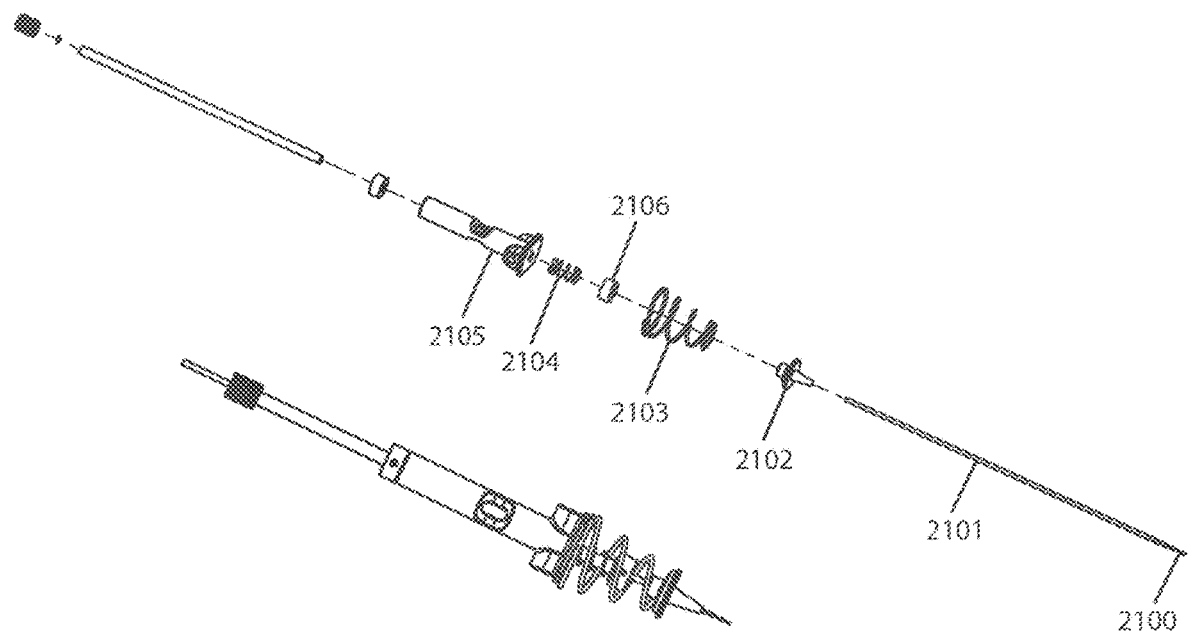
FIG. 21 shows a fluid aspirator.

FIG. 21—Fluid aspirator FIG. 21 shows a system for aspirating a fluid. The system comprises an aspiration conduit 2010 with an aspiration tip 2100, a seal piercer 2102, a first compliance spring 2103, a second compliance spring 2014, and an outer housing 2105. The seal piercer 2102 has a conical end that concentrically surrounds the aspiration conduit 2101 in a region near the aspiration tip 2100 and comprises a mechanical stop surface 2106. To aspirate a fluid, the entire assembly is vertically actuated toward the top surface of a fluid container until the mechanical stop surface 2106 contacts an upper surface of the fluid container. If the fluid container comprised a seal, the seal piercer 2102 breaks the seal. At the point that the mechanical stop surface 2106 contacts the upper surface of the fluid container, vertical motion of the seal piercer 2102 is arrested, but the first compliance spring 2103 provides compliance to allow the aspiration conduit 2101 to continue vertical motion. In certain embodiments, vertical motion is stopped when the aspiration conduit 2101 is submerged in the fluid contents of the fluid container. In certain embodiments, vertical motion is not stopped until the aspiration conduit 2101 contacts the bottom surface of the fluid container. Vertical motion of the outer housing may continue 2105 without motion of the aspiration conduit 2101 due to the compliance of the second compliance spring 2104. Such embodiments remove the requirement that the vertical position of the bottom of the fluid container be known to allow for maximal aspiration of fluid, avoidance of mechanical damage to the aspirator tip, or both.

Figure 22:
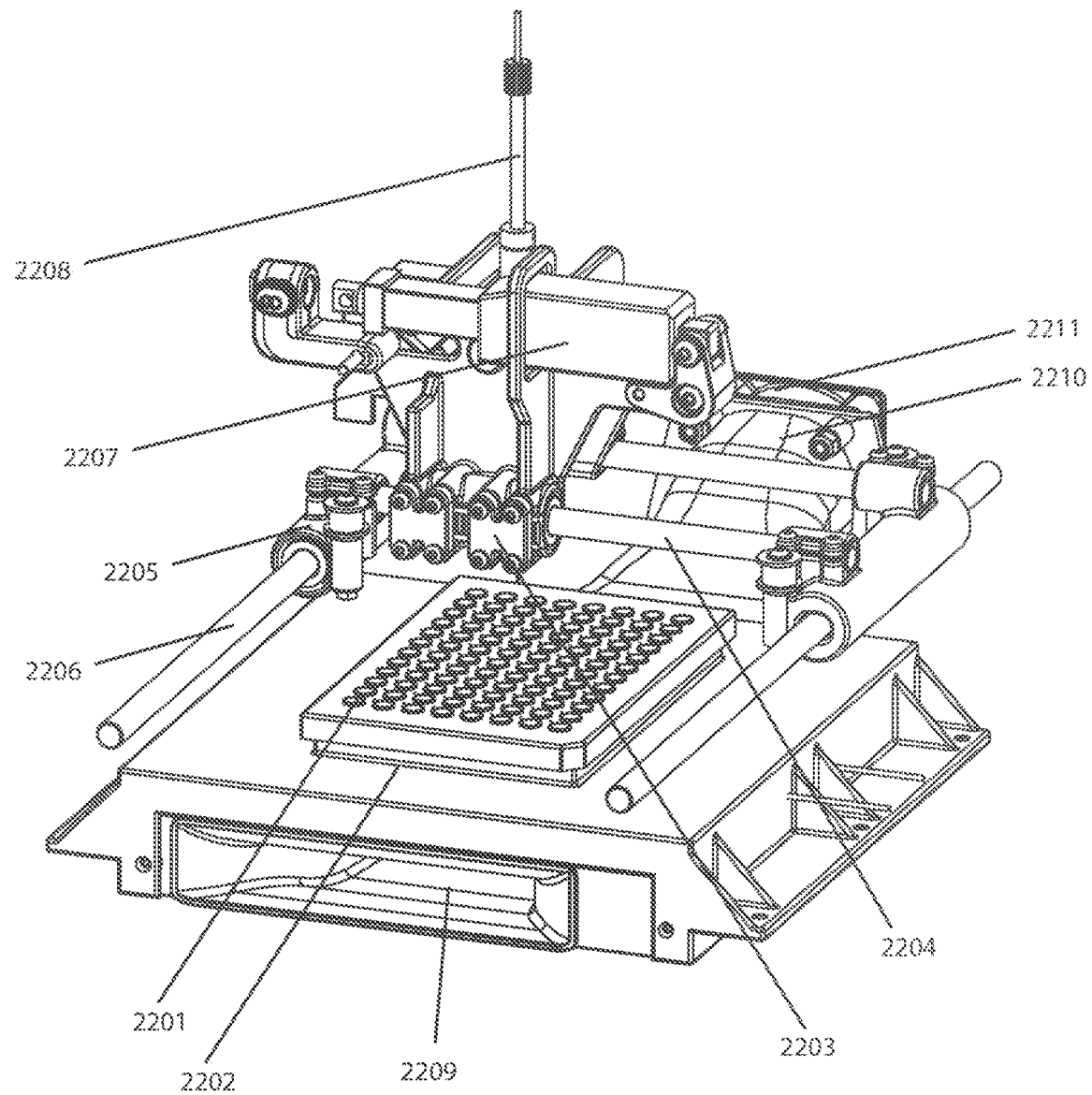
FIG. 22 shows a system for aspirating fluid.

FIG. 22—System for aspirating fluid FIG. 22 shows a system for aspirating fluids. The system comprises at least one fluid container 2201, a fluid container holder 2202, a first axis carriage 2203, a first axis drive 2204, a second axis carriage 2205, a second axis drive 2206, a vertical actuator 2207, and an aspiration conduit 2208. The fluid container 2201 contains fluids to be aspirated. In some embodiments, the fluid contents of the fluid container 2201 comprise dispersed phase, e.g., samples as described further herein. The first axis drive 2204 creates motion of the first axis carriage 2203 in a first axis and the second axis drive 2206 creates motion of the second axis carriage 2205. The second axis carriage holds the aspiration conduit 2208, and combined motion of the first axis drive 2204 and the second axis drive 2206 allow for arbitrary positioning of the aspiration conduit 2208 on the plane created by the first and second axes. In certain embodiments, the first and second axis drives are a screw/nut combination turned by a motor. In certain embodiments, the first and second axis drives are directly positioned by belts. In a certain embodiments, movement of a first belt positions the first axis carriage 2203 and movement of the second belt positions the second axis carriage 2205. In certain embodiments, two belts are arranged in an H-bot arrangement such that the combined motions of the two belts create movements of the first axis carriage 2203 and the second axis carriage 2205 together. Motors may be any suitable motors; in certain embodiments, the motors are DC brushed motors, DC brushless motors, or stepper motors. Motors may be operated in open-loop or closed-loop control. In certain embodiments, the system additionally comprises mechanical or electro-mechanical stops to prevent positioning the system beyond an allowable set of bounds. In certain embodiments, the system additionally comprises limit switches to indicate when the first or second axis positions of the carriages are at allowable limits. The limit switches may be any suitable switches; in certain embodiments, the limit switches are mechanical switches, optical interrupters, or proximity sensors. The vertical actuator 2207 moves the aspiration conduit 2208 in the vertical position, allowing it to be inserted into fluid containers for the purpose of aspirating fluids. In certain embodiments, the vertical actuator comprises a linear actuator and rotational motion-translation system. The vertical actuator may be any suitable actuator; in certain embodiments, the vertical actuator comprises a scotch yoke, rack-and-pinion, linear-actuator, or linear-belt drive.

In certain embodiments, the system additionally comprises an air intake 2209, an air outlet 2210, and an air fan 2211 for generating air flow between the air intake and air outlet. In certain embodiments, the air fan 2211 is closer to the air outlet 2210 than the air inlet 2209. In other embodiments, the air fan 2211 is closer to the air inlet 2209 than the air outlet 2210. The airflow may be used to remove thermal energy from the underside of the fluid container holder 2202. In certain embodiments, the system further comprises a thermoelectric cooler such that the temperature of the fluid container 2201 may be held below a maximum temperature and heat from the thermoelectric cooler may be removed by the airflow. In some embodiments, the maximum temperature is less than 27 C, less than 25 C, less than 21 C, less than 17 C, less than 15 C, less than 10 C, or less than 5 C. Maintaining a reduced temperature in the fluid container 2201 may slow or prevent unwanted chemical or physical reactions in the fluid contents of the fluid container 2201 prior to fluid aspiration.

Figure 23:
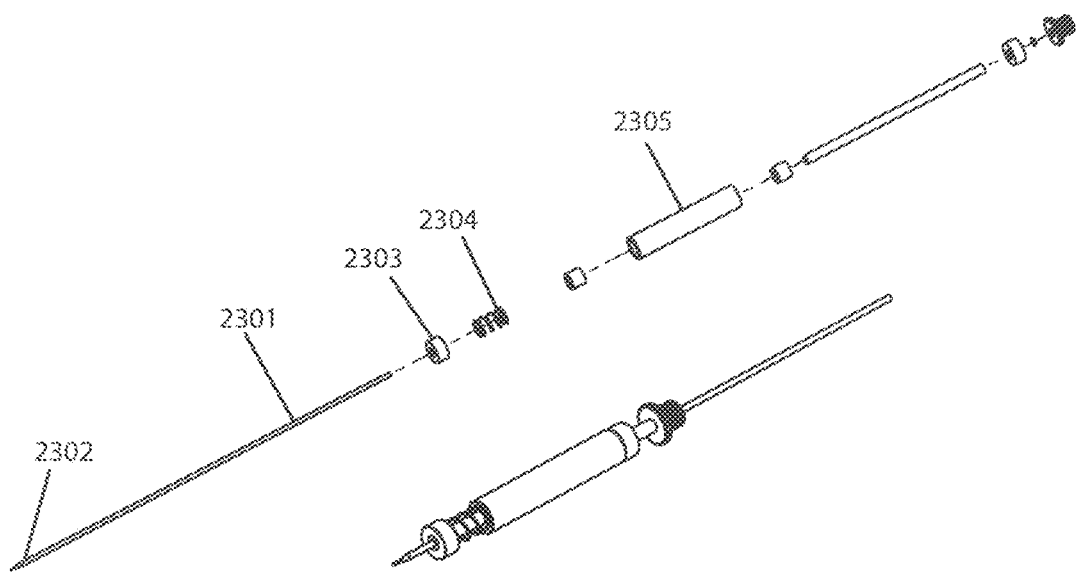
FIG. 23 shows a fluid aspirator.

FIG. 23—Fluid aspirator FIG. 23 shows a system for aspirating a fluid that eliminates the need to precisely position an aspiration tip, comprising an aspiration conduit 2301, an aspiration tip 2302, a mechanical counter-force surface 2303, a compliance spring 2304, and an outer housing 2305. The fluid aspirator is actuated into a fluid container until the aspiration tip 2302 contacts the bottom surface of the fluid container. At this point, compliance provided by compression of the compliance spring 2304 between the mechanical counter-force surface 2303 and the outer housing 2305 allows for continued travel of the outer housing 2305 without applying significantly increased forces to the aspiration tip 2302. In certain embodiments, positioning of the aspiration tip 2302 at the bottom of a fluid container is important to aspirate as much of the fluid contents of the fluid container as possible. This system reduces the need to know the vertical position of the aspiration tip 2302 accurately, as it may be guaranteed to be in contact with the bottom surface of the fluid container when the compliance spring is compressed. In certain embodiments, the system additionally comprises a force sensor such that a signal from the force sensor indicates when compression of the spring increases, allowing for detection of when the aspiration tip 2302 is in contact with the bottom of the fluid container. In certain embodiments, the aspiration tip 2302 is subsequently vertically positioned upward of the bottom of the fluid container once the bottom surface has been located prior to aspiration.

Figure 24:
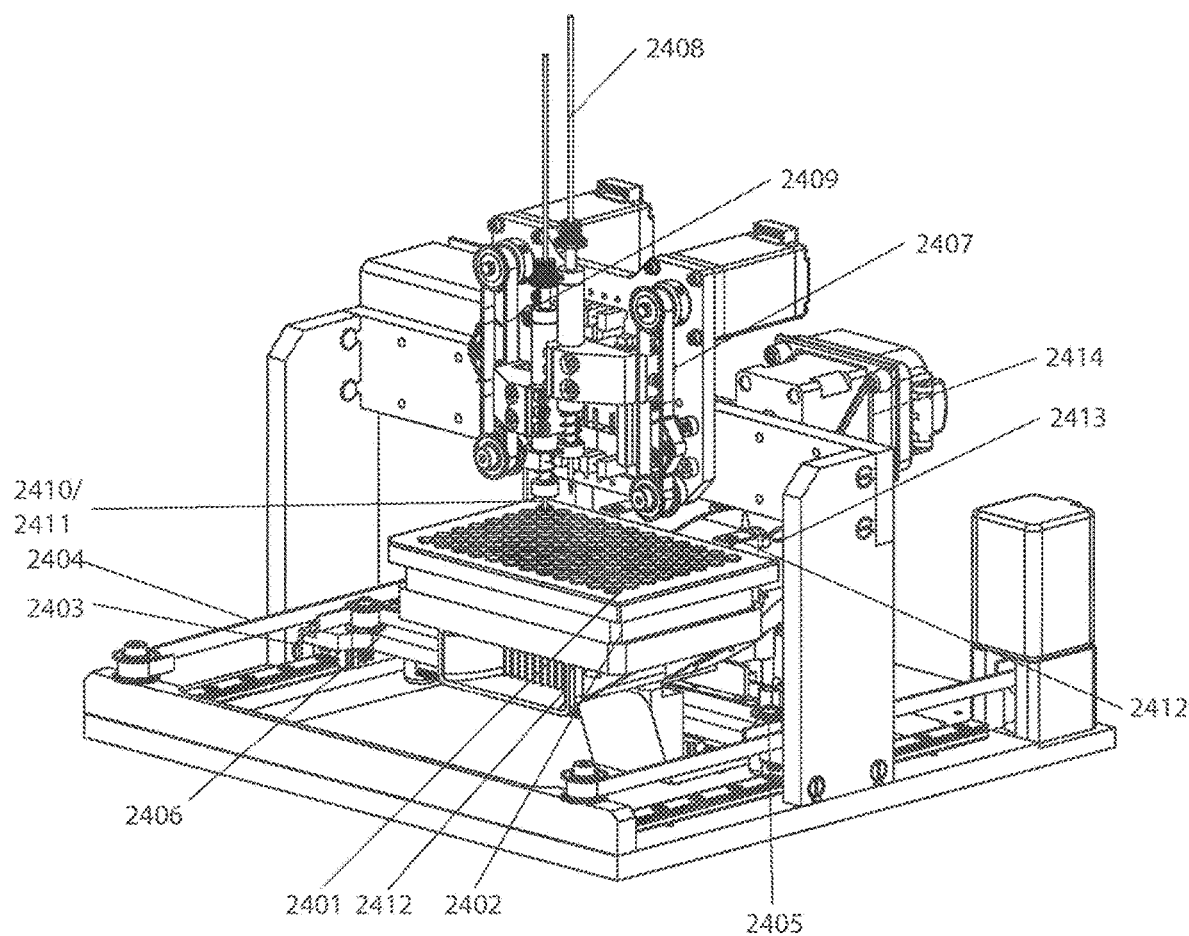
FIG. 24 shows a system for aspirating a fluid.

FIG. 24—System for aspirating a fluid FIG. 24 shows a system for aspirating fluid comprising at least one fluid container 2401, a fluid container holder 2401, a first axis carriage 2403, a first axis drive 2404, a second axis carriage 2405, a second axis drive 2406, a first vertical actuator 2407, and an aspiration conduit 2408. The fluid container 2401 contains fluids to be aspirated. In some embodiments, the fluid contents of the fluid container 2401 comprise dispersed phase, such as samples, e.g., as described herein. The first axis drive 2404 creates motion of the first axis carriage 2403 in a first axis and the second axis drive 2406 creates motion of the second axis carriage 2405. The second axis carriage holds the fluid container holder 2403, and combined motion of the first axis drive 2404 and the second axis drive 2406 allow for arbitrary positioning of the fluid container holder 2402 on the plane created by the first and second axes. In certain embodiments, the fluid container holder may be positioned so that a user may place a fluid container 2401 in the fluid container holder 2402. In certain embodiments, the first and second axis drives are a screw/nut combination turned by a motor. In certain embodiments, the first and second axis drives are directly positioned by belts. In certain embodiments, movement of a first belt positions the first axis carriage 2403 and movement of the second belt positions the second axis carriage 2405. In certain embodiments, two belts are arranged in an H-bot arrangement such that the combined motions of the two belts create movements of the first axis carriage 2403 and the second axis carriage 2405 together. Motors may be any suitable motors; in certain embodiments, the motors are DC brushed motors, DC brushless motors, or stepper motors. Motors may be operated in open-loop or closed-loop control. In certain embodiments, the system additionally comprises mechanical or electro-mechanical stops to prevent positioning the system beyond an allowable set of bounds. In certain embodiments, the system additionally comprises limit switches to indicate when the first or second axis positions of the carriages are at allowable limits. Any suitable limit switches may be used; in certain embodiments, the limit switches are mechanical switches, optical interrupters, or proximity sensors. The first vertical actuator 2407 moves the aspiration conduit 2408 in the vertical position, allowing it to be inserted into fluid containers for the purpose of aspirating fluids. In certain embodiments, the vertical actuator comprises a linear actuator and rotational motion-translation system. Any suitable vertical actuator may be used; in certain embodiments, the vertical actuator comprises a scotch yoke, rack-and-pinon, linear-actuator, or linear-belt drive.

Figure 25:
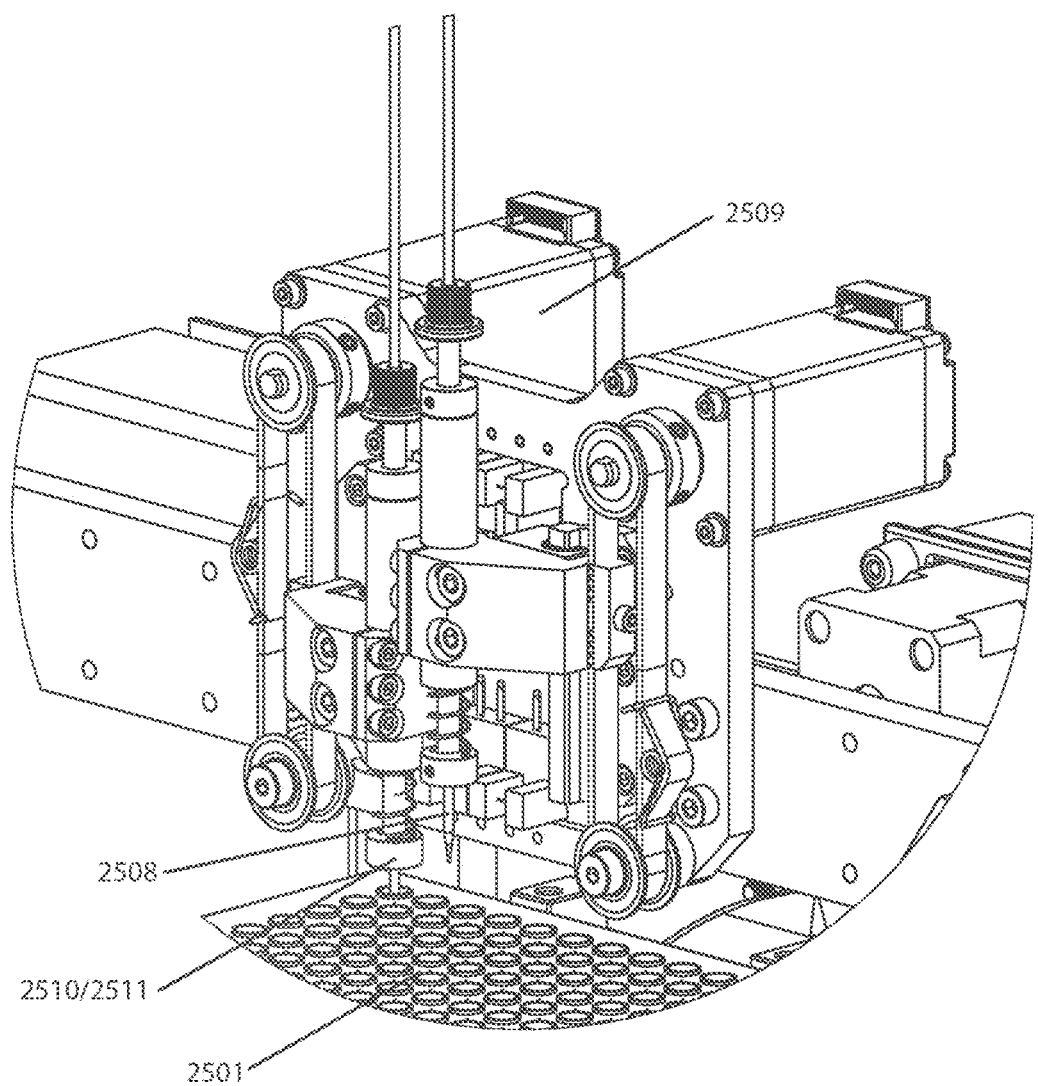
FIG. 25 shows a system with second vertical actuator.

In certain embodiments, the system comprises a second vertical actuator 2409 (FIG. 25). In certain embodiments, the system comprises a seal punch 2510 positioned by the second vertical actuator 2509 such that the seal punch may pierce seals covering the at least one fluid container 2501. In certain embodiments, the system comprises a second aspiration conduit 2511 positioned by the second vertical actuator 2509 such that the second aspiration conduit may aspirate fluid contents from or dispense fluid contents into the at least one fluid container 2501. In certain embodiments, the system comprises both the seal punch 2510 and the second aspiration conduit 2511.

In certain embodiments, the second aspiration conduit may aspirate at least one cleaning fluid contents that have been dispensed into the at least one fluid container 2501 by the first aspiration conduit 2508. In certain embodiments, the second aspiration conduit aspirates at least one cleaning fluid into a cleaning fluid waste reservoir.

In certain embodiments, the system additionally comprises an air intake 2512, an air outlet 2513, and an air fan 2514 for generating air flow between the air intake and air outlet. In certain embodiments, the air fan 2514 is closer to the air outlet 2513 than the air inlet 2512. In certain embodiments, the air fan 2514 is closer to the air inlet 2512 than the air outlet 2513. The airflow may be used to remove thermal energy from the underside of the fluid container holder 2502. In certain embodiments, the system further comprises a thermoelectric cooler such that the temperature of the fluid container 2501 may be held below a maximum temperature and heat from the thermoelectric cooler may be removed by the airflow. In certain embodiments, the maximum temperature is less than 27 C, less than 25 C, less than 21 C, less than 17 C, less than 15 C, less than 10 C, or less than 5 C. Maintaining a reduced temperature in the fluid container 2501 may slow or prevent unwanted chemical or physical reactions in the fluid contents of the fluid container 2501 prior to fluid aspiration.

Figure 26:
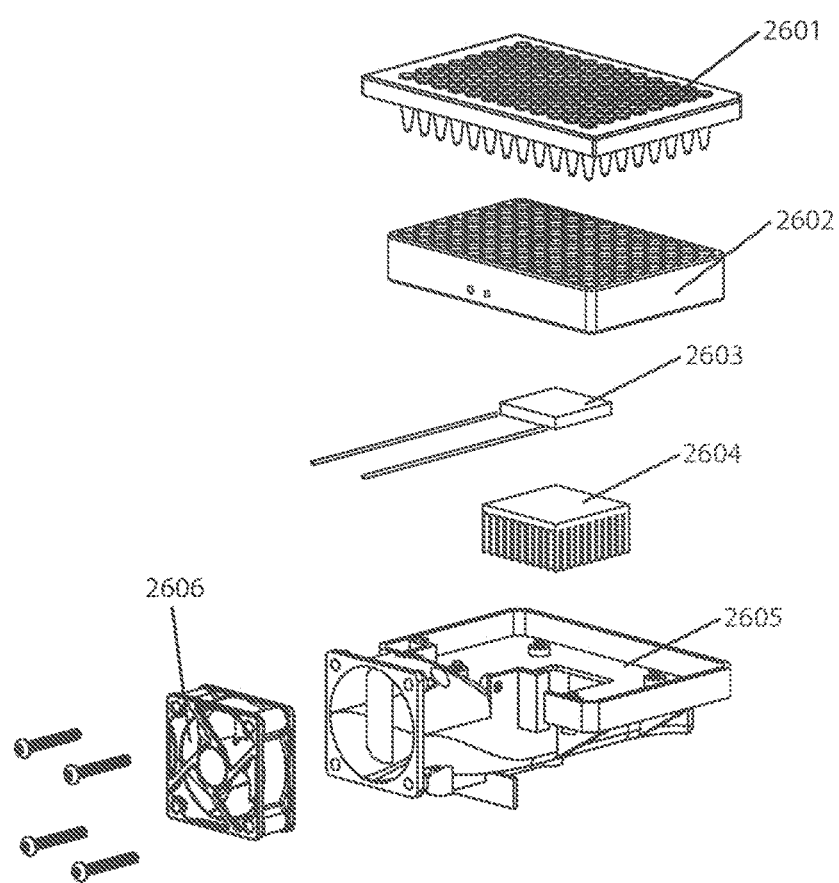
FIG. 26 shows a system for holding a fluid container.

FIG. 26—System for holding a fluid container FIG. 26 shows a system for holding a sample container comprising at least one fluid container 2601, a fluid container holder 2602, a thermoelectric cooler 2603, a heat sink 2604, an airflow assembly 2605, and a fan 2606. The fluid container 2602 holder has features such that the at least one fluid container 2601 may only be inserted into the fluid container holder 2602 in one way and that thermal contact is maintained between the fluid container holder 2602 and the at least one fluid container 2601. The fluid container can be any suitable fluid container; in certain embodiments, the fluid container is a microtiter plate, a tube strip, an individual test tube, or a cartridge. In certain embodiments, the fluid container is a 24-well plate, a 48-well plate, a 96-well plate, a 384-well plate, or a 1536-well plate. The thermoelectric cooler 2603 additionally comprises a temperature sensor and a temperature controller such that the temperature of the fluid container 2601 may be maintained in a constant temperature range. Any suitable method of control may be used; in certain embodiments, the temperature controller uses a proportional-integral method, a proportional-integral-differential method, or an on-off method of control. Maintaining the temperature of the fluid container 2601 in a constant temperature range may be beneficial to prevent biochemical or chemical reactions or physical changes to the fluid contents of the at least one fluid container 2601. In certain embodiments, the size of the temperature range is less than 5 C, less than 3 C, less than 1 C, or less than 0.1 C and the constant temperature is within the temperature range of 25 C, 20 C, 15 C, 10 C, or 5 C. The heat sink 2604 aids in heat transfer away from the thermoelectric cooler 2603 and the fan 2604 drives air through the airflow assembly to remove heat from the heat sink 2604.

In certain embodiments, the thermoelectric cooler 2603 may be run in reverse to add heat to the fluid contents of the at least one fluid container 2601 to increase the temperature of the fluid contents to an elevated temperature in order to create a biochemical, chemical, or physical change in the fluid contents of the at least one fluid container 2601. In certain embodiments, the reaction is a cellular lysis, reverse transcription, nucleic acid polymerization, protein denaturing, or any other suitable reaction. In certain embodiments, the elevated temperature is less than 96 C, less than 90 C, less than 80 C, less than 70 C. less than 60 C, or less than 50 C. In certain embodiments, multiple elevated temperatures are achieved.

FIGS. 27A, 27B, 27C, and 27D—System for cleaning a fluid aspirator FIG. 27 shows a system for cleaning a fluid aspirator comprising a body 2701, an internal volume 2702, and a port 2703. A first fluid aspirator is inserted into the port 2703 and exposed to at least one cleaning fluid. In certain embodiments, the first fluid aspirator dispenses the at least one cleaning fluid into the internal volume 2702. In certain embodiments, a second fluid aspirator dispenses the at least one cleaning fluid into the internal volume prior 2702 prior to insertion of the first fluid aspirator, and the external or internal surfaces of the first fluid aspirator may be cleaned by contact with or aspiration of the at least one cleaning fluid by the first fluid aspirator. In certain embodiments, a third fluid aspirator evacuates the at least one cleaning fluid from the internal volume 2702 after removal of the first fluid aspirator. In certain embodiments, the second and third fluid aspirator are the same aspirator. In certain embodiments, the system additionally comprises a drain 2703 for removal of the at least one cleaning fluid. In certain embodiments (FIGS. 27A and 27C) the system additionally comprises a first cleaning fluid channel 2704 with a first cleaning fluid inlet 2705 that dispenses at least one cleaning fluid into the internal volume 2702. In certain embodiments (FIGS. 27B and 27D), the system additionally comprises a second cleaning fluid channel 2706 with a second cleaning fluid inlet 2707. When the second cleaning fluid flows from the second cleaning fluid inlet 2707 through the second cleaning fluid channel 2706 into the internal volume 2702, it impinges on the tip of the first fluid aspirator so as to improve removal of at least one fluid from the outer surface of the first fluid aspirator.

Figure 28:
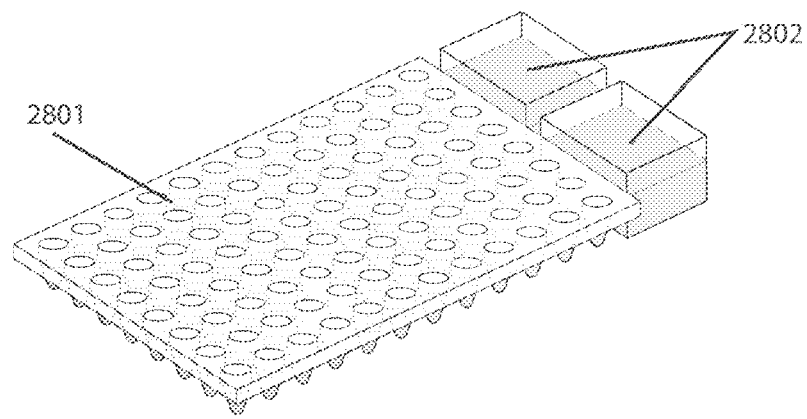
FIG. 28 shows a system for providing sample and cleaning fluids.

FIG. 28—System for providing sample and cleaning fluids FIG. 28 shows a system for providing sample and cleaning fluids comprising at least one sample container 2801 and at least one cleaning fluid container 2802. In certain embodiments, the at least one sample container is a microtiter plate and the at least one cleaning fluid container 2802 is an open tray. In certain embodiments, the microtiter plate is a 96-well plate and the system comprises two cleaning fluid containers 2802

Figure 2:
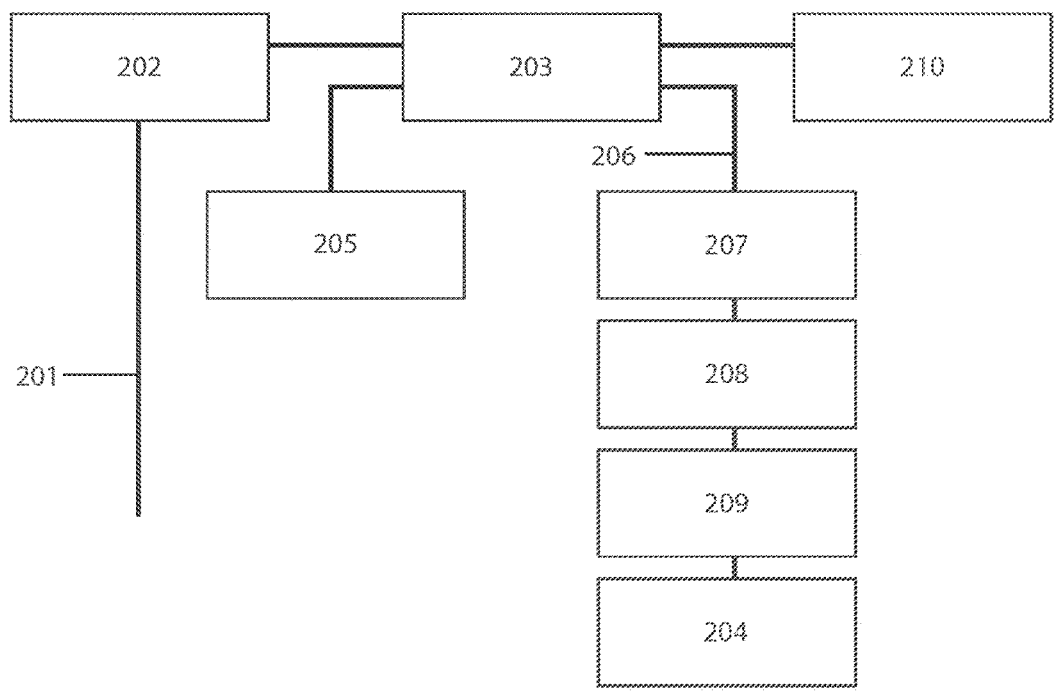
FIG. 2 shows an intake system with blowback.
Figure 3:
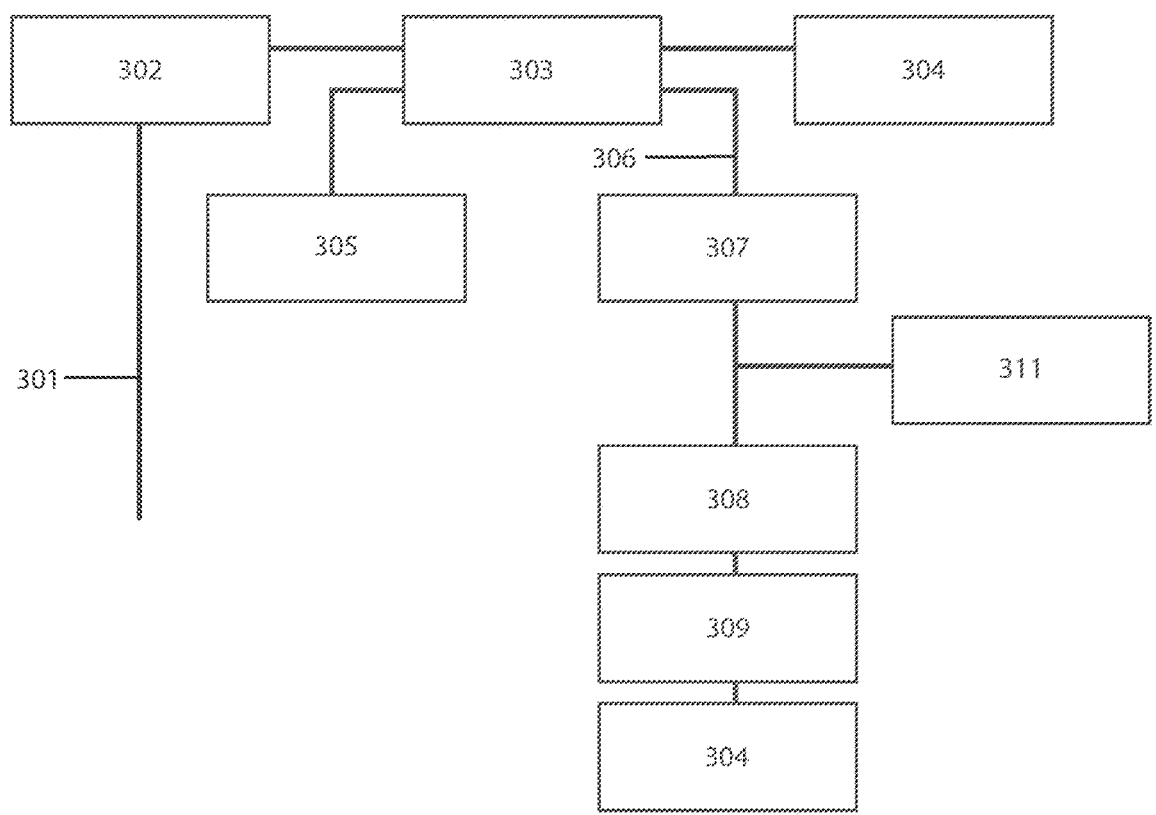
FIG. 3 shows an intake system with spacer fluid addition.

FIG. 1 shows an intake system with a waste FIG. 1 shows an embodiment of a system for conducting a process on one or more aliquots of sample fluid without cross-contamination of the sample fluids. The system comprises an intake system inlet 101, an autosampler assembly 102, an injector 103, at least one waste 104, a process continuous fluid source 105, and a process system inlet 106. The autosampler assembly 102 pulls sample fluids into the injector through the intake system inlet 101 and positions the fluids so that the process continuous fluid source 105 may displace the sample fluids into the process system inlet 106, as described elsewhere herein. Once re-positioned to be in fluid communication with the intake system, cleaning fluids may be pulled into the intake system inlet 101, displacing residual sample fluid into the waste 104, with the composition, order and amount of cleaning fluids as described elsewhere herein. The system may additionally comprise a partitioner 107 to sub-divide the aliquots of sample fluid, a reactor 108 to mediate at least one reaction on the aliquots or partitions of sample fluid, or a detector 109 to measure at least one property of the aliquots or partitions of sample fluid, or any combination thereof, each as described herein FIG. 2 shows an intake system with blowback FIG. 2 shows another embodiment of the system in FIG. 1 comprising a sample inlet 201, an autosampler assembly 202, an injector 203, and where the waste 104 is replaced by a source of purge or cleaning fluids 210. The system may additionally comprise a process continuous fluid source 205 and may comprise a partitioner 207, a reactor 208, a detector 209, and/or a process waste 204, as described in FIG. 1. During the cleaning steps, as described elsewhere herein, the purge or cleaning fluids are backflushed through the injector 203 and out the intake system inlet 201, and into a waste container, as described elsewhere herein FIG. 3 shows an intake system with spacer fluid partition FIG. 3 shows another embodiment of the system where a source of spacer fluid 311 is added on the process side of the system. The system comprises a sample inlet 301, an autosampler assembly 302, an injector 303, and a process continuous fluid source 305. The system may additionally comprise a partitioner 307, a reactor 308, a detector 309, and/or a process waste 304, as described in FIG. 1. In some embodiments, the source of spacer fluid is added after a partitioner 307, as shown. In other embodiments, the source of spacer fluid is added before or after the injector 303 but before the partitioner 307. In some embodiments, the source of spacer fluid may comprise a pump to move the spacer fluid into the process system. In some embodiments, the pump is actuated after a sample volume has been transferred through the process system elements upstream of the spacer fluid source so as to add a spacer fluid volume after the sample volume. In some embodiments, the pump is a metering pump, a positive displacement pump, a piston pump, a syringe pump, a diaphragm pump, or a peristaltic pump.

Figure 29:
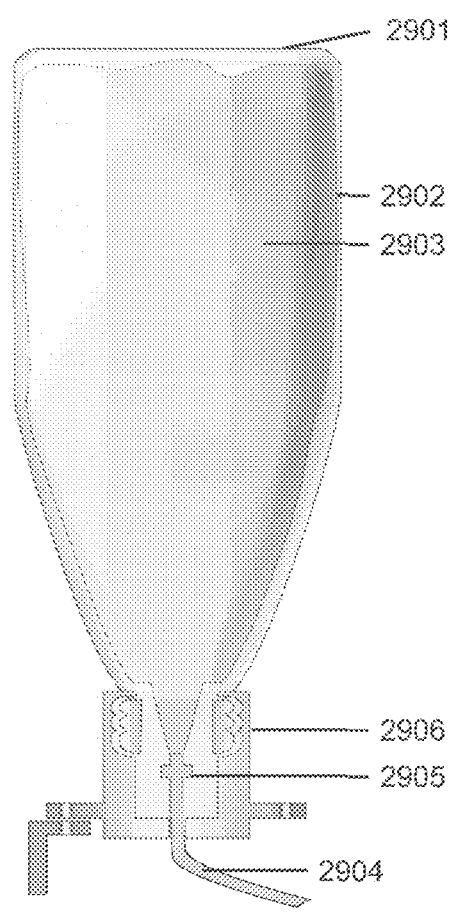
FIG. 29 shows a system for providing fluid reagents.

FIG. 29—System for providing fluid reagents FIG. 29 shows a system for providing fluid reagents comprising a rigid cartridge 2901, a collapsible bag 2902, a fluid volume 2903, a fluid delivery conduit 2904, a conduit coupling 2905 for connecting the fluid delivery conduit 2904 to the collapsible bag 2902, and a cartridge interface 2906. As fluid is delivered from the collapsible bag through the fluid delivery conduit 2904, the collapsible bag collapses, eliminating the need to vent the fluid delivery conduit 2904 to account for the reduced fluid volume. The rigid cartridge 2901 encloses the collapsible bag 2902, making it easier for users to handle. When the rigid cartridge 2901 is coupled to the cartridge interface 2906, the conduit coupling 2905 is simultaneously coupled, and when the rigid cartridge 2901 is decoupled from the cartridge interface 2906, the conduit coupling 2905 is simultaneously decoupled, eliminating the need for the user to directly couple and decouple the conduit coupling 2905, which may be difficult to do without introducing significant quantities of air into the system.

The conduit coupling can be any suitable coupling; in certain embodiments, the conduit coupling 2905 is a screw connector, a Luer connector, a press quick-disconnect connector, or a screw quick-disconnect connector. In certain embodiments, the conduit coupling 2905 has zero or very low dead volume. The collapsible bag may comprise any suitable material. In certain embodiments, the fluid delivery conduit 2904 may be a tube. The tube may comprise any suitable material. In certain embodiments, the fluid delivery conduit 2904 may have an internal volume capable of holding a minimum volume of fluid reagents. If each processing step requires an integral volume of fluid, the user may not be able to use all of the fluid in the collapsible bag 2902 because, at a point in time, an insufficient volume of fluid remains in the collapsible bag 2902 to complete all of the processing steps. By sizing the minimum volume such that the fluid delivery conduit 2904 may hold enough fluid for a minimum number of processing steps, the user can maximize usage of the fluid in the collapsible bag. In some embodiments, the minimum volume is greater than 1 mL, greater than 5 mL, greater than 10 mL, or greater than 20 mL.

Figure 30:
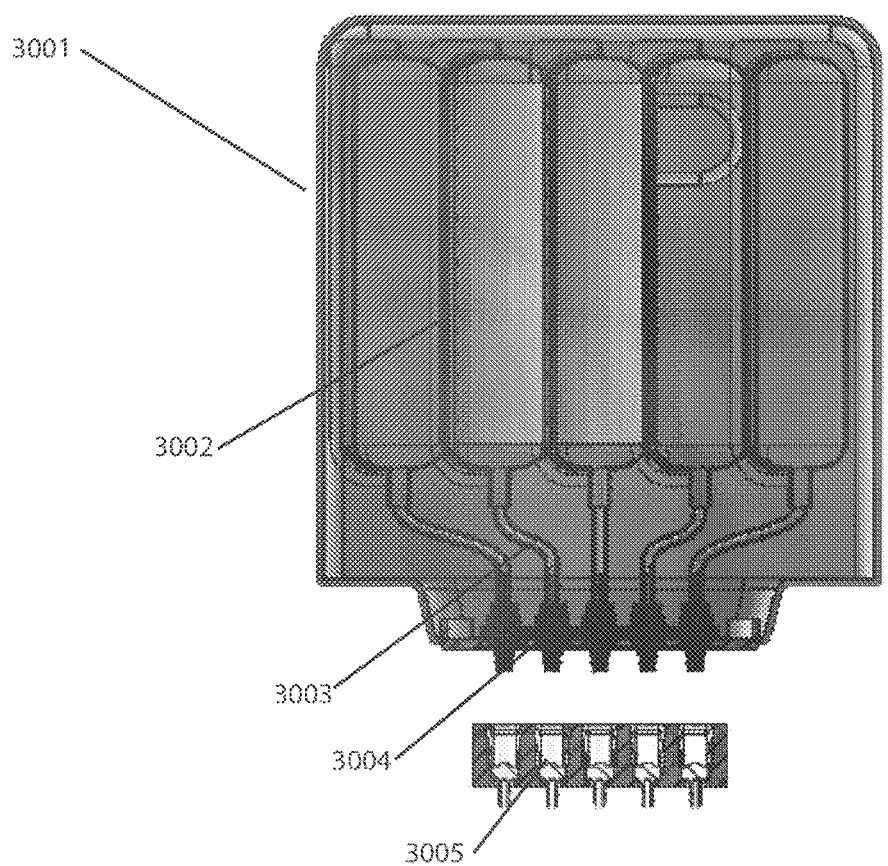
FIG. 30 shows a cartridge for supplying reagents or collecting waste.

FIG. 30. FIG. 30 shows a further embodiment where the rigid cartridge encloses a plurality of collapsible bags, each connected to a fluid conduit. This embodiment allows for the user to install multiple reagent reservoirs with a single replaceable cartridge. FIG. 30 shows embodiments of a multi-container cartridge for supplying reagents or collecting waste. The system comprises a cartridge 3001 to holds at least one fluid container 3002 with a fluid container line 3003 to connect to a primary fluid container connector 3004. In some embodiments, the fluid container 3002 comprises materials that are flexible, such that the volume of the fluid container 3002 may decrease as fluid is dispensed or increase as fluid is collected. The fluid container 3002 may be comprised of any suitable materials. In some embodiments, the fluid container comprises a polymer or a metal. The fluid container line 3003 may be comprised of any suitable material. In some embodiments, the fluid container line 3003 comprises a polymer or a metal. The cartridge 3001 may comprise a vent hole to allow air to enter or leave the cartridge as the volume of the at least one primary fluid container 3002 increases or decreases. The primary fluid container connector 3004 interfaces to a secondary fluid container connector 3005 that interfaces with one or more conduits on the intake system and/or process system. In some embodiments, the primary fluid container connector 3004 and secondary fluid container connector 3005 are quick disconnect connectors. In some embodiments, the primary fluid container connector 3004 and secondary fluid container connector 3005 are dry-break connectors so as to minimize fluid leak or loss when connecting or disconnecting the cartridge 3001. In some embodiments, the fluid container 3002 additionally comprises one or more additional outlets or vents to allow for draining or addition of fluid to the container. In some embodiments, the cartridge 3001 holds two or more fluid containers, each with a fluid container line, a primary fluid connector, and a secondary fluid connector, such that a user may connect all of the fluid connectors simultaneously when connecting any one fluid connector. In some embodiments, the fluid containers comprise reagents pre-loaded for use in the intake or process systems. In some embodiments, the one or more fluid containers are for collecting waste. In some further embodiments, the one or more fluid containers comprise a denaturing fluid for denaturing at least one detectable or potentially detectable component that may be added to the fluid containers 3002 in the operation of the intake and/or process system.

Thus, an external reservoir system may be used for systems and methods as described herein. The external reservoir may comprise a polymer bag, a tubular channel, or a luer-lock fitting, or other materials or components as described herein. In some instances, the polymer bag is a collapsible polymer bag. In some instances, the collapsible polymer bag allows fluid to flow by gravity into the reservoir as needed without air exchange back into the bag. In some instances, the polymer bag is placed inside a hard-sided bottle. The hard-sided bottle may have a threaded interface at the bottom that holds the luer-fitting for the polymer bag in a fixed position. In some instances, a mating threaded interface above the reservoir holds a mating luer-fitting in a fixed position.

Figure 31:
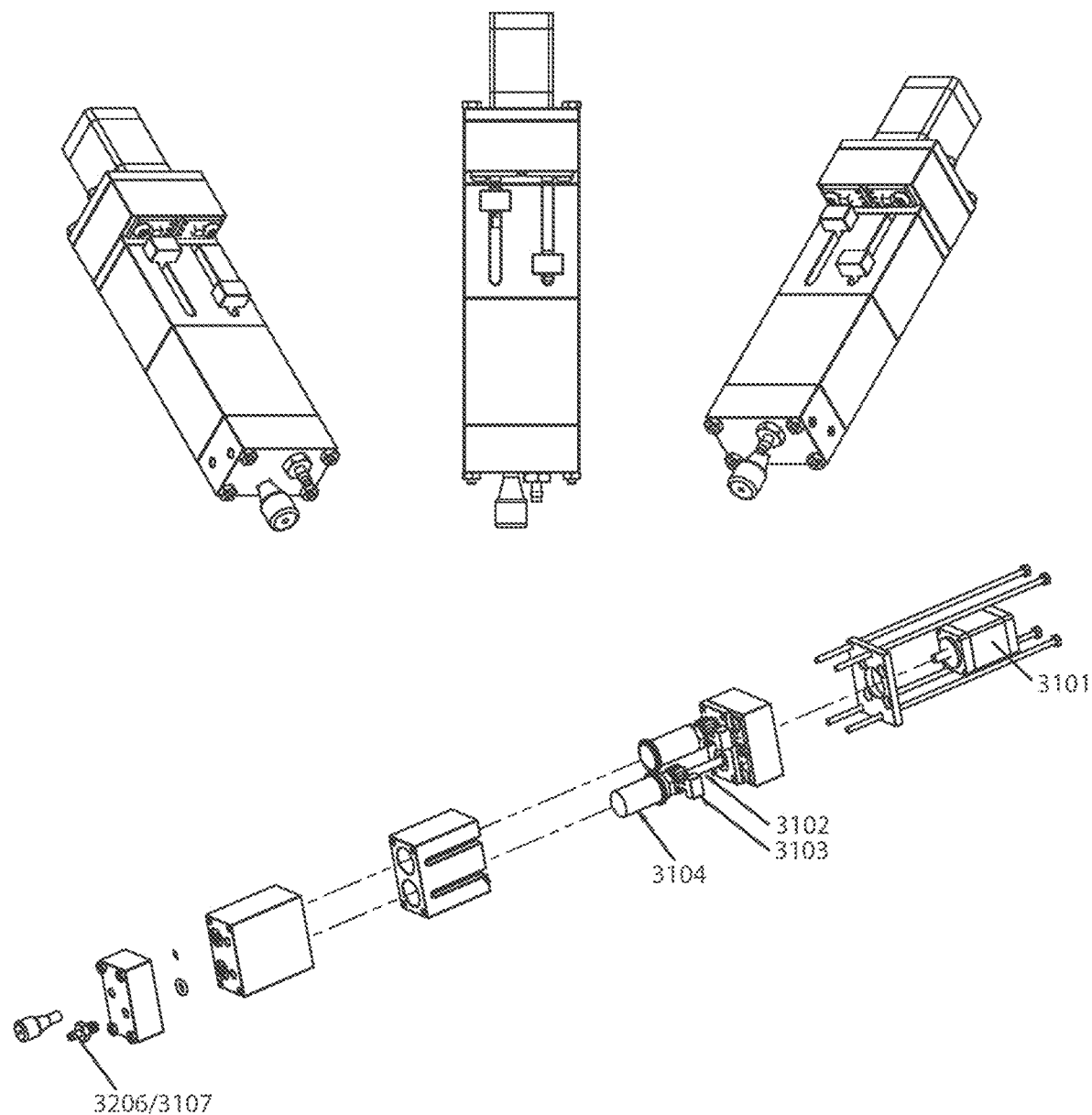
FIG. 31 shows a syringe pump.

FIG. 31 (syringe pump) FIG. 31 shows an embodiment of a system for pumping fluid phases through conduits within the system. The system comprises a motor 3101 that is coupled to a lead screw 3102, such that rotational motion from the motor is transferred to motion of the lead screw. A lead nut 3103 is threaded over the lead screw and is coupled to a piston 3104, that is mounted inside of a bore or cavity. As the lead screw rotates the piston travels along the lead screw, either towards the motor as the motor spins in one direction and away from the motor as it spins in the opposite direction. As the piston moves through the bore it either pulls fluid into the bore or pushes fluid out of the bore. The bore has inlet 3106, and outlet 3107 ports that can couple to tubing or other system components such as fluid reservoirs. The substrate of the bore may be comprised of any suitable material that is chemically resistant to the system fluids contained within the syringe pump.

In certain embodiments the system contains an inlet check valve at the inlet port and an outlet check valve at the outlet port. These check valves are oriented such that the inlet check valve will be opened, and the outlet check valve closed when the piston is being driven towards the motor such that fluids will flow into the bore from through inlet and will not exit the outlet. While the piston is being driven away from the motor the inlet check valve will seat closed and the outlet check valve will crack open allowing fluid to be pushed. In certain embodiments, the inlet to the syringe pump is connected to a reagent supply reservoir. In certain embodiments, the inlet port of the syringe pump is connected to a switching valve that is also connected to multiple reagent reservoirs such that the switching valve can position itself to allow one of multiple reagent reservoirs to feed into the syringe pump.

The motor may be any suitable motor; in certain embodiments the motor is a stepper motor, such a motor might be controlled such that it moves in micro stepping mode. In certain embodiments each micro step translates to a fluid displacement that is, e.g. 1%, 2%, 5%, 10%, 25%, 50%, 100%, 200% the size of the dispersed phase partitions that are created by the system partitioner. In certain embodiments a gear box is coupled between the motor shaft and the lead screw. In certain embodiments the motor is a brushed DC motor, or a brushless DC motor, or a servo motor.

In some embodiments an encoder is included as part of the assembly such that it can provide feedback to the rotation of the motor shaft. The encoder output can be used to help control the speed of the motor rotation, providing control over the rate of fluid flow into and out of the syringe pump. In certain embodiments, the fluids are pumped through the system not with a positive displacement pump, but with a pneumatic system where a pressure head is created to drive fluids to desired locations.

Further components can include one or more of a limit switch to home or find absolute position, an encoder to store memory of absolute position, an anti-backlash nut, various connector styles, orientation to avoid air being pulled into the syringe pumps, o-rings, a flag to prevent rotation, materials, multiway valves such as 3 way valves. In certain embodiments pump is configured to provide nonpulsatile flow, such that the flow is consistent enough to drive droplet formation where the coefficient of variation of droplet size is less than 5%, 4%, 3%, 2%, 1%.

In certain embodiments, 2 or more syringe pumps are contained within the system to drive the same system fluid such that if either pump fails the system can still dispense said system fluid. In certain embodiments pumps can be controlled such that one pump will stop dispensing while a second pump starts dispensing the same fluid into towards the same channel such that the fluid flow is not disrupted for more than 10 ms, 100 ms, 1 s, 5 s, 10 s or 20 seconds.

Figure 32:
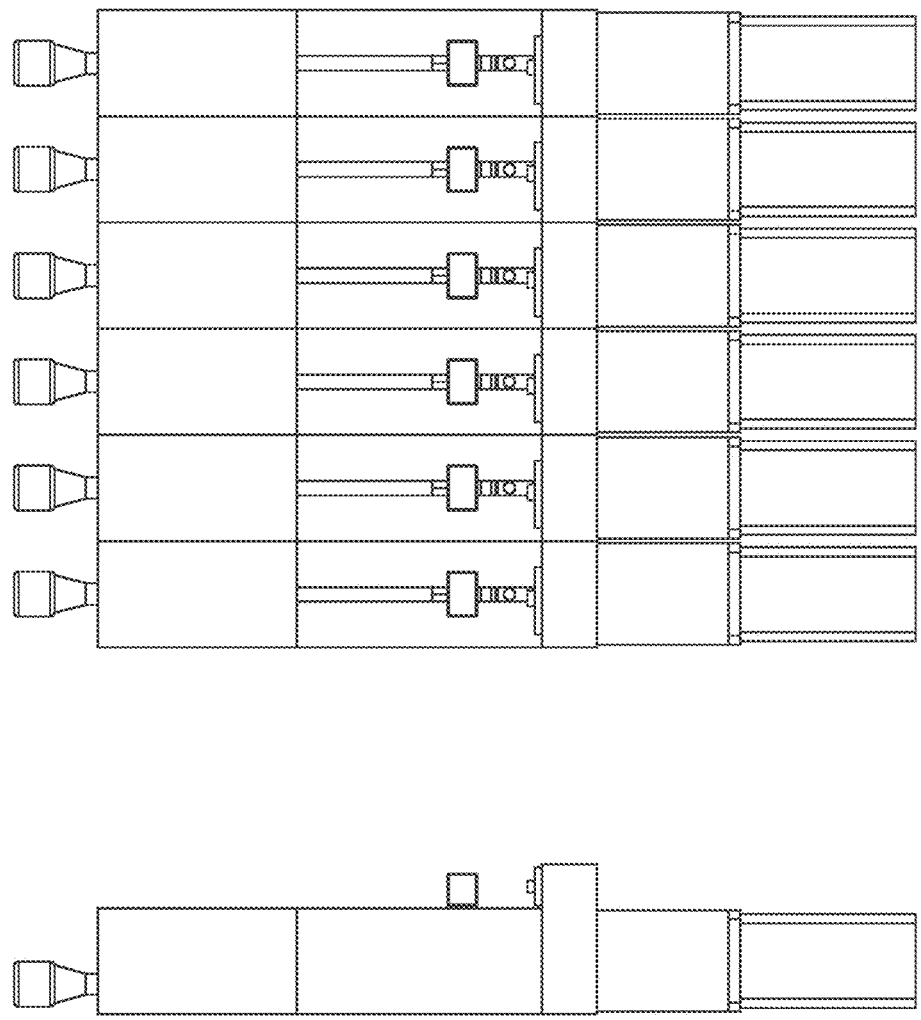
FIG. 32 shows a bank of syringe pumps.
Figure 87:
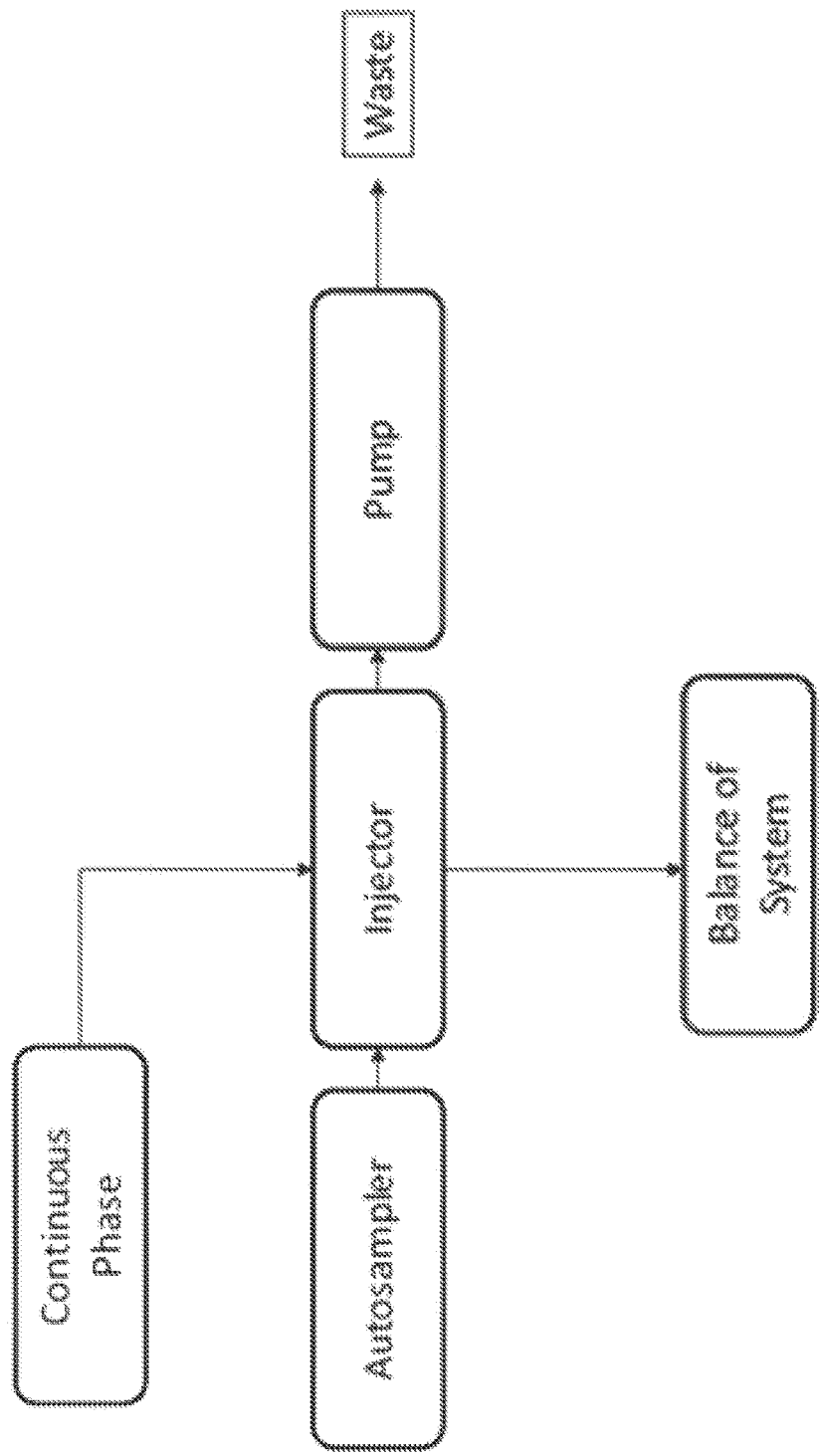
FIG. 87 shows a diagram comprising a sampler, pump, continuous phase, and inject.
Figure 88:
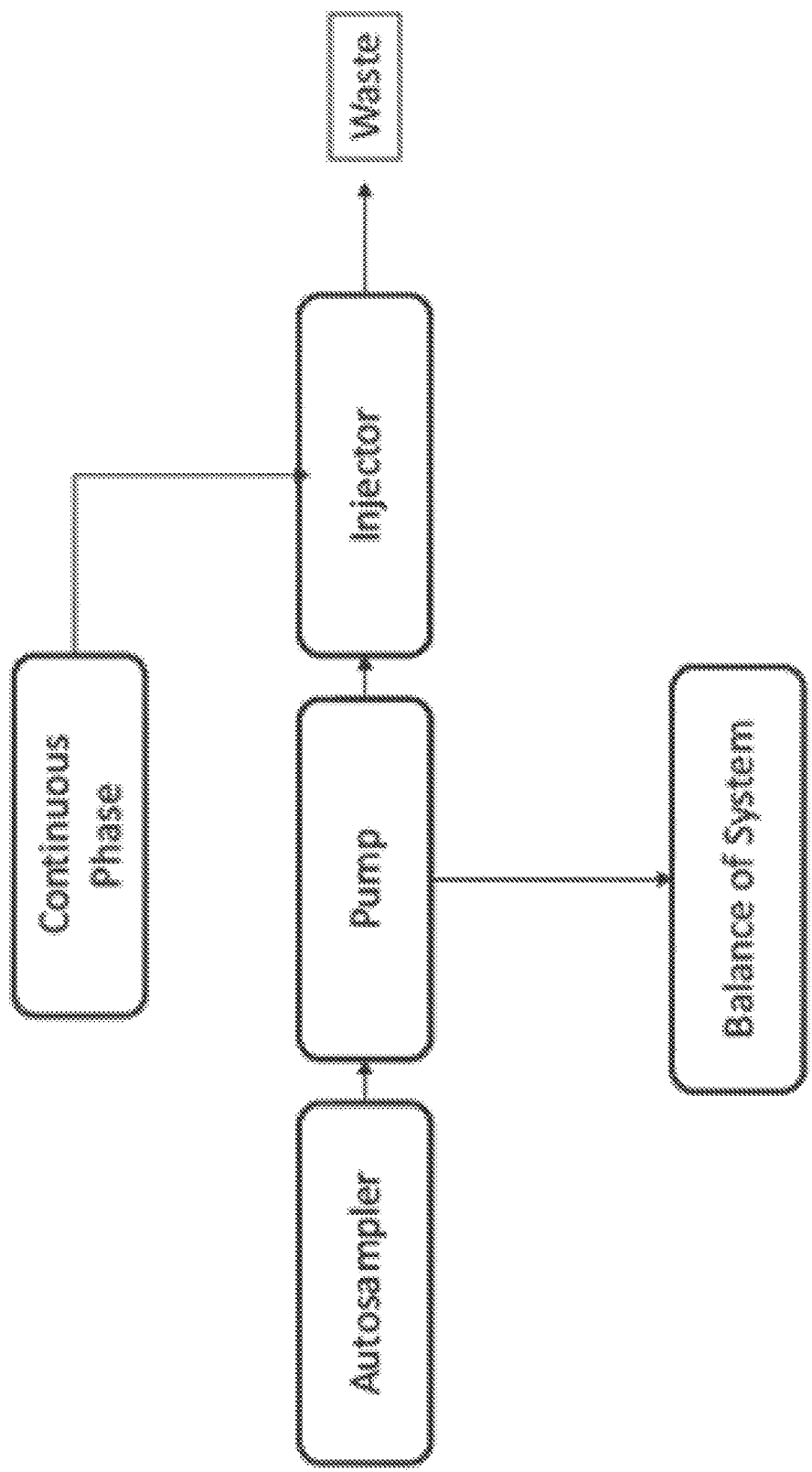
FIG. 88 shows a diagram comprising a sampler, pump, continuous phase, and inject.

FIG. 32 (bank of syringe pumps) In some embodiments at least 2, 3, 4, 5, 6, 7, 8, 9, or 10 syringe pumps are included in the system, e.g., to drive different system fluids and deliver them to components of the system. The design of the syringe pump allows large numbers of individual pumps to be arranged without taking up significant amount of space that would drive an increase in the overall system footprint Thus, described herein are systems and methods for serial flow emulsion reactions comprise use of a sampling device, wherein the sampling device comprises a pump. The pump may be used to provide a driving force to move fluid from the fluid injector, the decontamination fluid reservoir, the purge fluid reservoir, or combinations thereof into the injection device. See e.g. FIGS. 87-88. The pump may be located upstream or downstream of the injector. In some instances, the pump is a peristaltic pump. In some instances, the pump is reversible In some instances, the pump comprises a fluid channel that provides a physical barrier between mechanical elements of the pump and the working fluids of the system. In some instances, a pump motor is actuated by a controller to move a set volume of fluid from the fluid injector, fluid reservoir, purge fluid reservoir, or combinations thereof into the injection device. In some instances, the pump motor is a stepper motor. In some instances, the pump motor is a servo motor with a rotational encoder. In some instances, the controller operates in an open-loop mode. In some instances, the controller operates in closed-loop mode.

Thus, systems and methods as described herein may comprise a pump. The pump may be downstream of the fluid injector, decontamination fluid reservoir, and purge reservoir but upstream of the injection device. The pump may create suction in the fluid injector, decontamination fluid reservoir, or purge reservoir, drawing fluid from these elements and creating a positive pressure downstream that drives the fluid into the injection device. In some instances, the pump is downstream of the fluid injector, decontamination fluid reservoir, or purge reservoir, and the injection device. The pump may create suction throughout both the sampling device and injection device to draw fluid through both devices, which is deposited in a waste reservoir.

In some instances, the sampling device comprises a flush reservoir. The flush reservoir may comprise a fluid immiscible with a dispersed phase that forms a dispersed phase in the microfluidic channel. In some instances, the fluid contained in the flush reservoir comprises materials at least partially miscible with a dispersed phase comprising sample. In some instances, the fluid contained in the flush comprises water and PCR primers and fluorescent labels for a biological assay being performed on nucleic acids in the dispersed phase comprising sample. In some instances, the dispersed phase does not comprise nucleic acids and is used as a "no template control." In some instances, the flush comprises fluorescent markers to indicate a boundary between samples.

III. Injector

Systems and methods provided herein can include an injector, also referred to herein as an injection system. In certain embodiments, an injector serves as an interface between the intake system, also referred to herein as a sampler, autosampler, or similar wording, and the process system, where the injector can cycle between a configuration that is in fluid communication with the intake system and a configuration that is fluid communication with the process system. The injector can be configured to have additional configurations, e.g., configurations that allow cleaning of one or more parts of the intake system and injector. In certain embodiments, the injector comprises common conduit, also referred to herein as an injection chamber, or injection loop, where the common conduit can be in fluid communication with the intake system or in fluid communication with the process system, but cannot simultaneously be in fluid communication with both. Thus, the intake system and/or the injector can be treated between injections of dispersed phase, e.g., between samples, in order to reduce or eliminate traces of dispersed phase, e.g., sample, between rounds of intake of dispersed phase, e.g., sample. It will be appreciated that "intake system" can include the injector when the system is configured to be fluidly connected to the injector, as will be clear from context in the following description.

In certain embodiments, systems and methods provided herein may comprise an intake system, such as any of the intake systems described above, connected to an injector in such a way that in a first configuration there is fluid communication between the injector and the intake system and in a second configuration there is not fluid communication between the injector and the intake system. In further embodiments, in the second configuration the injector is in fluid communication with a process system. The process system can comprise a partitioner, such as a partitioner as described below. The process system can comprise a reactor, such a reactor as described below. The process system can comprise a detector, such as a detector as described below. The process system can comprise a disengager, such as a disengager as described below. In certain embodiments, the process system comprises a partitioner and a reactor. In certain embodiments, the process system comprises a partitioner, a reactor, and a detector. In certain embodiments, the process system comprises a partitioner, a reactor, a detector, and a disengager. In certain embodiments, the process system is a system for performing a digital process in partitions, such as a digital PCR system. In certain embodiments, surfaces of the injector that come in contact with a dispersed phase, such as a sample, have higher affinity for at least a first continuous phase than for the dispersed phase; in certain embodiments, surfaces of the injector that come in contact with dispersed phase, e.g., sample, comprise fluoropolymer and the at least first continuous phase comprises a fluorinated oil.

Figure 33:
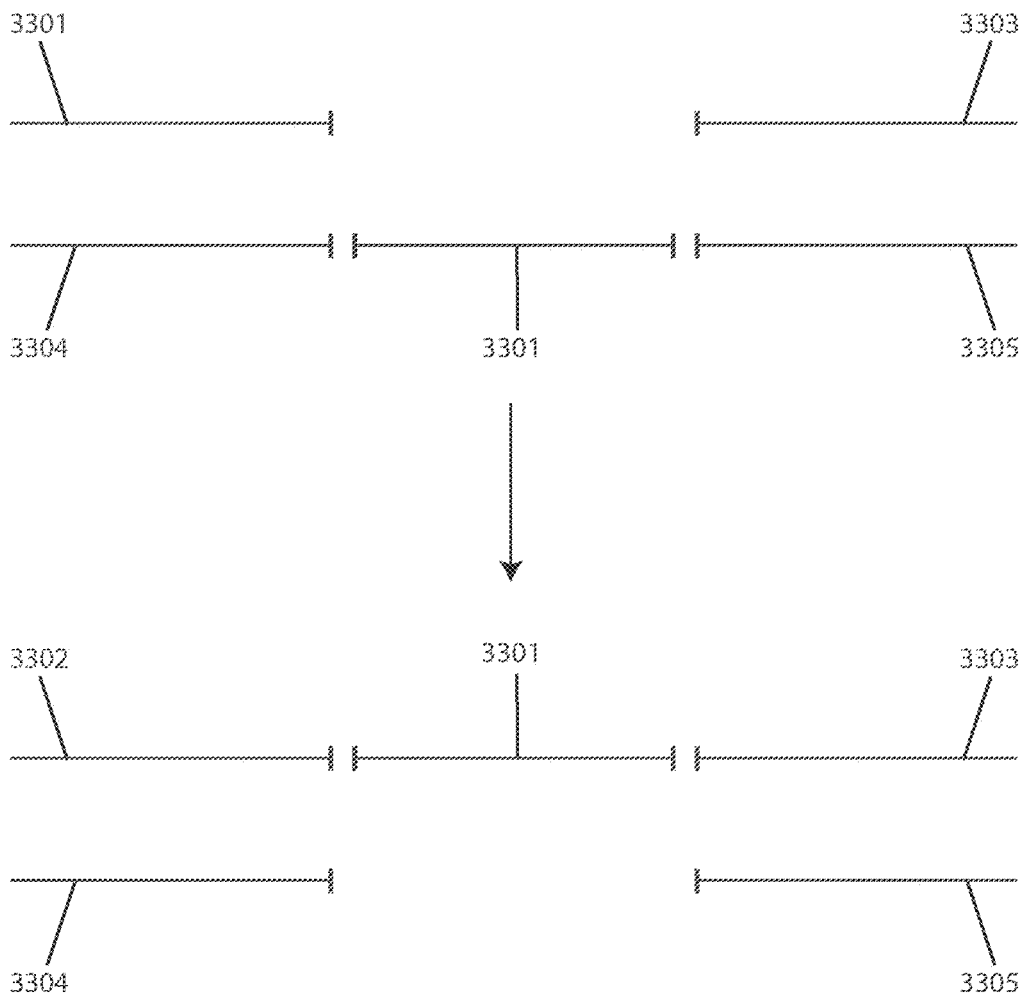
FIG. 33 shows an injector system.

FIG. 33—Basic injector concept FIG. 33 shows an embodiment of an injector. The injector comprises a common conduit 3301, a first intake system conduit 3302, a second intake system conduit 3303, a first process system conduit 3304, and a second process system conduit 3305. The injector may be positioned in at least two states. In the first state, the common conduit 3301 is in fluid communication with both the first intake system conduit 3302 and the second intake system conduit 3303. In the second state, the common conduit 3301 is in fluid communication with both the first process system conduit 3304 and the second process system conduit 3305. The injector may exist in at most one of these states at any given time. The injector may exist in neither of these states, for example while the injector is changing between the first state and the second state or vice versa. As such, the injector can never be positioned such that the first intake system conduit 3302 or the second intake system conduit 3303 are in fluid communication with either the first process system conduit 3304 or the second process system conduit 3305. In general, the common conduit 3301, first intake system conduit 3302, second intake system conduit 3303, first process system conduit 3304, and second process system conduit 3305 may be constructed of any suitable material. In certain embodiments, the conduits have surfaces that comprise a material that has a higher affinity for at least one continuous phase in the system than for any dispersed phase in the system, such that when the at least one continuous phase flows through the system it preferentially displaces volumes of dispersed phase from the surface of the conduit. In certain embodiments, the surface of the conduits in the system comprise a hydrophobic material, at least one continuous phase comprises a hydrophobic component, and at least one dispersed phase comprises an aqueous phase. In certain embodiments, the surface of the conduits in the system comprises a fluoropolymer, at least one continuous phase comprises a fluorinated oil, and the dispersed phase has a lower affinity for a fluoropolymer surface than the fluorinated oil. Here and elsewhere herein, a fluoropolymer may be any suitable fluoropolymer, such as polytetrafluoromethylene (PTFE), chlorotrifluoroethylene (CTFE), polyvinylidene difluoride (PVDF), perfluoroalkoxy polymer (PFA), fluorinated ethylene-propylene (FEP), or a combination thereof. In some embodiments, the surface of the conduits comprises a hydrophilic material, at least one continuous phase is hydrophilic, and at the dispersed phase is hydrophobic. In a further embodiment, the dispersed phase is an oil.

The common conduit 3301 may be constructed in any suitable manner. In certain embodiments, the common conduit 3301 comprises a tube. In certain embodiments, the common conduit 3301 comprises a fluoropolymer tube. In certain embodiments, the common conduit 3301 comprises a channel in a solid substrate. In certain embodiments, the channel is a microfluidic channel. In some further embodiments, the substrate comprises a fluoropolymer material. In some embodiments, the common conduit 3301 comprises both a channel in a solid substrate and a tube. In some embodiments, the volume of the common conduit 3301 is selected so as to deliver a specific aliquot of volume from the intake system to the process system. This volume may be any suitable volume, such as a volume between 0.1 uL and 500 uL, or between 0.1 and 200 uL, or between 0.5 and 200 uL, or between 1 and 200 uL, or between 2 and 200 uL, or between 2 and 100 uL, or between 2 and 50 uL, or between 2 and 30 uL, or between 5 and 200 uL, or between 5 and 100 uL, or between 5 and 50 uL, or between 5 and 40 uL, or between 5 and 30 uL, or between 10 and 200 uL, or between 10 and 100 uL, or between 10 and 50 uL, or between 10 and 30 uL.

Use of the injector system may allow for the movement of a specific volume of a dispersed phase from the intake system to the process system. In certain embodiments, a method for moving a specific volume of a dispersed phase from the intake system to the process system comprises positioning the injector such that the common conduit 3301 is in fluid communication with the first intake conduit 3302 and the second intake conduit 3303, flowing a dispersed phase through the first intake conduit 3302, into the common conduit 3301, and at least partially into the second intake conduit 3303. The injector is then positioned such that the common conduit is in fluid communication with the first process conduit 3304 and the second process conduit 3305. At least one continuous phase is flowed into the first process conduit 3304, displacing the dispersed phase from the common conduit 3301 and into the second process conduit 3305. A volume of dispersed phase substantially equal to the volume of the common conduit 3301 less at most the volume of a thin film of continuous phase near the surface of the common conduit 3301 is then transferred from the intake side to the process side. In some embodiments, this process is repeated to transfer multiple volumes of dispersed phase from the intake side of the system to the process side of the system, such as a series of at least 2, 5, 10, 50, 100, 200, 500, or 1000 separate volumes of dispersed phase.

In certain embodiments, the common conduit 3301 has a higher affinity for the at least one continuous phase than for the dispersed phase. For example, the common conduit can have a surface that is a fluoropolymer and the continuous phase can comprise a fluorinated oil. Thus, when at least one continuous phase is flowed through the first process conduit 3304 into the common conduit 3301, it preferentially displaces dispersed phase from the common conduit 3301 into the second process conduit 3305.

In embodiments where the common conduit 3301, first intake conduit 3302, first process conduit 3304, and the second intake conduit 3305 have a higher affinity for at least one continuous phase than for the dispersed phase to be transferred from the intake system to the process system, the injector may also be used to transfer a plurality of volumes of at least one dispersed phase from the intake system to the process system, such as a series of at least 2, 5, 10, 50, 100, 200, 500, or 1000 separate volumes of dispersed phase, without cross-contamination between volumes of the dispersed phase or phases, or with substantially no cross-contamination. Certain embodiments of the method comprise positioning the common conduit 3301 such that it is in fluid communication with the first intake conduit 3302 and the second intake conduit 3303, flowing a first volume of a dispersed phase through the first intake conduit 3303 such that flows into the common conduit 3301, positioning the common conduit 3301 such that it is in fluid communication with the first process conduit 3304 and the second process conduit 3305, flowing at least one continuous phase through the first process conduit 3304 into the common conduit 3301 such that the at least one continuous phase displaces or substantially displaces the first volume of dispersed phase from the common conduit 3301 into the second process conduit 3304, positioning the common conduit 3301 such that it is in fluid communication with the first intake conduit 3302 and second intake conduit 3303, flowing at least one continuous phase into the first intake conduit 3302 and through the common conduit 3301 such that it displaces or substantially displaces the residual volume of the first volume of dispersed phase into the second intake conduit 3303, flowing a second volume of dispersed phase through the first intake conduit 3302 into the common conduit 3301, positioning the common conduit 3301 such that it is in fluid communication with the first process conduit 3304 and the second process conduit 3305, and flowing at least one continuous phase through the first process conduit 3304 such that it displaces or substantially displaces the second volume of dispersed phase into the second process conduit 3305. In certain embodiments, the fraction of the first volume of dispersed phase or the second volume of dispersed phase displaced into the second process conduit 3305 is at least 80%, at least 90%, at least 95%, at least 98%, at least 99%, at least 99.9%, at least 99.99%, or at least 99.999%. In certain embodiments, the fraction of the residual volume of the first volume of dispersed phase or second volume of dispersed phase displaced into the second intake conduit 3303 is at least 80%, at least 90%, at least 95%, at least 98%, at least 99%, at least 99.9%, at least 99.99%, or at least 99.999%. As such, the common conduit 3301 and portions of the intake system that were exposed to the first volume of dispersed phase are cleaned or substantially cleaned of the first volume of dispersed phase so that the second volume of dispersed phase will not be contaminated with the first volume of dispersed phase in the intake system, common conduit 3301, or process system. In certain embodiments, the first intake conduit 3302 comprises a sample source and at least one continuous phase source and the second intake conduit 3303 comprises a waste. In certain embodiments, the first intake conduit 3302 may be positioned to be in fluid communication with a sample container and the second intake conduit 3303 comprises a motive force source. In certain embodiments, instead of flowing at least one continuous phase into the first intake conduit 3302 to displace residual volume of the first or second volume of dispersed phase into the second intake conduit 3303, at least one continuous phase may be flowed into the second intake conduit 3303 through the common conduit 3301 to displace residual dispersed phase into the first intake conduit 3302. In such embodiments, at least part of the second intake conduit 3303 comprises a material that has a higher affinity for the at least one continuous phase than for the dispersed phases. In certain embodiments, the second intake conduit 3303 comprises a continuous phase source and the first intake conduit comprises a sample source and a waste. In certain embodiments, the first intake conduit 3302 comprises a sample source and a waste.

In the above embodiments, a fixed volume of each sample may be transferred from the intake system to the process system if, when flowing each sample through the first intake conduit 3302 into the common conduit 3301, the sample substantially fills the common conduit 3301 (less the volume of a thin layer of at least one continuous phase at the surfaces of the common conduit 3301) and partially into the second intake conduit 3303 such that, when the common conduit 3301 is positioned to be in fluid communication with the first process conduit 3304 and the second process conduit 3305, the volume of the common conduit 3301 (less the volume of a thin layer of at least one continuous phase at the surfaces of the common conduit 3301) is transferred between the intake system and the process system. This may be useful where precise aliquots of samples are to be transferred between the intake system and the process system. Alternatively, in some embodiments the common conduit 3301 may be partially filled with dispersed phase, with the balance of the volume of the common conduit 3301 filled with at least one continuous phase, before positioning the common conduit 3301 so that that common conduit 3301 is in fluid communication with the first process conduit 3304 and the second process conduit 3305. This may be useful where it is important to transfer a high fraction of each volume of sample between the intake system and the process system.

The above methods may be repeated any number of times to transfer multiple aliquots of one or more dispersed phases from the intake system to the process system. In the above embodiments, there may be moments (e.g. while the common conduit 301 is transitioning between states) where there is no flow. As such, the system may be thought of as using discontinuous flow to transfer aliquots of dispersed phases between the intake system and the process system. In certain embodiments, there is a transition pause in flow as the common conduit transitions between states of at least 0.01, 0.05, 0.1, 0.5, 1, 2, 5, or 10 ms, and/or not more than 0.05, 0.1, 0.5, 1, 2, 5, 10 or 50 ms.

Figure 34:
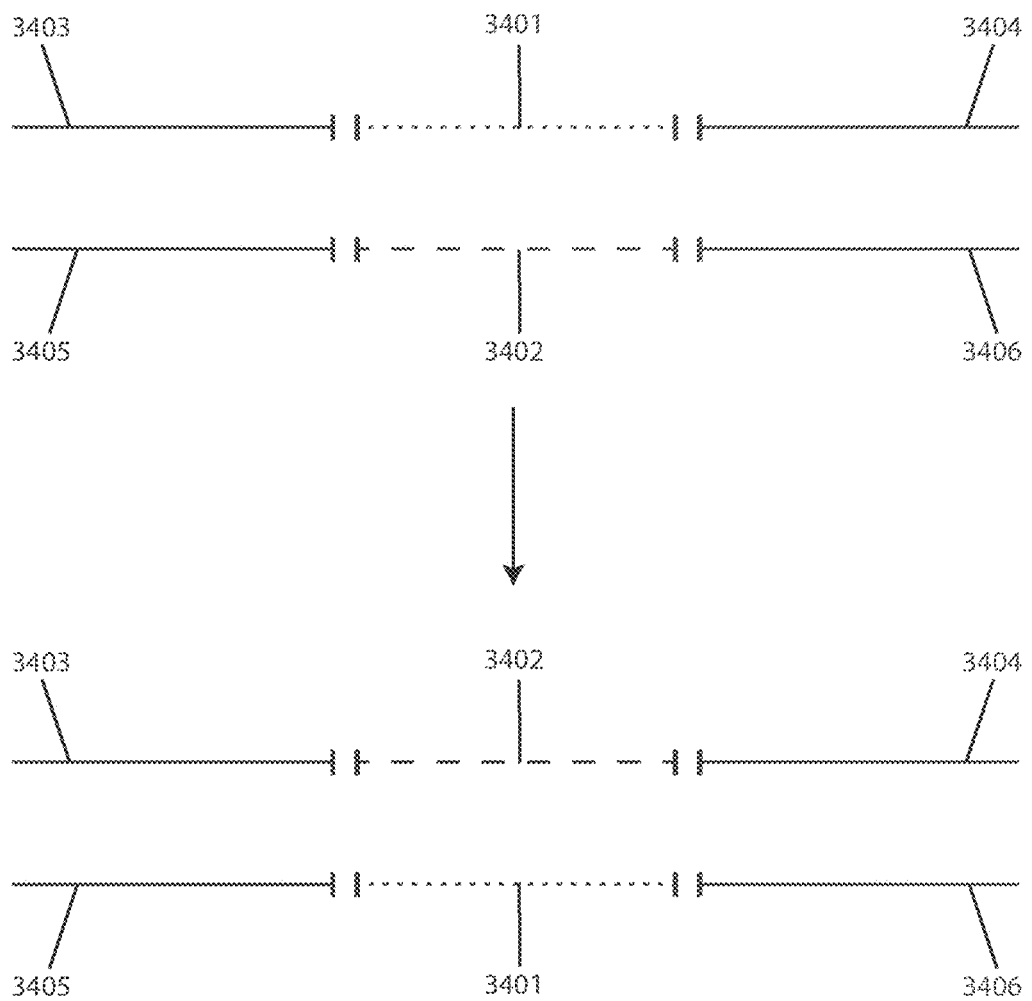
FIG. 34 shows an injector with a plurality of common conduits.

FIG. 34—Injector with a plurality of common conduits
FIG. 34 shows an embodiment of the injector where there is a plurality of common conduits. The system comprises a first common conduit 3401 and a second common conduit 3402, a first intake system conduit 3403, a second intake system conduit 3404, a first process system conduit 3405, and a second process system conduit 3406. Each common conduit has at least two states. In a first state of the first common conduit 3401, the first common conduit 3401 is configured such that it is in fluid communication with the first intake conduit 3403 and the second intake conduit 3404. In a second state of the first intake conduit 3401, the system is configured such that the first common conduit 3401 is in fluid communication with the first process conduit 3405 and the second process conduit 3406. The first common conduit 3401 may be in at most one of its first or second states at any given time, and the first common conduit 3401 may be in neither of the states (e.g. when it is changing between states). Likewise, the second common conduit 3402 has a first state where the second common conduit 3402 is positioned such that the second common conduit 3402 is in fluid communication with the first intake conduit 3403 and the second intake conduit 3404, and the second common conduit 3402 has a second state where the second common conduit 3402 is in fluid communication with the first process conduit 3405 and the second process conduit 3406. The second common conduit 3402 may be in at most one of its first and second states at any time, and it may be in neither of the first or second states (e.g. when it is changing between states). The first common conduit 3401 and the second common conduit 3402 may not simultaneously be in their respective $n^{th}$ state; for example, the first common conduit 3401 may not be in its first state while the second common conduit 3402 is in its first state, and the first common conduit 3401 may not be in its second state when the second common conduit 3402 is in its second state. However, other states are not mutually exclusive. Specifically, the first common conduit 3401 may be in its first state when the second common conduit 3402 is in its second state, and the first common conduit 3401 may be in its second state when the first common conduit 3402 is in its first state.

In further embodiments, the first common conduit 3401 is in its first state whenever the second common conduit 3402 is in its second state and the first common conduit 3401 is in its second state whenever the second common conduit 3402 is in its first state. Methods for efficiently transferring volumes of at least one dispersed phase from the intake system to the process system can comprise positioning the first common conduit 3401 such that it is in its first state (i.e. it is in fluid communication with the first intake conduit 3403 and the second intake conduit 3404); the second common conduit 3402 will then be in its second state. A first volume of dispersed phase is flowed through the first intake conduit 3403 and into the first common conduit 3401, and the first common conduit is positioned such that it is in its second state (simultaneously positioning the second common conduit 3402 in its first state). At least one continuous phase is flowed through the first process conduit 3405 and into the first common conduit 3401 such that it displaces all or a substantial fraction of the first volume of dispersed phase from the first common conduit 3401 and into the second process conduit 3406. While the at least one continuous phase is flowing through the first process conduit 3405, at least one continuous phase is flowed either through the first intake conduit 3403, into the second common conduit 3402, and into the second intake conduit 3404, displacing or substantially displacing residual dispersed phase into the second intake conduit 3404, or through the second intake conduit 3404, into the second common conduit 3402 and into the first intake conduit 3403, displacing or substantially displacing residual dispersed phase into the first intake conduit 3403. A second volume of dispersed phase is then flowed through either the first intake conduit 3403 or second intake conduit 3404 into the second common conduit 3402. Once the substantial fraction of the first volume of dispersed phase is displaced from the first common conduit 3401 and the second volume of dispersed phase is flowed into the second common conduit 3402, the injector is positioned such that the first common conduit 3401 is in its first state (simultaneously putting the second common conduit 3402 in its second state). At least one continuous phase is flowed through the first process intake 3405 and into the second common conduit 3402, displacing the second volume of dispersed phase or a second substantial fraction of the second volume of dispersed phase into the second process intake 3406. While the second volume of dispersed phase is being displaced into the second process intake 3406, at least one continuous phase is flowed through the first intake conduit 3403 and into the first common conduit 3401, displacing residual first volume of dispersed phase into the second intake conduit 3404, or at least one continuous phase is flowed through the second intake conduit 3404 and into the first common conduit 3401, displacing residual first volume of dispersed phase into the first intake conduit 3404. The first common conduit 3401 is then ready for intake of a subsequent volume of dispersed phase without cross-contamination of the dispersed phase volumes. These embodiments allow for cleaning of one common conduit while transferring volume from the second common conduit to the process system, reducing the amount of time required for a single volume of dispersed phase from the intake system to the process system without cross contamination.

Figure 35:
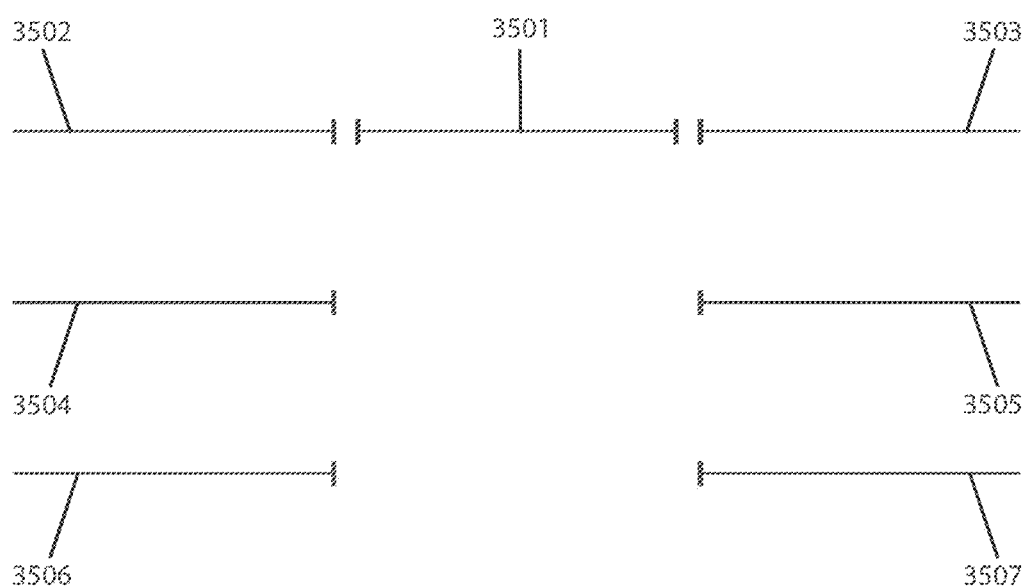
FIG. 35 shows a multi-position injector.

FIG. 35—Multi-position injector FIG. 35 shows an injector system that has more than two states for a common conduit. The system comprises a common conduit 3501, a first intake system conduit 3502, a second intake system conduit 3503, a first process system conduit 3504, a second process system conduit 3505, a first auxiliary system conduit 3506, and a second auxiliary system conduit 3507. The common conduit 3501 has at least three states. In the first state, the common conduit 3501 is in fluid communication with the first intake system conduit 3502 and the second intake system conduit 3503. In the second state, the common conduit 3501 is in fluid communication with the first process system conduit 3504 and the second process system conduit 3505. In the third state, the common conduit 3501 is in fluid communication with the first auxiliary system conduit 3506 and the second auxiliary system conduit 3507. The system may be in at most one state at any time. This concept may be extended to systems with two, three, four, or any number of auxiliary systems.

Figure 36A:
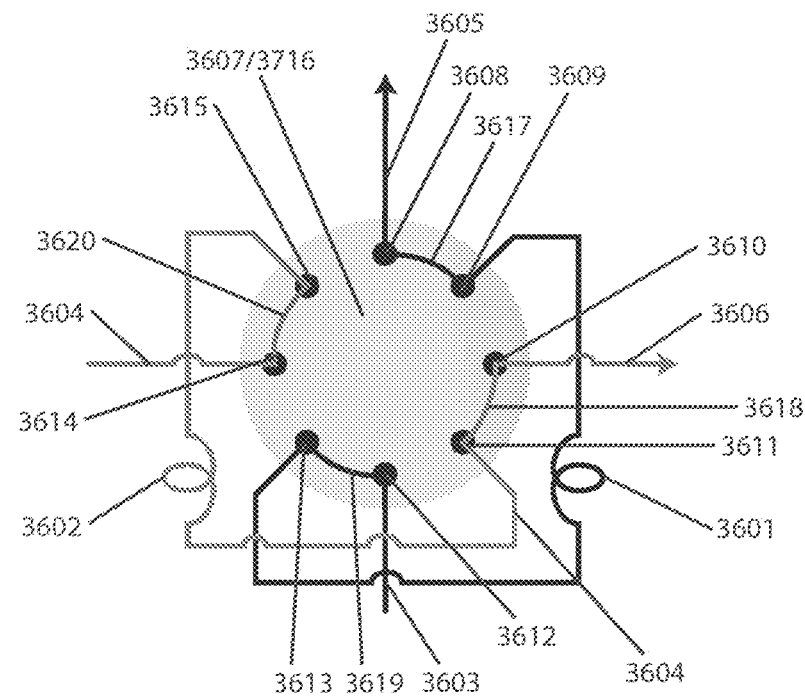
FIGS. 36A and 36B show a rotary single face injector in two different positions.
Figure 36B:
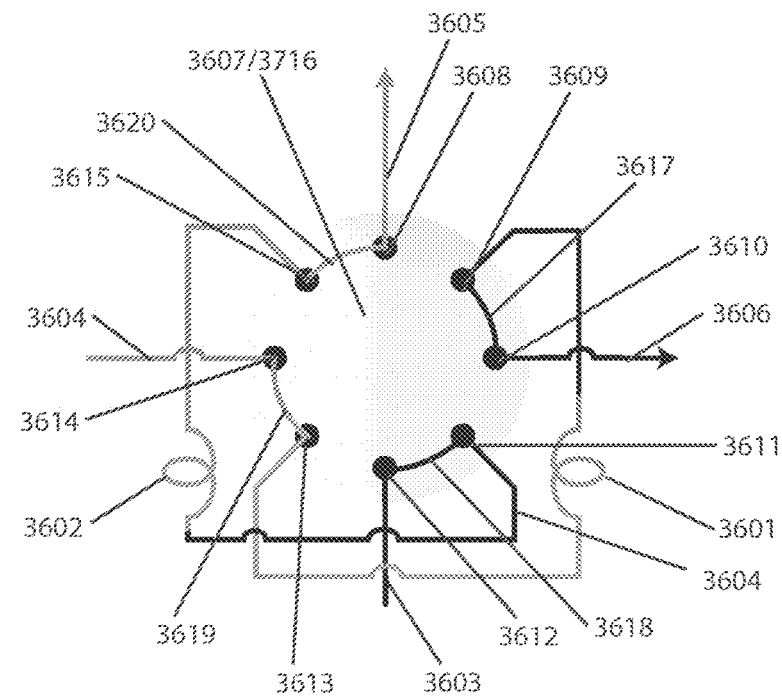

FIGS. 36A and 36B—Rotary single face injector FIG. 36 shows an embodiment of an injector system that comprises a rotary surface seal. The system comprises a first common conduit 3601 that comprises a first tube, a second common conduit 3602 that comprises a second tube, a first intake conduit 3603, a second intake conduit 3604, a first process conduit 3605, and a second process conduit 3606. The system additionally comprises a first substrate 3607 which comprises a first port 3608, a second port 3609, third port 3610, a fourth port 3611, a fifth port 3612, sixth port 3613, a seventh port 3614, and an eighth port 3615. The system additionally comprises a second substrate 3616 which comprises a first channel 3617, a second channel 3618, a third channel 3619, and a fourth channel 3620. The second substrate 3616 has at least two states, and the second substrate 3616 is moved between states by changing the relative rotational orientation of the first substrate 3607 and the second substrate 3616. In the first state, the first channel (FIG. 36A) 3617 is in fluid communication with the first port 3608 and the second port 3609, the second channel 3618 is in fluid communication with the third port 3610 and the fourth port 3611, the third channel 3619 is in fluid communication with the fifth port 3612 and the sixth port 3613, and the fourth channel 3620 is in fluid communication with the seventh port 3614 and the eight port 3615. In the second state (FIG. 36B), the first channel 3617 is in fluid communication with the first port 3608 and the sixth port 3613, the second channel 3518 is in fluid communication with the fourth port 3511, the third channel 3619 is in fluid communication with the third port 3610 and the fifth port 3612, and the fourth channel 3620 is in fluid communication with the second port 3609 and the eighth port 3615. The first intake conduit 3603 is in fluid communication with the first port 3608, the second intake conduit 3604 is in fluid communication with the fourth port 3611, the first process conduit 3605 is in fluid communication with the fifth port 3612, and the second process conduit 3606 is in fluid communication with the eight port 3615. The first common conduit 3601 additionally comprises a first conduit portion in fluid communication with the second port 3609 and the sixth port 3613, and the second common conduit 3602 additionally comprises a second conduit portion in fluid communication with the third port 3610 and the seventh port 3614. Thus, when the second substrate 3616 is in the first state, the first common conduit 3601 is in fluid communication with the first intake conduit 3603 and the second intake conduit 3604, and the second common conduit 3602 is in fluid communication with the first process conduit 3605 and the second process conduit 3606. When the second substrate 3616 is in the second state, the first common conduit 3601 is in fluid communication with the first process conduit 3605 and the second process conduit 3606 and the second common conduit 3602 is in fluid communication with the first intake conduit 3603 and the second intake conduit 3604. When the relative position of the first substrate 3607 and the second substrate 3616 is such that the second substrate 3616 is not in either state, the first common conduit 3601 and the second common conduit 3602 are not in fluid communication with either the intake system or the process system.

The first substrate 3607 and second substrate 3616 may be made of any suitable material. In some embodiments, the surfaces of the first substrate 3607 and/or second substrate 3616 have a higher affinity for at least one continuous phase than for at least one dispersed phase in the present system. In some embodiments, the surfaces of the first substrate 3607 and/or second substrate 3616 comprise fluorinated polymers, and at least one continuous phase comprises a fluorinated oil, as described herein. In some embodiments, the first substrate 3607 is moved relative to the second substrate 3616. In some embodiments, the second substrate 3616 is moved relative to the first substrate 3607. Motion can be achieved by any suitable mechanism. In certain embodiments, motion is achieved by using a motor. Any suitable motor may be used, such as a stepper motor, a brushed dc motor, or a brushless dc motor. In certain embodiments, the motor is a stepper motor and angular position is determined using open-loop control by counting the number of steps moved. In certain embodiments, the motor has an encoder for determining the angular position. In certain embodiments, the system comprises limit switches to detect an angular position.

Figure 37:
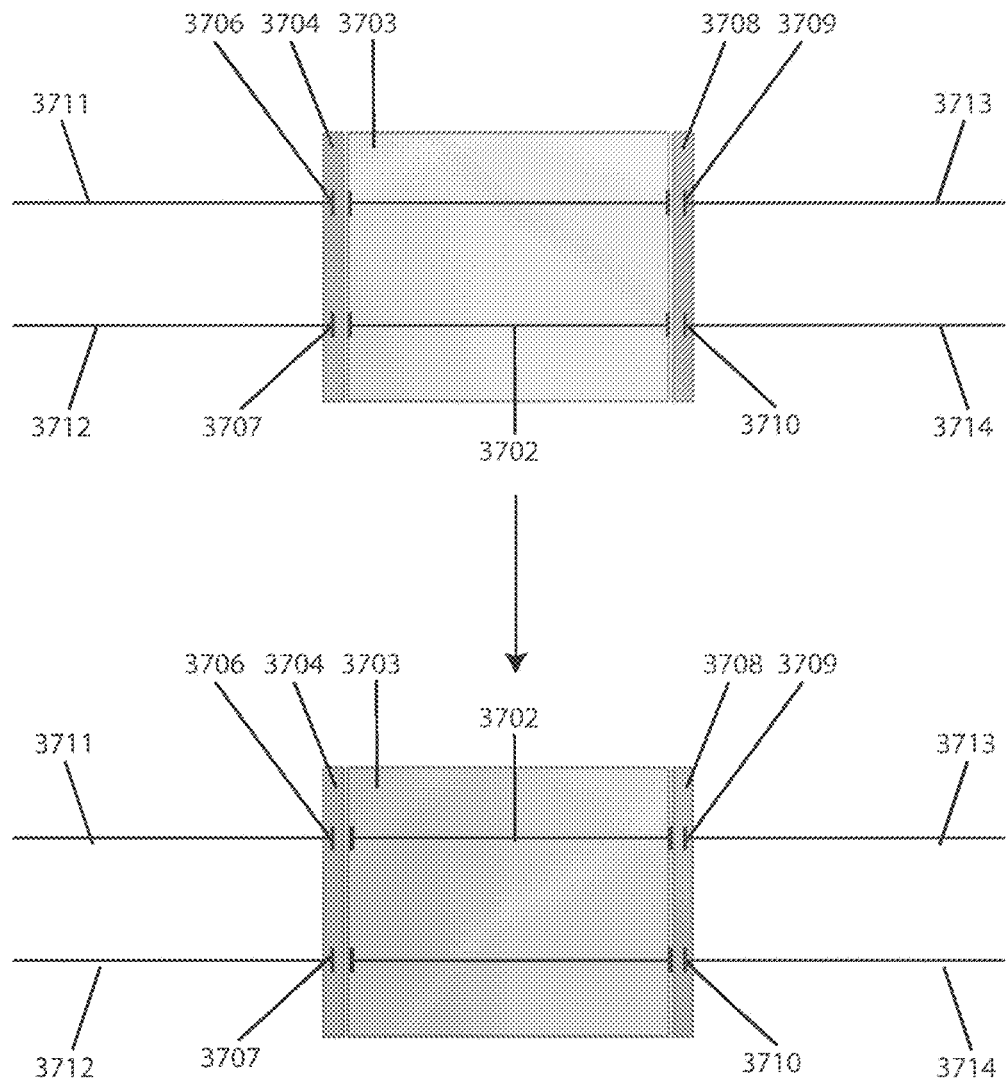
FIG. 37 shows a rotary dual face injector.

FIG. 37 Rotary dual face injector FIG. 37 shows an injector system that comprises two faces. The system comprises a first substrate 3701 comprising at least one common conduit 3702. The system additionally comprises a second substrate 3703 comprising a first port 3704 and a second port 3705; third substrate 3706 comprising a first port 3707 and a second port 3708; a first intake conduit 3709 and second intake conduit 3710; and a first process conduit 3711 and second process conduit 3712. The first intake conduit 3709 is in fluid communication with the first port 3704 of the second substrate 3703, the second intake conduit 3710 is in fluid communication with the first port 3707 of the third substrate 3706, the first process conduit 3711 is in fluid communication with the second port 3705 of the second substrate 3704, and the second process conduit 3712 is in fluid communication with the second port 3708 of the third substrate 3706. The common conduit 3702 may exist in at least two states. In the first state, the common conduit 3702 is in fluid communication with the first port 3704 of the second substrate 3703 and the first port 3707 of the third substrate 3706, and is thus in fluid communication with the intake system. In the second state, the common conduit 3702 is in fluid communication with the second port 3705 of the second substrate 3703 and the second port 3708 of the third substrate 3706, and is thus in fluid communication with the process system. The common conduit 3702 may exist in at most one of these states at any time, although it may not exist in either state, e.g. when changing between the states. In some embodiments, the common conduit 3702 is a channel or bore through a solid substrate. In some embodiments, the common conduit 3702 and ports 3704, 3705, 3706, and 3708 are arranged such that changes in relative rotational position of the first substrate 3702 and the second and third substrates (3703 and 3706, respectively) may position the common conduit 3702 in either of the states. In some embodiments, the first substrate 3702 is rotated and the second substrate 3703 and third substrate 3706 are held in a static position. As described for other embodiments of the injector, the system may have multiple common conduits with mutually exclusive states. In some embodiments, multiple common conduits are formed from channels in a first substrate 3702 whose centerlines lie on a common circular arc. Motion may be generated in substrate 3702 (or substrates 3703 or 3706) by the use of a motor. In some embodiments, the motor is a brushed dc motor, a stepper motor, a brushless dc motor. Position may be indicated by any appropriate methods. In some embodiments, step counts, encoders, limit switches, and/or optical interrupters are used to determine positions. The substrates 3702, 3703, and 3706 may be made of any suitable material. In some embodiments, as in other descriptions of injectors herein, the surfaces of the substrates in contact with fluids have a higher affinity for at least one continuous phase than for the dispersed phases in the system so as to allow preferential displacement of dispersed phases. In some embodiments, the substrates 3702, 3703, or 3706 comprise metals or polymers. In some preferred embodiments, the substrates 3702, 3703, or 3706 comprise fluoropolymers and at least one continuous phase comprises a fluorinated oil. In further embodiments, the substrates 3702, 3703, or 3706 comprise CTFE and/or PTFE.

Thus, the sampling device may introduce volumes of dispersed phase to an injector that then flows to a reactor and a detector. Injectors for use in systems and methods as described herein may comprise zero or low-dead volume valves. In some instances the zero or low-dead volume valves comprise one or more rotors. In some instances, one or dispersed phases pass through the rotor and injected through the injector. In some instances, the rotor comprises a calibrated volume. In some instances, the calibrated volume is at least or about 0.001 nanoliter (nL), 0.002 nL, 0.003 nL, 0.004 nL, 0.005 nL, 0.006 nL, 0.007 nL, 0.008 nL, 0.009 nL, 0.01 nL, 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.50 nL, 0.60 nL, 0.70 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL. In some instances, the calibrated volume comprises at least or about 100 nL, 200 nL, 300 nL, 400 nL, 500 nL, 600 nL, 700 nL, 800 nL, 900 nL, 1000 nL, 2000 nL, 3000 nL, 4000 nL, 5000 nL, 6000 nL, 7000 nL, 8000 nL, 9000 nL, 10000 nL, 20000 nL, 30000 nL, 40000 nL, 50000 nL, 60000 nL, or more than 60000 nL.

In some instances, the injector introduces one or more dispersed phases to a microfluidic channel or tube for subsequent reactions in a reactor. In some instances, the one or more dispersed phase is rejected to a waste stream not in fluid communication with the microfluidic channel or tube for subsequent reactions in a reactor. In some instances, the injector introduces one or more continuous phases. In some instances, the one or more continuous phases comprise oil.

Further embodiments of injectors useful in the systems and methods provided herein are described in PCT Publication No. WO2018098438, incorporated herein by reference.

IV. Process System

Systems and methods provided herein can include an injector, also referred to herein as an injection system. In certain embodiments, an injector serves as an interface between the intake system, also referred to herein as a sampler, autosampler, or similar wording, and the process system, where the injector can cycle between a configuration that is in fluid communication with the intake system and a configuration that is fluid communication with the process system. The injector can be configured to have additional configurations, e.g., configurations that allow cleaning of one or more parts of the intake system and injector. In certain embodiments, the injector comprises common conduit, also referred to herein as an injection chamber, or injection loop, where the common conduit can be in fluid communication with the intake system or in fluid communication with the process system, but cannot simultaneously be in fluid communication with both. Thus, the intake system and/or the injector can be treated between injections of dispersed phase, e.g., between samples, in order to reduce or eliminate traces of dispersed phase, e.g., sample, between rounds of intake of dispersed phase, e.g., sample. It will be appreciated that "intake system" can include the injector when the system is configured to be fluidly connected to the injector, as will be clear from context in the following description.

In certain embodiments, systems and methods provided herein may comprise an intake system, such as any of the intake systems described above, connected to an injector in such a way that in a first configuration there is fluid communication between the injector and the intake system and in a second configuration there is not fluid communication between the injector and the intake system. In further embodiments, in the second configuration the injector is in fluid communication with a process system. The process system can comprise a partitioner, such as a partitioner as described below. The process system can comprise a reactor, such a reactor as described below. The process system can comprise a detector, such as a detector as described below. The process system can comprise a disengager, such as a disengager as described below. In certain embodiments, the process system comprises a partitioner and a reactor. In certain embodiments, the process system comprises a partitioner, a reactor, and a detector. In certain embodiments, the process system comprises a partitioner, a reactor, a detector, and a disengager. In certain embodiments, the process system is a system for performing a digital process in partitions, such as a digital PCR system. In certain embodiments, surfaces of the injector that come in contact with a dispersed phase, such as a sample, have higher affinity for at least a first continuous phase than for the dispersed phase; in certain embodiments, surfaces of the injector that come in contact with dispersed phase, e.g., sample, comprise fluoropolymer and the at least first continuous phase comprises a fluorinated oil.

A. Partitioner

The systems and methods described herein can provide a partitioner, also referred to as a droplet partitioner or droplet generator herein, for dividing dispersed phase into partitions, also referred to as droplets herein.

In certain embodiments, systems and methods comprise use of an intake system and a process system that comprises a partitioner, such as a partitioner as described herein. The intake system can be a system that can be completely isolated from the process system, such as an intake system as described above, for example, an intake system that comprises a intake system and, in certain configurations, an injector, where the injector can alternate between fluid connection with the intake system and fluid connection with the process system, e.g., where the injector at no time provides a continuous fluid connection between the intake system and the process system. Such intake systems are described more completely elsewhere herein. The partitioner may be any suitable partitioner, e.g., a partitioner that is configured to partition a dispersed phase, such as a dispersed phase supplied by an injector (in some cases, packets of dispersed phase surrounded by a continuous phase and/or separated from each other by a spacer fluid), into a plurality of partitions flowing in emulsion in a continuous phase, which can be any suitable number of partitions, for example as described below, such as 1000-100,000 partitions, where the partitions are an average of any suitable volume, for example as described below, such as 0.05 nL to 5 nL. In certain embodiments, the partitioner is a reverse-y partitioner, e.g., a partitioner in which an outlet is positioned within 30 degrees of parallel with a gravitational field and flow through the outlet is counter to gravitational force, such as those described herein. In certain embodiments, the partitioner is one in which an inlet for dispersed phase and an inlet for continuous phase meet at an angle of 170-190 degrees, such as an angle of 180 degrees (e.g., coaxial).

In certain embodiments, the surfaces of the partitioner that come in contact with dispersed phase (e.g., sample coming from the injector, and partitions of dispersed phase flowing out of partitioner), and/or with all fluid, have greater affinity for continuous phase than for dispersed phase. Thus, the continuous phase preferentially wets the wall of the channel, and, for example, preventing wall effects on droplet formation or portions of the dispersed phase being held up in the channel. In certain embodiments, the surface of the channel (e.g., inlet channel for sample in dispersed phase, outlet channel for partitions of dispersed phase in continuous phase) comprises a fluoropolymer, the continuous phase comprises a fluorinated or perfluorinated oil, and the dispersed phase comprises water or water-based mixture. In certain embodiments, the partitioner can be constructed from one or more blocks of material that has a greater affinity for continuous phase than for dispersed phase, for example, one or more blocks of fluoropolymer when the continuous phase is, e.g., a fluorinated oil; the block can include connections for conduits to channels within the block, where one or more of the connections minimize or eliminate disruption of flow through the connection. In certain embodiments, the partitioner includes a first inlet channel and a second inlet channel, where the first and second inlet channels intersect at an angle 150-180 degrees, for example at an angle of 170-180 degrees, or at an angle of 180 degrees. In some cases, the inlet channels are oriented so that the direction of flow within the channels is within 45, or within 30, or within 20, or within 15 degrees of orthogonal to a gravitational field. In certain embodiments, the partitioner include an outlet channel at the intersection of inlet channels, where the outlet channel is oriented parallel or nearly parallel to an ambient gravitational field, e.g., within 20, 15, 10, or 5 degrees of parallel; in some cases, the direction of flow through the outlet channel is opposite to the direction of the gravitational field. In certain embodiments, after the partitioner produces an emulsion of dispersed phase in continuous phase, a portion of the continuous phase is removed from the emulsion; part or all of the removed continuous phase may be added back to the system, for example, prior to droplets flowing through a detector in order to separate the droplets before detection.

Partitioners described herein may be incorporated into systems for chemical, physical, or biological processing of the dispersed phase contents. In certain embodiments using injectors as described herein, dispersed phase is not fed to the partitioner continuously, but in packets already entrained/dispersed in a continuous phase, e.g., packets that each represent an individual sample that has been sampled by a sampling system; the packets may be separated by a spacer fluid, as described herein. Packets of dispersed phase may be any suitable volume, such as 0.1-100 uL, or 1-80 uL, or 5-50 uL, or 10-30 uL, or 15-25 uL, or any other volume as described herein. If a spacer fluid is used between packets, it may also be any suitable volume, such as 0.1-50 uL, or 0.1-20 uL, or 0.1-10 uL, or 1-10 uL, or 1-8 uL, or 2-7 uL, or 3-7 uL, or any other volume as described herein. Thus, dispersed phase may be supplied to the partitioner discontinuously, e.g., as a series of discrete packets, each of which corresponds to, for example, a discrete sample, and partitions (droplets) are generated discontinuously. This is a natural consequence of using certain embodiments of injector. As such, the flow will preferably be laminar to avoid breakup of that packet of dispersed phase or polydispersity of the produced droplets. In addition, in certain embodiments, the droplet partitioner is not greatly affected by variations in supply flow that may be a consequence of moving injector positions, which can allow, for example, the loading of a new sample or purge fluid into the continuous stream during droplet formation. Thus, at certain times in the injection cycle, flow from the injector to the partitioner may be interrupted. Further, in certain embodiments the partitioner is fabricated completely out of material with a higher affinity for the continuous phase than for the dispersed phase; for example, in certain embodiments, the partitioner can be fabricated out of fluoropolymer, for use with, e.g., a continuous phase comprising fluorinated oil.

Partitioners of the systems and methods described herein can be reusable, and can partition multiple packets of dispersed phase, e.g., during a process run, such as packets which each represent a different sample, in series, such as a series of at least 10, 20, 50, 100, 200, 300, 500, or 1000 packets and/or not more than 20, 50, 100, 200, 300, 500, 1000, or 10,000 packets.

Thus, described herein are systems for serial flow emulsion reaction, wherein a droplet generator (partitioner) generates droplets (partitions) for reactions. Methods for droplet (partition) generation include, but are not limited to, orifices, t-junctions, flow-focusing junctions, and v-junctions. In some instances, the v-junction is a reverse v-junction (also referred to herein as a reverse-y junction) in which, in certain embodiments, the channel cross-section restricts after the junction rather than before it. In some instances, the droplet generator comprises a fluoropolymer. In some instances, the v-junction does not comprise a restriction. In some instances, the droplets are generated where two channels meet at an angle less than about 90 degrees. In some instances, the angle is at least or about 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, or 80 degrees. In some instances, the combined channel goes through a reduction in channel diameter. The channel diameter may be reduced by at least 0.5×, 1.0×, 1.5×, 2.0×, 2.5×, 3.0×, 3.5×, 4.0×, 4.5×, 5.0×, or more than 5× as compared to a channel that is not reduced in channel diameter. In some instances, a first channel of the two channels comprises an emulsion of the dispersed phase in a first continuous phase. In some instances, a second channel of the two channels comprises a continuous phase. In some instances, an exit channel is orthogonal to the original channel and is oriented vertically. In some instances, the force that moves generated droplets out of the junction comprises buoyancy effects. In some instances, a droplet size is unaffected by the relative flow-rates of the emulsion and the second continuous phase. In some instances, a droplet size is determined by the cross-sectional area of the exit channel.

Thus, in certain embodiments V-junctions may be used for in systems and methods as described herein. In some instances, the v-junction is a reverse v-junction, also referred to herein as a reverse-y. In some instances, the v-junction comprises two channels. In some instances, a cross section of each of the two channels is the same. In some instances, the length of each of the two channels is the same. In some instances, the two flow channels combine to a single channel. In some instances, the single channel comprises a reduced cross section as compared to each of the two channels. In some instances, the cross-section of the single channel is at least or about 0.5×, 1.0×, 1.5×, 2.0×, 2.5×, 3.0×, 3.5×, 4.0×, 4.5×, 5.0×, 5.5×, 6.0×, 6.5×, 7.0×, 7.5×, 8.0×, 8.5×, 9.0×, 9.5×, or 10× reduced as compared to each of the two channels. In some instances, the cross section of the single channel is reduced to a cross section of a droplet. In some instances, the droplet (e.g., average droplet size) is at least or about 5 micron (um), 10 um, 20 um, 30 um, 40 um, 50 um, 60 um, 70 um, 80 um, 90 um, 100 um, 120 um, 140 um, 160 um, 180 um, 200 um, or more than 200 um in diameter, and or not more than 10 um, 20 um, 30 um, 40 um, 50 um, 60 um, 70 um, 80 um, 90 um, 100 um, 120 um, 140 um, 160 um, 180 um, 200 um, 300, 500, or 1000 um in diameter, such as 1-1000 um, or 10-500 um, or 50-500 um, or 100-400 um, or 100-300 um, or 150-250 um in diameter. In some instances, the droplet is at least or about 200 um, 300 um, 400 um, 500 um, 600 um, 700 um, 800 um, 900 um, 1000 um, or more than 1000 um in diameter In some instances, the droplet separation and an optical stage are combined. The droplet separation and optical stage may be on the same microfluidic chip. The emulsion stream coming from the thermal cycler may enter a first channel on the chip. A stream of continuous phase may enter a second channel on the chip. In some instances, the two channels both constrict and then meet at a t-junction. The combined streams flow through an extended region at the same constricted size, a portion of which may comprise the optical stage. The constricted channel may then expand to a larger diameter and leaves the chip through a press-fit connection. In some instances, the first channel and the second channel do not constrict before meeting in a t-junction. In some instances, a constriction occurs beyond the exit of the t-junction. In some instances, the constriction is smaller than the characteristic size of the droplets so that a droplet substantially fills the channel in the optical stage. A portion of the constricted channel may form the optical stage. In some instances, the channel then expands to a larger size so that it substantially matches the cross-section of an exit tube.

In some instances, the junction is a "v-junction." In some instances, the streams are combined at an angle substantially less than 90 degrees, for examples, at least or about 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, or 80 degrees.

In some instances, a reverse-v junction is used with a tubular optical stage. In some instances, an exit of the reverse-v junction is tubular and continues to form an optical stage of the detector.

Droplets may be partitioned using a droplet technique. In some instances, the droplet technique is passive or active. For example, passive techniques include passive flow and passive pressure. Exemplary active droplet techniques include, but are not limited to, techniques based on mechanical principles (e.g., external syringe pumps, pneumatic membrane pumps, vibrating membrane pumps, vacuum devices, centrifugal forces, piezoelectric/ultrasonic pumps and acoustic forces); electrical or magnetic principles (e.g., electroosmotic flow, electrokinetic pumps, ferrofluidic plugs, electrohydrodynamic pumps, attraction or repulsion using magnetic forces and magnetohydrodynamic pumps); thermodynamic principles (e.g., gas bubble generation/phase-change-induced volume expansion); other kinds of surface-wetting principles (e.g., electrowetting, and opto-electrowetting, chemically, thermally, structurally and radio-actively induced surface-tension gradients); gravity; surface tension (e.g., capillary action); electrostatic forces (e.g., electroosmotic flow); centrifugal flow (substrate disposed on a compact disc and rotated); magnetic forces (e.g., oscillating ions causes flow); magnetohydrodynamic forces; and vacuum or pressure differential.

The droplet generator may generate droplets comprising various volumes. In some instances, a volume of the droplet comprises at least or about 0.01 nanoliter (nL), 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.45 nL, 0.50 nL, 0.55 nL, 0.60 nL, 0.65 nL, 0.70 nL, 0.75 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or more than 100 nL and/or not more than 0.02 nL, 0.03 nL, 0.04 nL, 0.05 nL, 0.06 nL, 0.07 nL, 0.08 nL, 0.09 nL, 0.10 nL, 0.20 nL, 0.30 nL, 0.40 nL, 0.45 nL, 0.50 nL, 0.55 nL, 0.60 nL, 0.65 nL, 0.70 nL, 0.75 nL, 0.80 nL, 0.90 nL, 1.0 nL, 2.0 nL, 3.0 nL, 4.0 nL, 5.0 nL, 10.0 nL, 20 nL, 30 nL, 40 nL, 50 nL, 60 nL, 70 nL, 80 nL, 90 nL, 100 nL, or 200 nL. In some instances, a volume of the droplet comprises no more than 0.75 nL. In some instances, a volume of the droplet comprises about 0.01 nL to about 100 nL, about 0.05 nL to about 80 nL, 0.05 nL to about 50 nL, 0.05 nL to 25 nL, 0.05 nL to 10 nL, 0.05 nL to 5 nL, about 0.10 nL to about 60 nL, about 0.10 nL to about 40 nL, about 0.10 nL to about 20 nL, about 0.10 nL to about 10 nL, about 0.10 nL to about 5 nL, about 0.10 nL to about 1 nL, about 0.2 nL to about 40 nL, about 0.2 nL to about 20 nL, about 0.2 nL to about 10 nL, about 0.2 nL to about 1 nL about 0.2 nL to about 0.8 nL, about 0.3 nL to about 30 nL, 0.3 nL to about 10 nL, 0.3 nL to about 1 nL, 0.3 nL to about 0.7 nL, about 0.4 nL to about 20 nL, 0.4 nL to about 10 nL, 0.4 nL to about 1 nL, 0.4 nL to about 0.6 nL, about 0.5 nL to about 10 nL, about 0.6 nL to about 4 nL, or 0.7 nL to about 2.0 nL. In certain embodiments, average droplet volume is 0.1-1 nL.

In some instances in which droplets are formed from sample containing nucleic acid, the sample is partitioned into droplets having, on average, 0.001 to 200, 0.1 to 2, 0.5 to 2.0, 0.1 to 20, 0.5 to 1.3, or 0.1 to 1 nucleic acid molecules. In some cases, one or more droplets do not comprise a nucleic acid molecule. In some instances, one or more droplets comprise a single nucleic acid molecule. In some cases, one or more droplets comprise two or more nucleic acid molecule. In some instances, the nucleic acid molecule is DNA. In some instances, the nucleic acid molecule is RNA. In some instances, the nucleic acid molecule is single stranded or double stranded.

In some instances, a number of droplets generated by any of the methods described herein, e.g., from a single sample (packet, as described above), is at least 1, 2, 3, 4, 5, 6, 7, 8, 9, 10, 11, 12, 13, 14, 15, 16, 17, 18, 19, 20, 25, 50, 100, 200, 300, 400, 500, 600, 700, 800, 900, 1000, 2000, 4000, 6000, 8000, 10000, 12000, 14000, 16000, 18000, 20000, 25000, 30000, 40000, 50000, 100000, 500000, 1000000, or more than 1000000 and or not more than 2, 3, 4, 5, 6, 7, 8, 9, 10, 11, 12, 13, 14, 15, 16, 17, 18, 19, 20, 25, 50, 100, 200, 300, 400, 500, 600, 700, 800, 900, 1000, 2000, 4000, 6000, 8000, 10000, 12000, 14000, 16000, 18000, 20000, 25000, 30000, 40000, 50000, 100000, 500000, 1000000, or 10000000 droplets, for example, 100-1,000,000, or 500-500,000, or 1000-100,000, or 2000-50,000, or 10,000-50,000, or 15,000-30,000, or 15,000-25,000 droplets. In some cases, the number of droplets is about 1, 2, 3, 4, 5, 6, 7, 8, 9, 10, 11, 12, 13, 14, 15, 16, 17, 18, 19, 20, 25, 50, 100, 200, 300, 400, 500, 600, 700, 800, 900, 1000, 2000, 4000, 6000, 8000, 10000, 12000, 14000, 16000, 18000, 20000, 25000, 30000, 40000, 50000, 100000, 500000, 1000000, or more than 1000000 droplets. In some instances, at least or about 10, 20, 30, 40, 50, 100, 150, 200, 250, 300, 350, 400, 450, 500, 550, 600, 650, 700, 750, 800, 850, 900, 950, 1000, 2000, 4000, 6000, 8000, 10000, or more than 10000 droplets are generated per second. In some instances, a range of about 10-10000, 20-8000, 30-7000, 40-6000, 50-5000, 60-4000, 70-3000, 80-2000, 100-1000 droplets are generated per second. In some instances, droplets are generated at rate of at least or about 500 ul, 750 ul, 1 mL, 1.5 mL, 2 mL, 2.5 mL, 3 mL, 3.5 mL, 4 mL, 4.5 mL, 5 mL, 5.5 mL, 6 mL, 6.5 mL, 7 mL, 7.5 mL, 8 mL, or more than 8 mL per hour.

A partitioner typically includes a first inlet channel for dispersed phase (e.g., a programmed emulsion of dispersed phase in continuous phase, supplied by an intake system, such as by an injector), one or more second inlet channels for continuous phase, and an outlet channel through which an emulsion of droplets formed by the partitioner in the continuous pass to the rest of the system. Any suitable arrangement of inlets and outlet may be used. In some cases, the surfaces of the partitioner, e.g., inlet and outlet channels, that come into contact with dispersed phase have greater affinity for continuous phase than for dispersed phase, for example, a fluoropolymer if the continuous phase comprises a fluorinated oil. The channels may be formed in a solid block of suitable material, such as a material that has a greater affinity for continuous phase than for dispersed phase, and in these and other cases, all channels in the partitioner can have greater affinity for continuous phase than dispersed phase; additionally or alternatively, part or all of one or more channels may be formed by tubing inserted into channels in a block. In this case, the tubing carrying dispersed phase (e.g., dispersed phase inlet and outlet tubing) can have greater affinity for continuous phase than for dispersed phase. Tubing or channels carrying only continuous phase, e.g., a continuous phase inlet, does not necessarily have to have greater affinity for continuous phase than dispersed phase (though, for convenience of construction or other reasons it may), so long as it is constructed of material compatible with the continuous phase.

The dispersed phase can contain any suitable material, e.g., in certain embodiments the dispersed phase comprises biological sample, such as a sample comprising nucleic acids, for example a sample in a packet in any suitable volume range, such as any of the volume ranges described herein. In certain embodiments the dispersed phase may further comprise reagents for the amplification of nucleic acids, detection, and/or other suitable reagents.

Any suitable partitioner may be used in systems and methods described herein. Exemplary partitioners include, but are not limited to, reverse-y (also referred to as reverse-v) partitioners, T-junction partitioners, and flow-focusing partitioners, described below.

Reverse-y partitioners. In certain embodiments, the partitioner may be configured as a "reverse-Y", also referred to as a "v" or "reverse-v" herein. The reverse-y partitioner is advantageous in that it can produce partitions of the same or substantially the same size over a wide range of inlet flow rates. In certain embodiments, surfaces of the reverse-y partitioner that come in contact with dispersed phase (e.g., sample/dispersed phase inlet, and outlet), have greater affinity for continuous phase than for dispersed phase; in certain embodiments, all surfaces of the partitioner have greater affinity for continuous phase than for dispersed phase.

In certain embodiments, described herein are reaction systems and methods, such as a digital PCR system and methods, in which a reverse-y partitioner is used to partition sample into a plurality of partitions, which are reacted, e.g. thermally cycled, and detected. In these systems and methods, any suitable reverse-y partition generator, as described further herein, may be used.

The reverse-y droplet partitioner includes an outlet channel parallel to or close to parallel to the gravitational field and two inlet channels placed relatively orthogonal to the gravitational field. See, e.g., FIGS. 38, 39A and 39B, and 40. In the reverse-y partitioner, two inlet channels meet at an angle (theta) between 2 degrees and 180 degrees between the axes of the channels, for example, between 10 and 180 degrees, or between 30 and 180 degrees, or between 50 and 180 degrees, or between 90 and 180 degrees, or between 110 and 180 degrees, or between 130 and 180 degrees, or between 150 and 180 degrees, or between 160 and 180 degrees, or between 170 and 180 degrees between the two axes of the channels, for example, 180 degrees (e.g., coaxial or substantially coaxial). See, e.g., FIG. 40 for an embodiment where the inlet channels are co-axial. The inlet channels may be oriented above or below the plane orthogonal to the outlet channel (e.g., +/−60, 50, 45, 40, 35, 30, 25, 20, 15, 10, 5, 4, 3, 2, or 1 degrees) (alpha). The first and the second inlet channel can be oriented with a substantial component (e.g., axis of flow) orthogonal to the ambient gravitational field, for example, the first inlet channel and/or the second inlet channel can be within 45, 40, 35, 30, 25, 20, 15, 10, 5, 4, 3, 2, or 1 degrees of orthogonal to the ambient gravitational field. See, e.g., FIGS. 38 and 39A and 39B, which shows exemplary arrangements of the first and second inlet channels. In the first inlet channel, a mixture of a first continuous phase and dispersed phases is flowing, with the continuous and dispersed phases being mostly immiscible. This is the case, e.g., when a series of samples is injected from the injector; each sample is dispersed phase, surrounded or substantially surrounded by continuous phase, for example, an aqueous phase surrounded by an oil, e.g., a fluorinated oil. Thus, this continuous and disperse phases can comprise a programmed emulsion containing discrete sample plugs (packets) separated by continuous phase and/or a spacer fluid. In the second inlet channel, fluid miscible with the first continuous phase is flowed; e.g., a second continuous phase. Any suitable fluid may be used. In certain embodiments, the first continuous phase is of the same composition as the second continuous phase, e.g., an oil, such as a fluorinated oil. In some cases, the first and second continuous phases comprise an oil and surfactant, such as a surfactant of a type and concentration described herein. In some cases, the dispersed phase comprises an aqueous solution. The first and second continuous phase can be composed of the same oil with varying surfactant concentrations. Additionally or alternatively, surfactant composition and/or concentration in the first continuous phase can be different from surfactant in the second continuous phase. The outlet channel receives flow from the first inlet channel and the second inlet channel at the junction point of the first inlet channel and the second inlet channel, and this outlet channel can be oriented parallel or nearly parallel to the ambient gravitational field, for example, within 45, 40, 30, 35, 20, 15, 10, 5, 4, 3, 2, or 1 degree of parallel to the ambient gravitational field, such as within 30 degrees, e.g., within 15 degrees, or within 10, 5, or 2 degrees. Fluid flow in the outlet channel moves counter to the gravitational force.

Without being bound by theory, it is thought that in orienting the channels in such a way, buoyancy can play a role in droplet formation. It is possible that buoyancy accelerates the continuous phase resulting in a neck formed behind the droplet. As the neck grows thin enough, it eventually breaks due to Rayleigh-Plateau instability. Thus, orientation of the outlet channel may be important to ensure droplet formation as opposed to separated, two phase flow (as typically seen in Y-junctions in microfluidic systems). If the outlet channel is oriented orthogonally or substantially orthogonally to gravity (e.g., within 30 degrees of the direction of gravity) and fluidic flow is in the same direction as gravitational force, the heavier phase may settle to the bottom of the outlet channel and the lighter phase may flow above it, generating two phase flow rather than partitioning of the inlet dispersed phase into droplets. For example, if the droplet partitioner outlet is parallel to gravity, the partitioner may not produce monodisperse droplets but rather producer large polydisperse droplets.

The characteristic dimension of the first inlet channel may be larger than the characteristic dimension of the second inlet channel, vice versa, or the two characteristic dimensions may be similar or equal. The "characteristic dimension," (also referred to herein as "critical dimension," "characteristic length," and equivalent terms) as that term is used herein, includes any dimension that substantially determines the cross-sectional area of the channel; for example, a characteristic dimension can be a diameter, a hydraulic diameter, or any other suitable dimension. The first and/or second inlet channel can thus have any suitable characteristic dimension. In certain embodiments, the characteristic dimension of the first and/or second inlet channel, e.g., diameter if the channel has a circular cross-section, can be at least 1, 10, 20, 50, 70, 80, 90, 100, 110, 120, 130, 150, 170, 200, 250, 300, 400, 500, 600, 700, 800, or 900 um, and/or not more than 10, 50, 70, 80, 90, 100, 110, 120, 130, 150, 170, 200, 250, 300, 400, 500, 600, 700, 800, 900, or 1000 um, for example, 1-1000 um, or 10-800 um, or 10-600 um, or 20-400 um, or 50-300 um, or 100-300 um, or 150-250 um.

The characteristic dimension of the outlet channel can be smaller than or equal to the characteristic dimensions of the two inlet channels, and it is this dimension that controls the resulting equivalent spherical diameter of the droplets that are formed. The characteristic dimension of the outlet channel, e.g., diameter if the channel has a circular cross-section, can be at least 1, 10, 20, 50, 70, 80, 90, 100, 110, 120, 130, 150, 170, 200, 250, 300, 400, 500, 600, 700, 800, or 900 um, and/or not more than 10, 50, 70, 80, 90, 100, 110, 120, 130, 150, 170, 200, 250, 300, 400, 500, 600, 700, 800, 900, or 1000 um, for example, 1-1000 um, or 10-800 um, or 10-600 um, or 20-400 um, or 20-300 um, or 20-200 um, or 50-200 um, or 80-150 um, or 80-120 um, or 90-110 um, or about 70, 80, 90, 100, 110, 120, 130, or 140 um. Unless otherwise noted, dimensions for conduits are interior dimensions. Also unless otherwise noted, conduits may have any suitable cross-section, such as square, oblong, circular, and the like; in certain cases cross-section may be described as circular but it is to be understood that any suitable cross-section may be used. The outlet channel may or may not expand to a larger characteristic dimension after droplet formation. However, the outlet channel of the droplet partitioner should be a uniform characteristic dimension (e.g., diameter) for a length at least 1.25× that characteristic dimension (e.g., diameter), for example, at least 1.25, 1.5, 2, 3, 4, 5, 6, 7, 8, 9 or 10 times the characteristic (dimension, e.g., diameter, and/or not more than 1.5, 2, 3, 4, 5, 6, 7, 8, 9, 10, 12, or 15 times the characteristic dimension, e.g., diameter, for example, between 1.5× and 10×, or between 2× and 8×, such as between 3× and 7×. For example, if the outlet channel is circular with a diameter of 100 um, typically it should remain at 100 um diameter for a length of at least 125 um. Beyond this region, the outlet conduit, either within the partitioner (e.g., a block of material) or outside the partitioner (e.g., block), can change to a different characteristic dimension (e.g., diameter) e.g., expand to a greater characteristic dimension (e.g., diameter). In addition, in some embodiments, at some point after the outlet conduit its orientation will become perpendicular or nearly perpendicular to the gravitational field, e.g., when leading to a reactor and/or detector. This can help reduce buoyancy effects on partitions, which can lead to undesirable axial dispersion of partitions or other problems.

An advantage of this approach is that the droplet size is relatively insensitive to the relative flow rates of fluid in the first inlet channel and the second inlet channel, for example, over a range of at least 2-fold, or a range of at least 5-fold, or a range of at least 10-fold, or a range of at least 100-fold, or a range of at least 1000-fold, for example, in flow rates from 0.01-3000 uL/min. Mean droplet size can vary over these ranges by, e.g., not more than 100, 90, 80, 70, 60, 50, 40, 30, 25, 20, 15, 10, 5, 2, or 1%.

In certain embodiments, the partitioner, e.g., a reverse-y partitioner, is electrically grounded.

Figure 38:
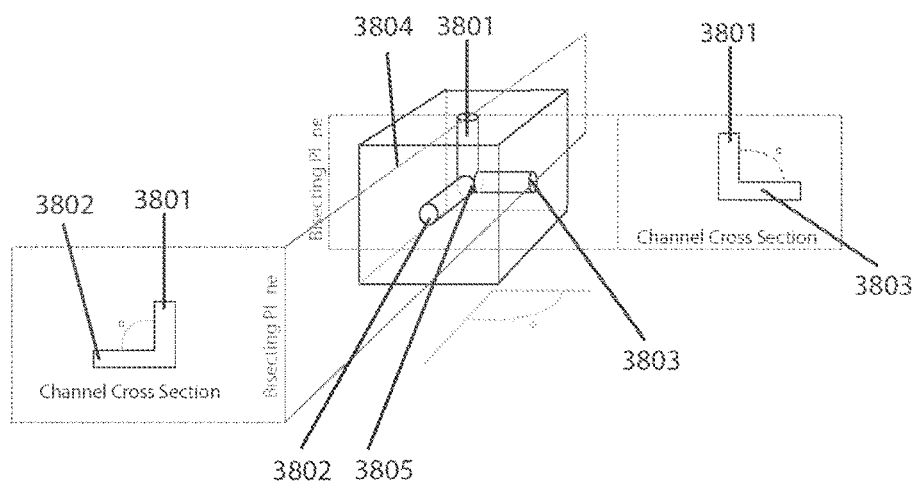
FIG. 38 shows a reverse-y partitioner, with a 90 degree intersect.
Figure 39A:
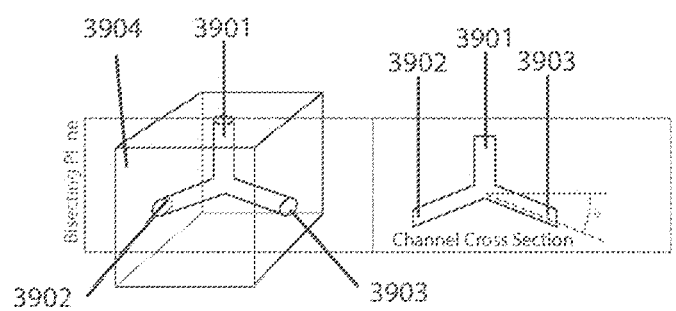
FIGS. 39A and 39B show different angles of intersect in reverse-y partitioner.
Figure 39B:
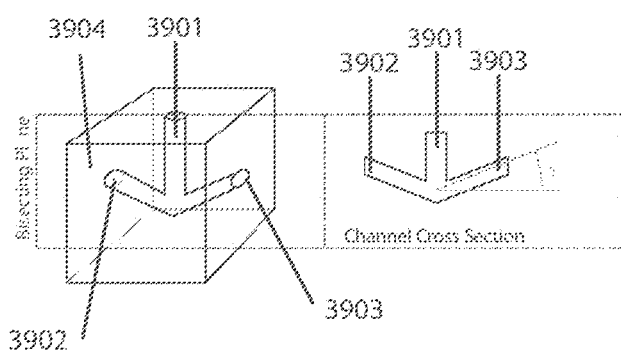
Figure 40:
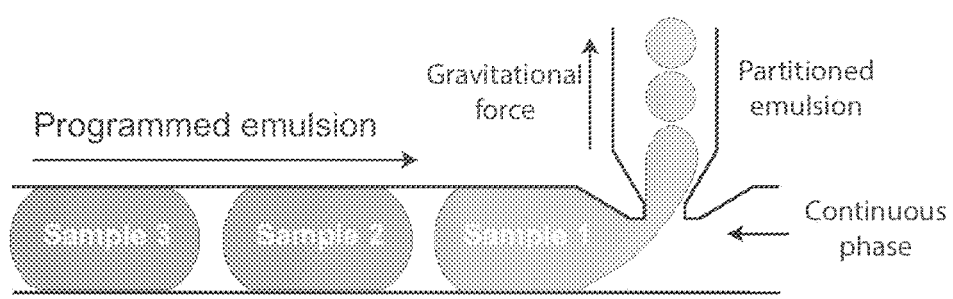
FIG. 40 shows a gravitational arrangement of channels.

FIGS. 38 and 39A and 39B show a reverse-y partitioner. The reverse-y droplet partitioner comprises an outlet channel 3801, 3901 substantially parallel and two inlet channels placed relatively orthogonal to the gravitational field. In the reverse-y partitioner, two small inlet channels 3802, 3902 and 3803, 3903 meet at an angle (theta) between 2 degrees and 180 degrees between the axes of the channels. The inlet channels may be oriented above or below the plane orthogonal to the outlet channel (+−45 degrees) (alpha). The first 3802, 3902 and the second 3803, 3903 inlet channels are oriented with a substantial component orthogonal to the ambient gravitational field. The channels may be formed in a substrate 3804, 3904. In a first inlet channel 3802, 3902, a mixture of continuous and dispersed phases is flowing, with the continuous and dispersed phases being mostly immiscible. This continuous and disperse phased comprises a programmed emulsion containing discrete sample plugs separated by continuous phase. In a second inlet channel 3803, 3903, fluid substantially miscible with the continuous phase is flowed. In certain embodiments, the first continuous phase is of the same composition as the second continuous phase. In certain embodiments, the first and second continuous phases comprise an oil and surfactant. In certain embodiments, the dispersed phase comprises an aqueous solution. In certain embodiments, the first and second phase are composed of the same oil with varying surfactant concentrations. In certain embodiments, the surfactant in the first continuous phase is different from the surfactant in the second continuous phase. An outlet channel 3801, 3901 receives flow from the first inlet channel 3802, 3902 and the second inlet channel 3803, 3903 at the junction point 3805, 3905 of the first inlet channel 3802, 3902 and the second inlet channel 3803, 3903, and this outlet channel 3801, 3901 is oriented substantially parallel to the ambient gravitational field. Fluid flow in the outlet channel 3801, 3901 moves counter to the gravitational force. In orienting the channels in such a way, buoyancy can play a role in droplet formation. The outlet channel 3801, 3901 may or may not expand to a larger length after droplet formation (25 um-2000 uM). The characteristic length of the first inlet channel 3801, 3901 may be larger than the characteristic length of the second inlet channel 3802, 3902, vice versa, or the two characteristic lengths may be substantially similar. The characteristic length can be a diameter, a hydraulic diameter, or any length scale that substantially determines the cross-sectional area of the channel. (1-1000 um) The characteristic length of the outlet channel 3801, 3901 is smaller than or equal to the characteristic lengths of the two inlet channels, and it is this length that controls the resulting diameter of the droplets that are formed. (1-1000 um) An advantage of this approach is that the droplet size is relatively insensitive to the relative flow rates of fluid in the first inlet channel and the second inlet channel. (0.01-3000 uL/min).

Figure 45:
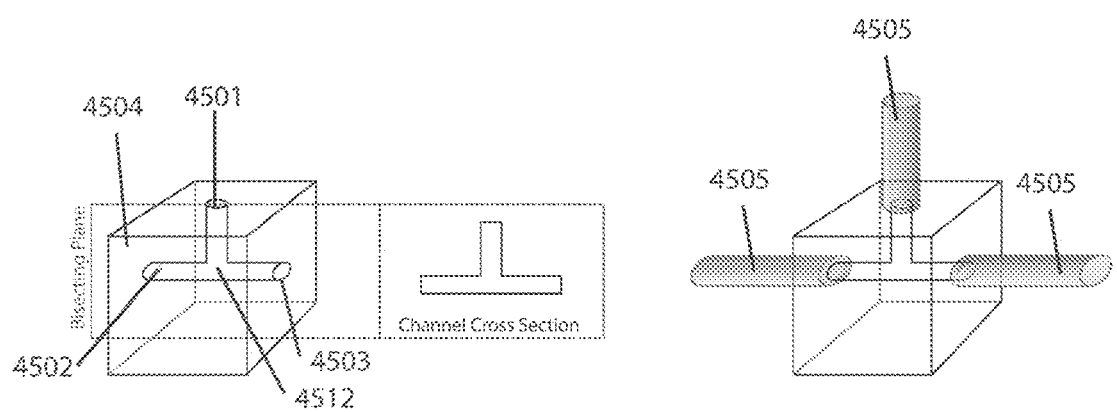
FIG. 45 shows partitioner connections for formed channels.

FIGS. 44A and 44B and 45 illustrate embodiments of a reverse-y partitioner in which the two inlet channels intersect at 180 degrees, are orthogonal to the gravitational field, and intersect with the outlet channel at an angle of 90 degrees, with the outlet channel oriented parallel to the gravitational field. In this embodiment, fluid flow of the first inlet channel collides with fluid flow of the second inlet channel. In certain embodiments, including that illustrated in FIGS. 44A, 44B, and 45, one, two, or all three of the channels are contained within a solid block. The channels of the partitioner, of any form, are connected to the rest of the system. FIGS. 44A and 44B and 45 also illustrate three ways in which tubing to connect the partitioner to the rest of the system may be used. FIG. 45 illustrates an embodiment in which tubing is attached with specialized adapters, where the channels of the partitioner are fluidic channels in the block. FIG. 44A illustrates an embodiment in which tubing is inserted partway into the block, where the channels are tubing channels connected to fluidic channels; in the case of FIG. 44B, tubing is inserted all the way into the block, thus the channels are tubing channels. Any combination of the three methods may be used. Thus, channels that come in contact with fluids may be formed by drilling or milling or similar operation, by tubing, or any combination thereof. Connections are described in more detail below. In instances in which tubing is inserted all the way into the block, the tubing itself serves as the channel (inlet and/or outlet). In all cases, in certain embodiments, surfaces that come in contact with fluids, such as with dispersed phase, have a higher affinity for continuous phase than for dispersed phase Thus in certain embodiments the channel geometries may be as described above. In certain embodiments, the first and second inlet channels are oriented 180 degrees apart, so that a single drilling or milling pathway is used to produce these channels. The outlet channel is created by a drilling or a milling operation that connects with the inlets channels. Each inlet or outlet channel may be comprised of a single drilled fluidic channel, a single drilled tubing channel, or a combination of the two. (A) Fluidic channels. (B) Tubing channels connected to fluidic channels. (C) Tubing channels.

In a first embodiment, e.g. as shown in FIG. 45, channels are generated with inner diameters equal to the characteristic length for droplet formation. The channels are generated by two or more drilling operations. The first of said drilling operations generates the two inlets channels 4502 and 4503. The second of said drilling operations generates the outlet 4501. The second drilling operation connects the second channel to the first channel generated by the first drilling operation forming a junction 4512. Tubing 4505 may be attached to the droplet partitioner in any suitable, manner, such as by a compression fitting using a nut and ferrule. The fitting generates a fluidic seal between the partitioner and tubing as the fitting is tightened.

In a second embodiment, e.g., as shown in FIG. 44A, channels are generated with two distinct inner diameters. The first inner diameter is equal to the characteristic length for droplet formation. The second inner diameter is of a size to connect tubing through an interference fit. The drilled channels comprise an outlet with a first channel 4401 with an inner diameter equal to the characteristic length for droplet formation and a second channel 4406 with an inner diameter equal to or smaller than the OD of the tubing 4405 to be inserted. When inserting tubing 4405 with a higher elastic modulus than the block material, a sufficient force is applied to the tubing forming a fluidic seal. The drilled channels also comprise two inlets with distinct inner diameters. For the first inlet, the drilled channels comprise a first channel 4402 with an inner diameter of a size capable of transporting the first fluid and a second channel 4407 with an inner diameter equal to or smaller than the OD of the tubing 4405 to be inserted. For the second inlet, the drilled channels comprise a first channel 4403 with an inner diameter of a size capable of transporting the first fluid and a second channel 4408 with an inner diameter equal to or smaller than the OD of the tubing 4405 to be inserted. The first 4402 and second 4403 inlet channels may be of equal or different sizes. The first inner diameter of the outlet channel 4401 is equal to the characteristic length for partition formation. The channels may be generated using one or more drilling operations that form a junction 4412 capable of partition formation. In a third embodiment, such as shown in FIG. 44B, channels are generated with a single distinct inner diameter equal to or smaller than the OD of the tubing 4405. The channels are generated by two or more drilling operations. The first of said drilling operations generates the two inlets channels 4410 and 4411. The second of said drilling operations generates the outlet 4409. The second drilling operation connects the second channel to the first channel generated by the first drilling operation forming a junction. When inserting tubing 4405 with a higher elastic modulus than the block material, a sufficient force is applied to the tubing forming a fluidic seal. Insertion of the tubing into the very center of the substrate 4404 forms a junction 4413. The inner diameter of the tubing is used as the channels and the critical diameter for partition formation is determined by the critical diameter of the inner diameter of the outlet tubing.

In certain embodiments, any combination of tubing connection methods may be used.

The droplet partitioner channels in the block, e.g., fluoropolymer block are made sufficiently small to ensure stable fluid flow reducing the possibility for hold up of sample in the channels.

In a preferred embodiment the tubing ID and channel ID are size matched to ensure stable fluid flow reducing the possibility for hold up of sample in the channels.

Droplet size for reverse-y partitioner. Methods for controlling the size of droplets produced in the droplet partitioner comprise controlling the cross-sectional area of the outlet channel, for example, controlling a characteristic dimension, also referred to herein as "characteristic length," or "critical dimension," such as a diameter or a hydraulic diameter. Droplets will be similar in diameter to this characteristic (critical) dimension, and/or have average cross-sectional areas similar to the cross-sectional area of the outlet channel. This differs from orifice-style droplet partitioners, where droplets that are formed will generally be substantially larger than the characteristic dimension of the orifice, generally larger than one and half times the characteristic dimension. An advantage of this style of droplet partitioner is that the droplet size is relatively insensitive to variability of the flowrate from the first inlet channel and the second inlet channel, as the characteristic dimension of the outlet channel generally controls the diameter of the produced droplets. This differs from shear-based (e.g. T-junction or cross-junction) or orifice droplet partitioner, which generally require stable flowrates to produce monodisperse droplets. As such, a system employing this droplet partitioner may be able to use less expensive, complicated, or bulky means of supplying the necessary driving force to introduce fluids into the first inlet channel and the second inlet channel. When referring to droplet diameter, it is meant the characteristic or equivalent spherical diameter (the diameter that the droplets would take as spheres suspended in the continuous phase). Droplets constrained within channels may elongate and have a critical dimension orthogonal to the channel axis shorter than this equivalent spherical diameter. Thus, in some embodiments, the systems and methods described herein, e.g., digital PCR methods, provide a plurality of partitions (droplets), such as at least 100, 1000, or 10,000 partitions, from a single sample (e.g., the dispersed phase that enters the partitioner in an inlet channel), where the partitions have an mean spherical diameter, such as a mean spherical diameter in the range of 10-1000, 20-800, 30-700, 40-500, 40-400, 40-300, 50-200, 50-150, or 75-125 um and wherein the coefficient of variation of the spherical diameters of the partitions is less than 50, 40, 30, 20, 15, 12, 10, 9, 8, 7, 6, 5, 4, 3, 2, or 1%, over a range of flow rates in inlet channels of at least 10-fold, or at least 100-fold, or at least 1000-fold.

Figure 41A:
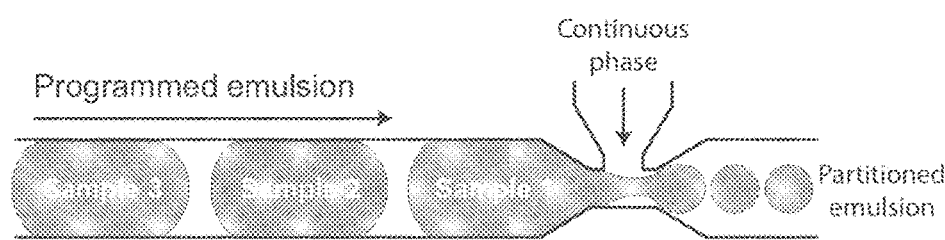
FIGS. 41A, 41B, and 41C show different configurations of T-junction partitioners.
Figure 41B:
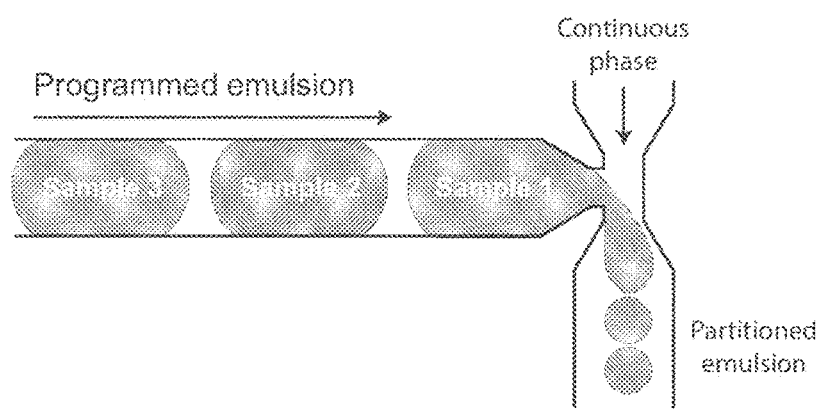
Figure 41C:
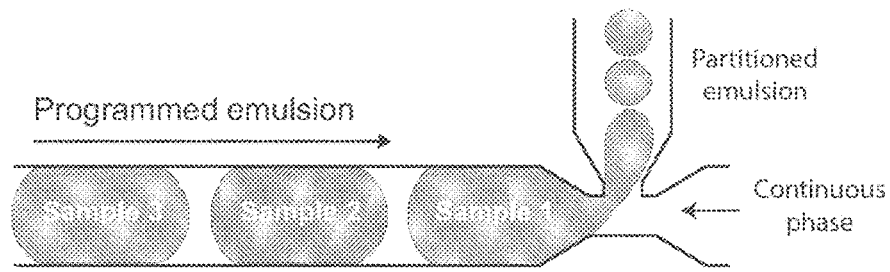

T-junction partitioners. FIGS. 41A, 41B, and 41C show another system for partitioning droplets (a "T-junction" droplet partitioner). In the T-junction partitioner, two inlet channels meet at an angle (theta) between 2 degrees and 90 degrees between the axes of the channels and converge to a single outlet channel. In some cases, the inlet channels meet at an angle between 90 and 180 degrees, or between 110 and 180 degrees, or between 130 and 180 degrees, or between 150 and 180 degrees, or between 160 and 180 degrees, or between 170 and 180 degrees, in some cases 180 degrees (co-axial); an arrangement in which the inlet channels are co-axial is shown in FIG. 41C. In a first inlet channel, a mixture of continuous and dispersed phases is flowing, with the continuous and dispersed phases being mostly immiscible. In a second inlet channel, fluid substantially miscible with the continuous phase is flowed. Continuous phases, surfactants, etc., can be as described for the reverse-y partitioner. The first and the second inlet channel can be oriented in any suitable plane relative to the ambient gravitational field, such as with a substantial component perpendicular to the ambient gravitational field. An outlet channel receives flow from the first inlet channel and the second inlet channel at the junction point of the first inlet channel and the second inlet channel, and this outlet channel is also oriented in any suitable manner, e.g., perpendicular or substantially perpendicular to the ambient gravitational field. In some cases, the flow of sample is perpendicular or nearly perpendicular (e.g., angle of 60-90, 70-90, 80-90, or 85-90 degrees) to the flow of the continuous phase (see, e.g., FIG. 41A), with sample phase parallel to the outlet. In some cases, the outlet and continuous phase are parallel and perpendicular or nearly perpendicular (e.g., angle of 60-90, 70-90, 80-90, or 85-90 degrees) to the sample phase. This results in droplets being pushed off into smaller partitions (see, e.g., FIG. 41B). In some cases, the sample phase and the continuous phase are parallel with each other (see, e.g., FIG. 41C), i.e., intersect at 180 degrees or nearly 180 degrees, and the outlet is perpendicular or nearly perpendicular (e.g., angle of 60-90, 70-90, 80-90, or 85-90 degrees) to the inlets. In this case, the two phases are colliding head-on. The outlet channel may or may not expand to a larger length after droplet formation. The characteristic dimension of the first inlet channel may be larger than the characteristic dimension of the second inlet channel, vice versa, or the two characteristic dimensions may be substantially similar. In certain embodiments, the characteristic dimension of the first and/or second inlet channel, e.g., diameter if the channel has a circular cross-section, can be at least 1, 10, 20, 50, 70, 80, 90, 100, 110, 120, 130, 150, 170, 200, 250, 300, 400, 500, 600, 700, 800, or 900 um, and/or not more than 10, 50, 70, 80, 90, 100, 110, 120, 130, 150, 170, 200, 250, 300, 400, 500, 600, 700, 800, 900, or 1000 um, for example, 1-1000 um, or 10-800 um, or 10-600 um, or 20-400 um, or 50-300 um, or 100-300 um, or 150-250 um. The characteristic dimension of the outlet channel is either smaller than, equal to, or larger than the characteristic lengths of the two inlet channels. In certain embodiments, the characteristic dimension of the outlet channel, e.g., diameter if the channel has a circular cross-section, can be at least 1, 10, 20, 50, 70, 80, 90, 100, 110, 120, 130, 150, 170, 200, 250, 300, 400, 500, 600, 700, 800, or 900 um, and/or not more than 10, 50, 70, 80, 90, 100, 110, 120, 130, 150, 170, 200, 250, 300, 400, 500, 600, 700, 800, 900, or 1000 um, for example, 1-1000 um, or 10-800 um, or 10-600 um, or 20-400 um, or 50-300 um, or 100-300 um, or 150-250 um. Droplet size is determined by the relative flow rates and geometry of the two inlet channels. As with other partitioners described herein, this partitioner can be fabricated using one or more solid blocks as a starting point, for example, a fluoropolymer block or similar block that has greater affinity for continuous phase than for dispersed phase, or can have coated surfaces, or conduits, or other features that convey greater affinity for continuous phase than for dispersed phase, in particular, in channels that come in contact with dispersed phase.

Figure 42:
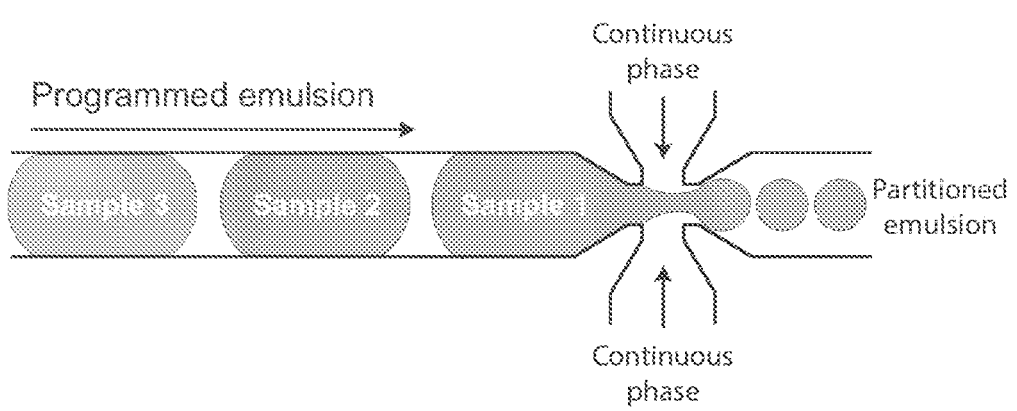
FIG. 42 shows a cross junction partitioner.

Flow-focusing droplet partitioner FIG. 42 shows another system for partitioning droplets (a "flow focusing" droplet partitioner, also referred to herein as a cross-junction partitioner). Two continuous phase flows result in the pinching of a plug into multiple smaller partitions. In the flow focusing partitioner, three inlet channels meet at an angle (theta) between 2 degrees and 90 degrees between the axes of the channels and converge to a single outlet channel. In some cases, the two outer channels are oriented perpendicular to the interior inlet channel, as shown in FIG. 42. In the interior inlet channel, a mixture of continuous and dispersed phases is flowing, with the continuous and dispersed phases being mostly immiscible. In the external inlet channels, a fluid substantially miscible with the continuous phase is flowed. Continuous phase, surfactants, and the like may be as described for the reverse-y droplet generator. All channels can be oriented in any suitable manner, e.g., with a substantial component perpendicular to the ambient gravitational field. An outlet channel receives flow from the three inlet channels and this outlet channel is also oriented in any suitable manner, e.g., substantially perpendicular to the ambient gravitational field. The outlet channel may or may not expand to a larger length after droplet formation. The characteristic dimension of the interior channel may be larger than the characteristic dimensions of the outer inlet channels, vice versa, or the characteristic dimensions may be substantially similar. In certain embodiments, the characteristic dimension of one or both of the outer inlet channels and/or the interior inlet channel, e.g., diameter if the channel has a circular cross-section, can be at least 1, 10, 20, 50, 70, 80, 90, 100, 110, 120, 130, 150, 170, 200, 250, 300, 400, 500, 600, 700, 800, or 900 um, and/or not more than 10, 50, 70, 80, 90, 100, 110, 120, 130, 150, 170, 200, 250, 300, 400, 500, 600, 700, 800, 900, or 1000 um, for example, 1-1000 um, or 10-800 um, or 10-600 um, or 20-400 um, or 50-300 um, or 100-300 um, or 150-250 um. The characteristic length of the outlet channel is either smaller than, equal to, or larger than the characteristic lengths of the two inlet channels. In certain embodiments, the characteristic dimension of the outlet channel, e.g., diameter if the channel has a circular cross-section, can be at least 1, 10, 20, 50, 70, 80, 90, 100, 110, 120, 130, 150, 170, 200, 250, 300, 400, 500, 600, 700, 800, or 900 um, and/or not more than 10, 50, 70, 80, 90, 100, 110, 120, 130, 150, 170, 200, 250, 300, 400, 500, 600, 700, 800, 900, or 1000 um, for example, 1-1000 um, or 10-800 um, or 10-600 um, or 20-400 um, or 50-300 um, or 100-300 um, or 150-250 um. Droplet size is determined by the relative flow rates and geometry of the two inlet channels. As with other partitioners described herein, this partitioner can be fabricated using one or more solid blocks as a starting point, for example, a fluoropolymer block or similar block that has greater affinity for continuous phase than for dispersed phase, or can have coated surfaces, or conduits, or other features that convey greater affinity for continuous phase than for dispersed phase Surfactants In some embodiments, the continuous phase, the dispersed phase, or both comprise a surfactant to stabilize the size of packets of continuous phase in dispersed phase. Surfactant composition and concentration may be as described elsewhere herein, e.g., see "Materials used in systems and embodiments provided herein," above. In certain embodiments, continuous phase flowing in an inlet of the partitioner, such as a fluorinated oil, comprises a surfactant, such as a fluorinated surfactant, at a concentration of 0.2-2%, such as 0.5-1.5%, or 0.8-1.2%, or any other concentration as described herein.

Partitioner integration into the overall system The partitioner is typically incorporated into a larger system for conducting chemical, physical, or biological processing. Systems and methods provided herein include a partitioner that is enclosed by a holder and/or that is connected to the overall system as described herein. Supply of continuous phase or mixtures of continuous phase and dispersed phase can be provided to the inlets of the droplet partitioner using tubes, pipes, microfluidic channels, or any other suitable systems and methods of supplying fluids. Mixtures of continuous phase and produced droplets can be connected to downstream processing elements using tubes, pipes, microfluidic channels, or any other suitable systems and methods of conveying fluids. In certain embodiments, polymer tubing is used to supply fluids to at least one of the inlets or convey fluid from the outlet. In some cases, tubing or other conduits that come in contact with dispersed phase have a greater affinity for continuous phase than for dispersed phase. In some cases, this tubing comprises a fluoropolymer It will be appreciated that, although connections are described in this section for connections to a partitioner, connections in other parts of the system (e.g., at a droplet separator, a detector, an injector, or any other suitable point) may also use similar or identical systems and methods, and the descriptions in this section apply to other areas in the system, as appropriate.

Typically, connections are formed in such a way as to reduce or eliminate dead spaces and other potential disruptions to flow in the system. In general, when flow moves in a conduit, connections or other effects that expand the characteristic dimension, e.g., diameter of the conduit are less likely to create dead spaces than connections or other effects where diameter remains constant; typically, it is not desirable to have connections where characteristic dimension, e.g., diameter decreases, especially if it decrease abruptly, as this can lead to dead zones or other disruptions. In certain embodiments, the cross-sectional outline of a conduit prior to a connection is matched with the cross-sectional outline of the conduit after the connection by the connection itself in such a manner that the two cross-sectional outlines are identical or nearly identical, and there is no or substantially no break at the junction between the two conduits. Conduits, e.g., tubing may be attached to the droplet partitioner in any suitable manner, e.g., by an interference fit or a compression fitting. See, e.g., FIGS. 43A, 43B, and 43C. In the first instance (FIG. 43C) holes are created in the block that is the droplet partitioner, e.g., drilled into a solid block, such as a block that has greater affinity for continuous phase than for dispersed phase, e.g., a fluoropolymer block for use with, e.g., fluorinated oils, with equal or slightly smaller diameter as the outer diameter of the tubing to be inserted. When inserting tubing with a higher elastic modulus than the block material, a sufficient force is applied to the tubing forming a fluidic seal. Since the drilled hole is smaller than the tube and the tube is more rigid than the block it forms a fluidically tight seal. In certain embodiments, the cross-sectional outline of the tubing is identical or nearly identical to the cross-section outline of the block when the tubing is inserted (e.g., with circular tubing and circular conduit in the block, the ID of the tubing is the same or nearly the same as the block when the tubing is inserted into the block, e.g., within 5, 2, 1, 0.5, 0.1, 0.05, 0.01, 0.005, or 0.001% of the same). The end of the tubing fits snugly against the block, so that, at flow rates and with compositions used in the tubing and the block, no disruption in flow or dead spots are created; in certain embodiments, the end of the tubing inserted into the block is configured to snug against the block material for the entire circumference of the tubing. Typically this can be accomplished by creating smooth cuts in the tubing that are perpendicular to the axis of flow in the tubing, and having a complementary surface for the tubing to butt against in the block. In the second instance (FIG. 43A), a compression fitting and nut is used to create a fluidic seal between the tubing and the channel in the block, e.g., block as described herein, such as fluoropolymer block. Any suitable combination of fluidic seals may be used. FIG. 43 also shows the partitioner block, e.g., block as described herein such as fluoropolymer block, that has been manufactured with the channels, contained in a holder, or housing material, to provide mechanical stability. This housing material may be composed of any suitable material that provides the desired mechanical stability, and capable of operations to shape the material, including machining, engraving, etching, ablating, embossing, molding, or printing for example, a metal, such as aluminum or stainless steel, for mechanical strength. FIG. 43B tubing is shown that is held in place using fittings that provide extra stability so the tubing doesn't get pulled out. FIGS. 43B and 43D show the use of specialized fittings. The fittings use a nut and ferrule to hold the tube in place against the polymer block. The ferrule crimps down on the tube while also providing pressure against the block. The nut should be able to reach down into the block so the housing material can't be so large that it does not reach. It is preferred that the tubing diameter matches the channel diameter to ensure stable fluid flow.

Thus, as in FIG. 43, in a first embodiment, a fluidic conduit 4305 is connected to the partitioner 4304 by a compression fitting using a nut 4314 and ferrule 4315. The fitting generates a fluidic seal between the partitioner and tubing as the fitting is tightened between the outer surface of the tubing and the inner surface of the partitioner. The internal cross-sectional diameter of the tubing 4317 may match the internal cross-sectional diameter of the conduits in the partitioner 4318 to ensure smooth fluid flow through the connection. The fittings material may be made out of any suitable material as long as that material is appropriate for the continuous phase solvents being used. In a second embodiment, channels are generated in a substrate 4304 with two distinct inner diameters. The first inner diameter 4318 is of ample size to allow flow of fluid to the partitioner junction 4319 and may be of equal size to the fluidic conduit being connected 4317 to ensure smooth flow through the connection. The second inner diameter 4320 is of a size to connect the fluid conduit through an interference fit. The diameter of second inner diameter 4320 is equal to or smaller than the outer diameter of the fluidic conduit to be inserted. When inserting a fluidic conduit 4305 made with a material of a higher elastic modulus than the block material, a sufficient force is applied to the tubing forming a fluidic seal.

The droplet partitioner may or may not be mounted using a supporting material 4316. The mounting material may be composed of any material capable of machining, engraving, etching, ablating, embossing, molding, or printing. The mounting material may be used to affix and stabilize the partition in a specified location in the system. The material may also be made of a conductive material to help dissipate any static build up at the partitioner. It may also be used to stabilize conduit connections to the partitioner. For example, when using an interference fit connection, the fluidic seal is generated inside of the partitioner at the interface of the inner surface of partitioner and the outer surface of the fluidic conduit. However, additional support may be required to further secure the union from disturbance and may be generated using a nut and ferrule assembly 4314 connected to a supporting mount 4316.

The channels in the partitioner may be generated through the use of tubing and/or drilled, milled, or otherwise formed channels in a solid block. Suitable characteristic dimension, e.g., diameter for circular channels, range from 50 um to 2 mm, such as 50 um to 1 mm, or 50 um to 500 um, or 100 um to 400 um, or 200 um to 2 mm, or any other range or dimension as described herein in specific embodiments. When tubing is used, the tubing is placed sufficiently into the block, e.g., fluoropolymer block to act as fluidic channels at the junction. When formed channels are used, the tubing is placed adjacent to drilled channels in the fluoropolymer block. Any suitable combination of fluidic channel types may be used, for inlet channels and/or outlet channel.

In certain embodiments, fluoropolymer tubing is inserted into the fluoropolymer block adjacent to formed channels, e.g., drilled or milled channels equal to or smaller than the tubing ID. The inlet and outlet channels can be produced in the fluoropolymer block in two passes. In the first pass, a channel is generated to accommodate either the interference or the compression forming a fluidic seal with the tubing. In the second pass, the liquid channel is generated.

The droplet partitioner channels in the fluoropolymer block are made sufficiently small to reduce the possibility for hold up of sample in the channels.

Channel diameters for the tubing (or other appropriate conduit) connecting to the inlet channels can take any dimension. However, it is generally preferable to avoid transitioning from smaller diameters to a larger diameter in the droplet partitioner inlet channels, because it can potentially cause breakup of the inlet train of dispersed phase (e.g. aqueous PCR reactions), holdup, sample adsorption or other problems that lead to, e.g., cross-contamination between samples and/or inaccurate readings for a sample due to partial removal of part of the sample. Also, there is little benefit to being very small in the connection conduits, for pressure drop reasons. Generally, the characteristic dimension, e.g., diameter, of these inlet conduits can be, at least 50, 75, 100, 125, 150, 200, 250, 300, 350, 400, or 450 um, and/or not more than 75, 100, 125, 150, 200, 250, 300, 350, 400, 450, 500, 600, 700, or 800 um, for example, between 75 and 800 um, or between 125 and 700 um, such as between 150 um and 500 um.

Connection to the outlet channel generally follows the same pattern. In certain embodiments, a conduit leading from the partitioner to the rest of the system can have a characteristic (critical) dimension, e.g., a diameter, of at least 50, 75, 100, 125, 150, 200, 250, 300, 350, 400, or 450 um, and/or not more than 75, 100, 125, 150, 200, 250, 300, 350, 400, 450, 500, 600, 700, or 800 um, for example, between 75 and 800 um, or between 125 and 700 um, such as between 150 um and 500 um.

Thus, systems and methods as described herein may comprise reducing contamination by of dead zones. "Dead zones" as described herein refer to regions or zones in the flow where droplets of the dispersed phase or continuous phase have low or zero velocity. In some instances, the system comprises multiple microfluidic tubes, channels, or modules that are interconnected to provide a flow pathway for the continuous phase, emulsion and/or dispersed phase. These interconnections may be locations at which dead zones could form. For example, an interconnection may be where there is an imperfect connection between one microfluidic tube or module and a second microfluidic tube or module, and a dead zone can form in the imperfect connection. Dead zones can lead to cross-contamination because a first portion of a first dispersed phase generated from a first sample may be trapped in the dead zone long enough to contact or be interspersed with a portion of a first dispersed phase generated from a second sample. To prevent formation of dead zones, one or more connections may be made between the one or more microfluidic channels or one or more tubes in the system. For example, one or more connections are made between the microfluidic channels or the tubes of the injector, droplet generator, reactor, or detector. For example, a press-fit connection can be made between a microfluidic tube and a microfluidic channel (a first conduit and a second conduit). The press-fit connection may comprise a recessed region in a polymer leading to the microfluidic channel. The cross-section of the microfluidic channel (first conduit) may substantially match the internal cross-section of the tube (second conduit). In some instances, the microfluidic channel and the microfluidic tube comprise different cross-sections. In some instances, an internal cross-section of the recessed region is smaller than the external cross-section of the tube. In some instances, an internal cross-section of the recessed region is the same as the external cross-section of the tube. The tube may comprise a material with a lower elastic modulus than the polymer containing the channel. Exemplary materials of the tube include, but are not limited to, silicon, polystyrene, polyacrylamides, PDMS, ceramic, metals, and glass. Exemplary polymers of the channel include, but are not limited to, a styrenic elastomer, an ethylene vinyl acetate elastomer, a polyolefin elastomer, a diene elastomer, fluoropolymers (e.g. PTFE, PVDF, PFA, and FEP), or combinations thereof.

Provided herein are systems and methods for serial flow emulsion reactions, wherein reducing contamination by preventing formation of dead zones may comprise creating a seal. In some instances, as a result of a connection between the tube and the polymer, a fluidic seal is created. In some instances, the fluidic seal prevents continuous flow of droplets.

In some instances, placement of the tube prevents creation of a dead zone. For example, placement of an end of the tube against an end of the recess prevents creation of a dead zone and a continuous flow. A continuous flow may also be a result of the cross-section of the channel and the cross-section of the tube being substantially the same.

Fabrication of partitioners. For partitioners described herein, such as reverse-y, T-partitioners, or flow-focusing partitioners, any suitable fabrication method may be used; for convenience, methods will be described for the reverse-y partitioner but it will be appreciated that T-partitioners and other design can employ the same or similar techniques Droplet partitioners can be fabricated from any suitable materials of construction, including glass, polymers, metal, ceramics, or any mixture of these. Any suitable fabrication method that creates the desired features, e.g., removes material from a solid piece or builds up material to have the specified feature geometries, may be used. Fabrication techniques include but are not limited to direct machining, engraving, etching, ablating, embossing, molding, printing.

Provided herein are methods of fabricating partitioners, e.g., from a solid block of material, or from a plurality of blocks joined together to provide a fluidically tight seal. In certain embodiments, the block or plurality of blocks comprise material that has greater affinity for continuous phase to be used in the system than for dispersed phase—this provides an easy and rapid method to manufacture a partitioner with the desired properties without requiring coating or otherwise altering the surface and produces partitioners that will continue to function properly even if the surfaces are subject to wear.

In some cases, suitable channels may be created by creating holes, e.g., drilling into a solid block. For example, for a reverse-y partitioner in a configuration such as shown in FIG. 44, where the inlet channels meet at 180 degrees, or any other type of partitioner where conduits of the same diameter meet at 180 degrees, a single drilling or similar operation can produce both inlet channels and a second drilling operation can produce the outlet channel; in the case of a partitioner as shown in FIG. 39, more than 2 drilling operations can be required. If press fittings or compression fittings are used, a larger hole to accommodate the tubing may be drilled first, then the smaller-diameter hole that will comprise the channel can be drilled. Suitable machining or other operations may be used to produce a junction of the larger with the smaller conduit that will butt firmly with tubing inserted into the larger-diameter conduit. Thus, in certain embodiments, the first and second inlet channels are oriented 180 degrees apart, so that a single drilling, milling, or other similar pathway is used to produce these channels. The outlet channel is created by a drilling, milling, or other similar operation that connects with the inlet channels. Each inlet or outlet channel may be a single drilled fluidic channel, a single drilled tubing channel, or a combination of the two.

However, other manufacturing procedures may be used. See, e.g., FIGS. 46A and 46B. FIG. 46A shows a combination of milling and drilling. The drill step creates the outlet. The mill step creates the two inlets. They may be at any angle from each other from 2-180 degrees (90 degrees is shown in the Figure). Once the two pieces are made they are joined by any suitable method, for example, fused together chemically or are held together tightly to create a fluidic seal. The first method is preferred. FIG. 46B shows a 3 piece assembly generated entirely by milling. The 3 pieces are then fused together. Any suitable number of pieces may be drilled or milled, then joined, such as at least 2, 3, 4, or 5 pieces. The surface chemistry of the channels after bonding should be consistent with the chemistry of the continuous phase. With a hydrophobic continuous phase the material should be hydrophobic; for an aqueous continuous phase and the material being hydrophilic. For example, if fabrication begins with a fluoropolymer material, the blocks may be sealed together, and the channels are still composed of fluoropolymer, thus simplifying manufacturing. If a chemistry is used that destroys the fluoropolymer surface, it can be restored to be fluorinated. In embodiments in which the partitioner is a block that is composed of material with higher affinity for the continuous phase than for the dispersed phase, e.g., a fluoropolymer block, there is a benefit that if there surface is degraded/etched over time, instead of losing the fluoropolymer surface, new fluoropolymer is exposed. This ensures that the surface chemistry of the partitioner is more robust than traditional PDMS/glass droplet partitioners coated with a fluoropolymer Thus, while the material of construction is not necessarily important for droplet formation, it may be desirable for the surface of the partitioner to comprise a material with a higher affinity for the continuous phase than for the dispersed phase; droplet partitioners constructed of materials with substantially similar affinities for the two phases or a higher affinity for the dispersed phase than for the continuous phase may be coated with a film comprising a material with a higher affinity for the continuous phase than for the dispersed phase on the appropriate surfaces, e.g., at least on surfaces that will contact the dispersed phase. This film may, over time, chemically or physically degrade, exposing the underlying surface to the emulsion and disrupting droplet partitioning or holding up a portion of the dispersed phase. This can affect droplet size distribution, stability, and cross-contamination in negative ways. For example, a droplet partitioner could be constructed of glass with a surface fluoropolymer coating, the continuous phase comprising a fluorinated oil, and the dispersed phase comprising water. This partitioner's coating may wear over time. If instead, the entire droplet partitioner was made of fluoropolymer, chemical or physical degradation of the surface would only reveal more fluoropolymer maintaining the intended surface properties. Thus, all other elements being equal, it is desirable that the droplet partitioner have a thick layer comprising a material with higher affinity for the continuous phase than for the dispersed phase. In a preferred embodiment, the droplet partitioner channels themselves comprise such a material.

Surfaces of the droplet partitioner that come in contact with sample can be composed of materials compatible with biological assays. Such materials do not interfere with biochemical reactions, do not have significant affinity for biological materials or biochemical reagents, and/or do not substantially destabilize the emulsion of droplets or interfere with droplet formation. General classes of these materials include thermoplastics, silicones, fluoropolymers. In certain embodiments, these materials comprise a fluoropolymer.

The manufacturing methods available to producing microfluidic devices out of fluoropolymer are limited. One method is to machine the fluoropolymer to create the first inlet channel and the second inlet channel as well as the outlet channel. In certain embodiments, the first inlet channel is created by a drilling, milling, or similar operation, the second inlet channel is created by a drilling, milling, or similar operation, and the outlet channel is created by a drilling, milling or similar operation. In certain embodiments, the first and second inlet channels are oriented 180 degrees apart, so that a single drilling, milling, or similar pathway can be machined to produce these channels. In this embodiment, the drilled channels are the liquid channels. When machining at this scale (<300 um), the length of channels that can be created can be limited by the length of tooling available. In certain embodiments, one or more of the drilled channels are produced to support a fluidically tight seal to an inserted tubing. In this instance, the inserted tubing forms the liquid channels. The characteristic dimension, e.g., diameter, of the inserted outlet tubing determines the droplet diameter.

In certain embodiments, such as that shown in FIG. 46A the first inlet channel 4602 and the second inlet channel 4603 can created by at least one milling or similar operation on a substrate 4605, e.g., fluoropolymer surface, at least one debossing or similar operation on a substrate, e.g., fluoropolymer surface, or a combination thereof. The outlet channel 4601 can be created by at least one milling, drilling or similar operation into a material 4604, e.g., comprising a fluoropolymer so that the surface of the channel is fluoropolymer. The droplet partitioner is created by fusing the material containing the outlet channel to the fluoropolymer surface containing the first and second inlet channels so that a fluidic seal is created outside of the first 4602 and second 4603 inlet channels and the outlet channel 4601. Methods of fusing are as described herein. In another embodiment (FIG. 46B), the partition is generated from three or more pieces. The first inlet channel 4602 and the second inlet channel 4603 are created by at least one milling operation in a first substrate 4607, e.g., comprising a fluoropolymer surface, at least one embossing operation on a, e.g., fluoropolymer surface, or a combination thereof. The outlet channel is created by at least one or more milling operations into a first material 4607 comprising a fluoropolymer forming a portion of the outlet channel 4608 and a second material 4609 forming another portion of the outlet channel 4610. The droplet partitioner is created by fusing the material containing the outlet channel to the fluoropolymer surface containing the first and second inlet channels so that a fluidic seal is created outside of the first 4602 and second 4603 inlet channels and the outlet channel 4603. This fluidic seal creates a junction 4606 where two fluidics meet and exit via the outlet channel 4601. Methods for fusing are as described herein.

In embodiments where two or more pieces are fused, any suitable method for fusing the materials may be used. Exemplary methods for fusing these materials together include fusion welding, ultrasonic welding, heat welded or chemical bonding. Chemical bonding requires etching the fluoropolymer surface to make it amenable to chemical bonding agents. The channel features may be generated before or after etching. In the first instance where the channels are generated before etching, both the surface to be bonded and the channels are no longer fluorinated. After bonding, the channels may once again be rendered fluorinated by chemical deposition. In the second instance where the channels are milled or otherwise created after etching, the bonding restores the channel material to its native properties. In some cases, the pieces may be physically crimped or clamped together if sufficient force is applied to generate a fluidically tight seal.

Connections of the partitioner with conduits to the rest of the system may be made as described herein, e.g., by press fit or compression fit, or other suitable method to provide a connection that does not disrupt fluid flow to a significant degree, e.g., to a degree where a dead space, eddy, swirl, or other disruption is formed.

In certain embodiments, fluoropolymer tubing is inserted into the fluoropolymer block adjacent to drilled or milled channels equal to or smaller than the tubing ID. The inlet and outlet channels are produced in the fluoropolymer block in two passes. In the first pass, a channel is generated to accommodate either the interference or the compression forming a fluidic seal with the tubing. In the second pass, the liquid channel is generated.

The droplet partitioner channels in the fluoropolymer block are made sufficiently small to ensure stable fluid flow reducing the possibility for hold up of sample in the channels.

In certain embodiments, the tubing ID and channel ID are size matched.

Concentrating droplets (disengagement). In certain embodiments, after partitions are formed at the partitioner, a portion of the continuous phase (e.g., oil, such as a fluorinated oil) is removed from the emulsion (disengagement), thus concentrating the droplets. The system for removing continuous phase and, in certain embodiments, adding removed continuous phase back to the system is referred to herein as a disengager. This can be useful to slow the fluidic velocity, since there is not as much liquid moving through the system at any given time. Low fluidic velocity can improve droplet stability and reduce the effect of unstable liquid flows that can induce droplet breakage, cross-contamination, droplet transit between samples, and the like. In certain embodiments, an amount of continuous phase is removed sufficient to slow fluidic velocity by at least 0.1, 0.5, 1, 2, 3, 4, 5, 6, 7, 8, 9, 10, 12, 15, 17, 20, 22, 25, 30, 35, 40, 45, 50, 55, 60, 65, 70, 75, 80, or 85% of the fluidic velocity before continuous phase removal, and/or at most 0.5, 1, 2, 3, 4, 5, 6, 7, 8, 9, 10, 12, 15, 17, 20, 22, 25, 30, 35, 40, 45, 50, 55, 60, 65, 70, 75, 80, 85, or 90% of the fluidic velocity before continuous phase removal. In certain embodiments, the amount of continuous phase removed is at least 0.1, 0.5, 1, 2, 3, 4, 5, 6, 7, 8, 9, 10, 12, 15, 17, 20, 22, 25, 30, 35, 40, 45, 50, 55, 60, 65, 70, 75, 80, or 85% of the continuous phase, and/or at most 0.5, 1, 2, 3, 4, 5, 6, 7, 8, 9, 10, 12, 15, 17, 20, 22, 25, 30, 35, 40, 45, 50, 55, 60, 65, 70, 75, 80, 85, or 90% of the continuous phase, such as continuous phase as described herein, e.g. an oil, for example a fluorinated oil, for example, 20%-80%, such as 30-70%, or 30-99%, or 80-99.5%, or 90-99.5%. It is desirable to remove continuous phase in such a way that droplets are not also removed, e.g., in such a way that less than 10, 9, 8, 7, 6, 5, 4, 3, 2, 1, 0.8, 0.6, 0.5, 0.4, 0.3, 0.2, 0.1, 0.05, 0.01, 0.005, 0.001, 0.0005, or 0.0001% of droplets are also removed. In certain cases, an impediment to droplet movement with the continuous phase, such as a filter, is used to ensure that droplets are not removed with the continuous phase. In certain cases, some or all of the removed continuous phase can be re-used, for example, to separate droplets prior to detection (see below); at the point or points of reintroduction, there may also be a second impediment, such as a filter, to ensure that droplets do not move into the continuous phase conduit. Some or all of the removed continuous phase may be returned to the system; e.g., continuous phase removed after the partitioner and before the reactor, e.g., thermal cycler, may be returned to the system before the interrogation region of the detector in order to separate partitions; for example, 10-100% of removed continuous phase may be returned, such as 50-100%, for example, 80-100%.

Figure 47A:
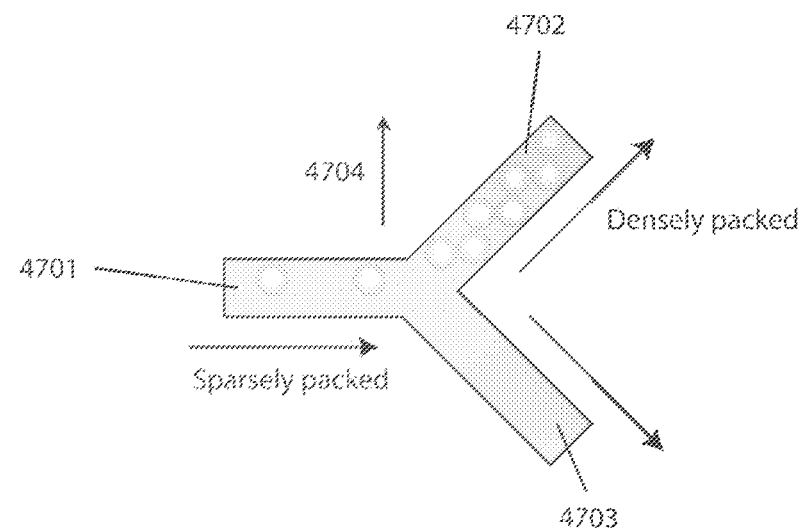
FIGS. 47A and 47B show removal of additional continuous phase.
Figure 47B:
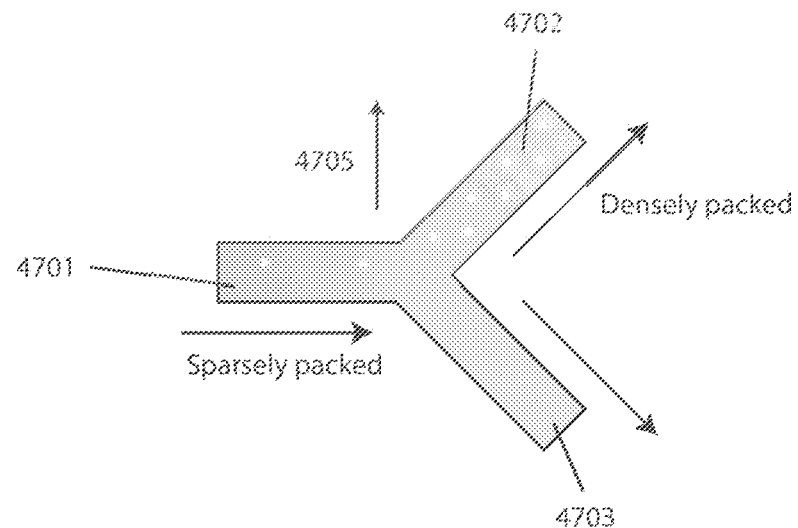

Removal of continuous phase can be active or passive. If the removal is active, any suitable method for producing a force to move droplets or continuous phase may be used. FIG. 47A illustrates active removal using an electrical feature that pushes or pulls droplets from one channel to another (dielectrophoretic sorting). Passive movement, as shown in FIG. 47B, can use fluidic resistance and/or buoyancy to prefer upward droplet movement in an embodiment of a system for reducing the amount of continuous phase fluidic between dispersed phase partitions. In FIG. 47A, the system comprises a substrate that comprises a main channel 4701, a first outlet channel 4702, and a second outlet channel 4703. The two outlet channels connect to the main channel at a common intersection. In this embodiment there is also an electrode that generates a non-uniform electric field 4704 and any grounding electrodes required. Loosely spaced partitions enter the main channel 4701, enter the non-uniform electric field 4704 and are moved towards the first outlet channel 4702 through dielectrophoretic force. The relative amount of continuous phase fluid that flows to the first 4702 and second 4703 outlet channels is based on the relative flow rates between the two channels. Droplets exiting through the first outlet channel 4702 are more packed than the droplet entering the main channel 4701. FIG. 47B shows another embodiment of a system for reducing the amount of continuous phase fluidic between dispersed phase partitions. The system comprises a substrate that comprises a main channel 4701, a first outlet channel 4702, and a second outlet channel 4703. The two outlet channels connect to the main channel at a common intersection. In this embodiment the planar orientation of the channels is parallel to the gravitational force 4705. In orienting the substrate in this manner, gravitational force 4705 and buoyance may play a part in droplet mobility. Loosely spaced partitions enter the main channel 4701, float towards the top of the conduit, and transit towards the first outlet channel 4702. Since the droplets are positioned at the top of the channel and the first outlet channel 4702 is present at the top of the substrate, the droplets preferentially exit through the first outlet channel 4702. The relative amount of continuous phase fluid that flows to the first 4702 and second 4703 outlet channels is based on the relative flow rates between the two channels. Droplets exiting through the first outlet channel 4702 are more packed than the droplet entering the main channel 4701.

Figure 48:
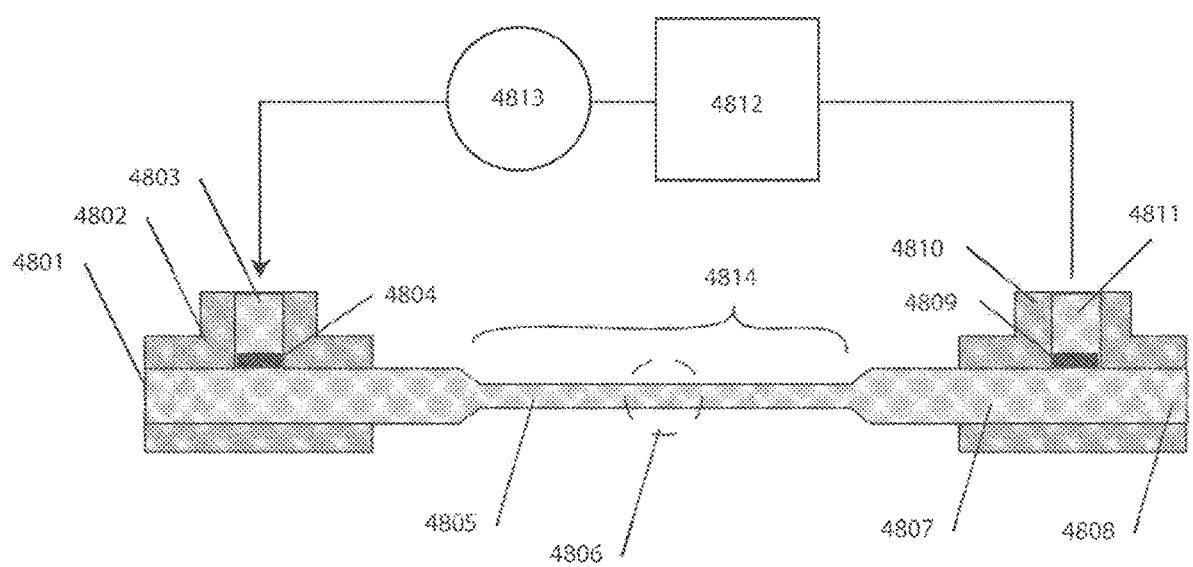
FIG. 48 shows recycle of oil with disengagers.

Continuous phase can be removed at any suitable location after the partitioner, and can be removed at 1, 2, 3, or more than 3 locations. Continuous phase that has been removed can also be reintroduced at any suitable point, before or after the point of removal, or both, and can be reintroduced at 1, 2, 3, or more than 3 locations. In certain embodiments, continuous phase is removed after droplets have passed through a detector. See FIG. 48. Some or all of the removed continuous phase can then be reintroduced into the system at one or more suitable locations; FIG. 48 shows continuous phase (oil) reintroduced at a point before the detector, in order to separate partitions as they enter the detection zone (see description of detection, below). The system comprises a T-connector 4802 connecting a main conduit 4801 flowing densely packed partitions, a second conduit flowing additional separation fluid, such as oil 4803, a physical barrier with pore sizes significantly smaller than the partition diameter 4804, and an outlet conduit 4805. The outlet conduit comprises a constricted region 4814. A first continuous phase and partitions of dispersed phase enter the main conduit 4801 while a second continuous phase miscible with the first continuous phase enters through the second conduit 4803. The additional continuous phase fluid is injected into the conduit 4803 from a reservoir 4812 using a pump 4813. Upon exiting the T-connector 4802, the average separation of the dispersed phase partitions (average distance between adjacent partitions) is greater than upon entering the T-connector. The spaced partitions enter the constricted region of the conduit 4814 and enter the interrogation region 4806 where a parameter of the partitions is interrogated. Spaced partitions enter a second T-connector 4810 through a conduit 4807. The partitions enter a branched connection. Continuous phase fluid flows through both the first outlet conduit 4811 and the second outlet conduit 4808 based on the relative flow rates through each conduit. Partitions are unable to enter the first outlet conduit 4811 due to the physical barrier generated by 4809. Since partitions are unable to enter the first outlet conduit 4811 and flow preferentially towards the second outlet conduit 4808, the partitions are more densely packed then when they were in the constricted region 4814. The additional continuous phase fluid entering the first T-connector 4802 is recycled upon reaching the second T-connector 4810.

Figure 49:
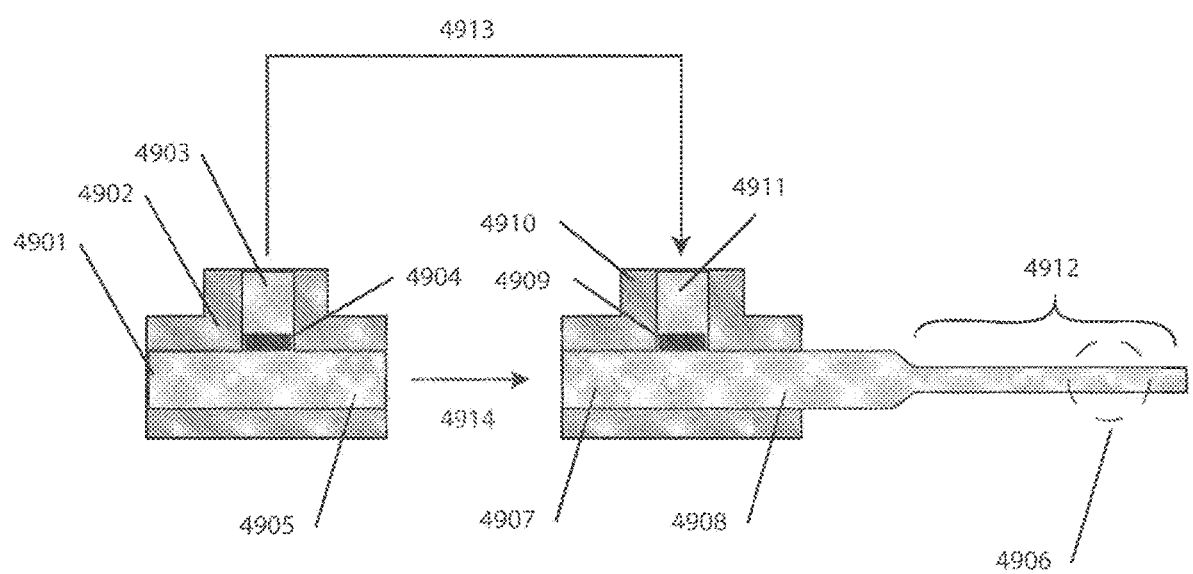
FIG. 49 shows disengagement for droplet slowing.

In certain embodiments, continuous phase is removed after droplets have been formed at the partitioner but before they move through a reactor. See FIG. 49, in which continuous phase is removed prior to a cycler (e.g., thermal cycler, such as for PCR). Some or all of the removed continuous phase can then be reintroduced into the system; FIG. 49 shows continuous phase (oil) reintroduced at a point before the detector, in order to separate droplets as they enter the detection zone (see description of detection, below). The system comprises a T-connector 4902, a main conduit 4901 flowing sparsely packed partitions, a first outlet conduit 4903 in which continuous phase fluid may flow, a physical barrier with pore sizes smaller than the partition diameter 4904, and a second outlet conduit 4905 flowing densely packed dispersed phase partitions. The outlet conduit leads to the larger partition handling system 4914. At the junction, continuous phase fluid may flow through both outlets based on the relative flow rates, but partitions may only flow towards the second outlet conduit 4905 due to the physical barrier 4904. As a result, the originally loosely packed partitions are more densely packed after transiting through the first T-connector system. Upon transiting the droplet handling system 4914, densely packed dispersed phase partitions enter a second T-connector 4910. The second T-connector comprises a first inlet conduit 4911, a physical barrier with pore size smaller than the partition diameter 4909, and a second outlet conduit 4908 that leads to a conduit constriction 4912. The additional continuous phase fluid exiting the first T-connector enters the second T-connector through the first inlet conduit 4911. The average spacing of the densely packed droplets entering the main inlet conduit 4907 of the second T-connector 4910 is increased as the transit the first inlet channel 4911. The loosely packed droplets enter the first outlet conduit 4908, enter a constricted region 4911. The spaced droplets enter the interrogation region 4906 where one or more parameters of the partitions are interrogated.

It will be appreciated that the embodiments exemplified in FIG. 48, and FIG. 49 can be combined in any suitable manner.

Similar construction and connection methods may be used for the disengagers as described for partitioners, with suitable modifications to account for, e.g., filter elements and the like.

In some instances, a system comprises a rotating pin. The rotating pin may have a cavity that is partially open. When the system is "collecting" droplets from a droplet generator, the droplets may move up or down into the cavity where the droplets are trapped at the roof or floor of the cavity. Once the droplets are all collected, the pin may rotate and the cavity is exposed to an open channel in a second part of the device, where another continuous flow input drives the droplets through the thermal cycler and detector. Once all of the droplets have passed the channel, the rotating pin may rotate back around and is ready to accept a new dispersed phase comprising droplets.

B. Reactor

The systems and methods provided herein can include moving partitions formed by the partitioner through a reactor. The reactor can be any suitable reactor that initiates and/or modulates one or more desired reactions in one or more of the partitions. Thus, a reactor can be a reactor that introduces energy, e.g., thermal energy, electromagnetic energy, acoustic energy, or other suitable energy, to partitions as they flow from the partitioner.

In certain embodiments, the reactor comprises a thermal cycler, e.g., a thermal cycler for cycling partitions through a plurality of temperature zones to cycle PCR reactions. Any suitable configuration may be used so long as it serves to expose partitions to temperature zones that are conducive to different parts of the PCR cycle. Generally, a conduit, such as a tube, is used to allow flow of partitions. In certain embodiments, the conduit is in contact with, e.g., wrapped around, a cylindrical or substantially cylindrical core that comprises at least 2 zones of different temperatures. The temperature zones may allow for a hot start reaction, thermal cycling, annealing, extension, polymerization, or protein denaturation. The conduit, e.g., tubing, thus forms a helical structure or substantially helical structure.

Figure 76:
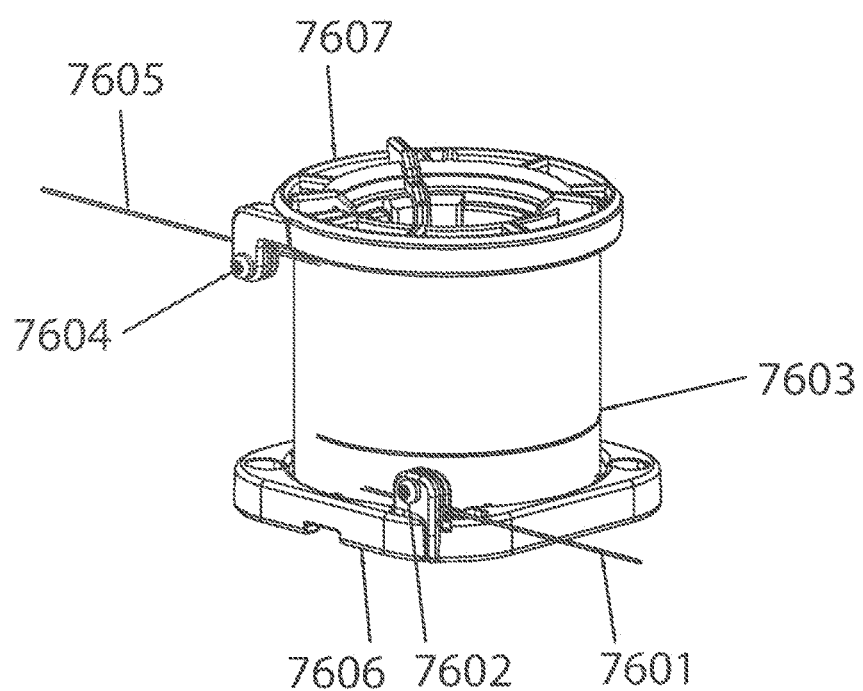
FIG. 76 shows a cylindrical heater-reactor.

It can be desirable to minimize buoyancy effects along sections of the conduit, e.g., at least in sections of the conduit in the thermal cycler. In certain embodiments, the radius of curvature and the rate of flow of the partitions in the conduit are in a range where flow in the conduit is laminar or substantially laminar. In certain embodiments, most or all of the conduit, for example, most or all of the conduit from just after the partitioner to the detector, can be kept in a plane that is orthogonal or nearly orthogonal to gravity; it will be appreciated that certain sections, such as coils around a racetrack thermal cycler, must, of necessity, deviate somewhat from the orthogonal plane but in general will remain nearly orthogonal to the plane. Thus, in certain embodiments, the conduit, such as the conduit from just after the partitioner to the detector, is configured so that no section of the conduit, or no significant section of the conduit, deviates from a plane that is orthogonal to gravity by more than 30, 20, 15, 10, 7, 5, 4, 3, 2, or 1 degree, where the angle is measured from the axis of flow in the conduit to the plane orthogonal to gravity. It will be appreciated that small sections of the conduit may deviate more than this from the orthogonal plane, e.g., up to 1, 2, 3, 4, 5% of the conduit, so long as the deviation does not produce significant buoyancy or other effects that lead to undesirable consequences, e.g., axial spreading of partitions to such a degree that one group of partitions may merge with another FIG. 76 shows a heater-reactor conduit. An embodiment of a system for providing distinct zones where droplets can be maintained at particular temperatures for set times FIG. 76. The system comprises a conduit that traverses one or more core heater elements that are maintained at a constant temperature. A core heater element is a block of material that is held at a specific temperature. The construction of a core heater element is such that it has a glass transition or melting temperature of at least 120, 200, 500 degrees Celsius. In a preferred embodiment the core heater elements are constructed out of a solid block of metal, for example aluminum, that has a high thermal conductivity, for example a thermal conductivity of more than 50, 100 or 200 W/m K. The temperature of the core heater elements is controlled with resistive heating elements. When current is applied across the resistive heating elements, they conduct heat into the core heater elements. Resistive temperature sensors are used to measure the temperature of the core heater elements. In some embodiments the resistive temperature sensors are thermally potted into the core heater elements to provide the most accurate measurements of the core heater element temperature. A control system is applied to read the temperature from the resistive temperature sensors and control the amount of current applied to the resistive heating elements. The control system is designed to hold the temperature of the zone within 2, 1, 0.5, 0.1 or less than 0.1 degree Celsius. The core heater elements are individually isolated to minimize conduction between the elements. The heated core elements of the heater-reactor can be flat or curved and the number of elements can vary from a single element to at least 3, 4, 5, 10, 20, 100 elements. The size and number of the core heater elements is used to determine the time a particular droplet that passes through the conduit of the heater reactor is held at specific temperatures. In a particular embodiment a single core heater element is a hollow cylinder that has a fluid conduit at the outer surface. In this example the diameter of the cylinder, the number of wraps of the conduit, and the fluid velocity in the conduit help determine the time each droplet spends at the desired reaction temperature. In certain embodiments where a single core heater element is used the system is designed to process dispersed phase samples for isothermal reactions. In other embodiments multiple core heater elements are combined such that they form a cylindrical shape that a conduit can wrap around. In embodiments where more than one core heater element is used the system can be designed to process dispersed phase samples for one or more isothermal reactions or for reactions that require temperature cycling. Some isothermal reactions may require two or more core heater elements.

In certain embodiments the conduit comprises tubing 7601 that enters at the bottom of the assembly where the conduit is held in place with a retaining system 7602 clamps the tubing to fix it in position but does not change the outer or inner diameter of the tubing by more than 1%, 2%, 5%, or 10%. The conduit is then wrapped around the exterior of the core heater element or elements 7603. The conduit leaves the top of the assembly where it is held in place with a retaining system 7604 clamps the tubing to fix it in position but does not change the outer or inner diameter of the tubing by more than 1%, 2%, 5%, 10%. The conduit then continues 7605 until connects to the next subunit in the instrument, such as a detector assembly. In some embodiments the core heater elements of the heater-reactor are held in place by structural elements that have low thermal conductivity 7606 and 7607, for example a thermal conductivity of less than 5, 1, 0.1 or 0.01 W/m K.

In some embodiments the cross-sectional area of the tubing is such that droplets must travel in a single file and there is insufficient room for droplets to pass each other. The diameter of the conduit may be larger, smaller, or equal to the equivalent spherical cross-sectional diameter of the partitions flowing through the channel. In some embodiments the cross-sectional area allows two droplets to move through the tubing side by side. In some embodiments the cross-sectional area allows more than two droplets to travel through the tubing side by side. In a preferred embodiment, the diameter of the conduit is larger than the equivalent spherical diameter of the dispersed phase partitions flowing through the conduit but is not large enough to have more than three full equivalent spherical diameters of the dispersed phase partitions flowing through a cross-section of conduit at a time. If the conduit through the heater-reactor is in direct fluid communication with the partitioner, then the fluid flow rate through the conduit is equal to flow rate leaving the partitioner and the rate remains constant throughout the conduit in the heater-reactor. In some embodiments a continuous phase flows through the heater during normal system function. When a first dispersed phase is partitioned in the partitioner it then moves through the conduit of the heater-reactor. In some embodiments the conduit is constructed out of flexible tubing that comprises a thermoplastic material such as polyolefins, polyurethanes, fluoropolymers, or blends of like materials. In a further embodiment the conduit comprises a material that has a higher affinity for the continuous phase than for the dispersed phase, such as PTFE, PFA, FEP or other like materials.

Radiant thermal energy from the heater-reactor is released to the greater system through convection. Air flow through the instrument is able to remove heat from the instrument the to help maintain a stable instrument operating temperature. The stable instrument operating temperature is below the temperature of the heater-reactor so that the heater-reactor can cool by convection. In some embodiments insulation is applied to exposed surfaces of the heater-reactor to control the rate of convective heat transfer. The insulation comprises materials that have low thermal conductivity for example a thermal conductivity of less than 5, 1, 0.1 or 0.01 W/m K.

In some embodiments more than one conduit can be wrapped around the same heated core materials. Such an embodiment provides the opportunity for a first dispersed phase, dispersed phase 1 to travel down one conduit, conduit A while the subsequent dispersed phase, dispersed phase 2 is directed down the second conduit, conduit B. Each subsequent dispersed phase that is added to the process side. The ability to switch the conduit can decrease the time between dispersed phase injections.

In some embodiments more than two conduits are wrapped around the same heated core materials. Such an embodiment provides the opportunity to switch the conduit path for each dispersed phase that is added to the process side.

In some embodiments where two or more conduits are wrapped around the same heated core materials, the individual conduits follow a helical path. In some embodiments the cross-sectional geometry of the conduit is circular, square, rectangular, triangular, oval, or some combination of these shapes.

In some embodiments the radius of curvature of the conduit is maximized to prevent the shear forces exerted on the partitions from exceeding the interfacial tension stabilizing the partition surface. In some embodiments the vertical rise of the conduit is minimized to reduce the ability of buoyant forces to move partitions relative to each other within a single dispersed phase sample. In some embodiments the fluid velocity helps to reduce motion of partitions relative to each other within a single dispersed phase sample.

Figure 77A:
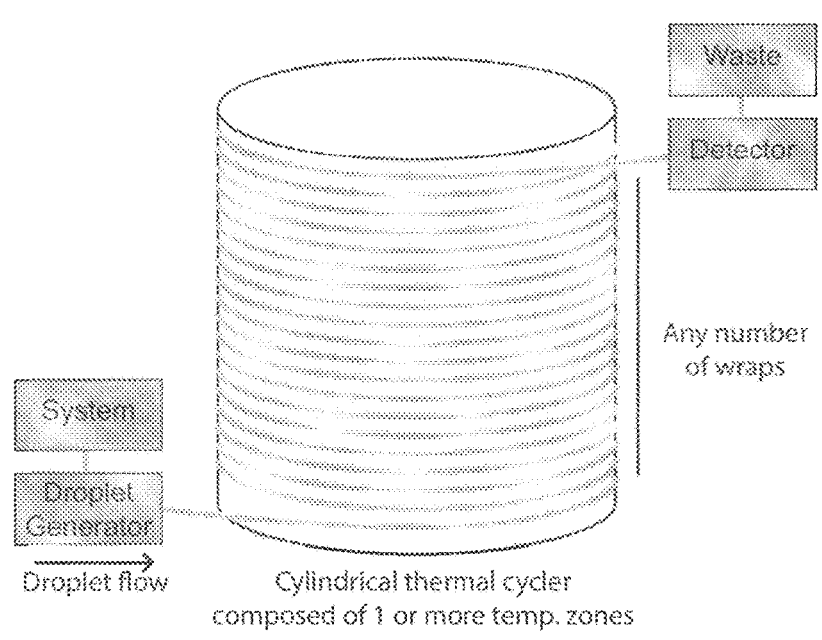
FIGS. 77A and 77B show a heater-reactor conduit.
Figure 77B:
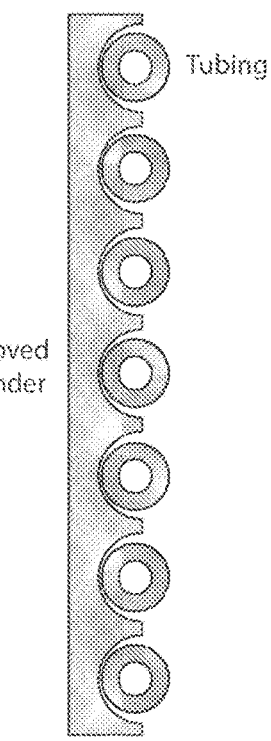
Figure 78:
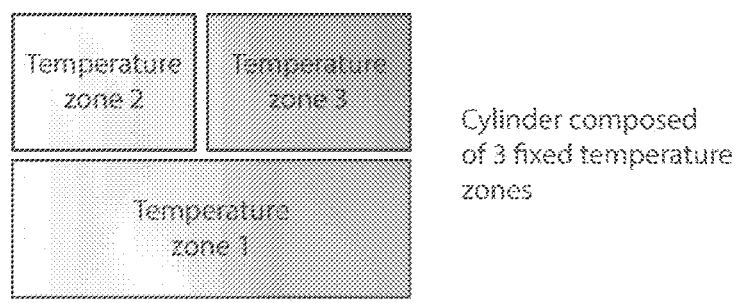
FIG. 78 shows a three temperature zone heater-reactor.

FIGS. 77A and 77B show a heater-reactor conduit An embodiment of a heater-reactor system for providing one or more distinct zones where droplets can be maintained at particular temperatures for one or more set times FIG. 77. The system comprises a conduit that travels from the dispersed phase partitioner through the heater-reactor and on to the detector assembly. In a particular embodiment a single core heater element is a hollow cylinder with the fluid conduit wrapped around outer surface. In some embodiments the number of wraps of the conduit can vary to change the amount of time the partitions spend at a particular temperature. The diameter of the cylinder can also be adjusted to vary the residence time of the partitions within the heater-reactor. In a preferred embodiment the core heater element has grooves (FIG. 77B) that capture the conduit and increase the contact surface area between the conduit and the core heater element. In some embodiments the groove depth allows at least 5, 10, 25, 50, 75 or 100% of the conduit to be captured. In some embodiments the groove is deeper than the diameter of the conduit such that the conduit is entirely captured and sits below the outer surface of the core heater element FIG. 78 shows a three temperature zone heater-reactor FIG. 78 shows an embodiment of a heater-reactor that contains three distinct core heater elements. Each of the core heater elements is independently controlled so that it is maintained at a particular temperature. In some embodiments the temperature of each core heater element is distinct. In other embodiments two or more of the core heater elements are maintained at the same temperature. In some embodiments the core heater elements are assembled so that they form a cylindrical shape. In some embodiments the conduit is wrapped around the core heater elements such that it forms at most a single 360 degree wrap around each core heater element. In some embodiments the conduit is wrapped around the core heater elements such that it makes more or more passes across each of the core heater elements.

Figure 79:
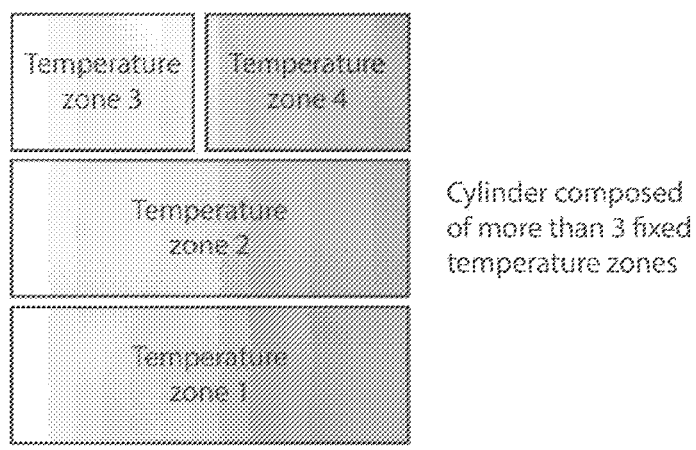
FIG. 79 shows a four temperature zone heater-reactor.
Figure 81A:
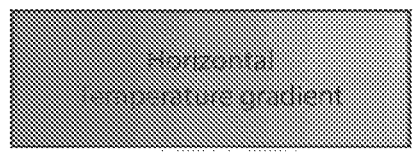
FIGS. 81A, 81B and 81C show a gradient heater-reactor.
Figure 81B:
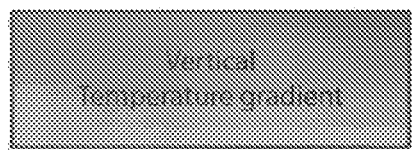
Figure 81C:
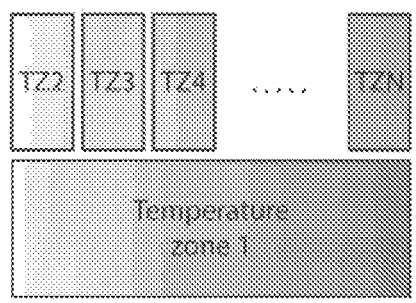

FIG. 79 shows a four temperature zone heater-reactor. FIG. 79 shows an embodiment of a heater-reactor that contains four distinct core heater elements. Each of the core heater elements is independently controlled so that it is maintained at a particular temperature. In some embodiments the temperature of each core heater element is distinct. In other elements two or more of the core heater elements are maintained at the same temperature. In some embodiments the core heater elements are assembled so that they form a cylindrical shape. In some embodiments the core heater elements are flat and the conduit passes back and forth across the elements in a serpentine arrangement. In some embodiments when the core heater elements are flat they at positioned perpendicular to the gravitational field so that the buoyant force is perpendicular to the fluid velocity to minimize the impact of buoyancy impacting the velocity of a partition within the conduit FIG. 80 shows a discrete four temperature zone heater reactor shows another embodiment of a heater-reactor that contains four distinct core heater elements that are arranged in distinct sub-assemblies. Each of the core heater elements is independently controlled so that it is maintained at a particular temperature. In some embodiments the temperature of each core heater element is distinct. In other embodiments two or more of the core heater elements are maintained at the same temperature. In some embodiments the core heater elements are assembled so that they form a cylindrical shape. In some embodiments the core heater elements are flat and the conduit passes back and forth across the elements in a serpentine arrangement. In some embodiments the core heater elements are assembled such that each distinct sub-assembly of core heater elements can be either flat or cylindrical. In some embodiments a valve is included such that partitions can either pass through all of the core heater element sub-assemblies or only through a sub-set of these sub-assemblies FIGS. 81A, 81B, and 81C show a gradient heater-reactor FIGS. 81A, 81B, and 81C show exemplary layouts for core heater elements that can be included as part of a heater-reactor. Each of the core heater elements is independently controlled to maintain a temperature profile that can be a distinct temperature or a gradient of temperatures. In some embodiments one or more core heater element can have a horizontal temperature gradient where there is a portion of the core heater element that is maintained to the highest desired temperature and a gradient of temperatures is formed where the rest of the core heater element has a lower temperature. In some embodiments this gradient is controlled by applying heat to particular portion of the core. The core is designed with materials that have a thermal conductivity to enable the formation of controlled gradient. In some embodiments one or more core heater element can have a vertical temperature gradient. As partitions of dispersed phase samples move through a conduit that is in thermal contact with the core heater element or elements, they are maintained at a temperature that matches the gradient of the core element. Such an embodiment enables the temperature of the partitions to be transitioned at controlled rates that might be critical for particular reactions to be performed efficiently. In some embodiments a large number of discreet core heater elements are arranged in a horizontal or vertical, or both, orientation to create a large number of distinct temperature holds for the partitions.

Figure 82A:
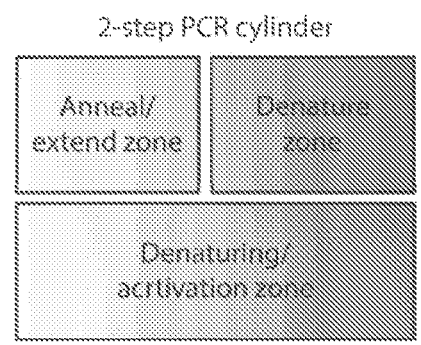
FIGS. 82A and 82B show a 2-step PCR heater-reactor.
Figure 82B:
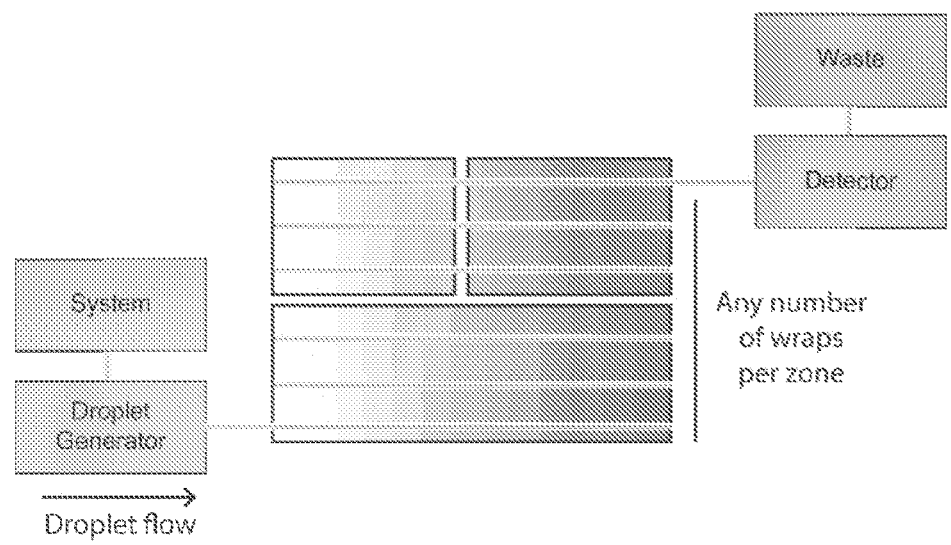
Figure 83A:
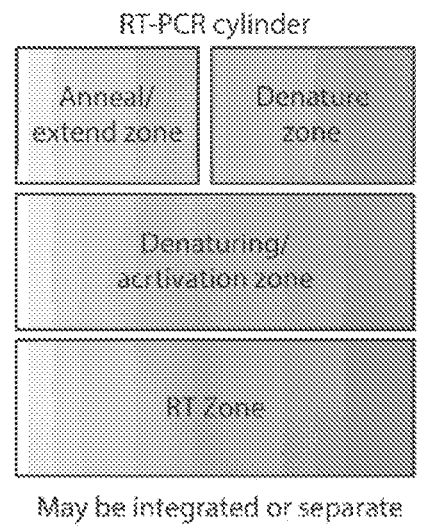
FIGS. 83A and 83B show a RT-PCR heater-reactor.
Figure 83B:
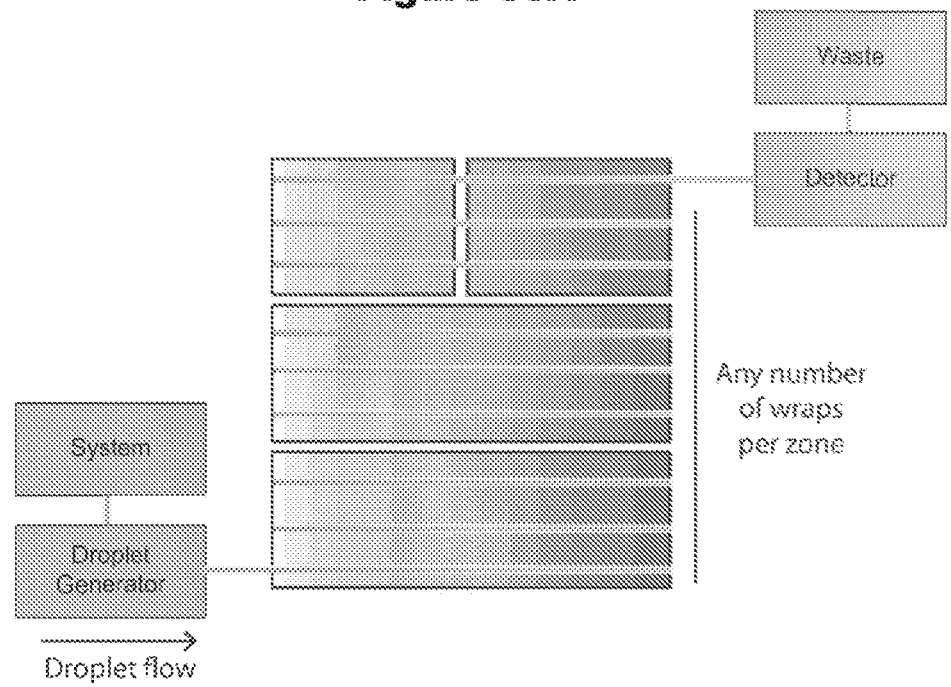

FIGS. 82A and 82B show a 2-step PCR heater reactor. FIG. 82 shows exemplary layout for a heater-reactor with three core heater elements. The system comprises a conduit that travels from the dispersed phase partitioner through the heater-reactor and on to the detector assembly. In a particular embodiment a single core heater element is a hollow cylinder with the fluid conduit wrapped around outer surface. In a particular embodiment the lowest core heater element is maintained at an elevated temperature of 95 degrees Celsius to act as an initial denaturation cycle for a PCR reaction. In this example zone two is also held at 95 degrees Celsius to provide further denaturation cycles and zone three is held at a temperature less than 95 degrees Celsius to provide an annealing and extension cycle for a PCR reaction. In this example the conduit is wrapped around zone one at least once and is wrapped around zones two and three at least 24, 28, 32, 36 or 40 times to provide that number of thermal cycles for the partitions to transition between a denaturing temperature and an annealing/extending temperature. The size of zones two and three are designed to control the timing of the denaturing and annealing/extension cycles FIGS. 83A and 83B show a RT-PCR heater-reactor. FIG. 83 shows exemplary layout for a heater-reactor with four core heater elements. The system comprises a conduit that travels from the dispersed phase partitioner through the heater-reactor and on to the detector assembly. In a particular embodiment a single core heater element is a hollow cylinder with the fluid conduit wrapped around outer surface. In a particular embodiment the lowest core heater element is maintained at a temperature optimized for reverse transcription reactions. As the conduit moves vertically the next core heater element it comes in contact with is held at an elevated temperature of 95 degrees Celsius to act as an initial denaturation cycle for a PCR reaction. In this example zone two is also held at 95 degrees Celsius to provide further denaturation cycles and zone three is held at a temperature less than 95 degrees Celsius to provide an annealing and extension cycle for a PCR reaction. In this example the conduit is wrapped around zone one at least once and is wrapped around zones two and three at least 24, 28, 32, 36 or 40 times to provide that number of thermal cycles for the partitions to transition between a denaturing temperature and an annealing/extending temperature. The size of zones two and three are designed to control the timing of the denaturing and annealing/extension cycles.

Thus, following generation of droplets, the droplets may flow to a reactor. In some instances, the reactor is a region where the microfluidic channel or tube passes through that causes a reaction. The region may comprise various temperature zones. For example, for polymerase chain reaction (PCR), the region comprises temperature zones at specific temperatures comprising tube wraps between the temperature zones. In some instances, the region comprises at least or about 1, 2, 3, 4, 5, 6, 7, 8, or more than 8 temperature zones. In some instances, the region comprises about 3 temperature zones. The temperature zones may allow for a hot start reaction, thermal cycling, annealing, extension, polymerization, or protein denaturation. In some instances, one or more cycles are performed in each temperature zone. In some instances, at least or about 1, 5, 10, 15, 20, 25, 30, 35, 40, 45, 50, 55, 60, 65, 70, 75, 80, or more than 80 cycles are performed. In some instances, about 30 to about 40 cycles are performed. In some instances, the region comprises a temperature zone for reverse transcription. In some instances, the region comprises a region where light impinges on the microfluidic channel or tube to initiate a photo-reaction. In some instances, the region comprises a region for focusing acoustic energy Following a reaction such as an amplification reaction, droplets may flow to a detector. In some instances, a detector detects droplet size. In some instances, a detector is used to quantify nucleic acids or protein. In some instances, a detector is used to quantify a product or products of a reaction or set of reactions in the droplet. In some instances, the quantity of product or products of the reaction or set of reactions can be correlated to a physical or chemical property of a species comprising the droplet.

C. Detector

Provided herein are systems and methods for detection of one or more detectable properties of partitions of at least one dispersed phase in a continuous phase, moving in serial flow through a conduit. Detection systems, also referred to as detectors herein, can include one or more of a system for separating partitions prior to detection, a narrowed detection channel through which partitions flow for detection, an optical restriction for restricting the amount of electromagnetic radiation that reaches a photodetector (restricting the field of view of the photodetector), and/or lock-in amplification. Systems and methods may further include a plurality of coplanar or nearly coplanar photo-detectors, use of one or more silicon photomultipliers, use of a conduit comprising a tube for detection, and/or other aspects as described herein.

The simplest embodiment of a detector includes a conduit through which partitions flow in single file, e.g., in an emulsion of partitions of dispersed phase in continuous phase, where the conduit includes an interrogation region (also referred to as an interrogation space or optical stage herein) at which detection occurs, and a detection element for detecting a signal from the emulsion, e.g., from a partition, as it flows through the interrogation region. In a fluorescence system, the detector also includes one or more excitation sources to provide electromagnetic radiation, e.g., light, to the interrogation region. Further possible components of detectors are described below.

In general, detectors can be used in any suitable serial flow system. In certain embodiments, systems and method provided herein provide a process system fluidly connected to a detector, such as a detector as described herein; for example, a detector that has at least one, two, three, four, five, or all of an optical restriction, separation system for separating partitions to be detected (increasing the average distance between partitions), and/or narrowed conduit at the interrogation region where the cross-sectional area of the conduit is less than or equal to the average equivalent spherical cross-section of the partitions (such as less than or equal to 100%, 95%, 90%, 80%, 70%, 60%, 50%, 40%, 30%, 20%, or 10% of the average equivalent spherical cross-section of the partitions); and/or a detector that utilizes lock-in amplification, e.g., for the detection of multiple signals from a single partition and/or to improve signal-to-noise ration of one or more signals from a single partition; and/or a detector that utilizes a conduit such as a tube at the interrogation region; and/or a detector that utilizes a coplanar or nearly coplanar array of a plurality of excitation sources and/or one or more detection elements, such as a detector where the conduit in the interrogation region is a tube or similar structure; and/or a detector where all or substantially all of the surfaces of parts of the detector that contact dispersed phase partitions have a greater affinity for continuous phase than for dispersed phase, for example, at least 90, 95, 99, or 99.9% of surfaces. The process system can be any suitable process system, for example a system that includes a partitioner for generating partitions, e.g., from a sample, such as any of the partitioners described herein; or a reactor for generating and/or modulating a reaction in at least a portion of partitions, such as any of the reactors described herein, e.g., a thermal cycler such as a thermal cycler for PCR, e.g., thermal cyclers as described herein, or a combination thereof.

In certain embodiments, systems and method provided herein provide a process system and a intake system, where the process system is fluidly connected to a detector, such as a detector as described herein, and where the intake system provides one or more samples to the process system, where the intake system and the process system are never in continuous fluid communication, such as any of the intake and process systems described herein, for example a intake system and a process system that are joined by an injector, where, e.g., the injector can cycle between connection to the intake system and connection to the process system, but does not provide a continuous connection between the intake system and the process system. The detector can be any suitable detector, such as a detector as described herein; for example, a detector that has at least one, two, three, four, five or all of an optical restriction, separation system for separating partitions (increasing the average distance between partitions) to be detected, and/or narrowed conduit at the interrogation region where the cross-sectional area of the conduit is less than or equal to the average equivalent spherical cross-section of the partitions; and/or a detector that utilizes lock-in amplification; and/or a detector that utilizes a conduit such as a tube at the optical stage; and/or a detector that utilizes a coplanar or nearly coplanar array of a plurality of excitation sources and/or one or more detection elements, such as a detector where the conduit in the interrogation region is a tube or similar structure; and/or a detector where all or substantially all of the surfaces of parts of the detector that contact dispersed phase partitions have a greater affinity for continuous phase than for dispersed phase.

Partitions moving through the conduit may be any size, e.g., volume, as described herein, such as 0.01-100 nL, 0.05-50 nL, 0.1-10 nL, 0.1-5 nL, 0.1-3 nL, or 0.1-2 nL, or any other suitable volume as described elsewhere herein. A series of partitions moves through the conduit in single file. In certain embodiments, the partitions arrive at the detector in groups, e.g., a group of partitions derived from a single sample; in some cases the groups of partitions are separated from each other by, e.g., spacer fluid; in certain embodiments, the spacer fluid, one or more partitions, or both, have one or more properties, such as one or more optical properties, that can be used to delineate boundaries between groups of partitions. A group of partitions can comprise any suitable number of individual partitions, for example, 10-10,000,000, 10,000-2,000,000, 100-1,000,000, 200-500,000, 500-500,000, 1000-200,000, 5000-200,000, 10,000-200,000, 10,000-40,000, 20,000-200,000, 25,000-45,000, or any number as described herein.

Systems and methods provided herein can allow for detection of a single partition at a time, with little or no signal overlap from adjacent partitions, for example, where signal that reaches a detection element from the interrogation region that is from a partition is at least 60, 70, 80, 90, 95, 99, 99.5, or 99.9% from a single partition in the interrogation region.

In certain embodiments, such as in digital assays (e.g., digital PCR), partitions are counted as either positive (containing a component of interest, for example, a nucleic acid that has been amplified) or negative (not containing a component of interest, for example, not containing a nucleic acid that has been amplified). In certain embodiments, at least 60, 70, 80, 90, 92, 95, 96, 97, 98, 99, 99.5, or 99.9% of the partitions flowing through the detector, for example, partitions in a group of partitions such as a group of partitions that corresponds to a sample, can be detected as individual partitions, e.g. with sufficient resolution to be counted as positive or negative. This resolution can be achieved by aspects of the system and methods as described herein, such as a detector as described herein; for example, a detector that has one, two, three, four, five, or all of an optical restriction, separation system for separating partitions to be detected (increasing average distance between partitions), and/or narrowed conduit at the interrogation region where the cross-sectional area of the conduit is less than or equal to the average equivalent spherical cross-section of the partitions; and/or a detector that utilizes lock-in amplification, such as in a detector with a plurality of excitation sources and at least one detection element; and/or a detector that utilizes a conduit such as a tube at the interrogation region; and/or a detector that utilizes a coplanar or nearly coplanar array of a plurality of excitation sources and/or one or more detection elements; and/or a detector where all or substantially all of the surfaces of parts of the detector that contact dispersed phase partitions have a greater affinity for continuous phase than for dispersed phase Systems and methods provided herein also can allow for determination of the volume of individual partitions as they flow through the detector; this, together with the number of partitions, can, e.g., allow calculation of an overall volume for, e.g., a group of partitions, such as a group of partitions that corresponds to an individual sample. This, together with other information, such as the number of partitions that give a positive signal in the group for a particular marker of a particular component, can allow accurate determination of the initial concentration of one or more components in the original sample from which the partitions were derived.

For convenience, detection systems will be described in terms of fluorescence systems, i.e., a system where a fluorophore is excited by electromagnetic radiation at one range of wavelengths and emits electromagnetic radiation at a second range of wavelengths, which is detected. However, any suitable method of detection may be used, and it will be appreciated that many aspects of the systems and methods described herein are applicable to a wide range of types of detection, e.g., chemiluminescence, radiation, absorbance, scattering, Raman scattering, electrical capacitance, electrical current, electrical resistance, thermal mass, image capture, and the like.

Detection systems and methods described herein are generally applicable to detection of signal from partitions moving in serial flow through a conduit. The source of the partitions may be any suitable source; in general, partition detection will be described in terms of detection following reaction, e.g., thermal cycling for PCR, but it will be understood that any suitable droplet source that produces partitions, at least some of which have or may have detectable properties, may be used.

It can be desirable to detect one or more signals from a single partition at a time, with little or no signal from adjacent partitions being detected, as the partitions flow through a conduit. Systems and methods provided herein can allow for detection of a single partition at a time, with little or no signal overlap from adjacent partitions, for example, where signal that reaches a detection element from the interrogation region that is from a partition is at least 60, 70, 80, 90, 95, 99, 99.5, or 99.9% from a single partition in the interrogation region. Systems and methods provided herein can include one or more, for example two or more, such as all three, of 1) increasing separation of partitions prior to or during detection (increasing average distance between partitions); 2) narrowing of the conduit at the interrogation region; and/or 3) an optical restriction to restrict the amount of electromagnetic radiation reaching a detection element, such as a photodetector. Using one or more of these systems and methods, it can be possible to detect signal from separate partitions, so that signal detected from an individual partition is at least 80, 90, 95, 96, 97 98, 99, 99.5, or 99.9% and/or not more than 90, 95, 96, 97 98, 99, 99.5, 99.9, or 100% due to signal produced by that partition, and not from adjacent partitions.

In certain embodiments, of the systems and methods provided herein, a system for increasing the average distance, i.e., separation, between partitions of dispersed phase in a continuous phase is used prior to and/or concurrent with partitions reaching an interrogation region in which detection of partitions occurs. Partition separation systems can increase separation of partitions (the average distance between partitions) by any suitable operation, for example, by adding a second continuous phase to a flow of partitions of dispersed phase in a first continuous phase (where the second continuous phase can be the same as or different from the first continuous phase), by narrowing the conduit through which partitions flow in continuous phase, or a combination thereof. Separation systems increase the average distance (separation) 'a' between partitions of dispersed phase in the continuous phases to a value 'b', where b>a. "a" and "b" can be, e.g., the distance between the geometric centers of adjacent partitions, or other suitable measuring point. In certain embodiments, systems and methods provided herein increase separation of partitions (average distance between partitions) so that b is at least 102, 105, 110, 125, 150, 175, 200, 225, or 300% of a, and/or b is at most 105, 110, 125, 150, 175, 200, 225, 300 or 400% of a, for example, b can be 102-400%, such as 102-300%, or in some cases 102-200% of a. Alternatively or additionally, separation of partitions can be described in terms of average distance from the surface of one partition to the surface of an adjacent partition. Thus, partitions can be separated prior to reaching the interrogation region so that the average distance from the surface of one partition to the surface of an adjacent partition is 20-500%, 20-400%, 30-300%, 50-200%, 75-200%, 50-150%, or 75-125% of the average spherical diameter of the partitions. Partitions can be separated prior to reaching the interrogation region so that the average distance from the surface of one partition to the surface of an adjacent partition is 20-500 um, or 20-400 um, or 30-300 um, or 50-200 um, or 75-200 um, or 50-150 um, or 75-125 um.

In certain embodiments, a second continuous phase is added to the flow of partitions of dispersed phase in a first continuous phase, prior to the partitions reaching the interrogation region, for example, just prior to droplets reaching an interrogation region. The composition of the first and second continuous phases can be the same or different. In certain embodiments, continuous phase is removed from the flow of partitions after they have passed through the interrogation region, and part or all of the removed continuous phase is reintroduced into the system, e.g., some or all of the removed continuous phase can be used as the second continuous phase in a separation system. Alternatively or additionally, continuous phase removed from the flow of partitions after the partitioner can serve as a source of second continuous phase for separation of partitions (increasing average distance between partitions). See, e.g., Disengagement, discussed for partitioners, for further discussion of removal and reintroduction of continuous phase. Sufficient second continuous phase may be added to the flow of partitions in the first continuous phase that the total continuous phase volume in the flow pathway is increased by a suitable amount to achieve a desirable separation of droplets, e.g., an increase of at least 2, 5, 7, 10, 15, 20, 25, 30, 35, 40, 45, 50, 55, 60, 65, 70, 75, 80, 85, 90, or 95% and/or not more than 5, 7, 10, 15, 20, 25, 30, 35, 40, 45, 50, 55, 60, 65, 70, 75, 80, 85, 90, 100, 120, 150, 170, 200, 250, or 300%, such as between 10-300%, for example 10-150%, in some cases 15-125%. Sufficient second continuous phase can be added to the flow pathway so that the average distance between partitions (e.g., as measured from the surface of one partition to the surface of an adjacent partition) is at least 1, 2, 5, 10, 30, 50, 70, 80, 90, 100, 110, 120, 130, 150, 170, 200, 250, or 300 um and/or not more than 2, 5, 10, 30, 50, 70, 80, 90, 100, 110, 120, 130, 150, 170, 200, 250, 300, 400, or 500 um, such as 30-300 um, or 50-250 um, or 50-150 um. Where the separation between partitions (e.g., as measured from the surface of one partition to the surface of an adjacent partition) is expressed in terms of the average spherical diameter of partitions, it can be, e.g. at least 10, 20, 50, 70, 80, 90, 100, 110, 120, 150, or 200% and/or not more than 20, 50, 70, 80, 90, 100, 110, 120, 150, 200, 300, or 500% of the average spherical diameter of partitions.

In certain embodiments, partitions are detected in an interrogation region of conduit, where the cross-sectional area of the interrogation region is equal to or less than the average spherical cross-sectional area of partitions of dispersed phase that pass through the interrogation region. Any suitable reduction in cross-sectional area may be used. In certain embodiments, the cross-sectional area of the conduit may be not more than 20%, 30%, 40%, 50%, 60%, 70%, 80%, 90% or 95% and/or at least 10%, 20%, 30%, 40%, 50%, 60%, 70%, 80%, or 90% and/or at least 1%, 5%, 10%, 20%, 30%, 40%, 50%, 60%, 70%, 80%, 90% or 95% and/or at least 10%, 20%, 30%, 40%, 50%, 60%, 70%, 80%, of the equivalent average spherical cross-sectional area of the partitions of the dispersed phase. For example, the cross-sectional area of the conduit in the interrogation region may be 10-100%, such as 20-100%, for example 40-60% of the equivalent average spherical cross-sectional area of partitions of the dispersed phase. The conduit prior to the interrogation region may be, e.g., 100-400 um in diameter (if circular cross-section) and the conduit in the interrogation region may be, e.g., 20-120 um in diameter (if circular cross-section).

In certain embodiments of the systems and methods provided herein, an optical restriction is placed in the path of electromagnetic radiation emitted from partitions in an interrogation region, so that only a fraction of the electromagnetic radiation reaches a detection element, e.g., photodetector, than could otherwise reach it, i.e., without the restriction. The optical restriction can be configured and positioned so that electromagnetic radiation emanating from partitions upstream and downstream of the partition in the interrogation region is reduced in its ability to reach the detection element, i.e., blocked; thus, the optical restriction will generally be positioned at a point that is at or near the middle of the interrogation region, and have a width or other suitable dimension that reduces or eliminates electromagnetic radiation from sources other than the partition in the interrogation region, given the likely spacing of partitions in the flow, volume of the partitions, and cross-sectional area of the conduit in the interrogation region. In certain embodiments, the optical restriction has a configuration and position that reduces electromagnetic radiation reaching the detection element to not more than 80, 50, 40, 30, 20, 10, 5, 2, 1, 0.1, 0.01, 0.001, 0.0001, or 0.00001%, and/or at least 50, 40, 30, 20, 10, 5, 2, 1, 0.1, 0.01, 0.001, 0.0001, 0.00001, or 0.000001% of the electromagnetic radiation that would reach the detection element without the optical restriction, e.g., under standardized conditions such as excitation of fluorophores in a partition that are present at a concentration that indicates, e.g., the presence and amplification of a single nucleic acid in the partition; in certain embodiments, the amount of electromagnetic radiation reaching the detection element is 0.000001-5% of the electromagnetic radiation that would otherwise reach the detection element. Other suitable methods of standardization will be apparent, based on the type and extent of the process that the partitions are likely to undergo in the system; in general, standardization is based on an "average" partition that contains a component that would, e.g., render the partition as a positive signal in the system. In the example above, this would be a partition in a PCR system that contained 1 nucleic acid that was amplified in the PCR reaction. In certain embodiments, the optical restriction is configured and positioned so that, either with the optical restriction alone or in combination with one or both of separation of partitions (increasing the average distance between partitions) and/or narrowing of the interrogation region, at least 30%, 40%, 50%, 60%, 70%, 80%, 85%, 90%, 95%, 97%, 98%, or 99% and/or not more than 30%, 40%, 50%, 60%, 70%, 80%, 85%, 90%, 95%, 97%, 98%, 99% or 100% of the electromagnetic radiation reaching the detection element was emitted by at least one component in a single partition of the dispersed phase, such as 60-100%, or 80-100%, or 90-100%, or 95-100%, or 98-100%, or 99-100%, or 99.5-100%, or 99.9-100% was emitted by a single partition. In certain embodiments, the optical restriction is configured and positioned so that, either with the optical restriction alone or in combination with one or both of separation of partitions and/or narrowing of the interrogation region, when a first partition is passing through the interrogation region, not more than 0.1%, 0.5%, 1%, 2%, 3%, 4%, 5%, 7%, 10%, 15%, 20%, 25%, 30%, 40%, or 50% and/or at least 0, 0.001%, 0.005%, 0.01%, 0.05%, 0.1%, 0.5%, 1%, 2%, 3%, 4%, 5%, 7%, 10%, 15%, 20%, 25%, 30%, or 40% of the electromagnetic radiation reaching the detection element due to one or more components in a partition is from one or more partitions other than the partition in the interrogation zone, such as not more than 50%, for example, not more than 30%, such as not more than 25%. Any suitable shape may be used for the optical restriction, e.g., a circle (pinhole), a slit, two slits (square), and other shapes as described herein. The optical restriction can be placed at any suitable distance from the interrogation region, e.g., 0.1-24 inches, or 1-5 inches, or 2-4 inches, such as about 3 inches. The optical restriction can be placed at any suitable distance from the surface of the detection element, e.g., 0.1-24 inches, or 0.1-5 inches, or 0.1-2 inches, or 0.1-0.5 inches, e.g., about 0.25 inches. The area of the optical restriction will be determined by its placement and by the desired proportion of light to reach the detection element, such as, for a pinhole (circle), an area corresponding to a diameter of 10-1000 um, such as 100-250 um; for example, in an embodiment where the optical restriction is a pinhole and is positioned 3 inches from the interrogation region and 0.25 inches from the detection element, the diameter of the optical restriction is 200 um. The thickness of material comprising the optical restriction is preferably thin, e.g., as thin as possible.

In certain embodiments, lock-in amplification is used as part of the detector systems and methods. Lock-in amplification provides a number of advantages, as detailed herein; for example, lock-in amplification can allow the separate measurements of signals emitted from a single partition dud to electromagnetic radiation from a plurality of excitation sources with only a single detection element. In lock-in amplification, a signal source (e.g. an excitation source) is modulated by a carrier periodic function. The resulting signal is multiplied by the carrier periodic function and integrated over multiple periods of the carrier periodic function. Because background noise, when transformed into frequency space, will typically contain components at a wide range of frequencies, use of this method allows for acceptance of only that noise in a small bandwidth around the frequencies of greatest relative magnitude in the Fourier series representative of the carrier periodic function (related to the integration time), while the signal is concentrated within this frequency range or set of frequency ranges. As a result, noise outside of this bandwidth is rejected, and the relative level of signal to the level of noise is greatly amplified. In some instances, signal-to-noise can be improved by more than six orders of magnitude As applied to the present systems and methods, lock-in amplification can be practiced by modulating each excitation source simultaneously at a set of unique frequencies. Exemplary methods include use of an optical chopper in front of the excitation source where there is a physical object that blocks then passes electromagnetic radiation at a prescribed frequency based on the size of the feature and the rate of spinning; or LED blinking by fast on/off current of the system, or any other suitable method.

In certain embodiments, a single photodetector is used and the periodic functions are sunusoidal. Because noise in these systems is concentrated in lower frequency bands (e.g. 1/f noise, power supply noise, mains voltage noise), it is desirable that the modulation frequency be at a much higher frequency than the portion of the spectrum with the most noise. In some cases, this will be at frequencies greater than 100 kHz. In other cases, this will be at frequencies greater than 1 MHz. For each channel, lock-in detection can be achieved by multiplying the resulting signal at the photodetector by that channel's modulation frequency and integrating over at least one period of the modulation frequency. This mathematical operation can be achieved by analog means (e.g. using a signal multiplier circuit followed by a low pass filter) or with digital algorithms (e.g. using analog-to-digital converters to digitize the signal, followed by either numerical integration, numerical filter algorithms, or Fourier transform/Fast-Fourier Transform operations and filtering). By choosing a small enough low-pass filter bandwidth (e.g. 2 kHz), only noise contained in a bandwidth of that size centered around the modulation frequency in the original signal will be retained. This allows for significant increases in the signal-to-noise ratio. Moreover, if the individual excitation sources are modulated at sufficiently spaced intervals (e.g. 1 MHz, 1.1 MHz, 1.23 MHz, and 1.32 MHz for a four channel system with a bandwidth of 1 kHz), when demodulating the signal for one of the modulation frequencies, the remaining modulation frequencies are rejected with the noise. By demodulating these signals in parallel, any number of channels may be multiplexed on a single photodetector simply by adding additional excitation sources modulated at unique frequencies.

Thus, in certain embodiments, lock-in amplification is used. This has the advantages of the simplicity of the optical arrangement, the improved signal-to-noise ratio (potentially allowing for the use of a lower cost photodetector), and the requirement for only a single photodetector. Further details on lock-in amplification are given in the description of FIG. 65. In certain embodiments, at least 2, 3, 4, 5, 6, 7, or 8 and/or not more than 3, 4, 5, 6, 7, 8, 9, 10, 12, or 15 excitation sources are used, for example, 2-10, such as 2-7, for example, 2-6 excitation sources with a single detection element, e.g., photodetector, to detect electromagnetic radiation emitted in response to all of the excitation sources, where lock-in amplification is used.

In certain embodiments, an interrogation region is used where the interrogation region comprises a conduit whose walls have the same or substantially the same transmittance for one or more wavelengths of electromagnetic radiation of interest, for example, one or more excitation wavelengths and one or more emission wavelengths, around the circumference of the conduit. In certain embodiments, the conduit is a tube, for example a tube with a circular or substantially circular cross-section. The conduit can comprise any suitable material, for example, a material that has higher affinity for the continuous phase than the dispersed phase; in embodiments, the conduit comprise fluoropolymer, e.g., for use with a fluorinated oil continuous phase.

Use of such a conduit, e.g., a tube, at the interrogation region means that a plurality of excitation sources, a plurality of detection elements, or both, can be arranged so that all of the excitation sources and/or detection elements are in the same plane or nearly in the same plane, where the plane is orthogonal to the long axis of the conduit as it passes through the interrogation region. For example, all of the excitation sources and/or detection elements can be within 50, 40, 30, 20, 15, 10, 5, 4, 3, 2, 1, 0.5, or 0.1 degree of a plane orthogonal to the long axis of the conduit, i.e., orthogonal to the direction of flow of partitions in the conduit. In certain embodiments, at least 2, 3, 4, 5, 6, 7, or 8 and/or not more than 3, 4, 5, 6, 7, 8, 9, 10, 12, or 15 excitation sources are used, for example, 2-10, such as 2-7, for example, 2-6 excitation sources, all of which are within 50, 40, 30, 20, 15, 10, 5, 4, 3, 2, 1, 0.5, or 0.1 degree of a plane orthogonal to the long axis of the conduit; in certain embodiments, in addition to a plurality of excitation sources, at least one detection element is also within 50, 40, 30, 20, 15, 10, 5, 4, 3, 2, 1, 0.5, or 0.1 degree of the plane orthogonal to the long axis of the conduit in which the excitation sources are situated.

In certain embodiments, surfaces of the conduit through which the partitions pass in the detector have a greater affinity for continuous phase than for dispersed phase. For example, the surfaces may be fluoropolymer when the continuous phase is, e.g., a fluorinated oil.

Thus, described herein are various systems and methods for detecting individual droplets (partitions). An individual droplet (partition) may be detected based on the fluorescence of the individual droplet (partition). In some instances, as the individual droplet (partition) enters the optical stage (interrogation region), a signal is detected that is an increased over baseline. In some instances, an individual droplet (partition) is distinguished by peaks in the optical signal. In some instances, fluorescent molecules are added to the dispersed phase prior to droplet (partition) generation to increase the optical signal over the baseline optical signal when droplets (partitions) are not in the center of the optical stage (interrogation region). In some instances, the fluorescent molecules are added to the dispersed phases without quenching molecules. In some instances, the fluorescent molecules comprise a similar excitation wavelength and/or emission wavelength as the fluorophores for the assay or reaction. In some instances, the fluorescent molecule comprises a different excitation wavelength and/or emission wavelength as the fluorophores for the assay or reaction.

In some instances, an arrangement for a detector detects a single droplet (partition) at a time. An excitation source may transmit electromagnetic radiation (e.g., light) in substantially a single direction. The light may pass through a filter and then passes through a lens. The lens may focus the light onto an optical stage. Droplets (partitions) may pass through the optical stage. Light may be emitted by the fluorescent molecules in the optical stage. In some instances, a detection lens, filter, optical restriction, or combinations thereof are placed substantially in line with the excitation source and on an opposite side of the optical stage. In some instances, a detector is placed beyond an optical restriction. Light may pass from the excitation source and may be limited to a single wavelength by the filter. The light may be focused by the lens on a droplet (partition) where emission occurs. The emission may be then collimated by the second lens so that an image of the optical stage may be produced on the plane of the optical restriction. The optical restriction may select only a portion of the light corresponding to a region of the optical stage that comprises the droplet (partition). The detector may then register a signal for the light. In some instances, the detector is substantially orthogonal to both the excitation source and the direction of droplet travel. Exemplary excitation sources include, but are not limited to, a LED, a laser, or any other light source substantially restricted to a small range of wavelengths. The detector may be a photodiode, PMT, SiPM, or any other optical detector where the signal level increases monotonically with light intensity. In some instances, the excitation source is mounted in a light tube. In some instances, an optical fiber with integral lens is used to position the excitation source over the optical stage. In some instances, the excitation filter is chosen so that only light near the excitation frequency passes the filter. In some instances, the emission filter is chosen so that only light near the emission frequency passes the filter.

In some instances, an arrangement comprises both emission and excitation light that travel on substantially the same path from an optical stage. The system may comprise an excitation source, an excitation filter, a dichroic mirror, an optical stage lens, an optical stage, a detection filter, a detection lens, a detection optical restriction, and a detector. The excitation source may emit light at substantially a single wavelength which is restricted to primarily that wavelength by the excitation filter. The light may strike the dichroic mirror, where it is turned approximately 90 degrees toward the optical stage lens, which focuses the light on the optical stage. The light may excite fluorescent molecules in droplets (partitions) in the optical stage, and light emitted by those molecules passes back through the optical stage lens, where it is collimated onto the dichroic mirror. The light may pass through the dichroic mirror, through the emission filter which restricts the light primarily to the wavelength emitted by the fluorescent molecules in the droplets (partitions), where it then passes through the detection lens and is focused on the plane containing the optical restriction. The optical restriction may restrict the light passing to the detector to only that portion corresponding to a single droplet (partition) in the optical stage. The light creates a signal on the detector that monotonically increases with the emission intensity from the fluorescent molecules in a single droplet (partition). In some instances, the further comprises a mirror behind the optical stage so as to collect more emitted light from the droplets (partitions) in the optical stage.

The detector is what senses the presence and/or level of detectable components in the partitions (here described in terms of fluorophores). Thus, for fluorescence systems, the detector is what senses the presence and/or level of fluorophores in the partitions and, e.g., allows discrimination between "positive" (e.g., contains a molecule of interest) and "negative" (e.g., does not contain a molecule of interest) partitions in digital assays. The underlying concentration of that molecule in the original sample can then be determined from Poisson statistics on the ensemble of partitions.

One basic principle of detection in fluorescence systems is excitation of a fluorophore in the partition, which then emits electromagnetic radiation that can be measured with a photodetector. The intensity of the electromagnetic radiation emitted for a given excitation intensity is proportional to the concentration and state of the fluorophore in the partition. Fluorophores may be associated with molecules of interest in any suitable manner. Fluorophores can be incorporated into larger molecular systems such that the intensity of emission for a given excitation intensity can be related to the concentration of another chemical entity in the partition. For example, if a nucleic acid binding dye (e.g. intercalating or bis-intercalating agents, minor or major groove binders, or external binders) is used (e.g. SYBR Green, EvaGreen), the intensity of emission can be related to the total amount of nucleic acid in the system in which the intercalating dye is intercalated. For a hydrolysis probe, in which a fluorophore is closely associated with a quencher in the unhydrolyzed state but is remote from the quencher in the hydrolyzed state, the emitted intensity can be associated with the concentration of dye released from the hydrolyzed probe; hydrolysis can occur during nucleic acid polymerization if the probe incorporates a oligonucleotide sequence complementary to the sequence of nucleic acid of interest when using a polymerase with $5' \rightarrow 3'$ exonuclease activity. Alternatively the addition of fluorescent dye-modified nucleotides (e.g. dye systems with tetra- or pentaphosphate linked fluorophores) may produce a fluorescent signal with intensity proportional to the total amount of nucleic acid polymerization. The ratio of unmodified nucleotides to modified nucleotides tunes the total potential intensity achievable in each reaction vessel.

Excitation sources can generally be anything that emits electromagnetic radiation at wavelength ranges where the fluorophores can absorb this energy to re-emit. Noise can arise in these systems due to background electromagnetic radiation from the excitation source as well as auto-fluorescence. Thus, it is generally preferable that the electromagnetic radiation that reaches the partitions be restricted to the wavelengths that will excite the fluorophores as much as practically possible. This can be done in any suitable manner, for example, by (1) using electromagnetic radiation sources that emit electromagnetic radiation primarily at the wavelengths that will excite the fluorophores of interest, (2) using electromagnetic radiation sources that primarily emit electromagnetic radiation in the direction of the partition containing the fluorophores of interest, (3) using refractory elements and/or reflective surfaces to concentrate the electromagnetic radiation onto the interrogation region, and/or (4) using optical filters to restrict the wavelengths of electromagnetic radiation reaching the partitions containing the fluorophores of interest, or any combination of these methods. For (1), examples of electromagnetic radiation sources are light-emitting diodes (LEDs); lasers, including but not limited to Helium Neon, Argon Ion, Krypton Ion, Xenon Ion, Carbon Dioxide, Neodymium Doped Crystal Yttrium, Aluminum Garnet, Titanium Sapphire Mode Locked, Excimer, Semiconductor Diode, or dye-based; excited phosphors; excited quantum dots; or arc discharge lamps. For (2), suitable electromagnetic radiation sources are lasers, which concentrate their energy into a small beam or cone rather than emitting hemispherically. Other options for (2) can be collimated light emitting diodes (LEDs), excited phosphors, excited quantum dots, or arc discharge lamps. For (3), refractory elements include lenses; any suitable lens may be used, such as achromats/asphericals, and the like, including but not limited to semi-apochromats, apochromats, meniscus, hemispherical, cone, rod, ball, and cylinder lenses. Reflective elements can include parabolic mirrors, dichroic mirrors, or any other suitable reflective element, including but not limited to prisms and beam splitters. For (4), filters are preferentially bandpass filters, passing only a narrow range of frequencies substantially near the frequencies of electromagnetic radiation emission by the excitation source. Short-pass, long-pass, notch, neutral density or polarizing filters may be used; dichroic mirrors may also be used.

Photodetectors provide signals that change monotonically with the intensity incident or power of electromagnetic radiation on their surfaces. The choice of photodetector in the detection system depends on the incident intensity or power. For arrangements with high incident intensity, relatively insensitive detectors (e.g. photodiodes) may be used, which has the advantage of low cost. For other arrangements with intermediate intensity, charge coupled device (CCD) detectors or silicon photomultipliers may be used. For arrangements with low incident intensity, very sensitive devices (e.g. photomultiplier tubes or silicon photomultipliers) will typically be used to improve signal-to-noise ratio. In certain embodiments, one or more silicon photomultipliers is used.

In some situations, it is desirable to detect and/or measure a quantity of more than one component in each partition ("multiplexing"). This can achieved by any suitable technique, for example: (1) associating a component to each fluorophore, exciting each fluorophore separately, detecting the emitted intensity from each fluorophore, and using the intensity to calculate a quantity for the component associated with each fluorophore; (2) associating all but one of the components to each fluorophore and incorporating a fluorophore that is proportional to the total amount of all of the components in the system, exciting each fluorophore separately, detecting the emitted intensity from each fluorophore, using the intensity to calculate a quantity for the component associated with each fluorophore, using the intensity from the non-specific fluorophore to calculate a quantity for the entire mixture, and using the total quantity and the quantity of each component other than the final component to determine the quantity of the final component; (3) associating two or more components to each fluorophore each of which generates a specific fluorescent intensity, exciting each fluorophore separately, detecting the emitted intensity from each fluorophore, and using the intensity to detect the quantity for each component associated with each fluorophore at each intensity level; (4) associating a component to each fluorophore, exciting each fluorophore simultaneously, detecting the emitted intensity from each fluorophore, and using the intensity to calculate a quantity for the component associated with each fluorophore; (5) associating all but one of the components to each fluorophore and incorporating a fluorophore that is proportional to the total amount of all of the components in the system, exciting each fluorophore simultaneously, detecting the emitted intensity from each fluorophore, using the intensity to calculate a quantity for the component associated with each fluorophore, using the intensity from the non-specific fluorophore to calculate a quantity for the entire mixture, and using the total quantity and the quantity of each component other than the final component to determine the quantity of the final component; (6) associating two or more components to each fluorophore each of which generates a specific fluorescent intensity, exciting each fluorophore simultaneously, detecting the emitted intensity from each fluorophore, and using the intensity to detect the quantity for each component associated with each fluorophore at each intensity level.

Signals from different fluorophores can be discriminated in any suitable manner. In a first method, a non-spectrally sensitive photodetection system may be used and the excitation source at any given time may be limited to excitation wavelengths that primarily excite only one fluorophore in the system. While the excitation bands for desired fluorophores may overlap and thus more than one fluorophore may be excited in this case, corrections to the detected intensity on the photodetector may be made from a set of standard calibrations. By cycling through the excitation sources, each of the fluorophores may be detected at the photodetector, and, by correlating the time that each excitation source was on with those measurements at the photodetector, a quantity may be calculated for each component (or group of components) associated with that fluorophore. Each excitation source may be activated immediately after de-activating the previous activation source, or there may be a period where no activation source is on. Each excitation source should be active for at least the amount of time required for the signal from its associated fluorophore to stabilize. A single data sample may be taken from the photodetector during this time. Alternatively, multiple data signals may be taken from the photodetector during this time and aggregated. An advantage of this approach is that it is very optically simple and only requires a single photodetector. Disadvantages are that the gain will typically be uniform across all wavelengths and the number of samples at each wavelength for a given sampling frequency will be smaller than they would be were all the wavelengths of interest excited simultaneously.

A second method for discriminating signals from different fluorophores is to excite one or more fluorophores simultaneously, spatially separate the electromagnetic radiation emitted from the fluorophores, and detect all or a subset of the separated electromagnetic radiation with one or more photodetection elements spatially distinct from each other ("spectrometer method"). Means of spatially separating electromagnetic radiation include resolving the emitted electromagnetic radiation by wavelength, e.g., with a diffraction grating (transmissive or reflective), mirrors, a refractive prism, a series of dichroic mirrors that selectively remove one wavelength range at a time, or other suitable means. The refracted electromagnetic radiation can be collected by one or more photodetectors. In an example, the photodetectors are either photodiodes or silicon photomultipliers that are spatially distinct from each other and are positioned so as to intercept the wavelengths primarily associated with each fluorophore. In another instance, a linear charge-coupled device (CCD) or complementary metal-oxide-semiconductor (CMOS) sensor is used as the photodetector, and it is positioned to intercept electromagnetic radiation across the wavelength range emitted by some or all of the fluorophores. In some instances, it may be desirable to minimize the size of the photodetection elements (e.g. for cost or compactness), and an optical concentrating element may be used (e.g. lens, focusing mirror) to concentrate a spatial band of electromagnetic radiation onto each photodetection element.

A third method of discriminating signals from different fluorophores while simultaneously improving signal-to-noise ratio is to use lock-in amplification. See description above and below for lock-in amplification.

Thus, detectors for use in systems and methods as described herein may allow for multiplexing. In some instances, multiple wavelengths are used to detect separate emission spectra by using separate signal channels. In some instances, the signals received by the signal channels are separated in time. In some instances, the signal channels are generated by different detectors. The separate channels may allow for measuring different levels of intensity of each wavelength. In some instances, the signal of each channel varies temporally or spatially.

Detectors for use in systems and methods as described herein may comprise multiple channels. In some instances, one channel is used for detecting droplet size. In some instances, the channel for detecting droplet size comprises a fluorophore having an intensity that does not vary with the state of one or more reactions in the droplet. In some instances, detectors further comprise one or more channels for measuring a chemical reaction. Such channels may have an emission intensity that depends on the state of the chemical or physical reactions that comprise the underlying assays. In some instances, use of one or more channels indicates whether a droplet (partition) is present or not. For example, if a portion of the one or more channels are above a threshold, the droplet (partition) is present. In some instances, if a portion of the one or more channels are below a threshold, the droplet (partition) is not present.

Droplets (partitions) may be detected in a system comprising multiple channels. In some instances, size of the droplet (partition) is determined by measuring a time from a signal from the channel to rise above a threshold to a time for a signal from the channel to fall below a threshold. In some instances, size of the partition is determined by measuring the width, in time, of a signal peak at a fraction of the maximum signal for that peak. In further instances, the fraction is between 0.25 and 0.35, 0.45, and 0.55, 0.2 and 0.8, 0.65 and 0.85, and 0.1 and 0.9. In some instances, one or more measurements are detected. In some instances, the one or more measurements improve resolution of the size. In some instances, at least or about 1, 2, 3, 4, 5, 6, 7, 8, 9, 10, 11, 12, 13, 14, 15, 16, 17, 18, 19, 20, 24, 28, 32, 36, 40, 44, 50, 60, 70, 80, 100, 200, 1000 or more than 1000 measurements are detected.

Figure 93:
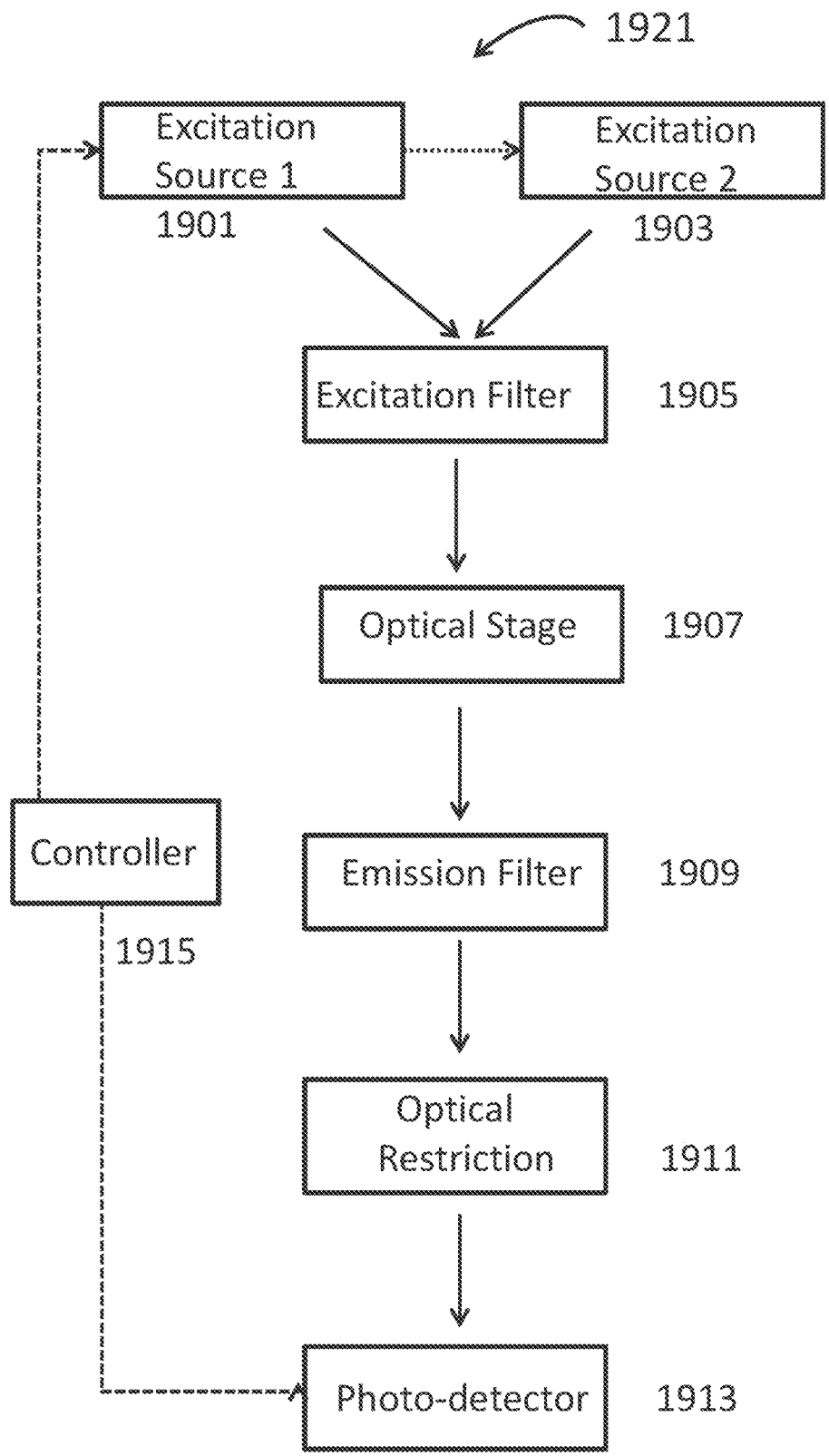
FIG. 93 shows a diagram of a system for achieving multiplexing.
Figure 94:
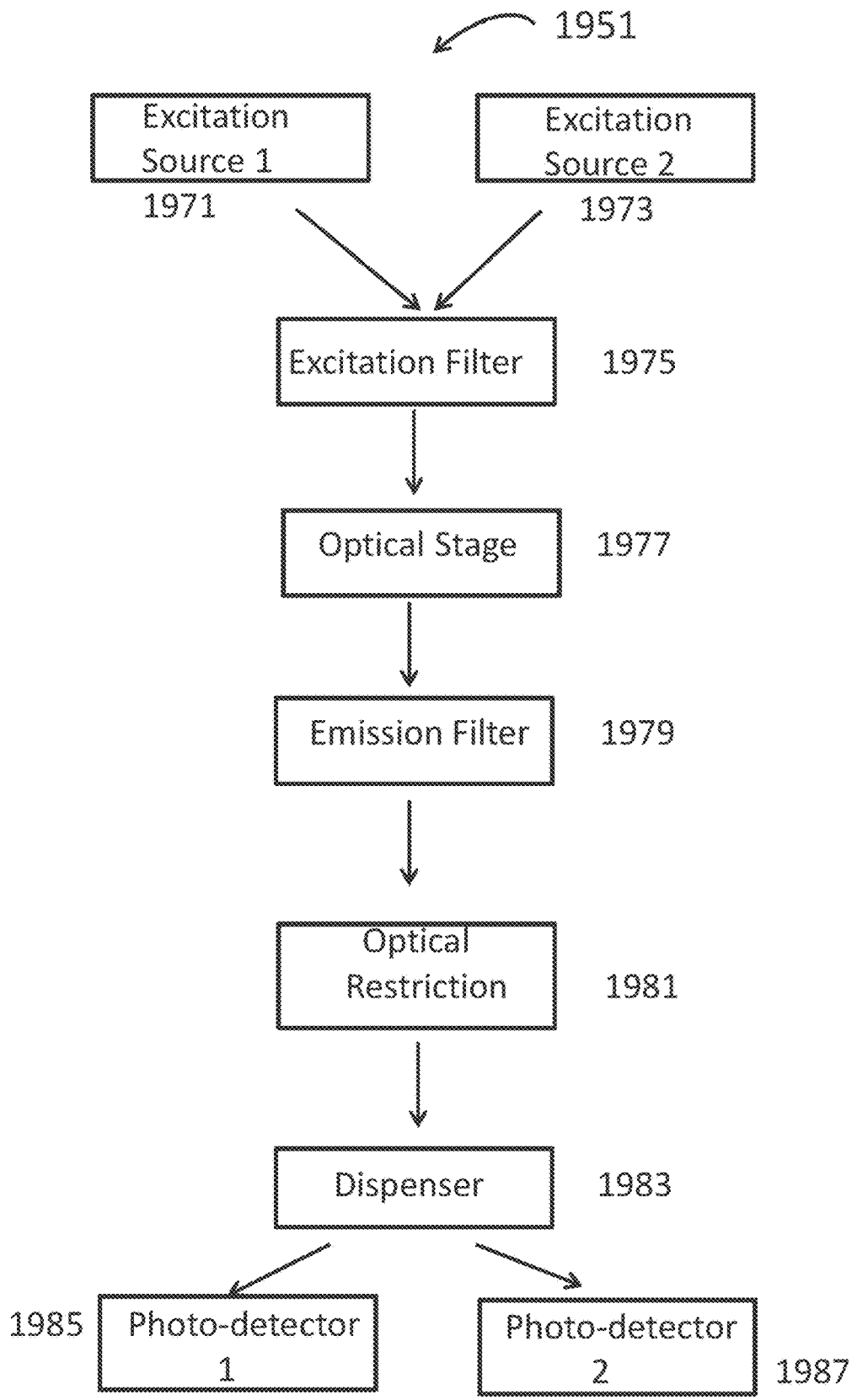
FIG. 94 show a diagram of a system for achieving multiplexing.

Thus, in certain embodiments detectors are configured for multiplexing. Exemplary diagrams of systems for achieving multiplexing are illustrated in FIG. 93 and FIG. 94. FIG. 93 illustrates temporal multiplexing. In some instances, multiple excitation sources and/or a controller is used. In some instances, the excitation filters and/or emission filters are converted to multiple bandpass filters. In some instances, the multiple bandpass filters substantially pass only those wavelengths corresponding to each of the excitation or emission wavelengths in the system. The controller may control whether the excitation sources are on or off. The system 1921 comprises multiple excitation sources 1901, 1903, an excitation filter 1905, an optical stage 1907, an emission filter 1909, an optical restriction (e.g. a pinhole or slit) 1911, a photo-detector 1913, and a controller 1915. Each of the excitation sources 1901, 1903 produces light over a range of wavelengths, where the wavelength range of each of the excitation sources does not substantially overlap with the wavelength range of any other of the excitation sources so that at least one fluorescent molecule in the dispersed phase is excited by each of the excitation sources 1901, 1903 and at least one fluorescent molecule in the dispersed phase is not excited by that excitation source. The controller 1915 is connected to the excitation sources 1901, 1903 and controls whether any of the excitation sources 1901, 1903 is on at any given time. By coordinating the times when a given excitation source is active with the timing of measurements made by the photo-detector 1913, the emission from only a specific fluorophore can be detected with a non-wavelength specific detector. Systems as described herein can comprise a time scale over which the fluorescent molecules react to changes in excitation, a time scale for changes in excitation intensity, and a time scale for making measurements on the detector that may be shorter than a time required for a droplet to move across the optical stage. The excitation sources may comprise LEDs, lasers, excited phosphorescent material, quantum dots, any other electromagnetic radiation (light) emitting material for which the light is emitted in a narrow range, or any combination thereof.

In some instances, a first excitation source is turned on by the controller for a first time. During this time, at least one measurement is taken by the detection element. In some instances, one measurement is taken by the detector. In some instances, multiple measurements are taken by the detector. For example, at least or about 2, 3, 4, 5, 6, 7, 8, 9, 10, 11, 12 or more than 12 measurements are taken by the detector. In some instances, at least 5 measurements are taken by the detector. These measurements may be averaged to get a noise-stabilized measurement. In some instances, at least one of the measurements at the start of the time when the first excitation source is on is rejected, and only the remaining measurements are aggregated. In some instances, no aggregation of the measurements is taken. In some instances, a median measurement is taken. After a first period of time has elapsed, the first excitation source may be deactivated and a second excitation source is activated. A second set of one or more measurements may be taken by the detector. In some instances, the one or more measurements of the second set are aggregated. In some instances, the one or more measurements are not aggregated. After a second period of time has elapsed, the second excitation source may be deactivated. If there are additional excitation sources, these may be activated and de-activated in turn, with each comprising its own time period of activation. After all of the sources have been turned on, the controller may loop back around to the first excitation source and the process repeats. Generally, the time period for each excitation source can all be different. In some instances, the time period for each excitation source is the same. In some instances, the time period for each excitation source is at least or about 50 microsecond (μs), 75 μs, 100 μs, 200 μs, 300 μs, 400 μs, 500 μs, 600 μs, 700 μs, 800 μs, 900 μs, 1.0 microsecond (ms), 1.5 ms, 2.0 ms. 2.5 ms, 3.0 ms, 3.5 ms, 4.0 ms, 4.5 ms, 5.0 ms, 5.5 ms, 6.0 ms, 6.5 ms, 7.0 ms, 7.5 ms, 8.0 ms, 8.5 ms, 9.0 ms, 9.5 ms, 10 ms, 10.5 ms, 11 ms, 12 ms, 13 ms, 14 ms, 15 ms, 16 ms, 17 ms, 18 ms, 19 ms, 20 ms, or more than 20 ms. In some instances, the time period is in a range of about 1 ms to about 10 ms. In some instances, the detection sampling is performed at least or about 1 kHz, 2 kHz, 5 kHz, 10 kHz, 15 kHz, 20 kHz, 25 kHz, 30 kHz, 35 kHz, 40 kHz, 45 kHz, 50 kHz, 55 kHz, 60 kHz, 65 kHz, 70 kHz, 75 kHz, 80 kHz, 85 kHz, 90 kHz, 100 kHz, 120 kHz, 140 kHz, 160 kHz, 180 kHz, 200 kHz, 220 kHz, 240 kHz, 280 kHz, 300 kHz, 320 kHz, 340 kHz, 360 kHz, 380 kHz, 400 kHz, 450 kHz, 500 kHz, 600 kHz, 700 kHz, 800 kHz, 900 kHz, 1000 kHz, 2000 kHz, 3000 kHz, 4000 kHz, or more than 4000 kHz. In some instances, the detection sampling is performed in a range of about 1 kHz to about 2 MHz. In some instances, the detection sampling is performed in a range of 10 kHz to about 500 kHz. In some instances, the detection sampling is performed in a range of 20 kHz to about 250 kHz.

In some instances, a first excitation source excites a molecule whose emission intensity is unrelated to the concentration of any target molecule or species to be measured. The excitation source is turned on in between each of the assay intensity measurement sources. In some instances, the channel is turned on interspersed between the other channels when its intensity is above a certain threshold. The channel may be turned and remains on when its intensity is below the certain threshold. In some instances, the system comprises time periods where no excitation source is turned on that are interspersed with time periods where a single excitation source is turned on. In some instances, a single detector is used that is not wavelength dependent. In some instances, multiple channels are used.

FIG. 94 illustrates a system for spatial multiplexing. In some instances, multiple excitation sources and/or a controller is used. In some instances, the excitation filters and/or emission filters are converted to multiple bandpass filters. In some instances, the multiple bandpass filters substantially pass only those wavelengths corresponding to each of the excitation or emission wavelengths in the system. The controller may control whether the excitation sources are on or off. In some instances, a wavelength-dispersion element and/or array of detectors are added behind the detection restriction. The system 1951 comprises a set of excitation sources 1971, 1973, an excitation filter 1975, an optical stage 1977, an emission filter 1979 an optical restriction (e.g. a pinhole or a slit), a wavelength-dependent disperser 1983 and an array of non-wavelength dependent detectors 1985, 1987 arranged spatially on an image plane of the wavelength-dependent disperser 1983. The disperser 1983 changes the angle at which rays of incoming light substantially impinging on the disperser 1983 at the same angle leave the disperser 1983. In some instances, an exit angle is dependent on the wavelength of the light impinging on the disperser. A light source comprising multiple wavelengths may be angularly resolved. In some instances, an angular distribution is created for each wavelength with a central angle and a measure of dispersion around the central angle. At any plane located a finite distance from the exit surface of the disperser 1983, an image is created where the angular distribution of light at the exit surface of the disperser 1983 is realized as a spatial distribution. By choosing a distance for this plane that is larger than some minimum value, an original source consisting light comprising a finite set of primary wavelengths may be resolved into a spatial distribution where the intensity within any spatial extent smaller than some fixed figure results primarily from at most one of the finite sets of primary wavelengths. By arranging the array of detectors such that the collection surface for each detector primarily intersects only one of the spatial extents, a wavelength-dependent detector may be created from non-wavelength dependent detectors. The detector may comprise photodiodes, photomultiplier tubes, silicon photomultipliers, any other optical transducer, or any combination thereof. In some instances, the detector comprises a photomultiplier (PMT). In some instances, the detector comprises a silicon photomultiplier (SiPM) or an array of silicon photomultipliers. In some instances, the detector is a charge-coupled device (CCD) or array of CCDs. The dispersion element may be a grating, a prism, or any object angularly disperses light. In some instances, the dispersion element is a grating. Gratings can be transmissive or reflective. In some instances, reflective gratings comprise a detector that is arranged at an angle for intersecting dispersed light.

Disclosed herein are methods for multiplexing using systems as described herein. For example, a method for multiplexing using the system of FIG. 94 comprises excitation sources that are all activated simultaneously. The detector may be sampled at least or about 100 Hz, 500 Hz, 1 kHz, 2 kHz, 5 kHz, 10 kHz, 15 kHz, 20 kHz, 25 kHz, 30 kHz, 35 kHz, 40 kHz, 45 kHz, 50 kHz, 55 kHz, 60 kHz, 65 kHz, 70 kHz, 75 kHz, 80 kHz, 85 kHz, 90 kHz, 100 kHz, 120 kHz, 140 kHz, 160 kHz, 180 kHz, 200 kHz, 250 kHz, 500 kHz, 1 MHz or more than 1 MHz.

Systems and methods as described herein for serial flow emulsion comprises multiplexing of sample, wherein various methods for analyzing multiplexed samples are used. In some instances, methods for analyzing multiplexed samples relates to detecting specific droplets (partitions). For example, each wavelength channel has a series of data of detector intensity as a function of time. For temporal multiplexing, the data may be obtained by pairing each detector measurement with the excitation source that was active when the measurement was taken. A subset of intensity data for each excitation source as a function of time may then be generated. For spatial multiplexing, the use of multiple detectors may produce a separate subset of intensity data as a function of time for each channel. As a droplet (partition) enters the optical stage, the intensity signal may increase until the droplet (partition) is approximately at a center of a region of the optical stage imaged by the optical restriction, after which the signal diminishes. A single measurement may be determined that represents a peak intensity for each droplet (partition). In some instances, a peak-finding algorithm is used for detecting the peak. In such an algorithm, the increase in intensity over adjacent signals may be used to determine whether the signal at a given time is a peak. In some instances, minimum relative or absolute thresholds are applied to the peaks located by a peak-finding algorithm. In some instances, smoothing algorithms are used. Smoothing algorithms may be used to reduce or eliminate local fluctuations in the data. In some instances, the smoothing algorithms are used before applying a peak algorithm. In some instances, the smoothing algorithms are used after applying a peak algorithm.

In some instances, analyzing multiplexed samples comprises methods for calibration. In some instances, systems and methods for analyzing multiplexed samples comprise measuring a peak at each channel. In some instances, if a peak is not detected, the peak is aligned with measured peaks. In some instances, calibration comprises examining at time at which a droplet (partition) peak was registered on one channel and ensuring that each other channel also has a peak at that time. In some instances, each channel comprises a peak within a fixed time window. In some instances, the fixed time window is determined when the peak is detected by another channel.

There are a number of ways of introducing partitions into the interrogation region. The partitions, coming from the portion of the system that prepares them for detection (e.g. in a PCR system, the thermal cycler), will be flowing in a conduit. That conduit may be any suitable conduit, e.g., a microfluidic channel in a chip, a tube of round, elliptical, rectangular, or other cross section, or any other conduit that can contain the partitions. The conduit should be oriented in such a way that the partitions can be illuminated by the excitation energy and electromagnetic radiation emitted by the fluorophores can be detected in a photodetector. The conduit may be oriented so that the excitation energy and the electromagnetic radiation emitted share a common pathway ("on-axis"), or it can be oriented so that they do not share a common pathway. For highest signal-to-noise ratio, it is preferred that the excitation electromagnetic radiation and emitted electromagnetic radiation do not share a common pathway. For this to occur, the material comprising the conduit through which the partitions are passing may not be strongly biased in terms of an illumination or emission direction. For example, when using a channel in a microfluidic chip comprising glass or polymer, illumination energy that is not substantially normal to the chip surface will have a relatively high fraction of that energy reflected away from the partitions in the chip without exciting the fluorophores. Likewise, emitted energy from the fluorophores in directions substantially deviating in angle from a normal vector to the chip surface will have a substantial fraction reflected or refracted away from those directions as well as absorbed by the material comprising the chip. To maximize illumination and detection efficiency, channels contained in microfluidic chips will preferentially have illumination and detection pathways that are on-axis or have a small angle of deviation between their axes.

In contrast, a conduit comprising a tube (e.g. a tube whose surface has higher affinity for continuous phase than dispersed phase, such as fluoropolymer tube when the continuous phase is, e.g., a fluorinated oil) has approximately isotropic illumination and emission frequency in the azimuthal angle, and so is relatively agnostic as to the direction for illumination and emission. In this case, off-axis solutions can be used, which, e.g., reduce the amount of stray electromagnetic radiation introduced into the detection system from the illumination system. Excitation sources can be arranged so that the focal point of the excitation is on a central point where a partition to be measured is passing. In one embodiment, the excitation sources are coplanar or nearly so with the photodetector and with each other, with the common plane substantially orthogonal to the tube through which the partitions are flowing. In other embodiments, at least one of the excitation sources is offset from the plane orthogonal to the partition conduit; the purpose of doing so would be to increase the number of excitation sources, which may be limited due to geometrical constraints. Where possible, the preferred embodiment is one where all of the sources are coplanar or nearly so with a plane orthogonal to the partition tube, because that will minimize reflection/refraction of excitation energy incident on the tube. Thus in certain embodiments the systems and methods provided herein include a detector comprising a plurality of excitation sources situated within 40, 30, 20, 15, 10, 5, 2, or 1 degree of a plane that is orthogonal to a conduit, for example, a tube, illuminated by the excitation sources. In certain embodiments, one or more photodetectors is also situated within 40, 30, 20, 15, 10, 5, 2, or 1 degree of the plane that is orthogonal to the conduit.

The cross-section of the detection conduit may be larger, the same as, or smaller than the equivalent average spherical cross-section of the partitions. Thus, the cross-sectional area of the conduit may be any suitable cross-section, depending on the equivalent average spherical cross-section of partitions. For example, for partitions that have an average diameter of 100 um, the average spherical cross-sectional area will be 7850 $um^2$, and appropriate calculation may be made of the cross-sectional area of the conduit, depending on whether the conduit is to be larger, smaller, or the same cross-sectional area as the average equivalent spherical cross-section of the partitions. Exemplary cross-sectional areas for the conduit in the interrogation region are 10-1,000,000 $um^2$, 10-100,000 $um^2$, 100-100,000 $um^2$, 100-50,000 $um^2$, 100-40,000 $um^2$, 500-50,000 $um^2$, 500-40,000 $um^2$, 1000-100,000 $um^2$, 1000-50,000 $um^2$, 1000-20,000 $um^2$, 2000-20,000 $um^2$, or 2000-10,000 $um^2$.

In certain embodiments, the cross-section of the interrogation region is smaller than or the same as the equivalent average spherical cross-section of the partitions. This ensures that partition position within the cross-section of the conduit does not affect the intensity measurement, because the partition consumes the entire cross section, or substantially the entire cross-section, of the conduit; it will be appreciated that in embodiments in which the surface of the conduit has greater affinity for continuous phase than for dispersed phase, a thin layer of continuous phase will be associated with the walls of the conduit and thus a partition flowing through the conduit will have a cross-section that is slightly smaller than that of the conduit. In certain embodiments, the cross-section of the conduit is smaller than that of the equivalent average spherical cross-section of the partitions. When this is the case, the partition becomes elongated in the conduit and, when the sampling frequency is at least twice as high as the frequency of partition arrival at the center point of the detection region in the conduit, multiple measurements may be made of each partition. By using the number of measurements above some minimum intensity in conjunction with the cross-section of the conduit and the liquid volumetric flowrate in the conduit, the size of the partitions may be calculated. This information may, in turn, be used to calculate various quantities about the components measured within the partitions (e.g. partition volumes, component concentrations, Poisson corrections based on the underlying distribution of partition sizes, etc.) and/or may be used to accept or reject partitions for quality reasons (e.g. too big or too small). Thus in certain embodiments, the detection conduit has a cross-sectional area that is not more than 20%, 30%, 40%, 50%, 60%, 70%, 80%, 90% or 95% and/or at least 10%, 20%, 30%, 40%, 50%, 60%, 70%, 80%, or 90% of the equivalent average spherical cross-section of partitions of dispersed phase flowing through it. The equivalent average spherical cross-section of the partitions is, e.g., the average cross-section of the partitions if their volume of each is contained in a sphere.

To perform assays with the system, it is important to measure and assign an emissive intensity in each wavelength range of interest to each partition. One such way to do this is to collect a relatively large fraction of the electromagnetic radiation emitted from the partitions illuminated in the interrogation region and to make mathematical corrections to the intensity based on the previous and subsequent measurements made on the partitions ahead of and behind the partition in the conduit, respectively. Another way to do this is to restrict the electromagnetic radiation reaching the photodetector(s) so that substantially only that electromagnetic radiation emitted from a single partition at a given time reaches the photodetector(s). This trades the efficiency of electromagnetic radiation collection (i.e. the fraction of the emitted electromagnetic radiation measured at a photodetector) for reduction in signal from other partitions than the partition being measured and has the potential to make data analysis simpler; it also enables the partition measurement technique described above. Methods to achieve this include placing an optical restriction (e.g. a slit or pinhole) between the conduit containing the partitions and the photodetection element(s). The size of the optical restriction will depend on its location in the optical path, but the intention is to reduce the field of view, e.g., so that only or substantially only electromagnetic radiation from a single partition is measured by the photodetector(s). The desired size and location of the optical restriction will depend on, e.g., the degree of separation of partitions of dispersed phase by continuous phase as they pass through the detection region (the greater the separation, the more electromagnetic radiation the optical restriction can let through from a given partition without allowing electromagnetic radiation from adjacent partitions through), the narrowness of the conduit in the detection region (conduits narrow enough to cause elongation of the partitions also essentially separate the center of one partition from others, decreasing the amount of electromagnetic radiation from others).

Thus, provided herein are systems and methods for detection of a single (partition) at a time, wherein the detection may comprise use of an optical stage. In some instances, a single droplet (partition) is measured by restriction of the excitation dimension and emission dimension of the optical stage. In some instances, the restriction is a geometric restriction. For example, geometric restrictions include use of a pinhole, slit, or any arrangement of openings in a surface that restrict the geometric and/or angular extent of light entering and exiting the optical stage and/or impinging on the photodetection element. In some instances, the restrictions allow for only the droplet (partition) to be detected. Following collection of emitted light, an image of the optical stage may be projected on a plane in front of the detector. By using a restriction in that plane such as a pinhole or slit or combination thereof, only a portion of the image comprising the droplet (partition) may be captured. In some instances, the restriction is located in a plane between the detector and its lens. In some instances, the restriction is located in front of the optical stage. In some instances, multiple restrictions are used. In some instances, at least or about 1, 2, 3, 4, 5, 6, or more than 6 restrictions are used. In some instances, the emitted light is at least or about $0.5$ $mm^2$, $0.75$ $mm^2$, $1.0$ $mm^2$, $1.25$ $mm^2$, $1.5$ $mm^2$, $1.75$ $mm^2$, $2.0$ $mm^2$, $2.5$ $mm^2$, $3.0$ $mm^2$, $3.5$ $mm^2$, $4.0$ $mm^2$, or more than $4.0$ $mm^2$.

Figure 90:
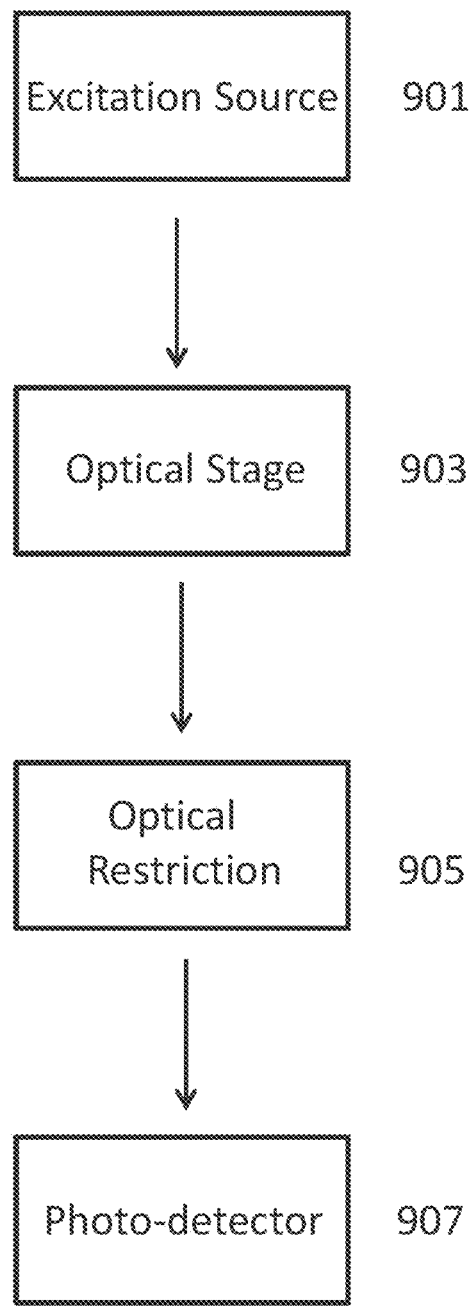
FIG. 90 shows a diagram of a detector.
Figure 91:
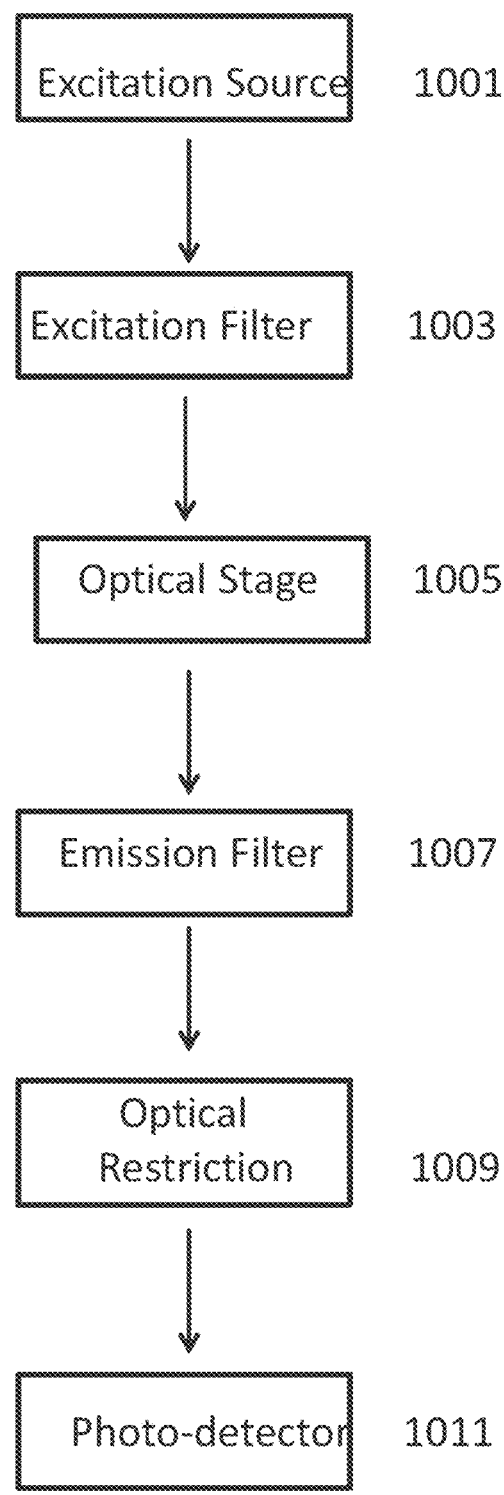
FIG. 91 shows a detailed arrangement of FIG. 90.

Hence, the detector may further comprise a pinhole (e.g. optical restriction). In some instances, the pinhole reduces the spatial extent of the excitation light source. In some instances, the pinhole allows the excitation light source to only illuminate one droplet (partition) in the optical stage at a given point in time. In some instances, the pinhole allows one droplet (partition) to be measured An exemplary diagram of a detector comprising an optical restriction is illustrated in FIG. 90. The detector comprises a light source (the "excitation" source) 901 to illuminate droplets (partitions) moving through an optical stage 903 and a photo-detector 907 to collect emitted light from the droplets (partitions) which corresponds to a fluorescent marker. FIG. 91 shows a detailed arrangement of FIG. 90. The detector comprises an excitation filter 1003 on the light source (the "excitation" source) 1001 and an emission filter between the optical stage 1007 and the photo-detector 1011. The filter for the excitation source may allow at least one wavelength range to pass through it. In some instances, the at least one wavelength that passes through the filter of the excitation source corresponds to an excitation wavelength of at least one fluorescent marker in a reaction or assay. In some instances, the filter for the photo-detector allows at least one wavelength range to pass through it. In some instances, the at least one wavelength that passes through the filter of the photo-detector corresponds to an emission wavelength of at least one fluorescent marker in a reaction or assay. In some instances, the filters improve a signal-to-noise ratio. In some instances, the signal-to-noise ratio is improved by only passing wavelengths that correspond to the reaction or assay.

Figure 92:
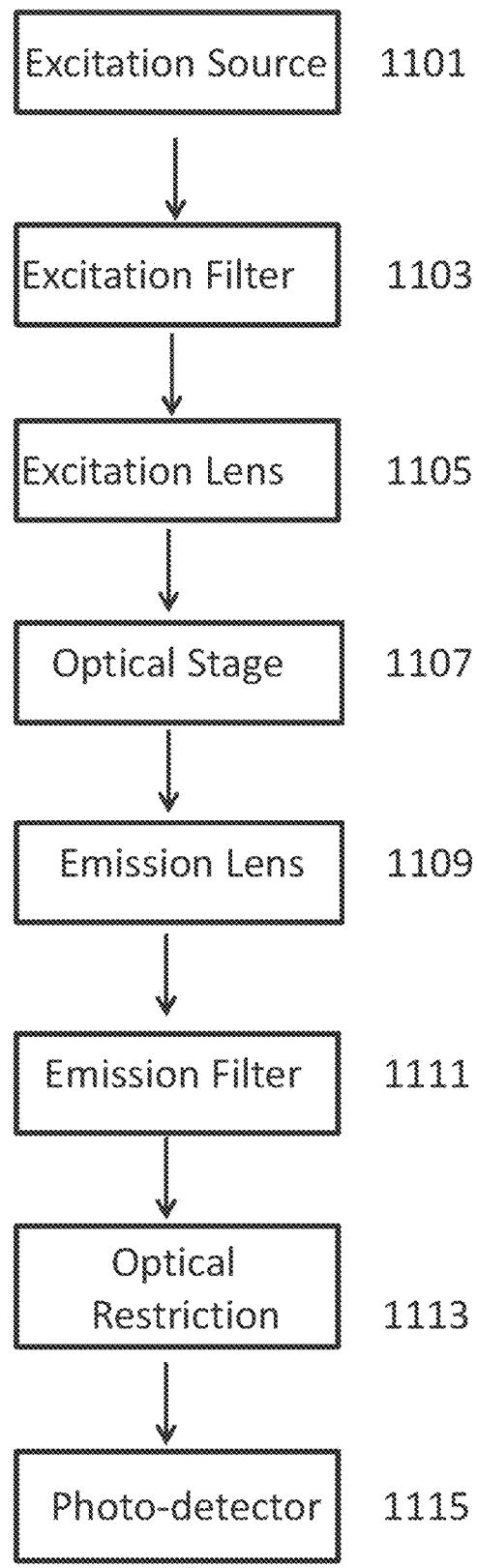
FIG. 92 shows a diagram of a detector comprising a pinhole.

An further exemplary diagram of a detector comprising an optical restriction, e.g., pinhole is illustrated in FIG. 92. Excitation lens 1105 on the excitation filter 1101 and emission lens 1109 on the emission filter 1111 allow for light to focus on the pinhole on the excitation side and collimate emission light such that light passes through the filter substantially normal to the filter surface.

The signal measured by the photodetector(s) (once demodulated, in the case of the lock-in detection system) is a time series of values correlated to the intensity or power of electromagnetic radiation incident on the photodetector. These values rise and fall as partitions pass through the system, with each partition having a relative maximum intensity value as the partition passes the portion of the conduit with highest optical collection efficiency. For many assays, it is important to assign a single value for each wavelength (or range of wavelengths) to each partition. As such, the time series data must be transformed into signal data in each wavelength (or wavelength range) as a function of partition number. This can be achieved with suitable peak finding algorithms. Peak finding can be complicated by noise in the data, which can be expressed as multiple relative maxima and minima within a specific partition. Smoothing the data can reduce the complexity of peak finding. Any suitable data smoothing technique may be used. Exemplary data smoothing techniques include convolution (1-D, 2-D, 3-D) with an averaging kernel (e.g. a Gaussian, a hat function, an impulse, a unit step function), moving averages, regression-based curve fitting to a model function, frequency-space transforms or filters with removal of high-frequency components (e.g. Butterfield filter, etc.).

Thus, systems and methods as described herein for detecting droplets (partitions) may comprise various algorithms. In some instances, the algorithms are peak-finding algorithms. The algorithms may be applied to a single wavelength channel or an accumulation of multiple wavelength channels. In some instances, a number of droplets (partitions) are known. In some instances, the number of droplets (partitions) is known because the average droplet size and total injection volume size is known. By counting the droplets (partitions), a sample may be delineated by the total droplet (partition) number reaching some minimum number of droplets (partitions). In some instances, samples with deviated distributions are identified.

In some instances, groups of droplets (partitions) are detected by measuring the number of distinct peaks with signal intensities above a baseline signal intensities, assigning the peaks to individual droplets (partitions), and counting the total number of droplets (partitions) observed in a time period. In some instances, by knowing a volumetric flow rate and injection volume, the group of droplets (partitions) comprises a minimum time period following detection of a first signal above the minimum threshold. A second group of droplets (partitions) may be determined by seeing a second signal above a minimum threshold.

In a system that includes an injector, discrete packets of samples can be injected into the system and individually partitioned into partitions. It can be important to be able to discriminate partitions that belong to a first sample from partitions that belong to a second sample. This can be done by, e.g., using intensity measurements from the photodetectors. For example, if a spacing fluid (e.g. a silicone-based or mineral oil) is added between injections of samples to be quantified, measurements made on the spacing fluid can provide information about where a first sample ends and a second sample begins. In certain embodiments, the spacing fluid does not contain a fluorophore capable of being excited by the illumination sources in the detector, the photodetectors should measure a relatively low intensity while that spacing fluid is moving through the detector. A period of continuous low intensity indicates a boundary between the first sample and the second sample. In certain embodiments, at least one dye excitable by the illumination sources in the detector is added to the spacing fluid. If the emission frequency for this dye overlaps with the emission frequency for dyes related to probes for analytes in the system, an extended period of high intensity for that dye (or dyes) indicates a boundary between the first sample and the second sample. If the spacing fluid is incapable of forming stabilized partitions near the size of the aqueous partitions in the continuous phase, this extended period should be much longer than the period of increased intensity representing a partition. Alternately, if the fluorophore in the spacing fluid has an emission band that does not substantially overlap (in wavelength) with the emission range of the other dyes in the aqueous phase, detection of a signal in this wavelength band will be enough to determine that a sample boundary has been reached. By choosing combinations of fluorophores (or the absence of any excitable fluorophores), samples can be labeled by the spacing fluid. For example, if two spacing fluids are available for injection, one without a fluorophore and one with a fluorophore, there are three combinations of labels that can be used to discriminate the samples arriving at the detector from each other. By alternating these spacing fluids, a problem in injection can be detected if two equivalent labels are detected in immediate series. If three spacing fluids are available for injection, one each with a different fluorophore (or possibly one without), seven labels are available if more than one spacing fluid may be injected between each sample. Alternatively or additionally, there can be just use one spacing fluid between each packet. Since there will be a spacing fluid before and after each packet, the data from both can be used to barcode the sample. For example, if 4 dyes are used with a 4-color detector, it is possible to barcode 256 samples with binary intensity and 6561 samples with trinary intensity. If 3 dyes are used with a 3-color detector it is possible to barcode 64 samples with binary intensity and 726 samples with trinary intensity. Alternatively or additionally, the volume of dyes (translated to a length of a high signal at the detector) can provide additional discrete states, expanding the number of unique states. Using the data from both increases sample injection speed since only one spacing fluid is needed. Suitable dyes and spacing fluid could be contained, e.g., in a consumable plate, e.g., in a second plate holder and the system can be designed, e.g., to include or not include it.

Thus, systems and methods as described herein may be used to detect groups of droplets (partitions). In some instances, the groups of droplets (partitions) represent different injections of dispersed phases (e.g. sample assays). In some instances, a first group of droplets (partitions) is distinguished from a second group of droplets (partitions) by the sequence of injection. For example, a purge fluid (spacer fluid) can be injected into the microfluidic path or channel between dispersed phases. In some instances, the purge fluid (spacer fluid) does not comprise fluorescent markers of the assay or reaction. The first group of droplets (partitions) may be distinguished from the second group of droplets (partitions) due to the purge fluid (spacer fluid) that is injected between the first group of droplets (partitions) and the second group of droplets (partitions) not emitting an optical signal above a threshold level within a specified wavelength range.

In some instances, groups of droplets (partitions) are detected using a fluorescent marker that is excited and/or emits light at a different wavelength than fluorescent markers in a dispersed phase. The fluorescent market may be miscible with the continuous phase but immiscible with the dispersed phase. In some instances, detection of the fluorescent wavelength at the different wavelength than that emitted by fluorescent markers in a dispersed phase indicates that no droplets (partitions) of the dispersed phase are passing through the detector. In some instances, a fluorescent marker is added to the purge fluid and/or separation (spacer) fluid between the dispersed phases. In some instances, the fluorescent marker is miscible with the purge fluid and/or separation fluid and immiscible with the dispersed phase. In some instances, the fluorescent marker is used to detect concentration of species in the dispersed phase.

In some instances, groups of droplets (partitions) are detected using a fluorescent marker that is emitted at a similar wavelength than a dispersed phase. In some instances, the fluorescent marker with an emission wavelength similar to the wavelength of the disperse phase is used to determine concentration of species in the dispersed phase. For example, the florescent marker is added to a purge fluid and/or separation fluid at a concentration resulting in an optical signal higher than the optical signal of droplets (partitions) of the dispersed phase. In some instances, the optical signal of the fluorescent marker is at least or about 0.5×, 1.0×, 1.5×, 2.0×, 2.5×, 3.0×, 3.5×, 4.0×, 4.5×, 5.0×, 5.5×, 6.0×, 6.5×, 7.0×, 7.5×, 8.0×, 8.5×, 9.0×, 9.5×, or 10× higher than the optical signal of the droplets (partitions) of the dispersed phase. In some instances, droplets (partitions) are distinguished from the purge fluid and/or separation fluid based on the difference in optical signal. In some instances, a number of optical signals of the purge fluid and/or separation fluid are detected between dispersed phases.

Partitions arriving at the detector may be measured as they enter the interrogation region. Due to fluidic restrictions, these partitions may be very close together. In this situation, signals will not follow a movement from baseline up to peak value for partitions, because for almost the entire time measurements are taken, partitions will be at the focal point in the system. Instead, there will only be a small break between partitions where the signal will be reduced. In this situation, the magnitude of the signal reduction will indicate whether the partition was a "positive" or a "negative" partition, and peak-finding methods may be used that either find "valleys" in the signal or operate on the inverse of the signal.

Alternatively, it may be desirable to separate partitions out by adding continuous phase to the system and/or by narrowing the conduit through which partitions flow. This can be performed ahead of the detector in a number of ways. In certain embodiments, another conduit may join the main flow conduit and add fluid, e.g., continuous phase, around the partitions, separating them. In certain embodiments, these conduits are part of a microfluidic device. The conduits can be machined out of a first substrate using an appropriate method (e.g. milling or other suitable method) and joined to a second substrate that contains at least one inlet port and at least one outlet port. The first and second substrate may be composed of one or more of a variety of materials, including but not limited to glass, silicon, or one or more polymers. In certain embodiments, the polymers comprise a fluoropolymer and the continuous phase comprises a fluorinated oil. In another embodiment, the first or second substrate (or both) are composed of glass coated with a coating comprising a fluoropolymer. One method of joining the first and the second substrate so that leaks do not occur is to form a chemical bond. In the case that the first and second substrate are fluoropolymers, a bonding method may comprise a step that removes at least some of the fluorine from the surface of the fluoropolymers, thus allowing a chemical bond to be formed. Another method of joining the first and second substrate together includes machining a surface of the first or second substrate such that only a small relief of the first or second substrate is available to contact the opposing substrate. A leak-resistant seal can be created by applying mechanical force to connect the first and second substrate together, that mechanical force creating pressure at the interface between the first and the second substrate. Another method of producing a leak-resistant seal is to use an elastomeric sealing material (e.g. an o-ring) to create a seal between the first and the second substrate. While this seal may not allow perfect contact between the first and the second substrate, if the effective space between the substrates is small enough and the substrates have a lower affinity for the dispersed phase (i.e. the partitions) than the continuous phase, substantially no dispersed phase will be able to flow through the space between the substrates and "short-circuit" the conduits.

In certain embodiments, conduits in the microfluidic device can be machined into a single substrate. One example of this is to drill coplanar conduits of cylindrical or substantially cylindrical cross-section into the substrate. These conduits can meet in a t- or cross-arrangement, or in any other suitable geometric relationship. In certain embodiments, the exit conduit may not be co-planar to the at least one inlet conduit.

In certain embodiments, continuous phase added to the system, e.g., partition spacing oil, is collected by removing, e.g., siphoning, excess oil after partition formation and reintroducing that partition oil for spacing purposes just before detection. See description elsewhere herein Any suitable method may be used for removing and/or reintroducing continuous phase. In certain embodiments, a small pored substrate is placed inline after the partition splitting junction. The pores are substantially small enough that a partition will not enter the oil siphon line and continue down the conduit, e.g., to a reactor such as a thermocycler. That continuous phase, e.g., oil, siphon line is then reintroduced in the separation system to provide a separation between each partition for detection. This evacuation and reintroduction of the separation continuous phase, e.g., oil, between partitions reduces the partition velocity during reaction, e.g., thermocycling, increasing the partition stability and reducing the tubing length required in the reactor, e.g., thermocycler.

Additionally or alternatively, continuous phase, e.g., partition oil, may be introduced before detection and then removed, e.g., siphoned, just after detection. This removed, e.g., siphoned continuous phase, e.g., oil may be transported to waste and/or recycled into a spacing continuous phase, e.g., oil, vessel for continuous partition separation.

Thus, in some instances, a microfluidic chip may be used to separate the droplets. The droplets (partitions) may then leave the microfluidic chip and enter a microfluidic tube that serves as the optical stage. Connections between the microfluidic chip and the microfluidic tube or channel or connections between the microfluidic chip and the optical stage tube may be made so that there are few or no dead flow regions for droplets. In some instances, droplets (partitions) are separated on a chip with either a t-junction or a v-junction (see below for v-junction embodiments). In some instances, a constricted region is continuous from a tubing interface to a chip. In some instances, the tube forms the optical stage. Thus, in some instances, the droplets (partitions) are separated from each other axially as they pass through the optical stage. In some instances, the droplets (partitions) are separated by addition of a continuous phase between each droplet (partition). In some instances, the continuous phase comprises a surfactant. In some instances, the continuous phase does not comprise a surfactant. Exemplary surfactants include, but are not limited to, a fluorocarbon, a hydrocarbon, a silicone, or an oil.

Additionally or alternatively, partition separation is achieved by reduction in the conduit dimensions; this alone can achieve greater separation of partitions, or it can be used in conjunction with a system that adds separation fluid, e.g., continuous phase. Since a conduit dimension reduction results in a volumetric reduction and there is a minimum amount of interstitial continuous phase, e.g., oil, between each partition, the volume reduction results in an increase in the partition-to-partition distance in the confined conduits. In certain embodiments, these conduits are constructed in an optically transparent substrate. In certain embodiments, partitions enter the constricted conduit, enter a partition imaging chamber sized to fit exactly or substantially exactly one partition, and then exit the chamber in a second constricted conduit. This allows for a single partition to be interrogated by the optical system while maximizing the spacing between each consecutive partition before and after the imaging chamber. See, e.g., FIG. 65. This partition imaging chamber can be fabricated in any suitable material, for example, fabricated in glass substrate coated with a fluorophilic surface chemistry.

Partitions arriving at the detector may be measured as they enter the interrogation region. Due to fluidic restrictions, these partitions may be very close together. In this situation, signals will not follow a movement from baseline up to peak value for partitions, because for almost the entire time measurements are taken, partitions will be at the focal point in the system. Instead, there will only be a small break between partitions where the signal will be reduced. In this situation, the magnitude of the signal reduction will indicate whether the partition was a "positive" or a "negative" partition, and peak-finding methods may be used that either find "valleys" in the signal or operate on the inverse of the signal Thus, systems and methods provided herein can achieve a separation of partitions of dispersed phase flowing in continuous phase prior to detection, where prior to separation, the average distance between partitions of dispersed phase in the continuous phase is a, and after separation, the average distance between partitions is b, where b>a. See, e.g., FIG. 51 for one way that a and b can be measured, e.g., as distance between geometric centers of partitions, such as distance between centers of spheres. It will be appreciated that in certain cases partitions alter geometry in going from an area before separation to an area after separation; for example, in certain embodiments separation is achieved by narrowing the conduit through which partitions flow to a cross-sectional area equal to or less than the average cross-sectional area of the partitions, and partitions may alter geometry from spherical to elongated. In such a case, a or b may be determined for what the distance would be if both partitions were spherical, so that, e.g., elongation of partitions does not in itself increase the measure but rather actual spacing between partitions increases the measure. In certain embodiments, b is at least 102, 105, 110, 125, 150, 175, 200, 225, or 300% of a, and/or b is at most 105, 110, 125, 150, 175, 200, 225, 300 or 400% of a.

Figure 52:
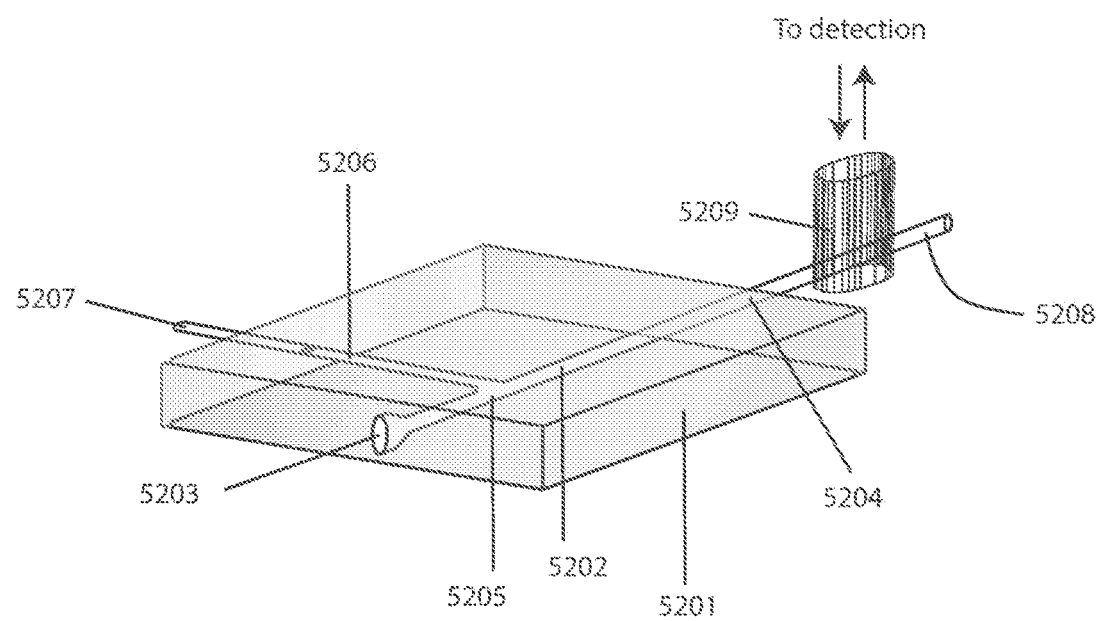
FIG. 52 shows a T-junction chip-based separator.

FIG. 52 (t-junction chip-based separator). An embodiment of a system for separating flowing dispersed phase partitions is shown in FIG. 52. The system comprises a substrate 5201 that comprises a main channel 5202, an inlet to the main channel 5203, and outlet to the main channel 5204, a branch channel 5206, and an inlet to the branch channel 5207 where the branch channel intersects the main channel within the substrate. A first continuous phase and partitions of dispersed phase enter through inlet 5203, while a second continuous phase is added at inlet 5207. In certain embodiments, the first continuous phase and second continuous phase have the same composition. In certain embodiments, the first continuous phase comprises an oil and a surfactant, while the second continuous phase does not comprise more than 5, 4, 3, 2, 1.5, 1.2, 1.1, 1.0, 0.9, 0.8, 0.7, 0.5, or 0.2% surfactant, e.g., not more than 2% surfactant, such as not more than 1% surfactant; this may be done to, e.g., save the cost of the surfactant. Continuous phases, oils, and surfactants are described in more detail elsewhere herein. The substrate 5201 may be any suitable material in which small channels may be manufactured. The surfaces of the substrate 5201, in particular, surfaces which contact flow of dispersed phase, can comprise a material that has a higher affinity for the continuous phase than for the dispersed phase. In certain embodiments, the first and second continuous phase comprise fluorinated oils and the surface of the substrate 5201, in particular, surfaces which contact flow of dispersed phase, comprises a fluoropolymer. Any suitable method may be used to fabricate the system; in some cases, methods similar or identical to those discussed for partitioners may be used. In certain embodiments, at least one of the main or branch channels is formed by creating relief features in at least one planar surface of the substrate and joining that surface to a second planar surface of the substrate to create an enclosed channel or set of channels. Suitable means of creating the relief include, but are not limited to, endmilling, laser machining, etching, photolithography. In certain embodiments, at least one of the main or branch channels are formed by creating hole features in a monolith of the substrate. The hole features can be created by any suitable method, such as drilling, e.g., mechanical drilling, laser drilling, etc.

The flow of first continuous phase and dispersed phase partitions is supplemented by flow of second continuous phase at the junction of the main and branch channels 5205. The cross-sectional area of at least one of the main or branch channels may be larger, smaller, or equal to the equivalent spherical cross-sectional area of the partitions flowing through the channel. For example, in channels with circular cross-sections, the diameter of at least one of the main or branch channels may be larger, smaller, or equal to the equivalent spherical cross-sectional diameter of the partitions flowing through the channel. In certain embodiments, the cross-sectional area of the main channel at the junction 5205 is larger than the equivalent spherical cross-sectional area of the dispersed phase partitions flowing through the main channel (e.g., diameter of main channel is greater than average spherical diameter of partitions, if the cross-section of the channel is circular or nearly circular), allowing the second continuous phase to be added to the space between more than one partition at a time.

The combined flow of dispersed phase partitions, first continuous phase, and second continuous phase exits the substrate at the main channel outlet 5204, where it enters a tube 5208. The tube passes through an interrogation region 5209, where at least one property of the dispersed phase partitions is detected. The tube is at least partially transparent to electromagnetic radiation in a first wavelength range and a second wavelength range, such that electromagnetic radiation incident on the tube in the first wavelength range may pass through the tube and, e.g., excite a reporter molecule in dispersed phase partitions positioned within the interrogation region 5209, with electromagnetic radiation emitted by the molecule in the second wavelength range may pass out of the tube to be detected. In some embodiments, the tube material allows at least 20%, 30%, 40%, 50%, 60%, 70%, 80%, 90%, 99% and/or not more than 30%, 40%, 50%, 60%, 70%, 80%, 90%, 99%, or 100% of the electromagnetic radiation in the first wavelength range to pass through it and least 20%, 30%, 40%, 50%, 60%, 70%, 80%, 90%, 99% and/or not more than 30%, 40%, 50%, 60%, 70%, 80%, 90%, 99%, or 100% of the electromagnetic radiation in the second wavelength range to pass through it. The tube may be constructed of any suitable material that meets the described requirements for translucence. In certain embodiments, the surface of the tube comprises a material that has a higher affinity for the first continuous phase, the second continuous phase, or both than it has for the dispersed phase. In certain embodiments, the cross-sectional area of the interrogation region of the tube is equal to or smaller than the cross-sectional area of the dispersed phase partitions, such that the dispersed phase partitions are in single file and they occlude all or substantially all of the cross-sectional area of the channel; in embodiments in which channels have greater affinity for continuous phase than dispersed phase, a thin layer of continuous phase is in contact with the wall, so that partitions occlude all of the channel except for the continuous phase film layer. This reduces optical contributions from more than a single dispersed phase partition.

Systems and methods as described herein may allow for estimation of droplet (partition) size. In some instances, systems and methods for estimating droplet (partition) size comprise detecting light emitted by a single droplet (partition). In some instances, systems and methods for estimating droplet (partition) size relate to a cross-section of a channel of an optical stage in which the channel of the optical stage is smaller than a cross-section of the droplet (partition). In some instances, as a result of cross-section of a channel of an optical stage being smaller than a cross-section of the droplet (partition) the droplet (partition) substantially fills the channel in the optical stage.

A length of a droplet (partition) may be estimated as it passes through the optical channel. For example, when a droplet (partition) enters the optical stage and is detected by the detector, a signal of the detector will rise above a minimum threshold and will remain above a minimum threshold until the droplet (partition) passes out of the optical stage and is no longer detected by the detector. Once the droplet (partition) passes out of the optical stage is no longer detected by the detector, the signal may drop. An amount of time from the signal being above a minimum threshold and the signal dropping may be correlated to the length of the droplet (partition). In some instances, a correction is applied. In some instances, the correction is due to velocity of flow in the channel. In some instances, the correction is applied based on a length or transit time of the droplet (partition) as the droplet (partition) pass through the optical stage. In some instances, the time is used to determine a droplet (partition) size. For example, the time that the droplet (partition) passes through the optical stage is multiplied by a volumetric flow rate to determine droplet (partition) size. Other correction values may be applied in determining droplet (partition) size. In some instances, a laminar flow correction is applied.

Exemplary droplet (partition) volume measured using systems and methods as described herein include, but are not limited to, at least or about 5 micron (um), 10 um, 20 um, 30 um, 40 um, 50 um, 60 um, 70 um, 80 um, 90 um, 100 um, 120 um, 140 um, 160 um, 180 um, 200 um, or more than 200 um. In some instances, droplet (partition) sizes are at least or about 200 um, 300 um, 400 um, 500 um, 600 um, 700 um, 800 um, 900 um, 1000 um, or more than 1000 um.

Connections between the droplet (partition) flow channel and the microfluidic channel or tube can result in little or no dead volume. An exemplary connection is a press-fit or compression connection as described herein. The droplet (partition) flow channel can narrow to the optical stage diameter at a t-junction with the continuous phase channel. The narrowed droplet flow channel extends beyond the t-junction to provide sufficient space for the optical excitation and detection system to be implemented. The distance between droplets (partitions) following the t-junction is greater than the distance between the droplets prior to entering the t-junction.

Figure 53A:
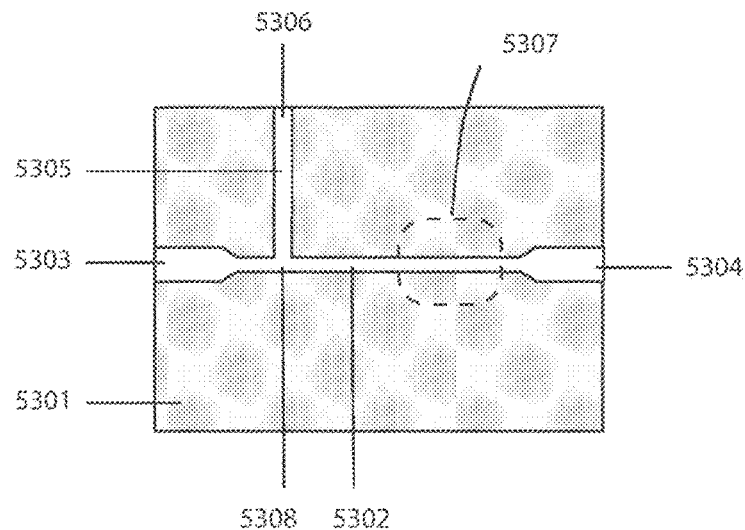
FIGS. 53A and 53B show two views of an on-chip interrogation region.
Figure 53B:
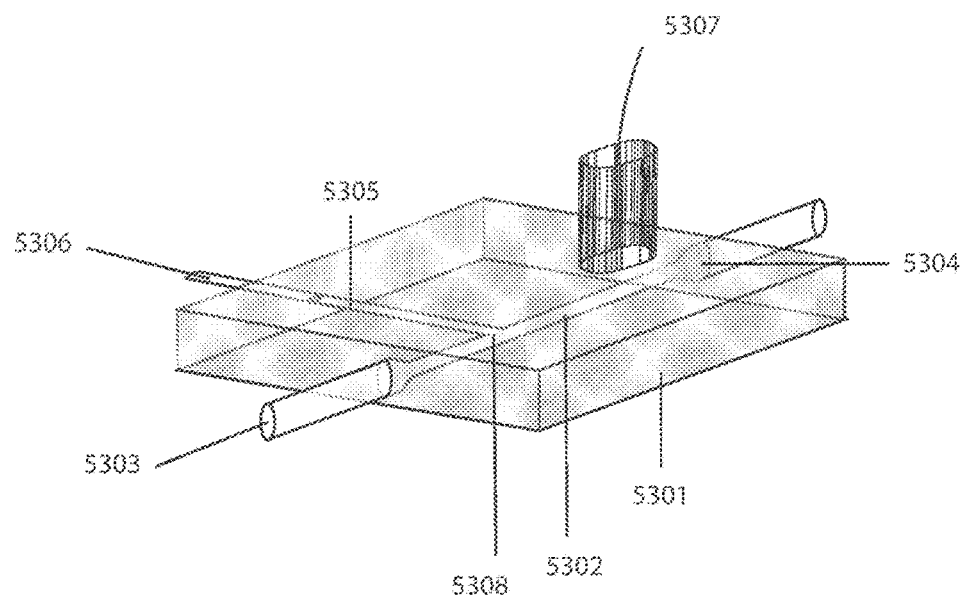

FIGS. 53A and 53B—On-chip interrogation region FIGS. 53A and 52B show different views of another embodiment of a dispersed phase partition separator and an interrogation region. The embodiment comprises a substrate 5301, a main channel 5302 comprising an inlet 5303 and an outlet 5304, a branch channel 5305 comprising an inlet 5306 and an interrogation region 5307. A first continuous phase and partitions of a dispersed phase enter the main channel 5302 through the inlet 5303 and a second continuous phase enters the branch channel 5306. The main channel and the branch channel meet at a junction 5308, where the addition of second continuous phase increases the average spacing between partitions of the dispersed phase in the channel. The dispersed phase partitions travel through the interrogation region 5307, where a property of the dispersed phase partitions is detected. In some embodiments, electromagnetic radiation of a first wavelength of light impinges on the main channel 5302 in the interrogation region 5307 and excites a molecule in the dispersed phase partitions, which emits electromagnetic radiation of a second wavelength of electromagnetic radiation. In some embodiments, the material and/or geometry of the interrogation region allows at least 20%, 30%, 40%, 50%, 60%, 70%, 80%, 90%, 99% and/or not more than 30%, 40%, 50%, 60%, 70%, 80%, 90%, 99%, or 100% of the incident electromagnetic radiation in the first wavelength range to pass through it and least 20%, 30%, 40%, 50%, 60%, 70%, 80%, 90%, 99% and/or not more than 30%, 40%, 50%, 60%, 70%, 80%, 90%, 99%, or 100% of the emitted electromagnetic radiation in the second wavelength range to pass through it. In certain embodiments, the cross-sectional area of the interrogation region 5307 of the main channel 5302 is equal to or smaller than the cross-sectional area of the dispersed phase partitions, such that the dispersed phase partitions are in single file and they occlude all or substantially all of the cross-sectional area of the channel; in embodiments in which channels have greater affinity for continuous phase than dispersed phase, a thin layer of continuous phase is in contact with the wall, so that partitions occlude all of the channel except for the thin continuous phase film layer. This reduces optical contributions from more than a single dispersed phase partition. Additionally, partitions that have an equivalent spherical cross-sectional area substantially the same or greater than the cross-sectional area of the main channel 5302 in the interrogation region 5307 reduce variability in detected optical signals due to dispersed phase position within the channel. Partitions with an equivalent spherical cross-sectional area greater than or equal to the cross-sectional area of the main channel in the interrogation region 5307 will become distorted so as to be longitudinally distributed along the channel. By measuring an optical property of a dispersed phase partition from when it enters the interrogation region 5307 to when it leaves the interrogation region 5307 and combining it with other information about the dispersed phase partition flow, a size property of the dispersed phase partition may be calculated. In certain embodiments, the cross-sectional area of the main channel at the junction 5308 is larger than the equivalent spherical cross-sectional area of the dispersed phase partitions (e.g., diameter of main channel is greater than average spherical diameter of partitions, if the cross-section of the channel is circular or nearly circular), allowing second continuous phase to be added between more than one pair of dispersed phase partitions simultaneously. In certain embodiments, the main channel 5307 reduces in cross-sectional area (e.g., reduces in diameter if the channel has a circular or nearly circular cross-section) after the junction 5308 before entering the interrogation region 5307 so as to reduce the cross-sectional area of the main channel 5302 in the interrogation region 5307 to a value equal to or below the equivalent spherical cross-sectional area of the dispersed phase partitions. In certain embodiments, the cross-sectional area of the main channel 5302 in the junction 5308 is less than or equal to the equivalent cross-sectional area of the dispersed phase partitions and remains so through the interrogation region 5307. The first continuous phase, second continuous phase, and partitions of dispersed phase exit the main channel 5302 at the outlet 5304. The cross-sectional area of the main channel 5304 beyond the optical stage may increase beyond the cross-sectional area of the main channel 5302 in the interrogation region 5307, to, e.g., facilitate fluidic connections. The cross-sectional profile of the main channel 5302 or branch channel 5306 may be any suitable cross-sectional profile. In some embodiments, one or more of the channels have a rectangular, semi-circular, or circular cross-sectional profile.

In certain embodiments, the first continuous phase and the second continuous phase have the same composition. The first continuous phase, the second continuous phase, or both can comprise a fluorinated oil. In certain embodiments, the first continuous phase additionally comprises a surfactant to stabilize dispersed phase partitions in the first continuous phase. In certain embodiments, the first continuous phase comprises an oil and a surfactant, while the second continuous phase does not comprise more than 5, 4, 3, 2, 1.5, 1.2, 1.1, 1.0, 0.9, 0.8, 0.7, 0.5, or 0.2% surfactant, e.g., not more than 2%, such as 1% surfactant; this may be done to, e.g., save the cost of the surfactant. Continuous phases, oils, and surfactants are described in more detail elsewhere herein. In some embodiments, the surface of the substrate 5301, in particular, surfaces which contact flow of dispersed phase, comprises a material that has a higher affinity for at least one of the continuous phases than for the dispersed phase, reducing the likelihood that dispersed phase will wet the surfaces of the substrate 5301. In a preferred embodiment, the entire substrate 5301 comprises a material that has a higher affinity for at least one of the continuous phases than for the dispersed phase. In a certain embodiments, the surface of or entire substrate 5301 comprises a fluoropolymer. The channels 5301 and 5306 may be formed in the substrate by any suitable method, as described elsewhere herein.

Thus, in some instances, the droplet (partition) separation and an optical stage are combined. The droplet (partition) separation and optical stage may be on the same microfluidic chip. The emulsion stream coming from the rest of the system, e.g. a reactor such as a thermal cycler may enter a first channel on the chip. A stream of continuous phase may enter a second channel on the chip. In some instances, the two channels both constrict and then meet at a t-junction.

The combined streams flow through an extended region at the same constricted size, a portion of which may comprise the optical stage. The constricted channel may then expand to a larger diameter and leaves the chip through, e.g., a press-fit connection. In some instances, the first channel and the second channel do not constrict before meeting in a t-junction. In some instances, a constriction occurs beyond the exit of the t-junction. In some instances, the constriction is smaller than the characteristic size of the droplets so that a droplet (partition) substantially fills the channel in the optical stage. A portion of the constricted channel may form the optical stage. In some instances, the channel then expands to a larger size so that it substantially matches the cross-section of an exit tube. In some instances, the junction is a "v-junction." In some instances, the streams are combined at an angle substantially less than 90 degrees, for examples, at least or about 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, or 80 degrees In some instances, a reverse-v junction is used with a tubular optical stage. In some instances, an exit of the reverse-v junction is tubular and continues to form an optical stage of the detector.

Figure 54:
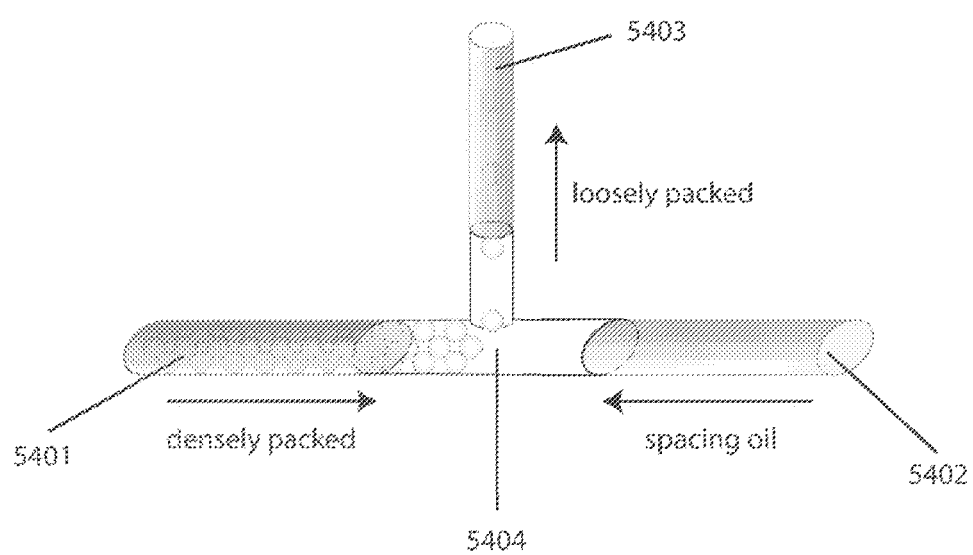
FIG. 54 shows a collision-style separator.

FIG. 54—Collision-style separator FIG. 54 shows a system of channels for increasing the spacing between partitions of dispersed phase. The system comprises a first inlet channel 5401 for a flow comprising a first continuous phase and partitions of at least one dispersed phase, a second inlet channel 5402 for a flow comprising a second continuous phase, and an outlet channel 5403 where the combined flow of the first inlet channel 5401 and second inlet channel 5402 exits. The first inlet channel 5401 and second inlet channel 5402 meet at a junction 5404, where their respective flows are combined into the flow of channel 5403. The channels 5401 and 5402 can have axes that are offset by an angle no greater than 45 degrees; in certain embodiments, the channels 5401 and 5402 are co-axial or substantially co-axial At the junction 5404, the second continuous phase is added between partitions of the first dispersed phase such that the spacing between the partitions of the dispersed phase is, on average, increased. The cross-sectional area of the first inlet channel 5401 and second inlet channel 5402 can be the same or substantially the same, an arrangement that may, e.g., simplify manufacturing. For example, the channels may be created in a substrate by a single set of machining operations. In certain embodiments, the cross-sectional area of the first inlet channel 5401 at a point just ahead of the junction region 5404 can be, e.g., equal to or less than the equivalent spherical cross-sectional area of the dispersed phase partitions such that the dispersed phase partitions enter the junction region 5404 in single file or substantially in single file. In such an embodiment, the second continuous phase may be added between the partitions of the first dispersed phase in a more controlled manner, making the spacing between partitions of the first dispersed phase more uniform. In certain embodiments, the outlet channel 5043 has a cross-sectional area equal to or less than the equivalent cross-sectional area of the dispersed phase partitions so as to only allow a single partition into the outlet channel 5403 at any one time. This may make the spacing between the dispersed phase partitions more uniform. The cross-sectional area of the outlet channel 5403 may increase to a size larger than the equivalent cross-sectional area of the dispersed phase partitions at some distance beyond the junction 5404. In some embodiments, this distance may be at least 1×, 2×, 3×, 4×, 5×, or 10×, and/or not more than 2×, 3×, 4×, 5×, 10×, or 15× the equivalent circular diameter of the cross-sectional area of the outlet channel 5403 at the junction 5404.

The embodiment shown in FIG. 54 may be constructed by any suitable method. In certain embodiments, the first inlet channel 5401, second inlet channel 5402, and outlet channel 5403 may comprise tubing. In certain embodiments, the first inlet channel 5401 and second inlet channel 5402 may be formed in a substrate and the outlet channel 5403 may comprise a tube that is connected to a hole in the substrate that intersects the first inlet channel 5401 and second inlet channel 5402 at the junction 5404. In certain embodiments, the first inlet channel 5401, second inlet channel 5402, and outlet channel 5403 are all formed in a substrate. Any suitable method or combination of methods for forming channels in substrates may be used including, but not limited to, mechanical drilling, end-milling, laser-drilling, wire EDM, chemical etching, photolithography. In preferred embodiments, the surfaces of the tubing and/or substrates, in particular, surfaces which contact flow of dispersed phase, comprise materials that have a higher affinity for at least one of the continuous phases than for the partitions of the dispersed phase so as to, e.g., prevent wetting of the surfaces of the tube and/or substrate by the dispersed phase, which could lead to cross contamination or coalescence of the dispersed phase partitions.

Figure 55:
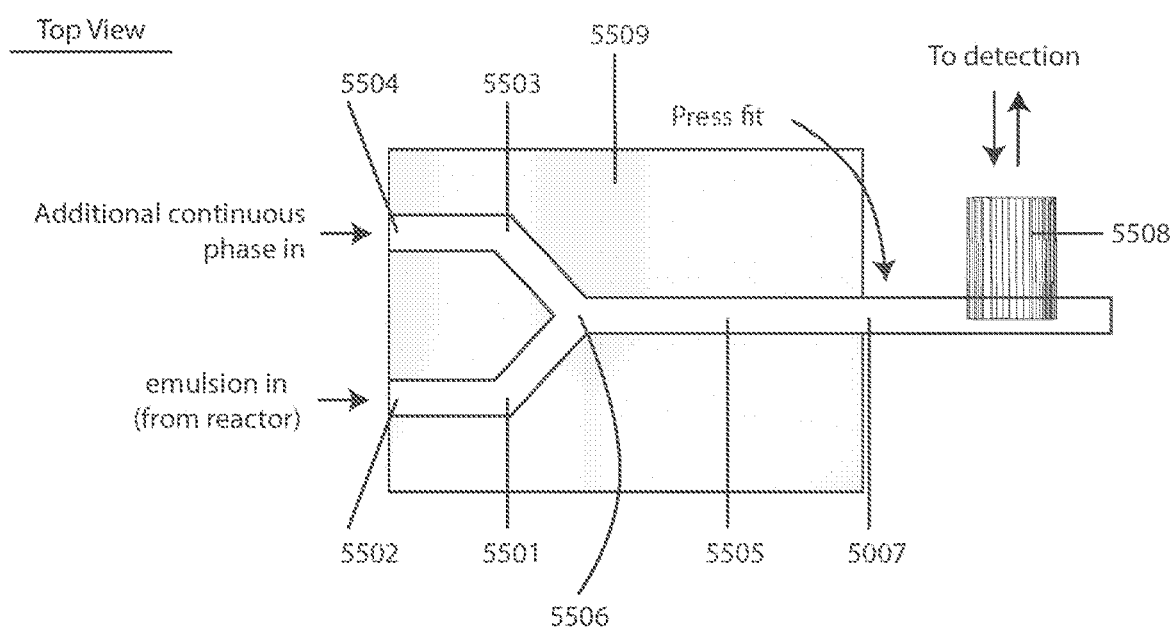
FIG. 55 shows a Y-style separator with off-chip detection.

FIG. 55—Y-style separator with off-chip detection FIG. 55 shows another arrangement for increasing the average spacing between partitions of dispersed phase, where the separation occurs in channels in a substrate and the interrogation region is in a tube. The arrangement comprises a first inlet channel 5501 with an inlet 5502, a second inlet channel 5503 with an inlet 5504, an outlet channel 5505, a junction 5506 where the first inlet channel 5501 and second inlet channel 5503 meet and exit in the outlet channel 5505, an outlet tube 5507, an interrogation region 5508, and a substrate 5509 in which the first inlet channel 5501, the second inlet channel 5503, and the outlet channel 5505 are formed. A first continuous phase and partitions of at least one dispersed phase enter the first inlet channel 5501 through the inlet 5502, and a second continuous phase enters the second inlet channel 5503 in the inlet 5504. The flows in the first inlet channel 5501 and the second inlet channel 5503 combine at the junction 5506, where the second continuous phase is added so as to increase the average spacing of partitions of dispersed phase. The angle at which the first inlet channel 5501 and the second inlet channel 5503 meet at the junction 5506 may vary. In certain embodiments, the first inlet channel 5501 and second inlet channel 5503 may meet at a relatively small angle between their respective axes, as in FIG. 54, such as an angle of less than 90, 80, 70, 60, or 50 degrees. In certain embodiments, the first inlet channel 5501 and second inlet channel 5502 may meet such that they are nearly or completely orthogonal, as in FIG. 52. In certain embodiments, the cross-sectional area of the outlet channel 5505 may be equal to or less than the equivalent cross-sectional area of the partitions of the dispersed phase at the junction 5506, and the cross-sectional area of the outlet channel 5505 remains equal to or less than the equivalent cross-sectional area of the partitions of the dispersed phase through the interrogation region 5508 so that the partitions of the dispersed phase do not substantially vary in position when projected onto the cross-section of the tube 5507. In other embodiments, the cross-sectional area of the outlet channel 5505 is larger than the equivalent cross-sectional area of the partitions of the dispersed phase at the junction 5506, but the cross-sectional area of the outlet channel 5505 subsequently decreases before entering the tube 5507 to a value equal to or less than the equivalent cross-sectional area of the partitions of the dispersed phase. In such embodiments, the second continuous phase can be simultaneously added around more than one partition of the dispersed phase, but the partitions of the dispersed phase would still substantially consume the entire cross-section of the tube 5507 at the interrogation region 5508, reducing variance in optical signal for partitions of dispersed phase with identical compositions. Such embodiments may reduce the pressure drop through outlet channel 5505 by only restricting the cross-sectional area near the interrogation region 5508. In certain embodiments, the outlet channel 5505 at the junction 5506 has a cross-sectional area that is at least 1×, 1.05×, 1.1×, 1.15×, 1.25×, 1.5× and/or not more than 1.05×, 1.1×, 1.15×, 1.25×, 1.5×, or 1.75× the equivalent spherical cross-sectional area of the dispersed phase partitions, or any value in between these values. In these embodiments, the outlet channel 5505 reduces to a cross-sectional area that is not more than 1×, 0.95×, 0.9×, 0.85×, 0.8×, 0.75×, 0.7×, 0.6×, 0.5×, or 0.4×, and/or at least 0.95×, 0.9×, 0.85×, 0.8×, 0.75×, 0.7×, 0.6×, 0.5×, 0.4×, or 0.3×, the equivalent cross-section area of the dispersed phase partitions at a point before the transition to the tube 5507. In some embodiments, the cross-sectional area of the tube 5507 is equal to or greater than the diameter of the outlet channel 5505 at the point where the tube 5507 and outlet channel 5505 meet so as to reduce break-up of partitions of dispersed phase when passing from the outlet channel 5505 to the tube 5507. While the cross-sectional area of the tube 5507 may be larger than the cross-sectional area of the outlet channel 5505 at the point where the channel and tube meet, it is preferred to limit the extent to which the cross-sectional areas differ so as to limit the formation of recirculation and dead zones in the tube 5507, which can broaden the residence time distribution of dispersed phase partitions in the system. In some embodiments, the cross-sectional area of the tube 5507 is at least 0%, 1%, 2%, 5%, 10%, 15%, 25%, 50%, or 100% larger and/or not more than 1%, 2%, 5%, 10%, 15%, 25%, 50%, 100%, or 150% larger than the cross-sectional area of the outlet channel 5505 at the point where the outlet channel 5505 and tube 5507 meet.

The first inlet channel 5501, second inlet channel 5503, and outlet channel 5505 are formed in a substrate 5509. The channels may be formed by any suitable method or combination of methods including, but not limited to, mechanical drilling, end-milling, laser-drilling, wire EDM, chemical etching, photolithography. In preferred embodiments, the surface of the substrate 5509, in particular the surfaces that come in contact with dispersed phase, comprises a material that has a higher affinity for at least one continuous phase than for the at least one dispersed phase so as to prevent wetting of the surface of the substrate 5509 by the at least one dispersed phase. In certain embodiments, more than 50%, 60%, 70%, 80%, 90%, 95%, 98%, or 99% of the substrate 5509 comprises a material that has a higher affinity for at least one continuous phase than or the at least one dispersed phase. In such embodiments, wear of the surface has a reduced risk of exposing material that has a higher affinity for at least one dispersed phase than at least one continuous phase. In some embodiments, at least one continuous phase comprises a fluorinated oil, at least one dispersed phase comprises water, and the surface of the substrate 5509 comprises a fluoropolymer. In certain embodiments, both the first continuous phase and the second continuous phase comprise fluorinated oils.

Thus, in some instances, a first channel may comprise a flowing emulsion leaving the thermal cycler meets a second channel comprising additional continuous phase at a v-based junction. At a portion of the junction, the cross-section of the combined flow channel may be substantially reduced to a cross-section smaller than the typical cross-section of a droplet (partition) in the system. In some instances, the combined flow channel is reduced at a 90 degree angle. In some instances, the combined flow channel is reduced at a 30 degree, 45 degree, 60 degree, 90 degree, 120 degree, 150 degree, 180 degree, or 360 degree angle. The continuous phase may be directly incorporated into the flow from the thermal cycler.

Figure 51:
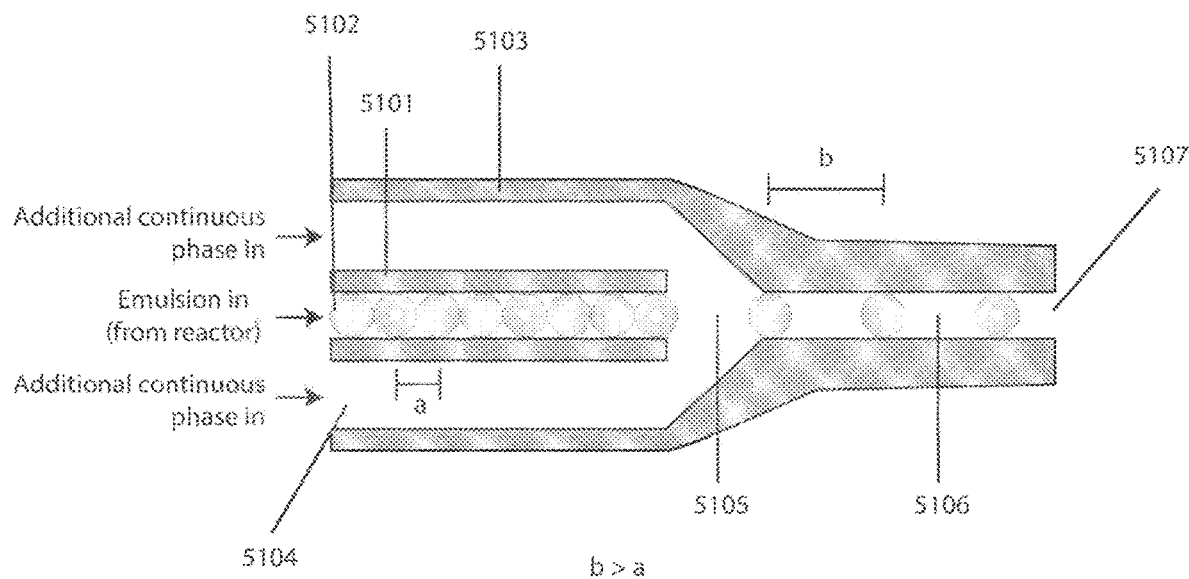
FIG. 51 shows a concentric tube separator.

FIG. 51—Tube-in-tube separator FIG. 51 shows another system for increasing the average spacing between partitions of dispersed phase. The system comprises a first inlet conduit 5101 with an inlet 5102 and a second inlet conduit 5103 with an inlet 5104, where the first inlet conduit 5101 is partially or completely surrounded by the second inlet conduit 5103. A first continuous phase and partitions of at least one dispersed phase enter the first inlet conduit 5101 at inlet 5102, and a second continuous phase enters the second inlet conduit 5103 at inlet 5104. The first continuous phase and partitions of dispersed phase exit the first inlet conduit at a junction region 5105, where they are combined with second continuous phase so as to increase the average spacing 'a' between partitions of dispersed phase in the continuous phases to a value 'b', where b>a. "a" and "b" can be, e.g., the distance between the geometric centers of adjacent partitions, or other suitable measuring point. In certain embodiments, b is at least 102, 105, 110, 125, 150, 175, 200, 225, or 300% of a, and/or b is at most 105, 110, 125, 150, 175, 200, 225, 300 or 400% of a. Additionally or alternatively, separation of partitions may be any suitable distance from one partition to adjacent partition, as described elsewhere herein. The system further comprises an outlet conduit 5106 and an outlet 5107. The outlet conduit 5106 may comprise an interrogation region for measuring an optical property of the partitions of the at least one dispersed phase. In some embodiments, the cross-sectional area of the outlet conduit 5105 is equal to or less than the equivalent spherical cross-sectional area of the partitions of the dispersed phase at the interrogation region so that the partitions of the dispersed phase occlude or substantially occlude the entire cross-sectional area of the outlet conduit.

In certain embodiments, the first inlet conduit 5101 and second inlet conduit 5103 are tubular, with the first inlet conduit 5101 substantially co-axial with the second inlet conduit 5103. Connections to the inlets 5102 and 5104 may be made in any suitable manner, such as those described for partitioners. The diameter of the first inlet conduit 5101 can be sized such that the partitions of the at least one dispersed phase are in single-file or substantially in single-file at the junction 5105. In certain embodiments, the cross-sectional area of the first inlet conduit 5101 at the junction 5105 is not more than 80%, 90%, 95%, 100%, 105%, 110%, or 120%, 125%, 150%, or 175% and/or at least 70%, 80%, 90%, 95%, 100%, 105%, 110%, or 120%, 125%, or 150% of the equivalent spherical cross-sectional area of the partitions of the at least one dispersed phase.

In other embodiments, the first inlet conduit 5101, the second inlet conduit 5103, and the outlet conduit 5106 are channels formed into a substrate. In certain embodiments, the inlets 5102 and 5104 are in fluid communication with interfaces to the substrate that are orthogonal or substantially orthogonal to the direction of flow in the first inlet conduit 5101 and second inlet conduit 5103 at the junction of the first inlet conduit 5101 and second inlet conduit 5103. In certain embodiments, the outlet conduit 5106 is co-planar or substantially co-planar with the first inlet conduit 5101 and second inlet conduit 5103. In other embodiments, the flow axis of the outlet conduit 5106 is orthogonal or substantially orthogonal to the flow axis of the first inlet conduit 5101 and the flow axis of the second inlet conduit 5103. In such embodiments, it is preferred that the direction of flow of the outlet conduit 5103 be oriented relative to gravity to use buoyant force to improve the achieved separation of the partitions of the at least one dispersed phase. For example, if at least one dispersed phase has a mass density lower than that of the first continuous phase and the second continuous phase, the direction of flow can be oriented in the direction of decreasing gravitational field strength so that the relative velocity of the partitions of the at least one dispersed phase and the continuous phases increases. The conduits may be formed in the substrate by any suitable method, as described elsewhere herein for use with substrates. In certain embodiments, the outlet conduit 5106 comprises an interrogation region. In other embodiments, another conduit interfaces to the outlet conduit 5106 at outlet 5107, and that conduit comprises an interrogation region for detecting at least one optical property of the partitions of the at least one dispersed phase.

The first inlet conduit 5101, second inlet conduit 5103, and outlet conduit 5105 may be constructed of any suitable material. In some embodiments, surfaces of the first inlet conduit 5101, second inlet conduit 5103, and outlet conduit 5105, in particular surfaces that encounter flow of dispersed phase, comprise materials that have a higher affinity for at least one continuous phase than for at least one dispersed phase so as to reduce the likelihood of wetting of the surfaces by the at least one dispersed phase. Continuous phase can be any continuous phase as described herein; in certain embodiments the continuous phase comprises a fluorinated oil, in some cases including a surfactant, such as a fluorosurfactant; fluorinated oils and fluorosurfactants are as described elsewhere herein.

Thus, an exemplary system for adding a continuous phase to separate each droplet (partition) may comprise a microfluidic channel or tube, e.g., from a reactor enters a junction where it becomes substantially concentric with a larger microfluidic tube or channel. Continuous phase may be added in the annular space between the larger microfluidic tube or channel and the smaller microfluidic tube or channel. At a point in the junction, the inner microfluidic tube or channel terminates, and the emulsion flow in that channel joins the additional continuous phase flowing in the larger microfluidic tube or channel. A converging section beyond the junction can bring the inner diameter of the droplet (partition) flow channel down to that required for the optical stage.

Figure 56A:
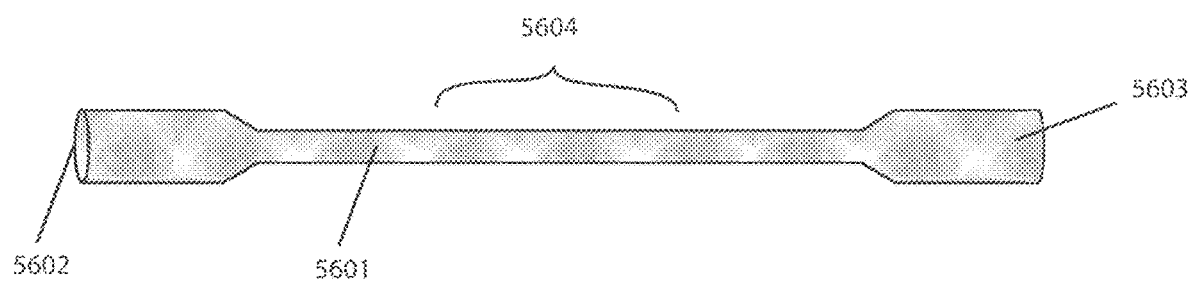
FIGS. 56A and 56B show two views of a constricted tube separator.
Figure 56B:
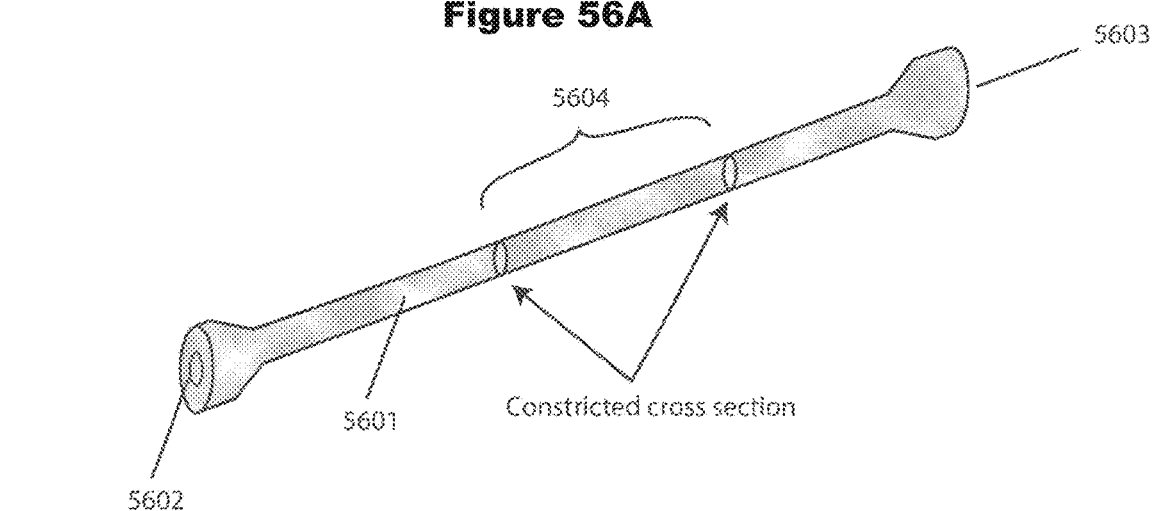

FIGS. 56A and 56B—Constricted tube separator. FIGS. 56A and 56B show different views of a system that may increase the separation between partitions of dispersed phase in a flow of a first continuous phase that does not require the addition of a volume of a second continuous phase. The system comprises a conduit 5601 that comprises an inlet 5602, an outlet 5603, and a region 5604 where the cross-sectional area of the conduit is smaller than at the inlet 5602 or the outlet 5603. At least one continuous phase and partitions of at least one dispersed phase enter the conduit at the inlet 5602. In the region 5604, the cross-sectional area is reduced to a value smaller than the equivalent spherical cross-sectional area of the at least one dispersed phase partitions, causing them to extrude longitudinally as they fill or substantially fill the cross-sectional area of the conduit. As the partitions of the at least one dispersed phase extrude, they displace fluid comprising the at least one continuous phase into the regions between the partitions of the at least one dispersed phase, increasing the distance (as measured along the conduit main axis) between the partitions of the at least one dispersed phase. In the region 5604, the cross-sectional area of the conduit may be not more than 20%, 30%, 40%, 50%, 60%, 70%, 80%, 90% or 95% and/or at least 10%, 20%, 30%, 40%, 50%, 60%, 70%, 80%, or 90% of the equivalent spherical cross-sectional area of the partitions of the dispersed phase. This increases both separation of partitions and the overall length of partitions in a manner and to a degree that can be calculated.

Figure 57A:
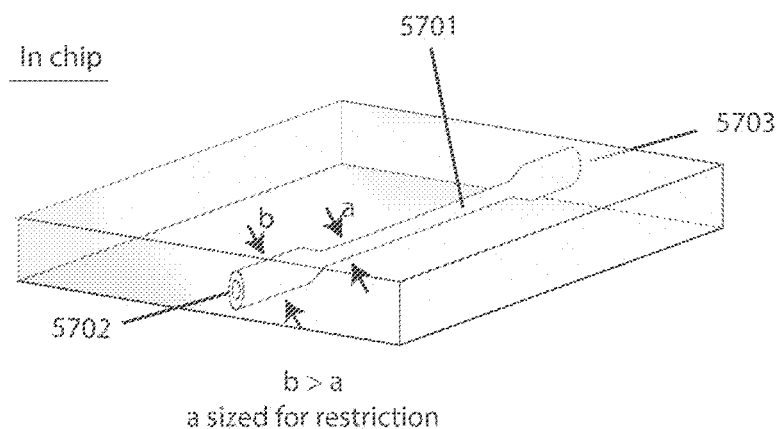
FIGS. 57A and 57B show a conduit formed in a substrate. 57A: in a chip; 57B: in a conduit.
Figure 57B:
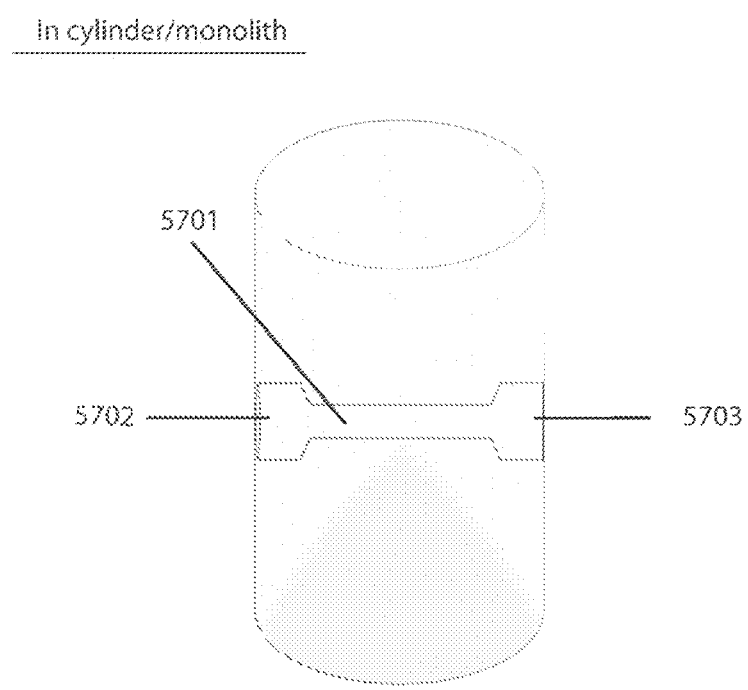

In certain embodiments, the conduit 5601 comprises the internal volume of a length of tubing. In these embodiments, the conduit 5601 may be formed in the tubing by any suitable method. In other embodiments, the conduit 5602 may be formed as a channel in a substrate. Some such embodiments are shown in FIGS. 57A and 57B. FIG. 57A shows an embodiment where the conduit 5701 is formed in a rectangular substrate. FIG. 57B shows an embodiment where the conduit 5701 is formed in a monolith, in this Figure depicted as a cylindrical monolith. The channel may be formed by any suitable method, including mechanical drilling, laser drilling, surface milling, end-milling, etching, photolithography. In certain embodiments, the surface of the conduit 5701 comprises a material that a higher affinity for the at least one continuous phase than for at least one dispersed phase, such that the likelihood that the at least one dispersed phase will wet the surface of the conduit 5701 is reduced.

Figure 58:
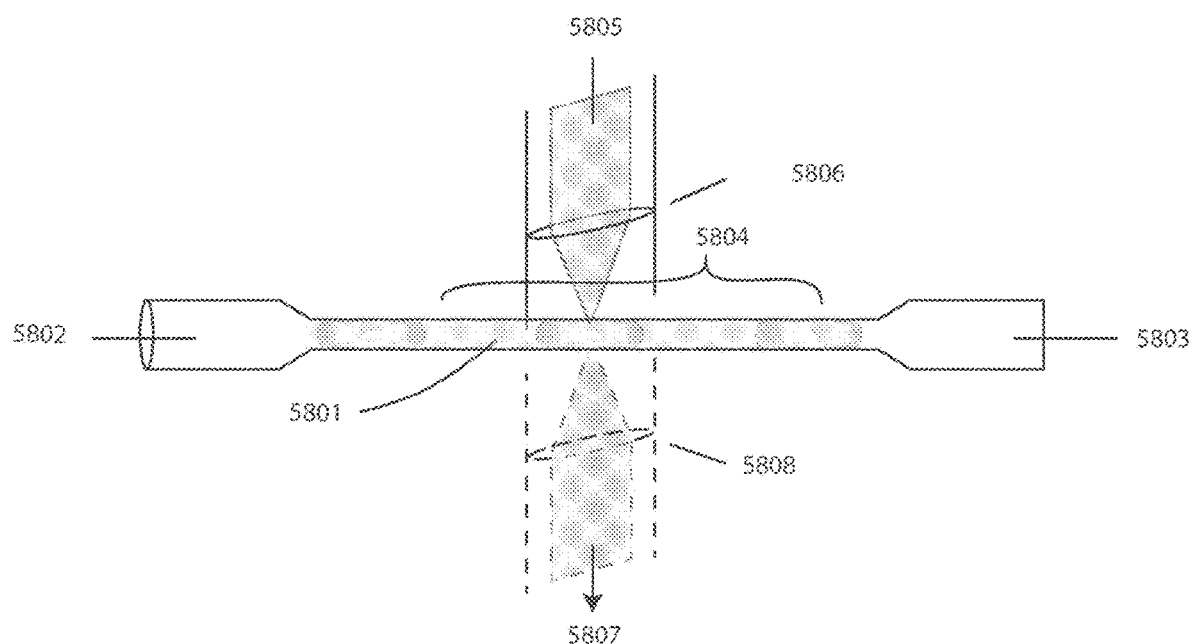
FIG. 58 shows an interrogation region.

FIG. 58—Typical interrogation region. A system for interrogating at least one optical property of partitions in a dispersed phase flowing in an emulsion with at least one continuous phase is shown in FIG. 58. The system comprises a conduit 5801, and inlet 5802, an outlet 5803, and an interrogation region 5804. In certain embodiments, the cross-sectional area of the conduit 5801 in the interrogation region 5804 is smaller than the cross-sectional area of the conduit 5801 at the inlet 5801 or the outlet 5803. For example, the cross-sectional area of the conduit 5801 in the interrogation region 5804 can be equal to or less than the equivalent spherical cross sectional area of the partitions of the dispersed phase such that the partitions of the dispersed phase fill or substantially fill the cross-sectional area of the conduit 5801. This reduces the variability of measurements of optical properties of the partitions of the dispersed phase due to variation in the position of the partitions of the dispersed phase as projected onto the cross-sectional area of the conduit 5801 in the interrogation region 5804. It will be appreciated that, as described for FIG. 56, such a narrowing both elongates partitions (if cross-sectional area of the conduit is less than that of partitions) and increases separation between partitions (because the same volume of continuous phase must fit into a smaller conduit, thus length must increase). In certain embodiments, in the region 5804, the cross-sectional area of the conduit may be not more than 20%, 30%, 40%, 50%, 60%, 70%, 80%, 90% or 95% and/or at least 10%, 20%, 30%, 40%, 50%, 60%, 70%, 80%, or 90% of the equivalent spherical cross-sectional area of the partitions of the dispersed phase. The system additionally comprises at least one excitation source 5805, one excitation lens 5806, one photodetection element 5807 and one emission lens 5808. The excitation lens 5804 has a first focal length and is positioned so that a first wavelength of electromagnetic radiation emitted by the excitation source 5805 is focused or substantially focused on the center of the conduit 5801 at a point in the interrogation region 5804. The emission lens 5804 has a second focal length and is positioned so that a second wavelength of electromagnetic radiation emitted by a first component comprising the partitions of dispersed phase is collimated as it passes in the direction of the photodetection element 5807. At least one continuous phase and partitions of dispersed phase flow into the inlet 5802 and pass into the interrogation region 5804. The first wavelength of electromagnetic radiation emitted by the excitation source 5805 is focused on the interrogation region 5804, where it may excite at least one component of one or more of the partitions of dispersed phase flowing through the interrogation region. This at least one component then emits electromagnetic radiation in the second wavelength that passes through the emission lens 5808, where it is collimated heading to the detection element 5807. Collimated electromagnetic radiation impinging on the excitation lens 5806 has a first axis parallel to the direction of collimation, and collimated electromagnetic radiation leaving the emission lens 5808 has a second axis parallel to the direction of collimation. In general, the first and second axes may have any relative angle. In certain embodiments, the first and second axis form an orthogonal or substantially orthogonal angle so that electromagnetic radiation emitted by the excitation source 5805 incident on the detection element is reduced relative to embodiments where the first and second axis are not orthogonal or substantially orthogonal. Thus, in certain embodiments, the angle between the first and second axes is between 45 degrees and 135 degrees, between 60 degrees and 120 degrees, between 75 degrees and 105 degrees, between 85 degrees and 95 degrees, or between 89 degrees and 91 degrees.

In certain embodiments, the conduit 5801 comprises the internal volume of a tube. Such embodiments have the advantage that the electromagnetic radiation impinging on the outer surface of the tube is normal to the outer surface of the tube at any position on a plane normal to the central axis of the conduit 5801, reducing the reflection of electromagnetic radiation from the outer surface of the tube. In other embodiments, the conduit 5801 comprises a channel in a substrate.

Figure 59:
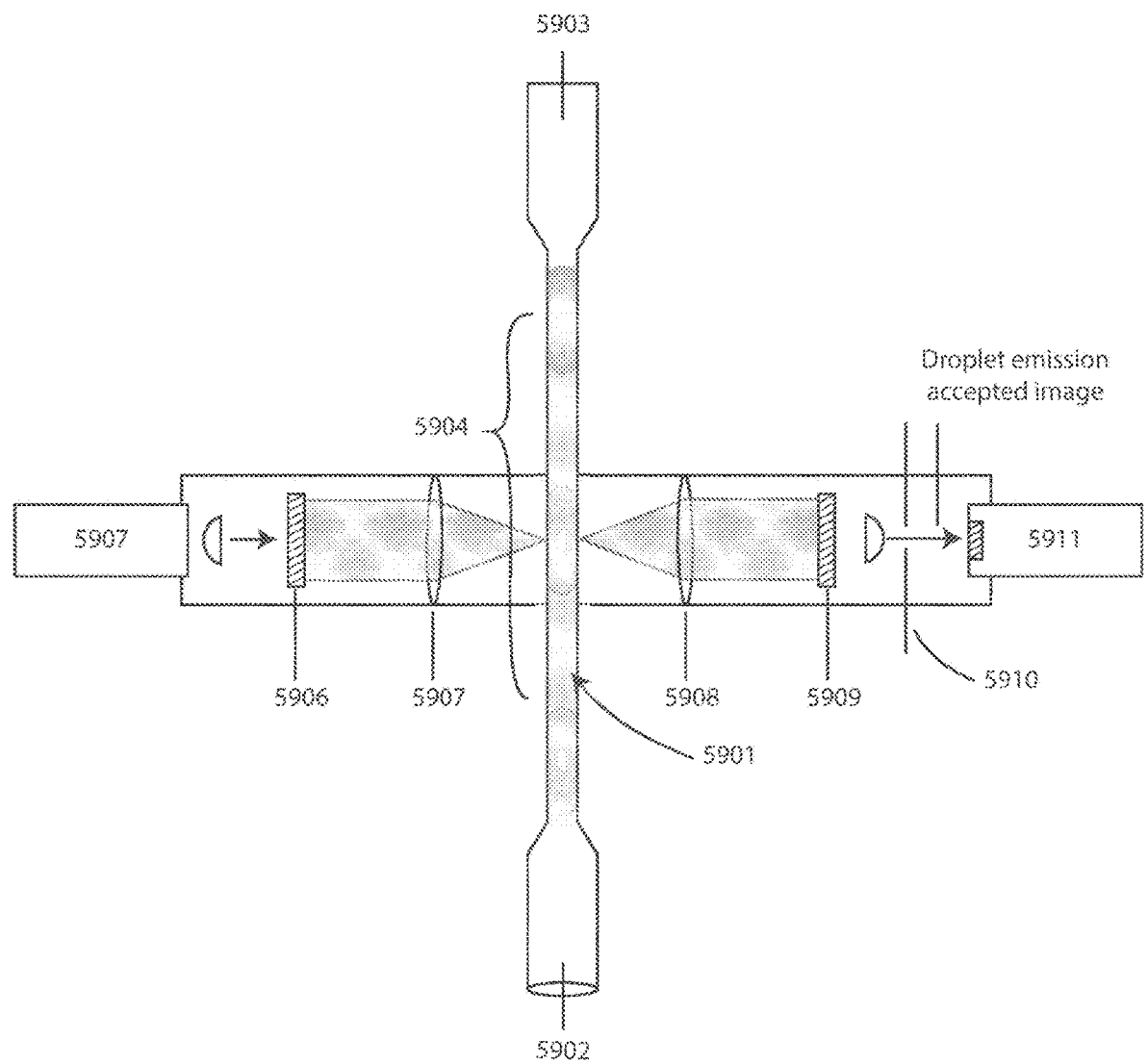
FIG. 59 shows a tubular interrogation region with opposing excitation/detection.

FIG. 59—Tubular interrogation region with opposing excitation/detection. FIG. 59 shows a further embodiment of the system shown in FIG. 58. The system comprises a conduit 5901, an inlet 5902, an outlet 5903, an interrogation region 5904, an excitation source 5905, an excitation filter 5906, an excitation lens 5907, an emission lens 5908, an emission filter 5909, an optical restriction 5910, and a detection element 5911. Electromagnetic radiation in a first wavelength range A is emitted by the excitation source 5905. In certain embodiments, the excitation source 5905 comprises an optical element to collimate the electromagnetic radiation in a first wavelength range A. The electromagnetic radiation passes through the excitation filter 5906 where electromagnetic radiation outside of a second wavelength range A' is reduced in intensity. In preferred embodiments, the second wavelength range A' coincides or substantially coincides with wavelengths where at least one component of one or more of the partitions of dispersed phase is excited so as to emit electromagnetic radiation in a third wavelength range B. After passing through the excitation filter 5906, the electromagnetic radiation passes through an excitation lens 5907 where it is focused on the conduit 5901 in the interrogation region 5904 and may excite at least one component of one or more of the partitions of dispersed phase in the interrogation region 5904 such that the component emits electromagnetic radiation in the third wavelength range B and passes into the emission lens 5907 where it is collimated onto the emission filter 5909. The emission filter 5909 is chosen so that it reduces the radiant power of electromagnetic radiation in the third wavelength range B outside of a fourth wavelength range B'. In certain embodiments, the fourth wavelength range B' is a subset of the third wavelength range B. The optical restriction 5910 is located between the emission filter 5909 and the detection element 5911 such that it restricts the field of view of the detection element so that the electromagnetic radiation reaching the detection element is limited or substantially limited to that emitted by at least one component in a single partition of the dispersed phase. This allows, in a practical manner, for the measurement of an optical property of only one partition of the dispersed phase at any specific time. In certain embodiments, at least 30%, 40%, 50%, 60%, 70%, 80%, 85%, 90%, 95%, 97%, 98%, or 99% and/or not more than 30%, 40%, 50%, 60%, 70%, 80%, 85%, 90%, 95%, 97%, 98%, 99% or 100% of the electromagnetic radiation reaching the detection element was emitted by at least one component in a single partition of the dispersed phase. In certain embodiments, when a first partition is passing through the interrogation zone, not more than 0.1%, 0.5%, 1%, 2%, 3%, 4%, 5%, 7%, 10%, 15%, 20%, 25%, 30%, 40%, or 50% and/or at least 0, 0.1%, 0.5%, 1%, 2%, 3%, 4%, 5%, 7%, 10%, 15%, 20%, 25%, 30%, or 40% of the electromagnetic radiation reaching the detection element due to one or more components in a partition is from one or more partitions other than the partition in the interrogation zone. Any suitable geometry may be used for the optical restriction. In certain embodiments, the optical restriction is a pinhole, i.e., a circular aperture. The pinhole can be any suitable size, for example, with a diameter less than 1000 um, 750 um, 500 um, 250 um, 150 um, 100 um, 80 um, or 50 um and/or at least 750 um, 500 um, 250 um, 150 um, 100 um, 80 um, 50 um, or 25 um. In other embodiments, the optical restriction 5910 is a slot or a star shape. In some embodiments, the emission filter 5909 additionally comprises a system for focusing the electromagnetic radiation onto the optical restriction 5910.

Figure 60:
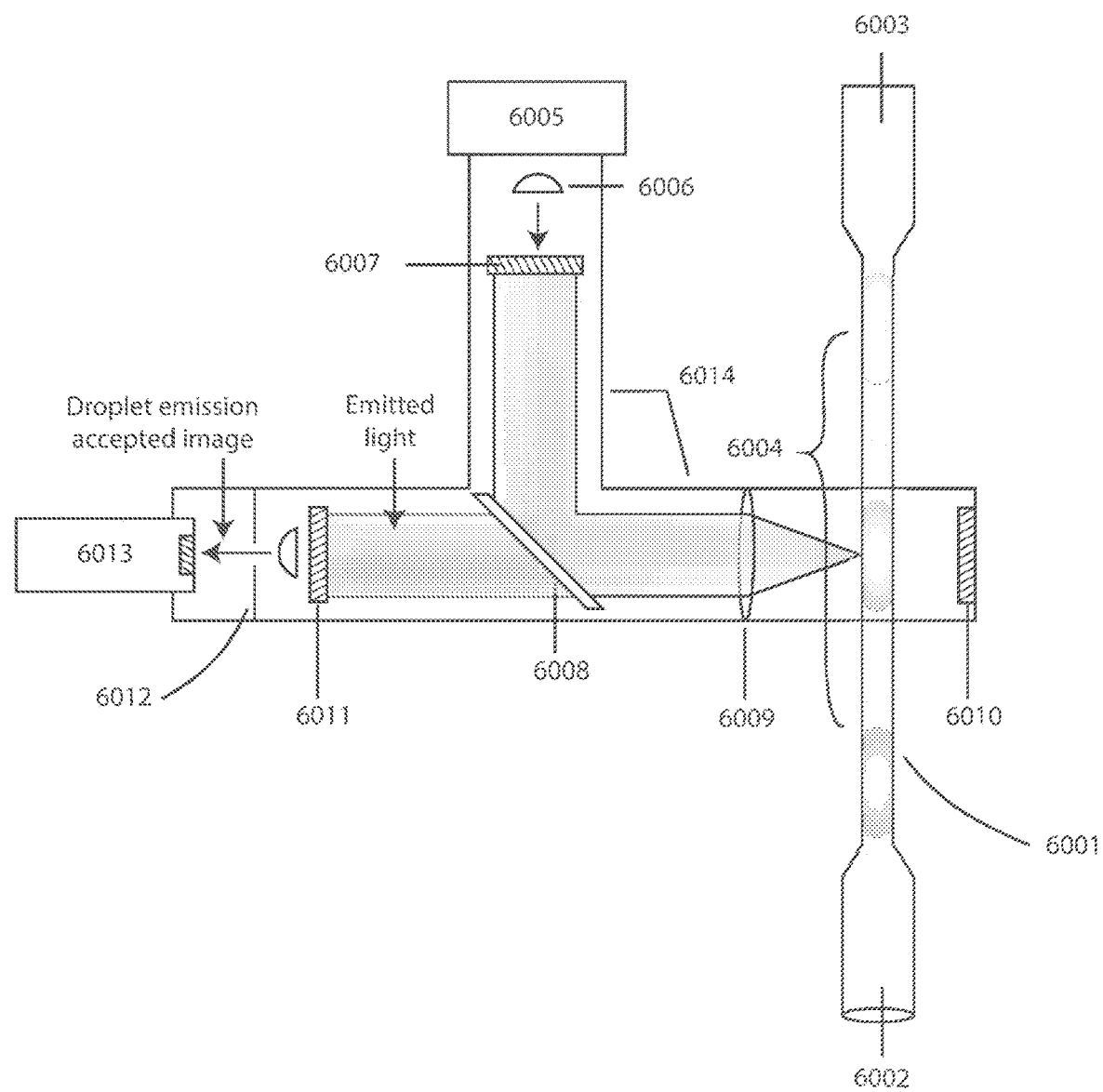
FIG. 60 shows a tubular interrogation region with in-path excitation/detection.

FIG. 60—Tubular interrogation region with in-path excitation/detection. FIG. 60 shows a system for measuring at least one optical property of the partitions of a dispersed phase where excitation electromagnetic radiation and emission electromagnetic radiation share a common optical pathway. The system comprises a conduit 6001, which comprises an inlet 6002, an outlet 6003, and an interrogation region 6004. In certain embodiments, the cross-sectional area of the interrogation region 6004 is reduced relative to the inlet 6002 and/or the outlet 6003 such that it has a value equal to or less than the equivalent spherical cross-sectional area of the partitions of the dispersed phase. In such embodiments, the partitions of the dispersed phase fill or substantially fill the cross-section of the conduit 6001 in the interrogation region 6004, reducing variability in the measurement of an optical property of the partitions of the dispersed phase due to variation in the position of the partitions of the dispersed phase in the cross-section of the conduit 6001. At least one continuous phase and partitions of at least one dispersed phase enter the conduit 6001 at the inlet 6002 and flow toward the outlet 6003. In certain embodiments, the partitions of the at least one dispersed phase enter the inlet 6002 in single file. In certain embodiments, the partitions of the at least one dispersed phase are separated along the axis of the conduit 6001 by a volume of the at least one continuous phase.

The system additionally comprises an excitation source 6005, an excitation collimator 6006, an excitation filter 6007, a turning mirror 6008, an interrogation region lens 6009, an emission filter 6011, an optical restriction 6012, a detection element 6013, and a collection tube 6014. The system may be used to detect at least one optical property of the partitions of the at least one dispersed phase as follows. Electromagnetic radiation with wavelengths in a first wavelength range A is emitted by the excitation source 6005 and collimated by the excitation collimator 6006. In certain embodiments, the collimator is a lens. In other embodiments, the collimator is a parabolic mirror. The electromagnetic radiation in the first wavelength range A passes through the excitation filter 6007, which reduces the power of the electromagnetic radiation outside of a second wavelength range A'. In certain embodiments, the second wavelength range A' is a subset of the first wavelength range A. In certain embodiments, the second wavelength range A' coincides or substantially coincides with a third wavelength range A" such that the third wavelength range A" excites a component contained in one or more of the partitions of the at least one dispersed phase, subsequently causing it to emit electromagnetic radiation in a fourth wavelength range B. The electromagnetic radiation in the second wavelength range A' transmitted by the excitation filter 6007 is then incident on the turning mirror 6008, where it is redirected at an angle alpha away from an axis normal to the surface of the excitation filter 6007. In certain embodiments, the angle alpha is between 85 degrees and 95 degrees. The turning mirror can be any suitable mirror, e.g., a dichroic mirror. Electromagnetic radiation in the wavelength range A' reflected from the turning mirror passes through an interrogation region lens 6009, where it is focused on the interrogation region. In certain embodiments, the focal length of the interrogation region lens 6009 is selected and the lens 6009 positioned such that the electromagnetic radiation in the wavelength range A' is focused or substantially focused on the center of the conduit 6001 in the interrogation region 6004. Electromagnetic radiation in the wavelength range A' excites a component contained in one or more partitions of the at least one dispersed phase, causing it to emit electromagnetic radiation in the fourth wavelength range B. The electromagnetic radiation in the fourth wavelength range B is collimated by the interrogation region lens 6009 and is then incident on the turning mirror 6008 and is substantially transmitted by the turning mirror 6008. The electromagnetic radiation in the fourth wavelength range B is then incident on the emission filter 6011, which reduces the radiant power outside of a fifth wavelength range B'. In some embodiments, the fifth wavelength range B' coincides with all or a substantial portion of the fourth wavelength range B so as to maximize transmitted power. The emission filter 6011 can further comprise a focusing optic that concentrates the electromagnetic radiation in the fifth wavelength range B' on the optical restriction 6012. The optical restriction 6012 is sized and positioned so that the field of view of the detection element 6013 is substantially restricted to electromagnetic radiation arriving from only at most a single partition of the at least one dispersed phase. In certain embodiments, at least 30%, 40%, 50%, 60%, 70%, 80%, 85%, 90%, 95%, 97%, 98%, or 99% and/or not more than 30%, 40%, 50%, 60%, 70%, 80%, 85%, 90%, 95%, 97%, 98%, 99% or 100% of the electromagnetic radiation reaching the detection element was emitted by at least one component in a single partition of the dispersed phase. In certain embodiments, when a first partition is passing through the interrogation zone, not more than 0.1%, 0.5%, 1%, 2%, 3%, 4%, 5%, 7%, 10%, 15%, 20%, 25%, 30%, 40%, or 50% and/or at least 0, 0.1%, 0.5%, 1%, 2%, 3%, 4%, 5%, 7%, 10%, 15%, 20%, 25%, 30%, or 40% of the electromagnetic radiation reaching the detection element due to one or more components in a partition is from one or more partitions other than the partition in the interrogation zone. As such, little or no correction in partition intensity must be made to account for the at least one emitting component comprising partitions of the dispersed phase preceding or following the partition of the dispersed phase emitting a plurality of electromagnetic radiation reaching the detection element.

In some embodiments, the conduit 6001 comprises the internal volume of a tube comprising a material that is at least partially transmissive in the third wavelength range A" and the fourth wavelength range B. In certain embodiments, the tube comprises a material at least partially transmissive in the third wavelength range A" and the fourth wavelength range B, such as at least 20%, 30%, 40%, 50%, 60%, 70%, 80%, 90%, or 99% and/or not more than 30%, 40%, 50%, 60%, 70%, 80%, 90%, 99%, or 100% transmissive of electromagnetic radiation of wavelength range A" and least 20%, 30%, 40%, 50%, 60%, 70%, 80%, 90%, or 99% and/or not more than 30%, 40%, 50%, 60%, 70%, 80%, 90%, 99%, or 100% transmissive of electromagnetic radiation of wavelength range B. In certain embodiments, the tube transmits at least 20%, at least 30%, at least 40%, at least 50%, at least 60%, at least 70%, at least 75%, at least 85%, at least 90% or at least 95% of the electromagnetic radiation incident upon it. In other embodiments, the conduit 6001 comprises a channel in a substrate. In some embodiments, the substrate comprises a material at least partially transmissive in the third wavelength range A" and the fourth wavelength range B such as at least 20%, 30%, 40%, 50%, 60%, 70%, 80%, 90%, or 99% and/or not more than 30%, 40%, 50%, 60%, 70%, 80%, 90%, 99%, or 100% transmissive of electromagnetic radiation of wavelength range A" and least 20%, 30%, 40%, 50%, 60%, 70%, 80%, 90%, or 99% and/or not more than 30%, 40%, 50%, 60%, 70%, 80%, 90%, 99%, or 100% transmissive of electromagnetic radiation of wavelength range B. In certain embodiments the substrate transmits at least 20%, at least 30%, at least 40%, at least 50%, at least 60%, at least 75%, at least 85%, at least 90%, or at least 95% of the electromagnetic radiation incident upon it.

Figure 61:
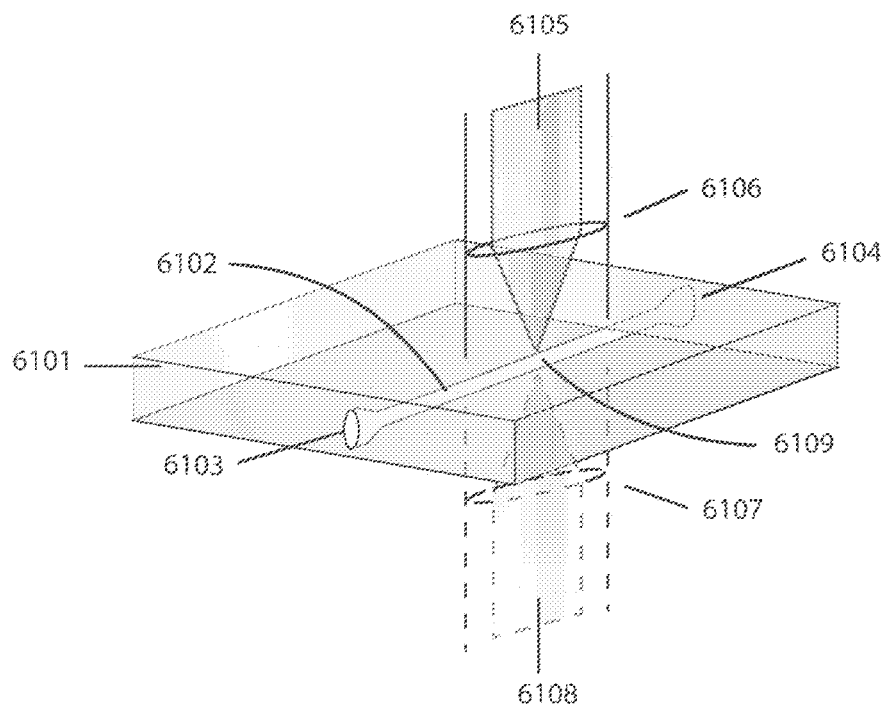
FIG. 61 shows on-chip interrogation region with opposing excitation/detection.

FIG. 61—On-chip interrogation region with opposing excitation/detection. FIG. 61 shows a system for detecting an optical property of partitions of a dispersed phase flowing in a channel. The system comprises a substrate 6101, a flow channel 6102, an inlet 6103, an outlet 6104, an excitation source 6105, an excitation lens 6106, an emission lens 6107, a detection element 6108, and an interrogation region 6109. The flow channel 6102 is formed in the substrate 6101. At least one continuous phase and partitions of at least one dispersed phase enter the flow channel 6102 at the inlet 6103 and flow toward the outlet 6104. In some embodiments, the flow channel 6102 is narrowed in the interrogation region 6109 so that the cross-sectional area of the flow channel 6102 in the interrogation region 6109 is less than or equal to the equivalent spherical cross-sectional area of the partitions of the dispersed phase.

The excitation source 6105 emits substantially collimated electromagnetic radiation in a first wavelength range A in the direction of the excitation lens 6106. The excitation lens 6106 focuses electromagnetic radiation in the first wavelength range A on the interrogation region 6104 of the flow channel 6102, where it excites at least one component of at least one of the partitions of the at least one dispersed phase, causing it to emit electromagnetic radiation in a second wavelength range B. The substrate 6101 possesses a first transmissivity in the wavelength range A and a second transmissivity in the second wavelength range B such that the substrate 6101 transmits a substantial fraction of incident electromagnetic radiation in each wavelength range. In some embodiments, the substrate 6101 transmits at least 20%, at least 30%, at least 40%, at least 50%, at least 60%, at least 70%, at least 80%, at least 90%, or at least 95% of the incident electromagnetic radiation in the first wavelength range A, at least 20%, at least 30%, at least 40%, at least 50%, at least 60%, at least 70%, at least 80%, at least 90%, or at least 95% of the incident electromagnetic radiation in the second wavelength range B, or any combination thereof. Electromagnetic radiation emitted in the second wavelength range B is transmitted through the substrate 6101, where it is incident on an emission lens 6107 and is collimated in a first axis.

Figures 62A, 62B:
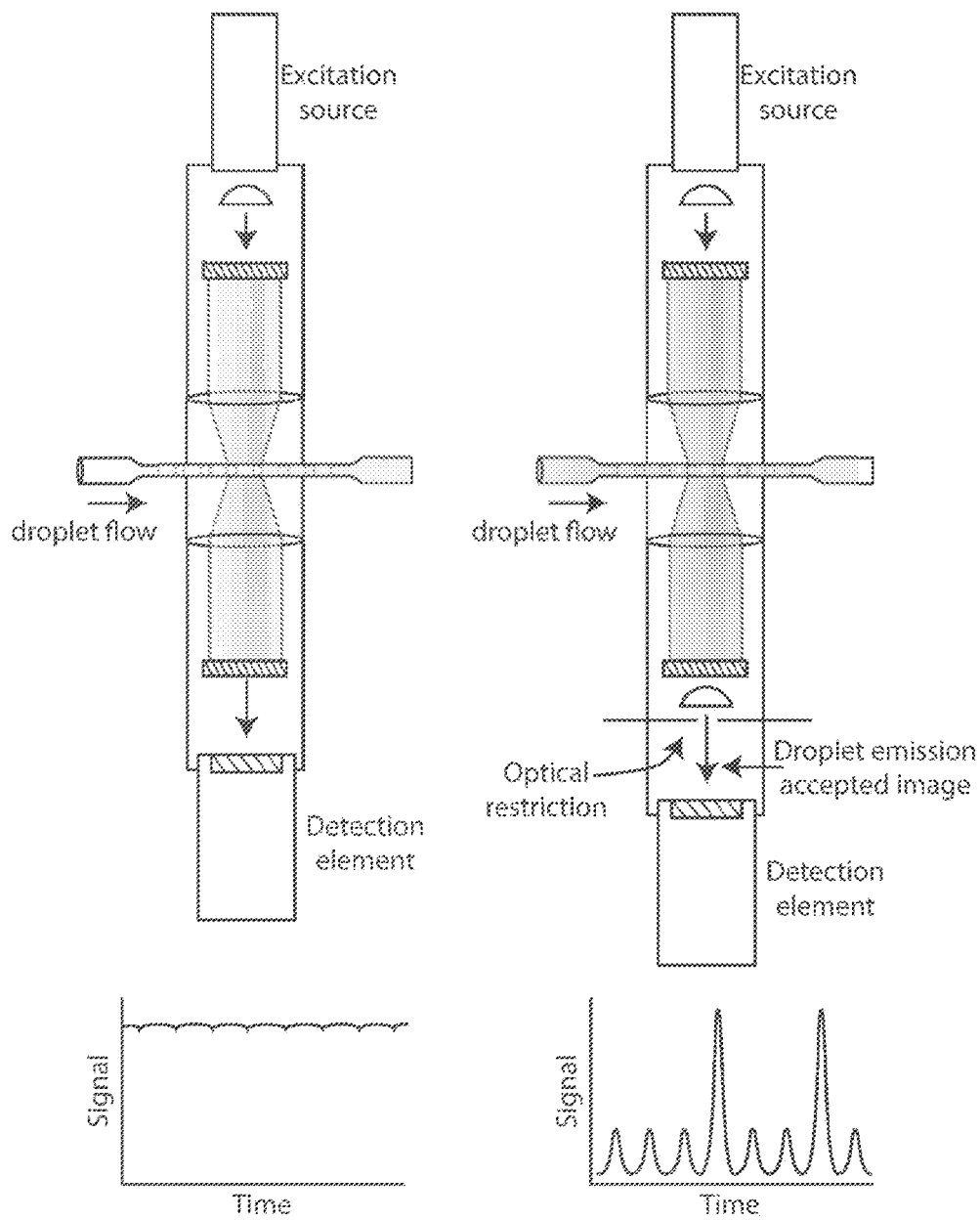
FIGS. 62A and 62B show use of an optical restriction to limit accepted electromagnetic radiation to a single partition.

FIGS. 62A and 62B—Use of an optical restriction to limit accepted electromagnetic radiation to a single partition. FIG. 62A shows a system for measuring an optical property of partitions of at least one dispersed phase that does not comprise an optical restriction between an emission filter and a photodetection element, and FIG. 62B shows a system for measuring an optical property of partitions of at least one dispersed phase that does comprise an optical restriction between an emission filter. In the system shown in FIG. 62A, the field of view of the interrogation region is not limited or substantially limited to a single partition. As a result, optical measurements at the detection element quantify energy from more than a single partition of the at least one dispersed phase at any one time, and the signal (as shown in the accompanying plot of intensity against time) has peaks representing the central portion of a single partition of the at least one dispersed phase that may be difficult to distinguish from the background signal. In contrast, the system shown in FIG. 62B comprises an optical restriction that limits the fraction of electromagnetic radiation reaching the detection element such that all or a substantial fraction of the energy emitted from partitions and reaching the detection element at any one time is from only a single partition of the at least one dispersed phase. In some embodiments, this fraction is greater than 20%, greater than 30%, greater than 40%, greater than 50%, greater than 60%, greater than 70%, greater than 80%, greater than 90%%, greater than 95%, greater than 98%, or greater than 99%. In certain embodiments, at least 30%, 40%, 50%, 60%, 70%, 80%, 85%, 90%, 95%, 97%, 98%, or 99% and/or not more than 30%, 40%, 50%, 60%, 70%, 80%, 85%, 90%, 95%, 97%, 98%, 99% or 100% of the electromagnetic radiation reaching the detection element was emitted by at least one component in a single partition of the dispersed phase. In certain embodiments, when a first partition is passing through the interrogation zone, not more than 0.1%, 0.5%, 1%, 2%, 3%, 4%, 5%, 7%, 10%, 15%, 20%, 25%, 30%, 40%, or 50% and/or at least 0, 0.1%, 0.5%, 1%, 2%, 3%, 4%, 5%, 7%, 10%, 15%, 20%, 25%, 30%, or 40% of the electromagnetic radiation reaching the detection element due to one or more components in a partition is from one or more partitions other than the partition in the interrogation zone. In the plot of intensity against time accompanying FIG. 62B, the amplitude difference between peak values and trough values is relatively larger than in the optical restriction-free system shown in FIG. 62A. This is due to the reduced contributions to the overall intensity signal from partitions of the at least one dispersed phase upstream or downstream of the partition of the at least one dispersed phase nearest the system focal point in the interrogation region. The optical restriction may take any suitable shape provided it reduces the fraction of electromagnetic radiation incident on the detection element to a portion of the energy that would otherwise reach it; for example, it can reduce the fraction of electromagnetic radiation incident on the detection element not emitted by a component of the partition of the at least one dispersed phase most proximate to the focal point of the interrogation region. In some embodiments, the optical restriction is circular. In certain embodiments, the optical restriction has a size of 10-500 um (diameter of circular optical restriction), e.g., 30-400 um, such as 50-350 um, in certain embodiments 150-250 um. Other sizes and positioning are as described elsewhere herein. In other embodiments, the optical restriction is shaped like a rectangular slot, triangle, star, pentagon, hexagon, square, heptagon, octagon, or any other n-sided polygon.

Figure 63:
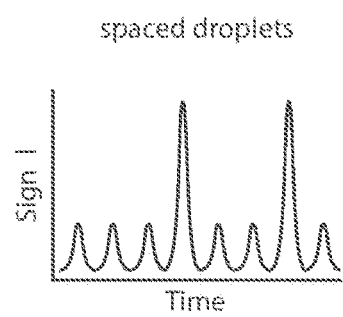
FIG. 63 shows positive signal detection.

FIG. 63—Positive signal partition detection. FIG. 63 shows the photodetector signal as a function of time as partitions of the at least one dispersed phase pass through an interrogation region and are spaced such that there is a volume of a continuous phase between the partitions of the at least one dispersed phase and no point of the surface of a first partition of the at least one dispersed phase is in contact with the surface of any other partition of the at least one dispersed phase in the interrogation region. As partitions of the dispersed phase enter the interrogation region and a component contained in one or more the partitions of the at least one dispersed phase is excited by electromagnetic radiation in a first wavelength range, a signal (e.g., voltage) measured at the photodetector increases due to electromagnetic radiation emitted in a second wavelength by the component contained in one or more the partitions of the at least one dispersed phase. The signal rises until the partition of the at least one dispersed phase is centered in the interrogation region, after which the signal falls until the partition of the at least one dispersed phase is no longer in the interrogation region. Each peak in signal corresponds to a single partition of the at least one dispersed phase. The magnitude of the signal corresponds to a property of the excited component in the partitions of the at least one dispersed phase. In certain embodiments, the signal increases with increasing concentration of an optical dye, such as described elsewhere herein. In certain embodiments, the concentration of the optical dye can be related to the concentration of a second component in the at least one dispersed phase. The second component can be any suitable component, e.g., a nucleic acid, protein, molecule, atomic species, solid particulate species, or ion. In some cases, it is desired only to determine which, of a discrete set of value bins, the concentration of the second component is in, and so signals may be classified into "high", "low", or any series of discrete values. In some cases, the assay is a digital assay where the concentration of the second component may be determined by estimating a statistical distribution from the number of "high" and "low" concentrations measured for the second component contained in one or more of the partitions of the dispersed phase. In certain embodiments, the assay is digital polymerase chain reaction and the second component is a nucleic acid.

Figure 64:
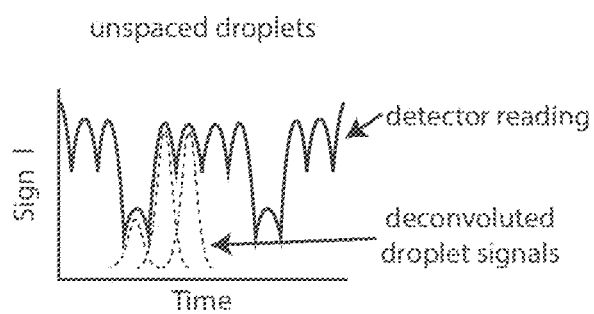
FIG. 64 shows negative signal detection.

FIG. 64—Negative signal partition detection. FIG. 64 shows the photodetector signal as a function of time as partitions of the at least one dispersed phase pass through an interrogation region and are not spaced so that no point of the surface of a first partition of the at least one dispersed phase is in contact with the surface of any other partition of the at least one dispersed phase in the interrogation region. In such a case, the signal at the photodetector may comprise electromagnetic radiation contributions from more than one partition of the at least one dispersed phase at a given time and the signal does not fall to a baseline in between signal peaks. Each relative peak still corresponds to a point where a single partition of the at least one dispersed phase is centered in the system, and a measurement of the signal intensity for that partition may be made. In certain embodiments, a correction to the signal for a first peak representing a first partition is made by accounting for the value of the signals at the peaks of the partitions following and preceding the first peak representing the first partition. In a certain embodiments, the intensity of the first peak is reduced by a first coefficient multiplied by the value of the signal of the peak immediately preceding the first peak in time and reduced by a second coefficient multiplied by the value of the signal of the peak immediately following the first peak. In certain embodiments, the first and second coefficient are proportional to the size and position of an optical restriction relative to the interrogation region. In a further embodiment, the first and second coefficient have the same value.

Figures 65A, 65B:
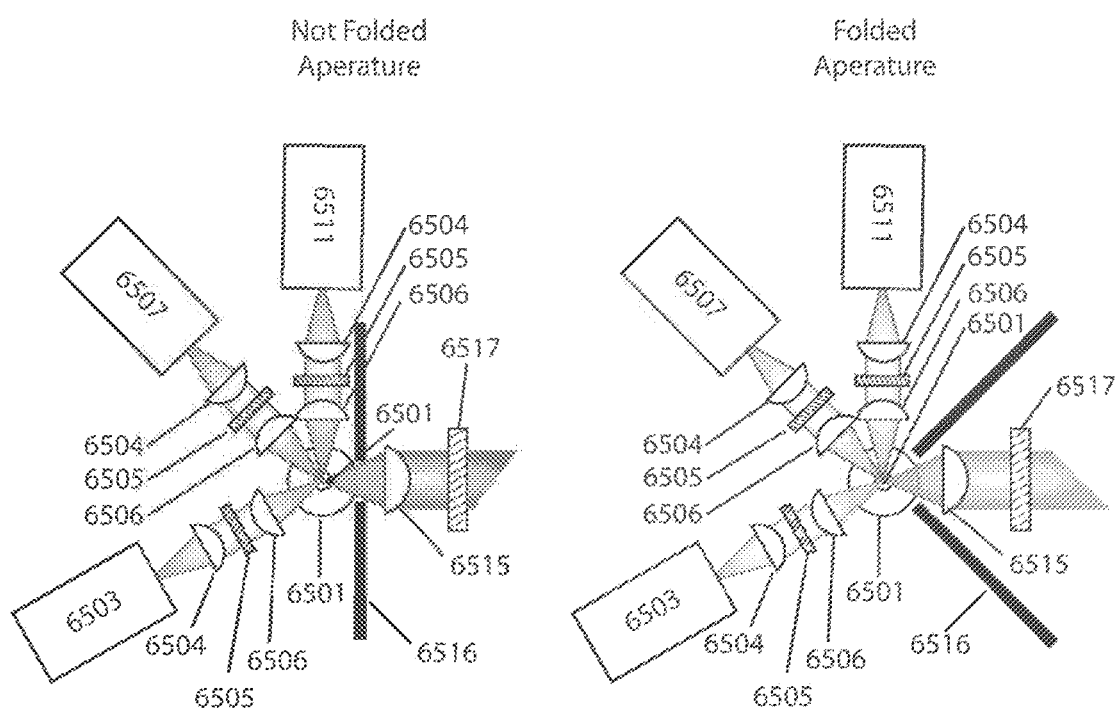
FIGS. 65A and 65B show a multiexcitation source. 65A: not folded aperture. 65B: folded aperture.

FIG. 65A—Multi-excitation source in tubular arrangement; FIG. 65B. FIG. 65 shows systems for measuring an optical property of one or more partitions of at least one dispersed phase flowing in at least one continuous phase where the flow is in a tubular conduit. The system comprises a tubular conduit with an outer surface 6501 and an inner surface 6502. A first excitation source 6503 emits electromagnetic radiation in a first wavelength range A that is collimated by a first excitation collimating lens 6504 onto a first excitation filter 6505, which substantially reduces the radiant power transmitted through the filter outside of a wavelength range A'. In some embodiments, the fraction of incident radiant power outside of the wavelength range A' transmitted by the filter is less than $10^{-1}$, $10^{-2}$, $10^{-3}$, $10^{-4}$, $10^{-5}$, $10^{-6}$, $10^{-7}$, or $10^{-8}$. A first excitation focusing lens 6506 focuses the radiant power in the wavelength range A' onto a focal point in or near the tubular conduit. The tubular conduit has a wall constructed of a material that at least partially transmits the radiant power in the wavelength range A' focused by the first focal lens and has a distance between the outer surface 6501 and the inner surface 6502 such that the total reduction in radiant power is small. In some embodiments, the total reduction is radiant power from the outer surface 6501 to the inner surface 6502 is less than 75%, 65%, 55%, 50%, 40%, 30%, 20%, 10%, 5%, 1%, 0.1%, or 0.01% and/or at least 65%, 55%, 50%, 40%, 30%, 20%, 10%, 5%, 1%, 0.1%, 0.01%, 0.001%, or 0%. In some embodiments, the focusing lens 6506 is positioned such that the collimated electromagnetic radiation in the wavelength range A' has a first axis normal or substantially normal to the outer surface 6501, which may minimize reflection of the electromagnetic radiation in the wavelength range A' off of the outer surface 6501. The electromagnetic radiation in the wavelength range A' excites at least one component in one or more of the partitions of the at least one dispersed phase, causing it to emit electromagnetic radiation in a wavelength range B. The system comprises an aperture 6516 that limits the field of view of a region of the system to an angle alpha in the plane normal to the flow axis of the conduit. Doing so may reject some, most, or substantially all of the electromagnetic radiation in the wavelength range A' emitted by the first excitation source 6503 and filtered by the first excitation filter 6505 reaching an emission collimating lens 6515 and any subsequent photodetection element beyond the lens 6515.

In certain embodiments, the aperture 6516 is folded such it increases, e.g., maximizes the angular extent available to excitation sources without allowing substantial electromagnetic radiation from the excitation sources to pass through the aperture, as shown in FIG. 65B. The system additionally comprises a detection element. The detection element may be any suitable element. In certain embodiments, the detection element is one of a photodiode, silicon photomultiplier (SiPM), avalanche photodiode, complementary metal oxide semiconductor (CMOS) detector, charge-coupled device (CCD) camera, or photomultiplier tube (PMT). The detection element can be positioned so as to measure an intensity or a power of electromagnetic radiation passing through the aperture 6516. In certain embodiments, the detection element is positioned so as to measure an intensity or a power of electromagnetic radiation passing through collimation lens 6515. In further embodiments, the system additionally comprises one or more of an emission filter, an emission focusing lens, and emission optical restriction. The emission filter is configured to substantially reduce the electromagnetic radiation passed outside at least one wavelength range B'. In preferred embodiments, the wavelength range B' coincides or substantially coincides with the wavelength range B. The emission focusing lens focuses electromagnetic radiation onto the emission optical restriction, restricting the field of view, for example, restricting the field of view such that the electromagnetic radiation reaching the detection element originated primarily from a single partition of the at least one dispersed phase.

In certain embodiments, the system further comprises a second excitation source 6507 that emits electromagnetic radiation in a wavelength range C, a second excitation collimating lens 6508, a second excitation filter 6509 that reduces the radiant power transmitted through the filter outside of a wavelength range C', and a second excitation focusing lens 6510 that focuses the electromagnetic radiation in the wavelength range C' on partitions of the at least one dispersed phase flowing through the conduit. The electromagnetic radiation in the wavelength range C' may excite at least one component contained in one or more of the partitions of the at least one dispersed phase to emit electromagnetic radiation in a wavelength range D. In further embodiments, the system comprises a third excitation source 6511 that emits electromagnetic radiation in a wavelength range E, a third excitation collimating lens 6512, a third excitation filter 6513 that reduces the radiant power transmitted through the filter outside of a wavelength range E', and a third excitation focusing lens 6514 that focuses the electromagnetic radiation in the wavelength range E' on partitions of the at least one dispersed phase flowing through the conduit. The electromagnetic radiation in the wavelength range E' may excite at least one component contained in one or more of the partitions of the at least one dispersed phase to emit electromagnetic radiation in a wavelength range F. In general, embodiments may be extended to comprise four, five, six, seven, eight, or more sets of an excitation source, an excitation collimating lens, an excitation filter, and an excitation focusing lens that expose partitions of the at least one dispersed phase flowing through the conduit to electromagnetic radiation in a wavelength range specific to each excitation set that may excite at least one component contained in on or more of the partitions of the at least one dispersed phase. Each excitation wavelength range corresponds to a component contained in one or more of the partitions of the at least one dispersed phase such that the radiant power emitted by each component when excited by each excitation wavelength corresponds to a property of the component in the partitions of the dispersed phase. In certain embodiments, the property is a molar or mass concentration of each component in the partitions of the dispersed phase. In certain embodiments, the property of each component in the partitions of the dispersed phase may be related to another property of the partitions of the dispersed phase. In an example, the components excited by the electromagnetic radiation in the excitation wavelength ranges are fluorescent dyes, the radiant power emitted by the fluorescent dyes may be quantitatively related to their molar concentration, and the molar concentration of each fluorescent dye, or a combination of the molar concentrations of a plurality of fluorescent dyes, may be related to a molar or mass concentration of at least one more component of the system. In certain embodiments, such a component would be a nucleic acid, a protein, a molecule, an atomic species, a solid particulate species, or an ionic species. By associating an excitation wavelength range with at least one component of the partitions of the dispersed phase, the use of at least two excitation wavelength ranges can allow the measurement of at least two properties of components contained in one or more of the partitions of the dispersed phase.

Figure 66:
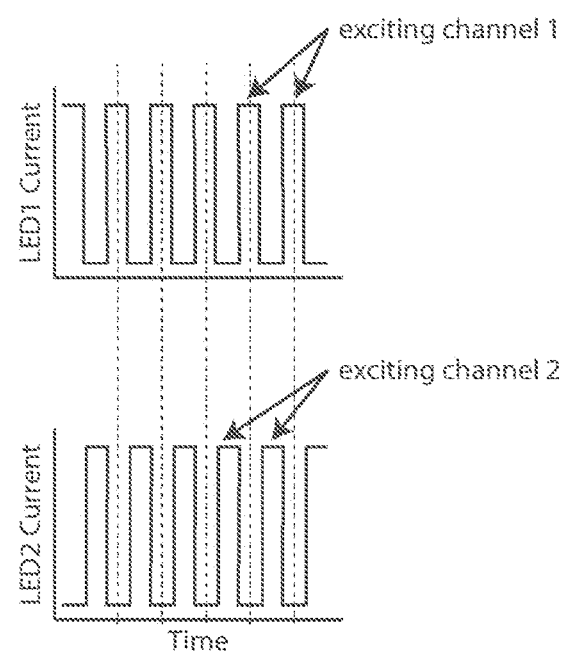
FIG. 66 shows temporal modulation.

In some embodiments, the photodetection element produces a signal proportional to the incident energy across a wavelength range Z, where the wavelength range Z at least partially coincides with at least two of the wavelength ranges B', D', F', or more, depending on the number of excitation sources. In such cases, multiplexing measurements of at least two components in the partitions of the at least one dispersed phase can require methods for deconvoluting signals at the single photodetection element. In certain embodiments, the excitation sources are cycled between active and inactive states such that, at any given time, a maximum of one excitation source is active. By cycling through the excitation sources at a rate at least equal to 1/(n*t), where n is the number of excitation sources and t is the time required for a single partition of the at least one dispersed phase to pass through the field of view of the detection element, at least one measurement may be made at the detection element for each component of the partitions of the at least one dispersed phase that may be associated with at least one excitation source. In preferred embodiments, the cycling frequency is 1/(n*t*g), where g is a coefficient equaling the number of measurements to be made, on average, for the duration of each excitation source, where g is greater than or equal to 4. In some preferred embodiments, g is greater than 4, 5, 6, 8, 10, 20, or 100. The limit to g is related to the response time of both the photodetection element and the at least one excited component in the partitions of the at least one dispersed phase. A schematic representation of this is shown in FIG. 66.

In certain embodiment, lock-in amplification is used to deconvolute the signals from the at least one component, for example at least two components, excited by the at least two wavelengths of electromagnetic radiation transmitted by the at least two excitation filters, increase the signal-to-noise ratio of the detection element, or both. The first excitation source 6503 is modulated in a first periodic function, which translates to a modulation in the electromagnetic radiation passed by the first excitation filter 6505 by the first periodic function and a modulated response of the electromagnetic radiation emitted by a first component of the partitions of the at least one dispersed phase in the wavelength range B. When represented as a Fourier series, the first periodic function will have an infinite set of coefficients, one for each frequency term in the Fourier series. In certain embodiments, the relative magnitude of each of a finite subset of the coefficients is at least greater than any other coefficient not in the finite subset of the coefficients by a minimum multiple. In certain embodiments, the minimum multiple is greater than 10, greater than 100, greater than 1000, greater than 10,000, greater than 100,000, or greater than 1,000,000. To improve analysis, it is desired that the finite subset has a limited number of coefficients. In some embodiments, the number of coefficients is fewer than 1000, fewer than 100, fewer than 10, fewer than 5, fewer than 2, or 1. In certain embodiments, the first periodic function is sinusoidal and the number of coefficients in the finite subset is 1. Due to the orthonormality of sinusoidal functions and the mathematical completeness of the Fourier series, integration of the product of the first periodic function and the signal measured by the detection element over multiple periods of the first periodic function will result in lower measured amplitudes of components of the signal corresponding to terms of the Fourier series representation of the first periodic function whose coefficients are not in the finite subset and relative amplification of the terms of the Fourier series representation of the first periodic function whose coefficients are in the finite subset. If the relative magnitude of the coefficients of the Fourier series representation of the components of the signal measured by the detection element that are not related to the electromagnetic radiation in the wavelength range B in the finite subset are not relatively larger than the coefficients of the Fourier series representation of the components of the signal measured by the detection element that are not related to the electromagnetic radiation in the wavelength range B not in the finite subset, components of the signal measured by the detection element related to the electromagnetic radiation in the wavelength range B will be preferentially amplified to components of the signal measured by the detection element not related to the electromagnetic radiation in the wavelength range B. As such, signals measured by the detection element that may be related to a property of at least one component of the partitions of the dispersed phase may be amplified by this method to have a multiple of their signal-to-noise ratio over signals measured when this method is not applied. In certain embodiments, the multiple is greater than 2, greater than 5, greater than 10, greater than 100, greater than 1000, greater than $10^5$, or greater than $10^6$.

In certain embodiments, the first periodic function is chosen such that it preferentially avoids terms of the Fourier series representation of the components of the signal measured by the detection element that are not related to the electromagnetic radiation in the wavelength range B whose coefficients are relatively larger than other coefficients in the wavelength range B. For example, in many electronics systems, noise has a power spectrum with higher coefficient frequencies at lower frequencies. In certain embodiments, these are frequencies less than 10 Hz, less than 100 Hz, less than 1 kHz, less than 10 kHz, less than 20 kHz, or less than 100 kHz. By selecting a first periodic function such that the coefficients of the terms of the Fourier series representation of the first periodic function representing these frequencies are not in the finite subset, this low frequency electronic noise may be preferentially rejected in the integrated measurement. For example, the first periodic function may be a sinusoidal function with a frequency of 1 MHz and the terms of the Fourier series representation of the signal measured by the detection element that are not related to the electromagnetic radiation in the wavelength range B representing frequencies greater than 100 kHz are not in the finite subset.

In applying the method to obtain an amplified signal from the signal measured by the detection element, the signal measured by the detection element typically must be integrated over multiple periods of the first periodic function. In general, the signal-to-noise ratio achieved increases as the number of periods over which the signal measured by the detection element is integrated increases. However, increasing the number of periods increases the time constant for response of the amplified signal (or equivalently, reduces the effective rate at which the amplified signal may be sampled). As partitions of the at least one dispersed phase move through the interrogation region, the signal measured by the detection element rises then falls. If individual partitions are to be distinguished, a minimum number of measurements of the signal of the detection element must be made when each individual partition of the first dispersed phase is in the interrogation region. At a very minimum, this minimum number is 1. In some embodiments, the minimum number is at least 3, at least 5, at least 7, at least 8, at least 10, or at least 20. In preferred embodiments, the minimum number is at least 10, at least 20, at least 50, or at least 100. This minimum number of measurements practically limits, in conjunction with each other, the number of periods over which the signal measured by the detection element is integrated and the rate at which the partitions of the dispersed phase move through the interrogation region. To increase the rate at which the partitions of the dispersed phase move through the interrogation region while maintaining the minimum number of measurements of the signal of the detection element made when each individual partition of the first dispersed phase is in the interrogation region, the number of periods over which the signal measured by the detection element is integrated must be decreased, relatively reducing the effective signal-to-noise ratio. Conversely, to increase the signal-to-noise ratio while maintaining the minimum number of measurements of the signal of the detection element, the rate at which partitions of the dispersed phase move through the interrogation region must be decreased. In an embodiment, a rate at which partitions of the dispersed phase move through the interrogation region is at least 10,000 partitions per minute and the rate at which measurements of the signal of the detection element are made is at least 40,000 times per minute.

The method also allows for the simultaneous measurement of properties of multiple components of the partitions of the at least one dispersed phase, where the properties multiple components of the partitions of the at least one dispersed phase may be related to electromagnetic radiation in multiple wavelength ranges emitted by the multiple components of the partitions of the at least one dispersed phase as a result of being irradiated by electromagnetic radiation in multiple wavelength ranges emitted by a plurality of excitation sources, each modulated in time by a distinct periodic function The planar arrangement shown in FIGS. 65A and 65B allows for the positioning of multiple excitation sources around a single interrogation region where the direction of the collimating electromagnetic radiation leaving each excitation collimating lens is normal or substantially normal to the outer wall 6501. This effectively allows for a high level of measurement multiplexing for a single interrogation region, reducing cost and allowing for multiple measurements to be made on each partition of the at least one dispersed phase as it passes through the single interrogation region.

In certain embodiments, the excitation sources may be electromagnetic radiation emitting diodes, organic electromagnetic radiation emitting diodes, arrays of electromagnetic radiation emitting diodes, lasers, or any combination thereof. Some excitation sources, such as electromagnetic radiation emitting diodes, have very low costs. Other sources, such as lasers, have higher costs but effectively smaller wavelength ranges of emission.

Figure 67A:
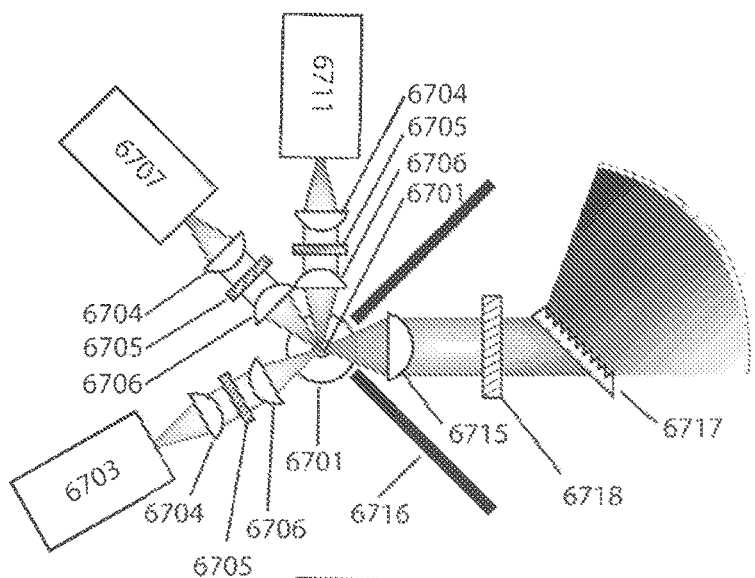
FIGS. 67A, 67B and 67C show different configurations of tubular spectrometer arrangements with diffraction.
Figure 67B:
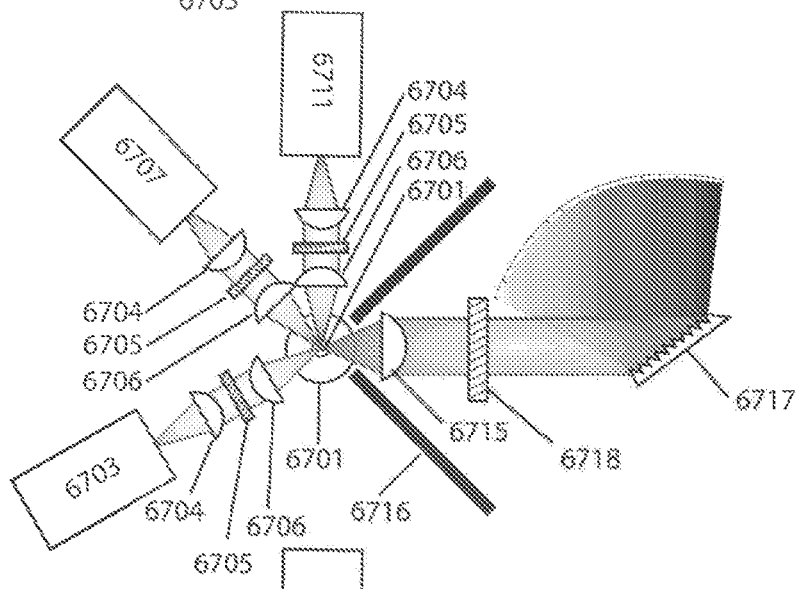
Figure 67C:
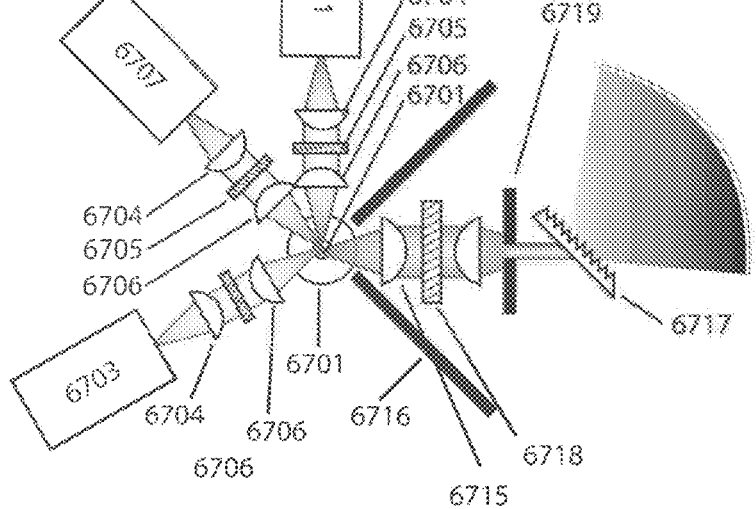

FIGS. 67A, 67B, and 67C—Tubular spectrometer arrangements with diffraction gratings/CCD. FIGS. 67A, 67B, and 67C show further embodiments of the system represented in FIG. 65 that allows for multiplexing by spatially resolving the spectral content of the electromagnetic radiation passing through the aperture 6716. The lens 6715 collimates the electromagnetic radiation passing through the aperture 6716. The system further comprises an emission filter 6718 that reduces the electromagnetic radiation passing through the aperture 6716 outside of a wavelength range H. The system further comprises a diffraction grating 6717; the electromagnetic radiation passing through the aperture is incident on the diffraction grating 6717, which disperses the electromagnetic radiation in a range of angles according to a monotonic function of the wavelength of the electromagnetic radiation. A solid angle projected from the surface of the diffraction grating 6717 at an angle alpha will subtend a portion of the electromagnetic radiation dispersed by the diffraction grating 6717, with the portion representing a fraction of the overall wavelength range H. The magnitude of the fraction is monotonically related to the size of the solid angle, with larger solid angles covering larger fractions of the overall wavelength range H. The system comprises at least one detection element 6718 that subtends a first solid angle covering a wavelength range H'. The wavelength range H' is selected so that the electromagnetic radiation in the wavelength range H' is primarily resultant from the excitation of a single component of the partitions of the at least one dispersed phase. In some embodiments, at least 50%, at least 60%, at least 70%, at least 75%, at least 80%, at least 90%, or at least 95% of the electromagnetic radiation in the wavelength range H' is primarily resultant from the excitation of a single component of the partitions of the at least one dispersed phase. The concept may be extended so that the system may comprise a second detection element subtending a second solid angle intercepting a second wavelength range H", in some cases, a third detection element subtending a third solid angle intercepting a third wavelength range H''', and so on, with each wavelength range containing electromagnetic radiation primarily resultant from the excitation of a single component of the partitions of the at least one dispersed phase. Any suitable detection element or combination of detection elements may be used. In certain embodiments, the detection elements may be a charge-coupled device (CCD) array, a set of photomultipliers, a set of photodiodes, a set of avalanche photodiodes, a set of silicon photomultipliers, or any combination thereof.

FIG. 67A shows an embodiment where the diffraction grating 6517 is transmissive, and FIG. 67B shows an embodiment where the diffraction grating is reflective. FIG. 67C shows the system that further comprises an optical restriction 6719, such that the electromagnetic radiation incident upon the diffraction grating 6717 results primarily from emission by components of the partitions of the at least one dispersed phase in a single partition of the at least one dispersed phase. In an embodiment, the fraction is greater than 50%, greater than 60%, greater than 70%, greater than 80%, greater than 90%, greater than 95%, greater than 98%, or greater than 99%.

Figure 68A:
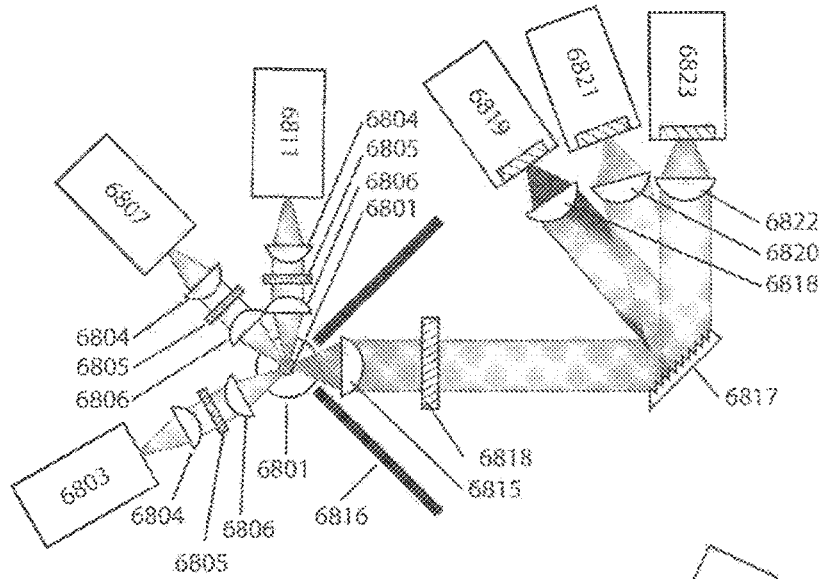
FIGS. 68A and 68B show a tubular spectrometer arrangements with diffraction.
Figure 68B:
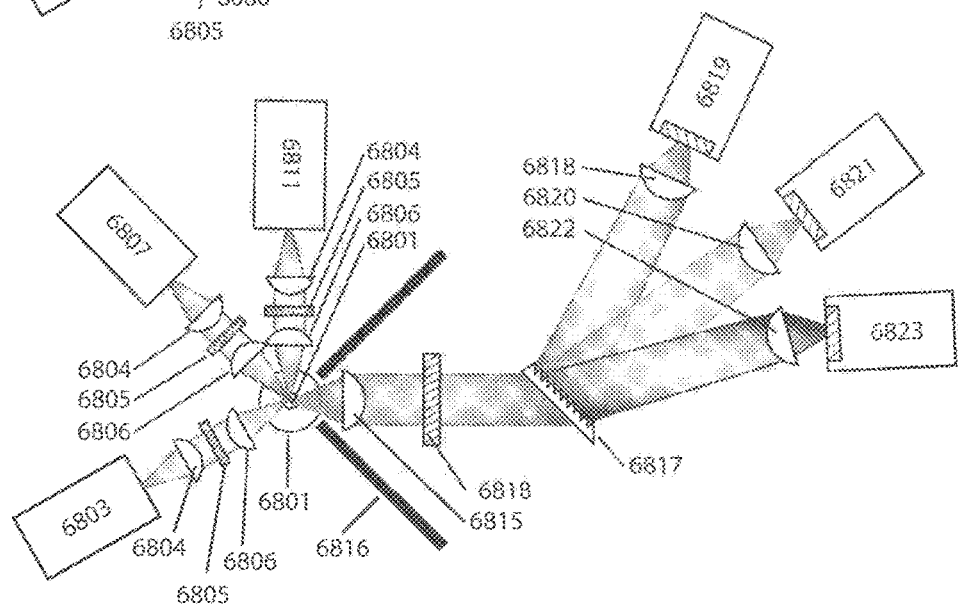

FIGS. 68A and 68B—Tubular spectrometer with SiPM detectors. FIGS. 68A and 68B show further embodiments that additionally comprises at least one focusing lens 6820 that focuses electromagnetic radiation on at least one detection element 6818. In FIG. 68A, the diffraction grating 6817 is reflective, and in FIG. 68B the diffraction grating is transmissive.

Figure 69:
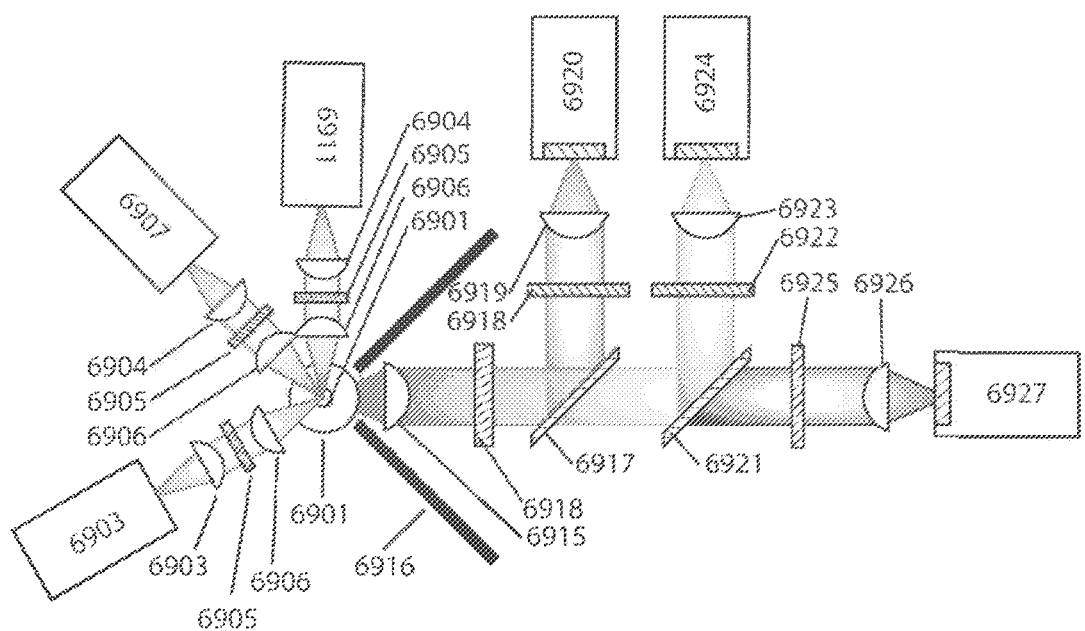
FIG. 69 shows a tubular spectrometer with turning mirror.
Figure 70:
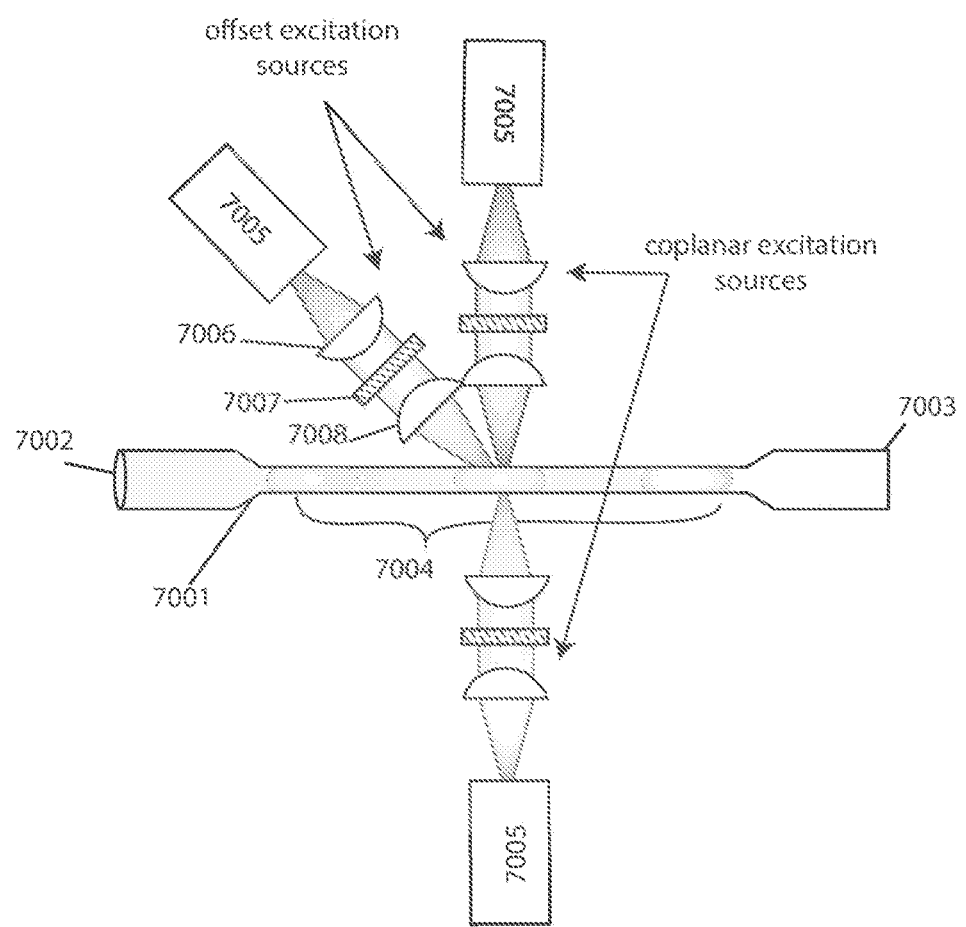
FIG. 70 shows offset excitation sources.

FIG. 69 shows another further embodiment of the system in FIG. 65 for multiplexing. The system additionally comprises at least one turning mirror 6917. The turning mirror preferentially reflects a subset V of the wavelength range of electromagnetic radiation passing through the aperture 6916, where the subset V represents electromagnetic radiation primarily emitted by only a single component of the partitions of the at least one dispersed phase. A first detection element 6920 measures the intensity or power electromagnetic radiation in the subset V, whereas a second detection element 6927 measures the intensity or power of the electromagnetic radiation not in the subset V. The system may additionally comprise one or more additional turning mirrors, each turning mirror preferentially reflecting a different subset of the electromagnetic radiation passing through the aperture 6916 and corresponding to electromagnetic radiation primarily emitted by a single component of the partitions of the at least one dispersed phase. In certain embodiments, the turning mirror is a dichroic mirror. In certain embodiments, the system comprises an emission filter 6921 that reduces the power or intensity of the electromagnetic radiation passing through the aperture 6916 outside of a wavelength range Z, where Z substantially coincides with the wavelengths of electromagnetic radiation emitted by the components of the partitions of the at least one dispersed phase FIG. 70—Offset excitation sources. FIG. 70 shows an embodiment of an excitation system for a tubular interrogation region where one or more excitation sources are offset from a plane normal to a central axis of the interrogation region. The system comprises a conduit 7001 that comprises an inlet 7002 and an outlet 7003 and an interrogation region 7004. Partitions of at least one dispersed phase flow from the inlet 7002 through the interrogation region 7004 toward the outlet. The conduit 7001 comprises an axis perpendicular to the cross section of the conduit in the interrogation region, and a plane co-planar with the cross-section of the conduit and normal to the axis. Excitation sources placed in a co-planar manner with the plane will minimize reflection of excitation radiant energy off the outer surface of the conduit 7001, but there may be a spatial limitation to the number of excitation sources that may be placed in this plane. In the embodiment shown, at least one excitation source 7005 is placed so that radiant energy passing through an excitation collimator 7006, an excitation filter 7007 to restrict the wavelengths of radiant energy passing through the filter to a subset that substantially coincides with the ranges of wavelengths for excitation of at least one component of the partitions, and a focusing lens 7008 to focus light on the interrogation region, where the focusing lens 7008 focuses light at an angle alpha offset from the plane normal to the axis. Doing so may allow for relieving spatial crowding and fitting more excitation sources around the interrogation region, at the penalty of additional radiant energy loss due to reflection. In some embodiments, alpha is less than 30 degrees, less than 20 degrees, less than 15 degrees, or less than 10 degrees.

FIG. 66—Temporal modulation pattern (one LED on at a time). FIG. 66 shows a representative diagram of temporal modulation, showing that excitation channel 1 is on when excitation channel 2 is off, and vice versa.

Figure 71:
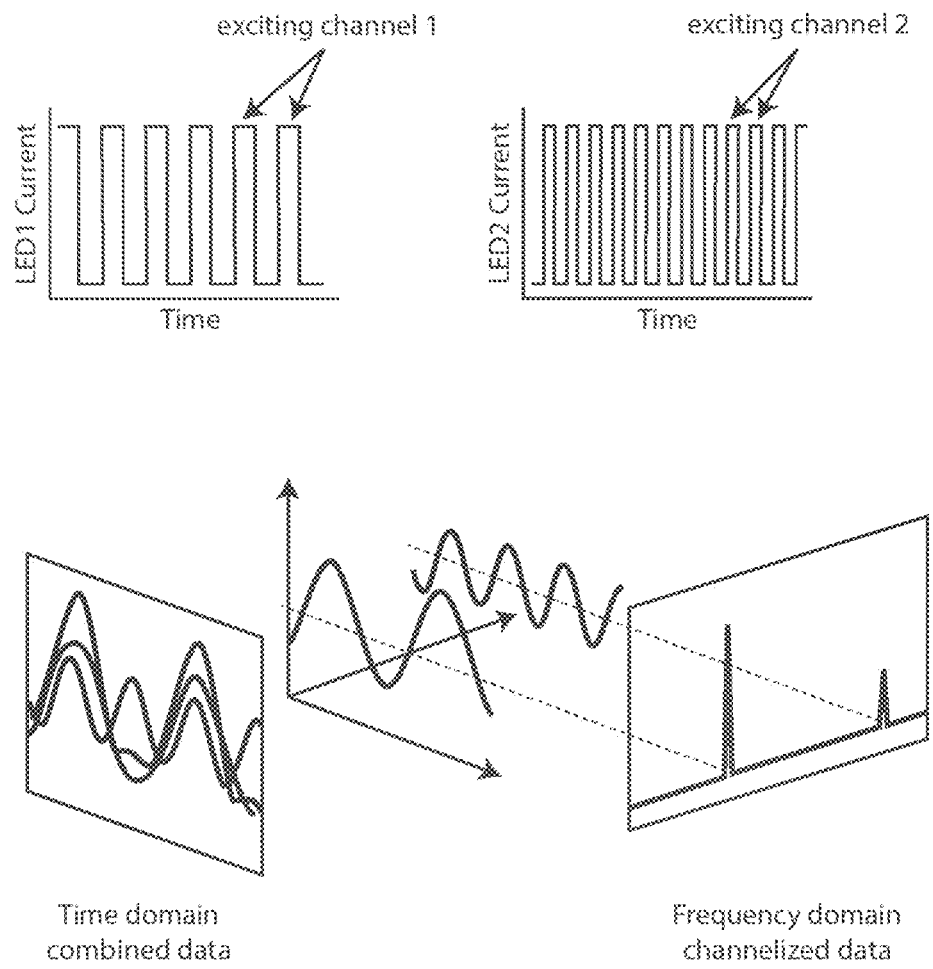
FIG. 71 shows lock-in detection for partitions.

FIG. 71—Lock-in detection in partitions. FIG. 71 shows examples of exciting two radiant energy sources with separate periodic functions, each having a at least partially non-overlapping subset of terms in its Fourier series representation whose coefficients are at least a multiple greater than the coefficients of all the other terms in their respective Fourier series representations. The resultant time-domain signal, with the total signal being the superposition of the contributions from each modulated excitation source and random noise, shows distinct peaks around the main terms of the respective Fourier series expansions of each modulated source when transforming to the frequency domain. Selecting each subset of frequency corresponding to each modulated excitation source and performing an inverse transform back to the time domain of that subset, a set of amplified time-domain signals corresponding primarily to the contribution for each modulated excitation source may be obtained.

Figure 72A:
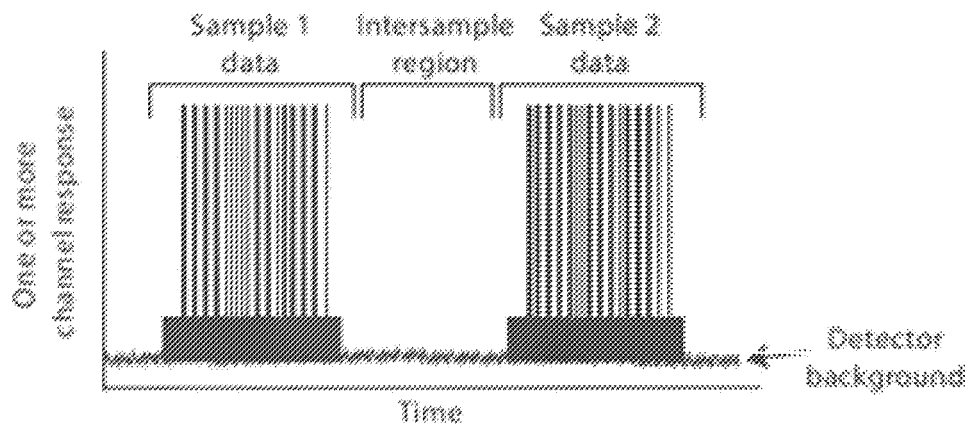
FIGS. 72A and 72B show blank sample discrimination.
Figure 72B:
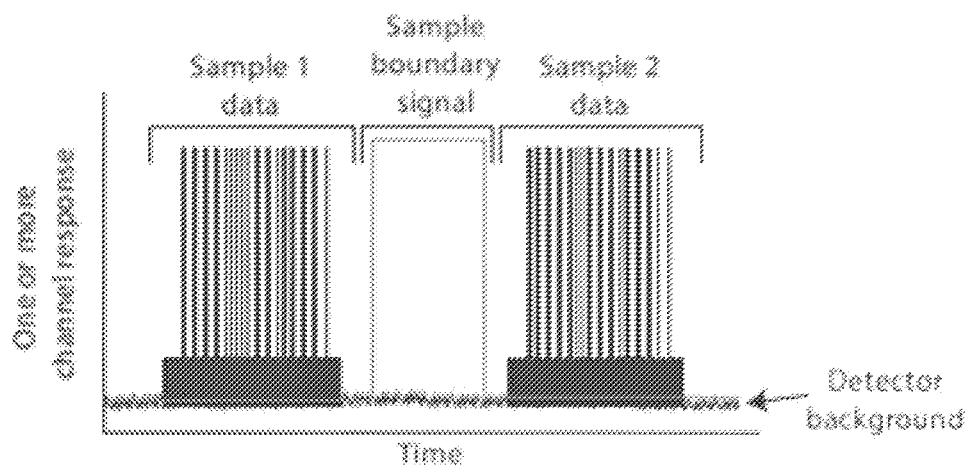

FIGS. 72A and 72B—Blank sample discrimination. FIG. 72 shows representative signals associated with the discrimination of boundaries between samples. In FIG. 72A a first sample comprising a plurality of partitions passes through the interrogation region at a first time range, generating high and low peaks in signal intensity for the one or more signal channels corresponding to emission by at least one component in the partitions of the at least one dispersed phase in the first sample. The first sample is followed by a spacer fluid that does not comprise a component that emits electromagnetic radiation with relatively high intensity when exposed to electromagnetic radiation from the excitation sources, and the intensity of the signal measured at the detection element is very low for a second time period. Finally, a second sample comprising a plurality of partitions passes through the interrogation region over a third time range, generating high and low peaks in signal intensity for the one or more signal channels corresponding to emission by at least one component in the partitions of the at least one dispersed phase in the second sample. The first time period precedes the second time period which precedes the third time period, and the length of the second period, where intensity is below a threshold value for a major fraction of the second time period, indicates a boundary between samples. In certain embodiments, the major fraction is at least 80%, at least 85%, at least 90%, at least 95%, at least 98%, at least 99%, at least 99.9%, or at least 99.99% of the time in the second time interval. In certain embodiments, the length of the second time interval is at least 1 second, at least 5 seconds, at least 10 seconds, at least 30 seconds, at least 60 seconds, or at least 120 seconds. FIG. 72B shows another embodiment where the spacer fluid comprises at least one component that may be excited by at least one of the excitation sources. In the second time interval, the signal of at least one of the detection channels increases to a value above a threshold value for a major fraction of the second time interval. In certain embodiments, the major fraction is at least 80%, at least 85%, at least 90%, at least 95%, at least 98%, at least 99%, at least 99.9%, or at least 99.99% of the time in the second time interval. In certain embodiments, the wavelength range at which the at least one component of the spacer fluid is excited coincides with at least one wavelength range at which at least one component of the partitions of the at least one dispersed phase are excited. In other embodiments, the wavelength range at which the at least one component of the spacer fluid is excited does not coincide with at least one wavelength range at which at least one component of the partitions of the at least one dispersed phase is excited. The arrangement where the excitation ranges do overlap allows for the use of one of the detection channels for multiple purposes.

Figure 73:
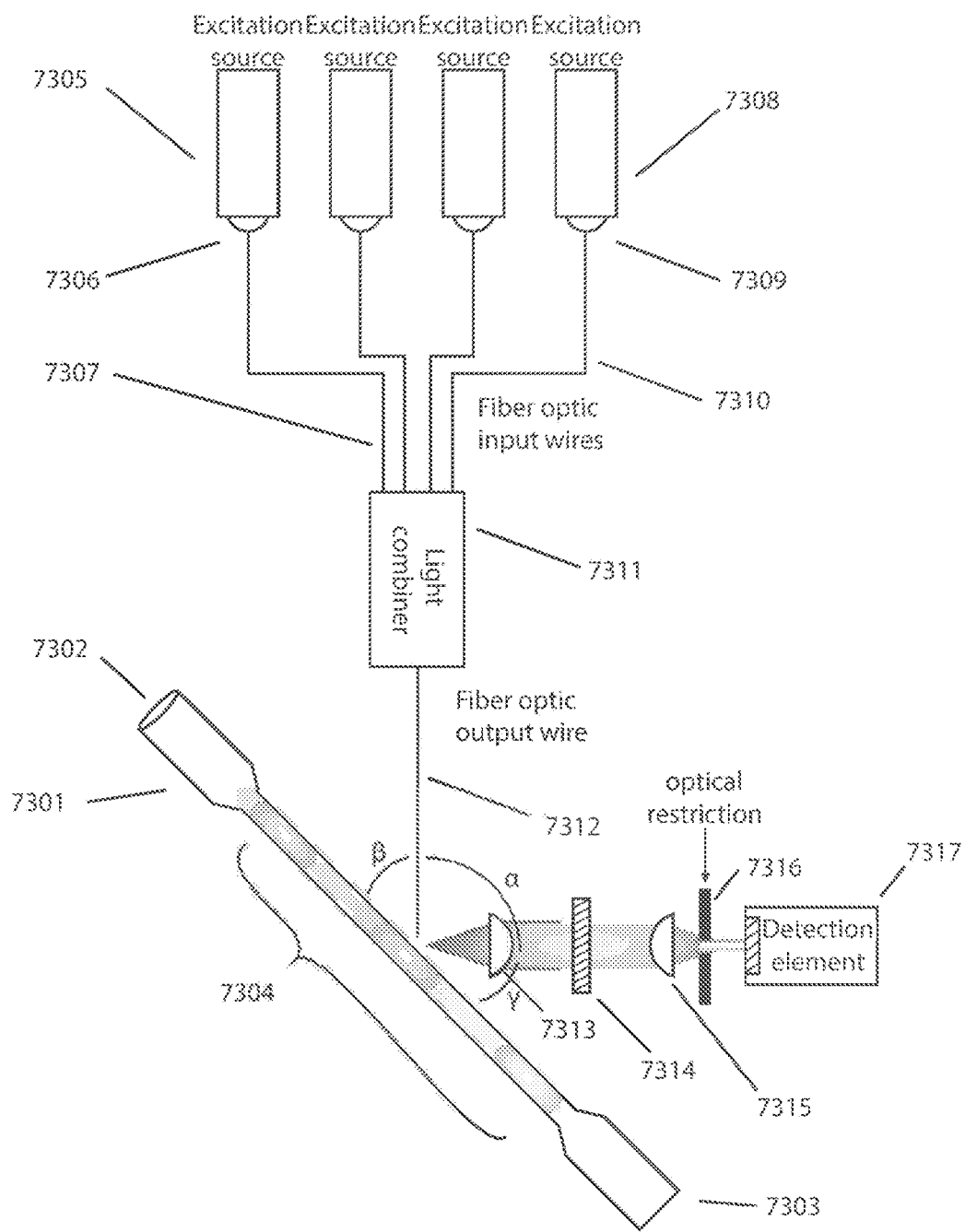
FIG. 73 shows fiber excitation on tube.

FIG. 73—Fiber excitation on tube. FIG. 73 shows a system for providing radiant energy to partitions. The system comprises a conduit 7301 that comprises an inlet 7302 and an outlet 7303 and an interrogation region 7304. The system additionally comprises a first excitation source 7305 that comprises a focusing element 7306 and an optical fiber 7307. The first excitation source provides radiant energy in a first wavelength range to excite one or more components of partitions of at least one dispersed phase flowing in the interrogation region 7304. The focusing element 7306 focuses radiant energy into an optical fiber 7307 that may be focused onto the interrogation region 7304. In some embodiments, the system additionally comprises a second excitation source 7308 that comprises a second focusing element 7309 and a second optical fiber 7310, as well as a light combiner 7311 that combines radiant energy into a fiber optic output 7312 to provide the combined radiant energy from the first and second optical sources onto the interrogation region 7304. The system may comprise three, four, or more excitation sources, with all of the radiant energy from the excitation sources provided to the interrogation region 7304 through the fiber optic output 7312. In some embodiments, the focusing elements comprise lenses. The system may additionally comprise an emission collimator 7313, an emission filter 7314, an emission focuser 7315, an optical restriction 7316, and a detection element 7317. Energy emitted from partitions in the interrogation region after excitation by the one or more wavelength ranges provided by the one or more excitation sources is collimated by the emission collimator 7313 and restricted to a subset of wavelengths that preferentially coincide with the wavelengths of relatively largest emission of one or more excited components in the partitions by the emission filter 7314. Radiant energy leaving the emission filter 7314 is focused on the aperture of the optical restriction 7316, through which passes radiant energy substantially originating from a single partition. The radiant energy passing through the optical restriction 7316 is incident on the detection element 7317, where a property of the radiant energy is detected. In some embodiments, the property is a radiant intensity or a radiant power. In some embodiments, the light combiner 7311 additionally comprises an excitation filter to limit the range of wavelengths passing through the fiber optic output 7312 to those that substantially coincide with wavelengths that will excite one or more components in the partitions passing through the interrogation region. In some embodiments, one or more excitation source may be a laser or a light emitting diode.

Figure 50:
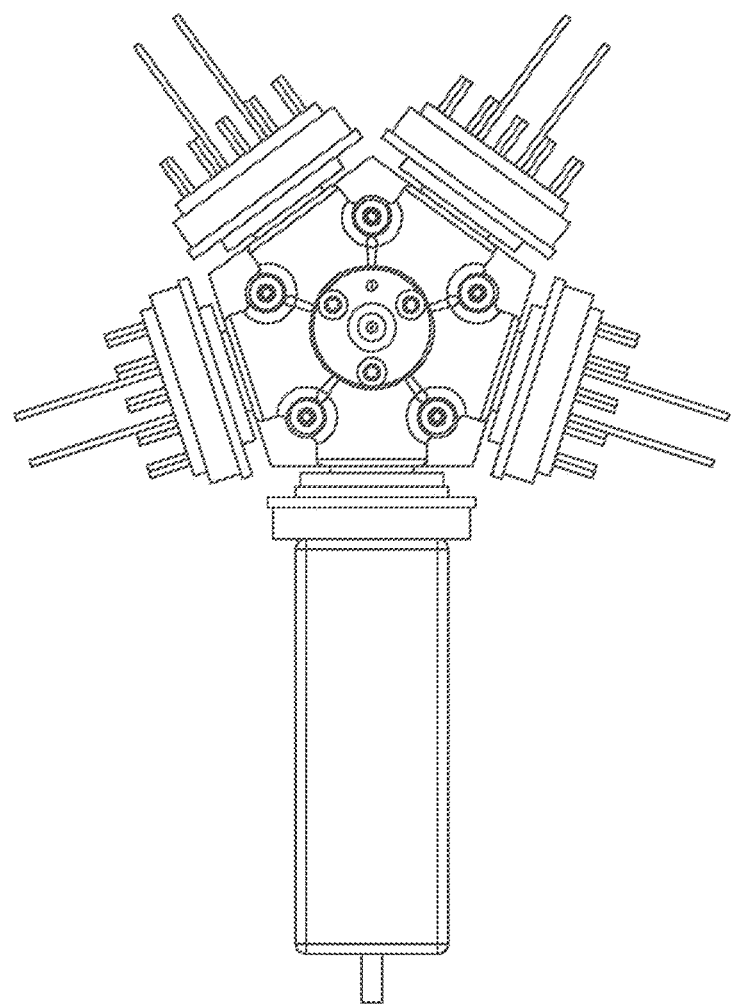
FIG. 50 shows a star-shaped detector.
Figure 74:
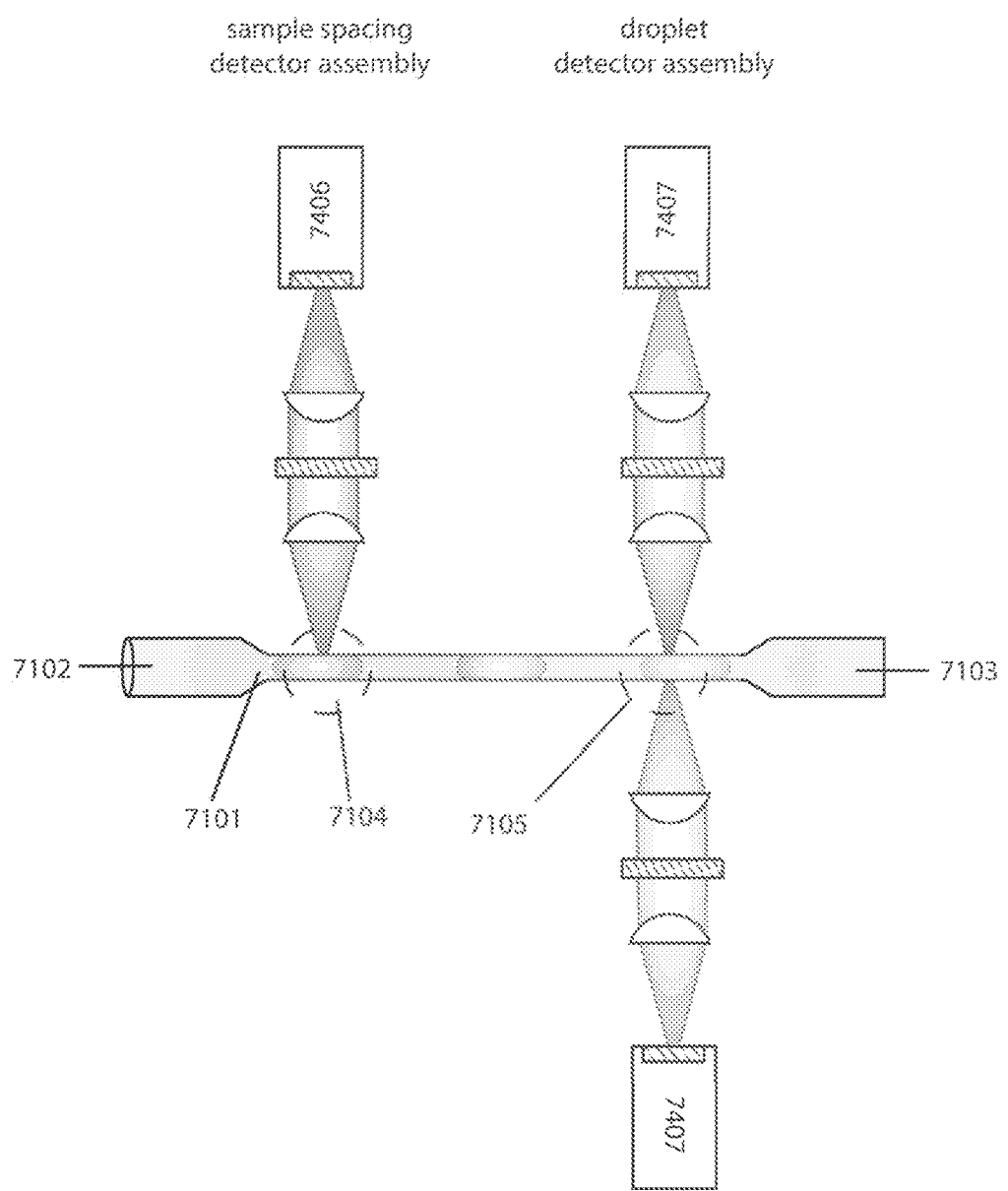
FIG. 74 shows two detector sample discrimination.
Figure 75:
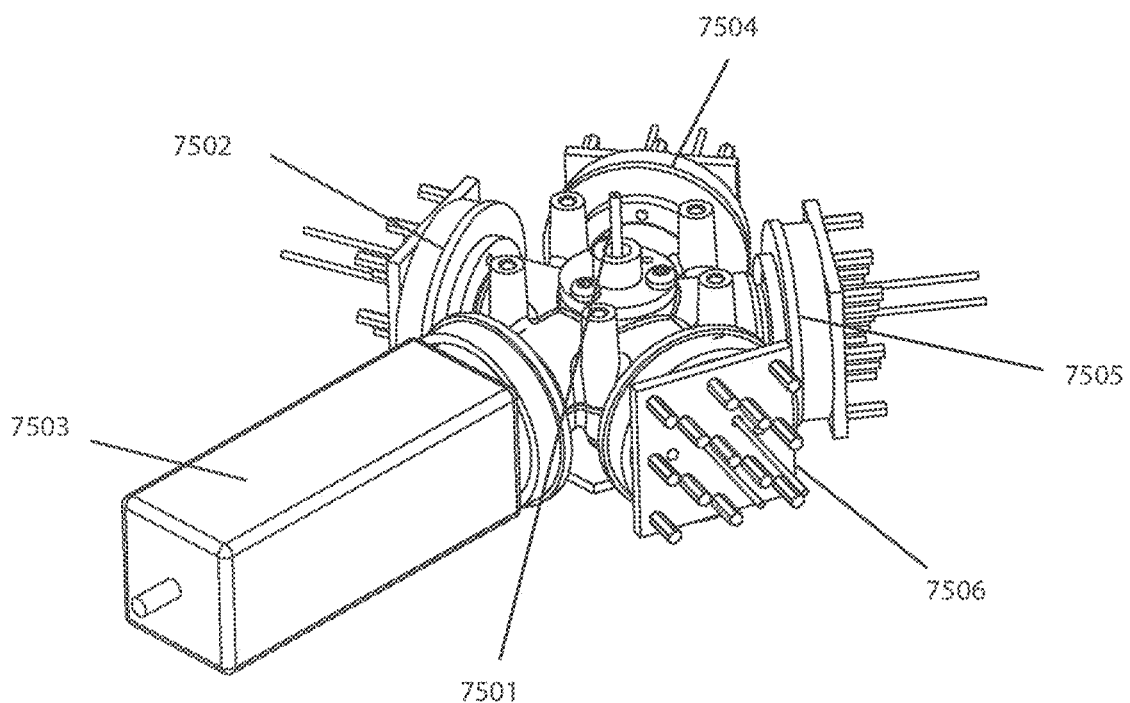
FIG. 75 shows a star-shaped detector.

FIG. 74—two detector sample boundary detection. FIG. 74 shows a system for detecting a sample boundary. The system comprises a conduit 7101, an inlet 7102, an outlet 7103, a first interrogation region 7104, a second interrogation region 7105, a first electromagnetic radiation detector 7406, and a second electromagnetic radiation detector 7407. At least one continuous phase and partitions of at least one dispersed phase enter the conduit 7101 at the inlet 7102, flow through the first interrogation region 7104, the second interrogation region 7105, and out the outlet 7103. A first electromagnetic radiation detector 7406 detects an optical property of partitions of the at least one dispersed phase that indicates the boundary between two samples. The second electromagnetic radiation detector 7407 measures at least one additional optical property of the partitions of the at least one dispersed phase related to a property of the at least one component of the partitions of the at least one dispersed phase. In certain embodiments, the first electromagnetic radiation detector 7406 is positioned to measure the absorbance of electromagnetic radiation through the partitions of the at least one dispersed phase. In certain of these embodiments, the spacer fluid comprises a component that preferentially absorbs electromagnetic radiation in a wavelength range, and a decrease in the electromagnetic radiation measured by the detector 7406 indicates a sample boundary. In certain further embodiments, the wavelength range is infrared. In certain embodiments, the samples comprise a component that preferentially absorbs electromagnetic radiation in a wavelength range, and an increase in the electromagnetic radiation measured by the detector 7406 indicates a sample boundary. In other embodiments, the electromagnetic radiation detector 7406 comprises an excitation source and an emission detector, and the excitation source excites a component in the partitions of the at least one dispersed phase to emit electromagnetic radiation in a wavelength range. In further embodiments, the spacer fluid comprises a component that is excited by electromagnetic radiation emitted by the excitation source and an increase in the electromagnetic radiation measured by the electromagnetic radiation detector 7406 indicates a boundary between samples. In other embodiments, the samples comprise at least one component that is excited by the electromagnetic radiation emitted by the excitation source and a minimum period of time where the intensity or power of the electromagnetic radiation measured by the detector 7406 is below a threshold indicates the boundary between samples FIGS. 50 and 75 Star-shaped detector. FIG. 50 shows a detector arrangement that might be used for lock-in amplification of optical signals from partitions. As shown, the embodiment comprises up to four excitation sources but only a single detection source arranged around a central tube. This shows a key advantage of lock-in detection, i.e. that a single detection element may measure emission from multiple excited components in a partition of a dispersed phase. Other embodiments, as described elsewhere herein, may comprise any number of excitation sources and/or detection elements arranged around a tubular interrogation region. FIG. 75 shows a system for detecting emission of radiant energy from partitions using one or more detectors. The system comprises an interrogation tube 7501, a first excitation source 7502, and a detection element 7503. As described elsewhere herein, the first excitation source may comprise collimating elements, filters, and/or focusing elements to focus radiant energy on a partition in the interrogation tube 7501 of a first wavelength range A so as to excite one or more components in the partition to emit energy in a second wavelength range A'. The detection element 7503 may additionally comprise an optical restriction, collimating elements, filters, and/or focusing elements to collect radiant energy in the second wavelength range A' from a single partition in the interrogation tube 7501 and measure an optical property of at least one component in the partition. In some embodiments, the first excitation source 7502 is substantially coplanar with a plane normal to the axis of flow in the interrogation tube 7501. In some embodiments, lock-in amplification is used to improve a signal-to-noise ratio. In some embodiments, the system may comprise a second excitation source 7504, a third excitation source 7505, and/or a fourth excitation source 7506, or more excitation sources, as needed. In some embodiments, lock-in amplification may be used to measure emission of radiant energy excited by at least two excitation sources, as described herein. As described elsewhere herein, the detection element 7503 may be any suitable measurement element. In some embodiments, the detection element 7503 comprises a photomultiplier tube, a silicon photomultiplier, a photodiode, a avalanche photodiode, a charge coupled device, or an array of charge coupled devices.

An optical stage (interrogation region0 may be used for measuring droplets flowing through systems as described herein. In some instances, droplet flow through a tube substantially parallel to a plane of the pinhole and near a common optical focal point of the two lenses. An internal diameter of the tube may allow free-flow spherical diameter of the droplets to have a larger internal diameter. In some instances, the optical stage is a microchannel on a microfluidic chip. In some instances, a region of the microchannel where a dimension of the microchannel is smaller than a spherical diameter of the droplets is a region for the excitation and emission lenses. The optical stage may comprise a material with a greater affinity for the continuous phase than the dispersed phase.

V. Definitions

Unless otherwise defined, all technical terms used herein have the same meaning as commonly understood by one of ordinary skill in the art to which this system and methods belongs.

As used herein, the term "comprising" and its grammatical equivalents specifies the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range. As used herein, the singular form "a", "an" and "the" include plural references unless the context clearly dictates otherwise.

As used herein, the terms "amplifying" and "amplification" are used interchangeably and generally refer to producing one or more copies of a nucleic acid.

As used herein, the terms "nucleic acid" and "nucleic acid molecule" are used interchangeably and generally refer to a polymeric form of nucleotides of any length, either deoxyribonucleotides (dNTPs) or ribonucleotides (rNTPs), or analogs thereof. Nucleic acids may have any three dimensional structure, and may perform any function, known or unknown. Non-limiting examples of nucleic acids include deoxyribonucleic acid (DNA), ribonucleic acid (RNA), a peptide nucleic acid (PNA), coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs such as, for example, locked nucleic acids (LNA), fluorinated nucleic acids (FNA), bridged nucleic acids and thio-nucleotides. If present, modifications to the nucleotide structure may be made before or after assembly of the nucleic acid. The sequence of nucleotides of a nucleic acid may be interrupted by non-nucleotide components, such as, for example a linker or other type of spacer. A nucleic acid may be further modified after polymerization, such as by conjugation or binding with a detectable species. In some instances, a nucleic acid may be a primer that, in some embodiments, can be used to amplify another nucleic acid molecule.

As used herein, the term "primer" generally refers to a nucleic acid molecule that is capable of hybridizing with a template nucleic acid molecule and capable of being extended in a template-directed manner via the template nucleic acid molecule.

As used herein, the terms "target nucleic acid" and "target nucleic acid molecule" are used interchangeably and generally refer to a nucleic acid molecule in a starting population of nucleic acid molecules having a target sequence whose presence, amount, and/or nucleotide sequence, or changes in one or more of these, are desired to be determined. In some instances, a target nucleic acid molecule may be double-stranded. In some instances, a target nucleic acid molecule may be single-stranded. In general, the term "target nucleic acid strand" refers to a single-stranded target nucleic acid molecule. In general, the term "target nucleic acid sequence" refers to a nucleic acid sequence on a strand of target nucleic acid. A target nucleic acid molecule or target nucleic acid sequence can be a portion of a gene, a regulatory sequence, genomic DNA, cDNA, RNA including mRNA, miRNA, rRNA, or others. The target nucleic acid sequence or target nucleic acid molecule can be a target nucleic acid sequence or target nucleic acid molecule from a sample or a secondary target such as a product of an amplification reaction.

As used herein, the term "sample" includes any volume of a dispersed phase to be processed in the process system. Samples may or may not comprise a sub-volume of a larger volume. A sample may include chemical or biological components to be one or more of categorized, sorted, analyzed, assayed for one or more qualitative or quantitative properties, reacted, separated, or subjected to physical changes in temperature, pressure, phase, state, electric potential, pH, or any other properties of interest. Samples may comprise a hydrophilic material (e.g. water) to be dispersed in a continuous phase comprising a hydrophobic material (e.g. oil), or may comprise a hydrophobic material (e.g. an oil) to be dispersed in a continuous phase comprising a hydrophilic material (e.g. water). Samples may additionally comprise biochemical or chemical reagents, catalysts, co-factors, co-solvents, buffers, salts, enzymes, dyes, reporter systems, or any other components that would aid in the desired process or processes to be conducted on the samples in the process system As used herein the term "partition" includes any subset of a volume of a dispersed phase dispersed in a continuous phase. Partitions may be any volume up to the volume of the original volume of a dispersed phase. The term "droplet," as used herein, is taken to mean partition.

As used herein the term "dispersed phase" includes any fluid that, when flowing in a conduit in the process system in contact with a continuous phase, will be nearly completely or substantially completely surrounded by fluid of a continuous phase. As such, dispersed phase refers to fluids even before they are actually dispersed in the continuous phase, as some or all of the volume of fluid referred to as dispersed phase becomes surrounded by a continuous phase when in the process system. Dispersed phase may include sample and/or spacer fluid, as defined in the present systems and methods. Dispersed phase may be in one or more volumes or partitions. Dispersed phase includes fluids nearly completely or completely immiscible with a continuous phase.

As used herein the term "continuous phase" includes any fluid that, when flowing in a conduit in the process system, it nearly or substantially completely surrounds fluids of dispersed phases such that the fluids of the dispersed phase become entrained in the continuous phase flow. As such, continuous phase refers to fluids even before they are actually in contact with dispersed phase fluids, as some or all of the volume of fluid referred to as continuous phase nearly completely or completely surrounds volumes of dispersed phase when in the process system.

VI. Numbered Embodiments

Numbered embodiment 1 comprises a system for producing a serial flow emulsion comprising (i) an intake system to sequentially transport a plurality of separate samples or portions of samples from a series of sample containers; (ii) a process system, wherein the process system comprises a partitioner to generate a plurality of partitions in a continuous phase from each of the samples; and (iii) an injector positioned between the intake system and the process system, wherein the injector is configured to be in fluid communication with the intake system, or to be in fluid communication with the process system, but not both simultaneously. Numbered embodiment 2 comprises the system of numbered embodiment 1 and further comprises (iii) a reactor fluidly connected to the partitioner to initiate or modulate one or more reactions in one or more of the partitions. Numbered embodiment 3 comprises the system of numbered embodiments 1-2 wherein the reactor is configured so all partitions flow through the reactor. Numbered embodiment 4 comprises the system of numbered embodiments 1-3 wherein the reactor supplies electromagnetic radiation, heating, cooling, sonic energy, or particulate radiation or a combination thereof to the partitions. Numbered embodiment 5 comprises the system of numbered embodiments 1-4 wherein the reactor comprises at least one thermal zone at a set temperature. Numbered embodiment 6 comprises the system of numbered embodiments 1-5 wherein the reactor comprises at least two thermal zones wherein each thermal zone is at a different temperature. Numbered embodiment 7 comprises the system of numbered embodiments 1-6 wherein the reactor comprises a conduit fluidly connected to the partitioner through which partitions flow, wherein the conduit repeatedly contacts the at least two different thermal zones. Numbered embodiment 8 comprises the system of numbered embodiments 1-7 wherein the conduit is arranged as a helix around a central core, wherein the central core comprises at least two different thermal zones at two different temperatures, and wherein the conduit is wrapped around the core so as to contact the core at the at least two different thermal zones. Numbered embodiment 9 comprises the system of numbered embodiments 1-8 further comprising (iv) a detector fluidly connected to the reactor to detect a characteristic of one or more of the partitions. Numbered embodiment 10 comprises the system of numbered embodiments 1-9 wherein the intake system is configured to be cleaned between samples without contact with the process system. Numbered embodiment 11 comprises the system of numbered embodiments 1-10 wherein the intake system is configured to be fluidly connected to at least one of (a) a purge fluid reservoir; (b) a denaturing fluid reservoir; and/or (c) a spacer fluid reservoir. Numbered embodiment 12 comprises the system of numbered embodiments 1-11 wherein the detector comprises at least one of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 13 comprises the system of numbered embodiments 1-12 wherein the detector comprises at least two of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 14 comprises the system of numbered embodiments 1-13 wherein the detector comprises at least three of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 15 comprises the system of numbered embodiments 1-14 wherein the intake system comprises a sampler, wherein the sampler is configured to remove a sample or a portion of a sample from a sample container and transport the sample or portion of sample to the injector, and the injector is configured to inject a fixed volume of the sample or portion of sample into a conduit fluidly connected to the process system. Numbered embodiment 16 comprises the system of numbered embodiments 1-15 wherein the intake system is configured to provide a sample comprising a first fluid to the process system and the process system is configured to provide a second fluid to the system after the first fluid, and wherein at least 80, 90, 95, 96, 97, 98, 99, 99.5, 99.9, 99.99% surfaces of all components of the system that come into contact with the sample or portions of the sample have greater affinity for the second fluid than for the first fluid. Numbered embodiment 17 comprises a method comprising (i) transporting a first sample comprising a first dispersed phase from a first sample container into an intake system; (ii) flowing the first sample from the intake system to an injector that is fluidly connected to the injection system but not to a process system; (iii) repositioning the injector so that it is fluidly connected to the process system but not the intake system; (iv) flowing the first sample from the injector into the process system; (v) partitioning the first sample into a plurality of partitions of the first dispersed phase in a continuous phase; (vi) repositioning the injector so that it is fluidly connected to the injection system but not to the process system; (vii) transporting a second sample comprising a second dispersed phase from a first second container into the intake system and into the injector; (viii) repositioning the injector so that it is fluidly connected to the process system but not the intake system; (ix) flowing the second sample from the injector into the process system; and (x) partitioning the second sample into a plurality of partitions of the second dispersed phase in the continuous phase. Numbered embodiment 18 comprises the method of numbered embodiment 17 comprising cleaning the intake system comprises at least one of (a) purging remaining sample from the intake system; and/or (b) denaturing remaining sample in the intake system. Numbered embodiment 19 comprises the method of numbered embodiment 17-18 wherein cleaning the intake system comprises both of (a) purging remaining sample from the intake system; and (b) denaturing remaining sample in the intake system. Numbered embodiment 20 comprises the method of numbered embodiments 17-19 further comprising transporting a spacer fluid from a spacer fluid reservoir into the intake system, and flowing the spacer fluid into the process system, wherein the spacer fluid is flowed into the process system between the first and second samples. Numbered embodiment 21 comprises the method of numbered embodiments 17-20 further comprising flowing the partitions of the first and second samples in a reactor for initiating and/or modulating one or more reactions in one or more of the partitions. Numbered embodiment 22 comprises the method of numbered embodiments 17-21 further comprising flowing the partitions through a detector fluidly connected to the reactor to detect one or more of the partitions. Numbered embodiment 23 comprises the method of numbered embodiments 17-22 wherein the detector comprises at least one of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 24 comprises the method of numbered embodiments 17-23 wherein the detector comprises at least two of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 25 comprises the method of numbered embodiments 17-24 wherein the detector comprises at least three of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 26 comprises the method of numbered embodiments 17-25 further comprising performing a reaction in at least a portion of the partitions. Numbered embodiment 27 comprises the method of numbered embodiments 17-26 the portion of the partitions comprise at least one nucleic acid per partition, and the reaction is a polymerase chain reaction (PCR). Numbered embodiment 28 comprises the method of numbered embodiments 17-27 wherein the samples comprise a first fluid and the process system provides a second fluid to the system after the first fluid, and wherein at least 80, 90, 95, 96, 97, 98, 99, 99.5, 99.9, 99.99% surfaces of all components of the system that come into contact with the sample or portions of the sample have greater affinity for the second fluid than for the first fluid. Numbered embodiment 29 comprises a system for conducting a serial flow emulsion reaction comprising components, the system comprising (i) an intake system to sequentially transport a plurality of separate samples or portions of samples from a series of sample containers; (ii) a process system, wherein the process system comprises a reactor to initiate or modulate a reaction in the samples or portions of the samples; and (iii) an injector positioned between the intake system and the process system, wherein the injector is configured to be in fluid communication with the intake system, or to be in fluid communication with the process system, but not both simultaneously. Numbered embodiment 30 comprises the system of numbered embodiment 29 wherein the reactor supplies electromagnetic radiation, heating, cooling, sonic energy, particulate radiation or a combination thereof to the one or more portions of the sample. Numbered embodiment 31 comprises the system of numbered embodiments 29-30 further comprising (iv) a detector fluidly connected to the reactor to detect a characteristic of the one or more portions of the sample. Numbered embodiment 32 comprises the system of numbered embodiments 29-31 wherein the detector comprises at least one of Numbered embodiment 23 comprises the method of numbered embodiments 17-22 wherein the detector comprises at least one of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 33 comprises the system of numbered embodiments 29-32 wherein the detector comprises at least two of Numbered embodiment 23 comprises the method of numbered embodiments 17-22 wherein the detector comprises at least one of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 34 comprises the system of numbered embodiments 29-33 wherein the detector comprises at least three of Numbered embodiment 23 comprises the method of numbered embodiments 17-22 wherein the detector comprises at least one of (a) an optical restriction that limits the amount of electromagnetic radiation that reaches a detection element in the detector from an interrogation region in the detector where partitions are detected to less than 10% of the electromagnetic radiation that would reach the detection element without the optical restriction; (b) an interrogation region comprising a conduit wherein partitions flow in single file through the conduit, and wherein the cross-sectional area of the conduit is less than 90% of the average spherical cross-sectional area of the partitions; (c) an excitation source to provide electromagnetic radiation to the interrogation region and a system to provide lock-in amplification of the excitation source; (d) a system to separate partitions prior to the interrogation region of the detector. Numbered embodiment 35 comprises the system of numbered embodiments 29-34 wherein the intake system is configured to be cleaned between samples while the injector is configured to be in fluid communication with the intake system. Numbered embodiment 36 comprises the system of numbered embodiments 29-35 wherein the intake system is configured to be transiently fluidly connected to at least one of (a) a purge fluid reservoir; (b) a denaturing fluid reservoir; and/or (c) a spacer fluid reservoir. Numbered embodiment 37 comprises the system of numbered embodiments 29-36 wherein the injector is configured to inject a fixed volume. Numbered embodiment 38 comprises the system of numbered embodiments 29-37 wherein the injector is configured to be fluidly connected to the intake system to receive a sample or a portion of a sample, or fluidly connected to the process system to move sample or a portion of sample into the process system, but not both. Numbered embodiment 39 comprises the system of numbered embodiments 29-38 further comprising a partitioner fluidly connected on an upstream side to the intake system and on a downstream side to the reactor, for portioning the sample or portion of sample into a plurality of partitions to be flowed through the reactor. Numbered embodiment 40 comprises the system of numbered embodiments 29-39 wherein the intake system is configured to provide a sample comprising a first fluid to the process system and the process system is configured to provide a second fluid to the system after the first fluid, and wherein at least 80, 90, 95, 96, 97, 98, 99, 99.5, 99.9, 99.99% surfaces of all components of the system that come into contact with the sample or portions of the sample have greater affinity for the second fluid than for the first fluid. Numbered embodiment 41 comprises a system comprising (i) an intake system for removing a series of samples from a series of sample containers, fluidly connected to (ii) an injector for injecting at least a portion of the sample from the sampler into a process system, wherein one, two, three, four, five, six, or seven of the series of sample containers comprises a barrier for each sample container to separate it from the environment, the intake system is configured to clean an external surface of an intake conduit of the intake system that comes in contact with sample, at least 90% of surfaces of the system that come in contact with sample comprising a first fluid have a lower affinity for the first fluid than for a second fluid with which the surfaces come in contact, the intake system is configured to be cleaned between samples, the system is configured to add a spacing fluid between samples in the series of samples, conduits in the system are configured to allow laminar flow, or a conduit in the system between a partitioner and a partition separation system or a partitioner and a detector are oriented so that flow in the conduit is within 20 degrees of orthogonal to gravity, or a combination thereof. Numbered embodiment 42 comprises the system of numbered embodiment 41 wherein the injector is configured to be isolated from the process system during a cleaning phase. Numbered embodiment 43 comprises the system of numbered embodiments 41-42 further comprising a reservoir comprising purge fluid operably connected to the intake system, the injector, or both the intake system and the injector. Numbered embodiment 44 comprises a system comprising a detector for detecting one or more partitions in a flowing series of partitions comprising (i) a conduit configured to flow the partitions within the conduit in single file, comprising an interrogation region wherein partitions are detected; (ii) a detection element for detecting the electromagnetic radiation emitted by the partitions in the interrogation region, if present; and (iii) an optical restriction configured and positioned between the interrogation region and the detection element so that only a portion of the electromagnetic radiation from the interrogation region that can be detected by the detection element is actually detected. Numbered embodiment 45 comprises the system of numbered embodiment 44 wherein the portion of electromagnetic radiation that can be detected due to the optical restriction is less than 10% of the amount that would be detected without the optical restriction. Numbered embodiment 46 comprises the system of numbered embodiments 44-45 wherein the interrogation region has a cross-sectional area equal to or less than 90% of the average spherical cross-sectional area of the partitions. Numbered embodiment 47 comprises the system of numbered embodiments 44-46 wherein the interrogation region has a cross-sectional area equal to or less than 50% of the average spherical cross-sectional area of the partitions. Numbered embodiment 48 comprises the system of numbered embodiments 44-47 further comprising (iv) an excitation source for supplying electromagnetic radiation to the interrogation region of the conduit. Numbered embodiment 49 comprises the system of numbered embodiments 44-48 comprising a plurality of excitation sources, each of which supplies electromagnetic radiation to the interrogation region. Numbered embodiment 50 comprises the system of numbered embodiments 44-49 wherein the excitation source or sources comprises a lock-in amplifier. Numbered embodiment 51 comprises the system of numbered embodiments 44-50 further comprising a partitioner fluidly connected to the detector, wherein the partitioner is configured to generate partitions of dispersed phase in a continuous phase from a sample. Numbered embodiment 52 comprises the system of numbered embodiments 44-51 further comprising a reactor for initiating or modulating a reaction in the partitions. Numbered embodiment 53 comprises the system of numbered embodiments 44-52 wherein at least a portion of the partitions comprise a single nucleic acid molecule and the reactor comprises a thermal cycler for polymerase chain reaction (PCR) reactions. Numbered embodiment 54 comprises the system of numbered embodiments 44-53 wherein the partitioner is configured to produce partitions of an average volume of 0.05-50 nL. Numbered embodiment 55 comprises the system of numbered embodiments 44-54 further comprising a partition separation system configured to add a separation fluid to the flow of partitions prior to the interrogation region of the detector. Numbered embodiment 56 comprises the system of numbered embodiments 44-55 further comprising an intake system that can be fluidly connected to a sample container and an injector that can be fluidly connected to the intake system or fluidly connected to the partitioner for supplying sample to the partitioner. Numbered embodiment 57 comprises the system of numbered embodiments 44-56 wherein the injector is configured to inject a fixed volume. Numbered embodiment 58 comprises a method for detecting partitions continuously flowing through an interrogation region of a conduit comprising detecting at least one detectable component in single partitions as they flow through the interrogation region by detecting electromagnetic radiation emitted from the detectable component by a detection element, wherein an optical restriction is configured and positioned between the interrogation region and the detection element so that only a portion of the electromagnetic radiation from the interrogation region that can be detected by the detection element is actually detected. Numbered embodiment 59 comprises the method of numbered embodiment 58 wherein the portion of electromagnetic radiation that can be detected due to the optical restriction is less than 10% of the amount that would be detected without the optical restriction. Numbered embodiment 60 comprises the method of numbered embodiments 58-59 wherein the interrogation region of the conduit is configured to have a cross-sectional area equal to or less than 100, 95, 90, 80, 70, 60, 50, 40, 30 20, 10%, for example less than 90%, such as less than 50% the average cross-sectional area of the partitions. Numbered embodiment 61 comprises the method of numbered embodiments 58-60 further comprising supplying electromagnetic radiation from an excitation source to the interrogation region. Numbered embodiment 62 comprises the method of numbered embodiments 58-61 further comprising performing lock-in amplification on the electromagnetic radiation from the excitation source. Numbered embodiment 63 comprises the method of numbered embodiments 58-62 comprising supplying electromagnetic radiation from a plurality of excitation sources to the interrogation region, and performing lock-in amplification on the plurality of excitation sources. Numbered embodiment 64 comprises the method of numbered embodiments 58-63 further comprising partitioning a sample into the partitions. Numbered embodiment 65 comprises the method of numbered embodiments 58-64 wherein the partitioning produces partitions of an average volume of 0.05-50 nL. Numbered embodiment 66 comprises the method of numbered embodiments 58-65 further comprising initiating or modulating one or more reactions in the partitions in a reactor. Numbered embodiment 67 comprises the method of numbered embodiments 58-66 wherein at least a portion of the partitions comprise a single nucleic acid molecule and the reactor provides thermal cycling to perform PCR on the nucleic acid. Numbered embodiment 68 comprises the method of numbered embodiments 58-67 further comprising adding a separation fluid to the flow of partitions before they reach the interrogation region. Numbered embodiment 69 comprise a system comprising a detector for detecting one or more partitions in a flowing series of partitions comprising (i) a conduit configured to flow the partitions within the conduit in single file, comprising an interrogation region; (ii) one or more excitation sources for supplying electromagnetic radiation to the interrogation region, wherein, if a plurality of excitation sources is used, each of the excitation sources supplies electromagnetic radiation at a different wavelength, wherein the different wavelengths excite one or more different molecules in the partition, if present; (iii) a detection element for detecting electromagnetic radiation emitted by the molecules, if present, in response to the electromagnetic radiation from the one or more excitation sources; wherein the excitation source or sources are configured to provide lock-in amplification. Numbered embodiment 70 comprises the system of numbered embodiment 69 comprising at least 2, 3, 4, 5, or 6, such as at least 3, different excitation sources, supplying electromagnetic radiation at 2, 3, 4, 5, or 6, such as at least 3 different wavelengths. Numbered embodiment 71 comprises the system of numbered embodiments 69-70 wherein the detection element comprises an avalanche photodiode. Numbered embodiment 72 comprises the system of numbered embodiments 69-71 further comprising (iv) an optical restriction configured and positioned between the interrogation region and the detection element so that only a portion of the electromagnetic radiation, such as less than 10% of the electromagnetic radiation, from the interrogation region that can be detected by the detection element is actually detected. Numbered embodiment 73 comprises the system of numbered embodiments 69-72 wherein the interrogation region has a cross-sectional area equal to or less than 90%, 80, 70, 60, 50, 40, 30, 20, or 10%, such as less than 90%, for example, less than 50%, of the average spherical cross-sectional area of the partitions. Numbered embodiment 74 comprises the system of numbered embodiments 69-73 further comprising a partitioner fluidly connected to the detector, wherein the partitioner is configured to generate partitions of dispersed phase in a continuous phase from a sample. Numbered embodiment 75 comprises the system of numbered embodiments 69-74 further comprising a reactor for initiating or modulating a reaction in the partitions. Numbered embodiment 76 comprises the system of numbered embodiments 69-75 wherein at least a portion of the partitions comprise a single nucleic acid molecule and the reactor comprises a thermal cycler for polymerase chain reaction (PCR) reactions. Numbered embodiment 77 comprises the system of numbered embodiments 69-76 wherein the partitioner is configured to produce partitions of an average volume of 0.05-50 nL. Numbered embodiment 78 comprises the system of numbered embodiments 69-77 further comprising a partition separation system configured to add a separation fluid to the flow of partitions prior to the interrogation region of the detector. Numbered embodiment 79 comprises the system of numbered embodiments 69-78 further comprising an intake system fluidly connected to at least one sample container and to an injector, wherein the injector is configured to reposition to move at least part of sample to the partitioner. Numbered embodiment 80 comprises the system of numbered embodiments 69-79 wherein the injector is configured to inject a fixed volume. Numbered embodiment 81 comprises a method for detecting molecules in partitions flowing through a conduit comprising (i) flowing the partitions through an interrogation region in the conduit in single file; (ii) supplying electromagnetic radiation to the interrogation region from one or more excitation sources wherein, if a plurality of excitation sources is used, each of the excitation sources supplies electromagnetic radiation at a different wavelength, wherein the different wavelengths excite one or more different molecules in the partition, if present; and (iii) detecting electromagnetic radiation emitted by the molecules, if present, in response to the electromagnetic radiation from one or more of the excitation sources with a detection element, wherein the excitation source or sources provide lock-in amplification. Numbered embodiment 82 comprises the method of numbered embodiment 81 comprising supplying electromagnetic radiation from at least 2, 3, 4, 5, 6, such as at least 3, different excitation sources, supplying electromagnetic radiation at 2, 3, 4, 5, 6, such as at least 3 different wavelengths. Numbered embodiment 83 comprises the method of numbered embodiments 81-82 wherein an optical restriction is configured and positioned between the interrogation region and the detection element so that only a portion, for example less than 10%, such as less than 5%, of the electromagnetic radiation from the interrogation region that can be detected by the detection element is actually detected. Numbered embodiment 84 comprises the method of numbered embodiments 81-83 wherein the interrogation region has a cross-sectional area equal to or less than 90%, 80, 70, 60, 50, 40, 30, 20, or 10%, such as less than 90%, for example, less than 50%, of the average spherical cross-sectional area of the partitions. Numbered embodiment 85 comprises the method of numbered embodiments 81-84 further comprising partitioning a sample into the partitions of dispersed phase in a continuous phase. Numbered embodiment 86 comprises the method of numbered embodiments 81-85 wherein the average volume of the partitions is 0.05-50 nL. Numbered embodiment 87 comprises the method of numbered embodiments 81-86 comprising initiation or modulating one or more reactions in the partitions in a reactor. Numbered embodiment 88 comprises the method of numbered embodiments 81-87 wherein at least a portion of the partitions comprise a single nucleic acid molecule and the reactor thermal cycles the partitions to perform polymerase chain reaction (PCR) reactions. Numbered embodiment 89 comprises the method of numbered embodiments 81-88 further comprising adding a separation fluid to the flow of partitions prior to the interrogation region of the detector. Numbered embodiment 90 comprises the method of numbered embodiments 81-89 further comprising supplying sample to the partitioner from an intake system via an injector which can be fluidly coupled to a sample container containing the sample, or fluidly coupled to the partitioner, but not both simultaneously. Numbered embodiment 91 comprises the method of numbered embodiments 81-90 further comprising cleaning the intake system. Numbered embodiment 92 comprises a system comprising a detector for detecting one or more partitions in a flowing series of partitions comprising (i) a conduit configured to flow the partitions within the conduit in single file, comprising an interrogation region, wherein the interrogation region is configured to have a cross-sectional area equal to or less than 100, 95, 90, 80, 70, 60, 50, 40, 30 20, 10%, such as equal to or less than 90%, for example equal to or less than 50%, the average cross-sectional area of the partitions; (ii) a detection element for detecting electromagnetic radiation emitted by the partitions, if present, in the interrogation region. Numbered embodiment 93 comprises the system of numbered embodiment 92 further comprising (iii) an optical restriction configured and positioned between the interrogation region and the detection element so that only a portion of the electromagnetic radiation, such as less than 10% of the electromagnetic radiation, from the interrogation region that can be detected by the detection element is actually detected. Numbered embodiment 94 comprises the system of numbered embodiments 92-93 further comprising (iv) an excitation source for supplying electromagnetic radiation to the interrogation region of the conduit. Numbered embodiment 95 comprises the system of numbered embodiments 92-94 comprising a plurality of excitation sources, each of which supplies electromagnetic radiation to the interrogation region. Numbered embodiment 96 comprises the system of numbered embodiments 92-95 wherein the excitation source or sources comprises a lock-in amplifier. Numbered embodiment 97 comprises the system of numbered embodiments 92-96 further comprising a partitioner fluidly connected to the detector, wherein the partitioner is configured to generate partitions of dispersed phase in a continuous phase from a sample. Numbered embodiment 98 comprises the system of numbered embodiments 92-97 further comprising a reactor for initiating or modulating a reaction in the partitions. Numbered embodiment 99 comprises the system of numbered embodiments 92-98 wherein at least a portion of the partitions comprise a single nucleic acid molecule and the reactor comprises a thermal cycler for polymerase chain reaction (PCR) reactions. Numbered embodiment 100 comprises the system of numbered embodiments 92-99 wherein the partitioner is configured to produce partitions of an average volume of 0.05-50 nL. Numbered embodiment 101 comprises the system of numbered embodiments 92-100 further comprising a partition separation system configured to add a separation fluid to the flow of partitions prior to the interrogation region of the detector. Numbered embodiment 102 comprises the system of numbered embodiments 92-101 further comprising an intake system fluidly connected to a sample container and to an injector which can be repositioned to connect to the partitioner for supplying sample to the partitioner. Numbered embodiment 103 comprises the system of numbered embodiments 92-102 wherein the intake system is configured to be cleaned between samples. Numbered embodiment 104 comprises a system comprising a detector for detecting one or more partitions in a flowing series of partitions comprising (i) a conduit configured to flow the partitions within the conduit in single file, comprising an interrogation region; (ii) a plurality of excitation sources for supplying electromagnetic radiation to excite molecules within a partition in the conduit, if present, wherein each of the plurality of excitation sources supplies electromagnetic radiation at a different wavelength; (iii) a detection element for detecting electromagnetic radiation emitted by the molecules, if present, in response to the electromagnetic radiation from one of the excitation sources; wherein the excitation sources and the emission detector are situated less than 40, 30, 20, 15, 10, 5, 2, or 1°, such as less than 5 degrees, for example less than 2 degrees, away from a plane that is perpendicular to the direction of flow of the partitions through the interrogation region. Numbered embodiment 105 comprises the system of numbered embodiment 104 wherein the conduit is a tube. Numbered embodiment 106 comprises the system of numbered embodiments 104-105 wherein the interrogation region is configured to have a cross-sectional area equal to or less than 100, 95, 90, 80, 70, 60, 50, 40, 30 20, 10%, such as equal to or less than 90%, such as less than 10%, of the average cross-sectional area of the partitions. Numbered embodiment 107 comprises the system of numbered embodiments 104-106 wherein the plurality of excitation sources comprises at least 2, 3, 4, 5, 6, for example, at least 3 different excitation sources. Numbered embodiment 108 comprises the system of numbered embodiments 104-107 wherein the excitation sources comprise a lock-in amplifier. Numbered embodiment 109 comprises the system of numbered embodiments 104-108 comprising a plurality of emission detectors wherein the excitation sources and the emission detectors are situated less than 40, 30, 20, 15, 10, 5° away from a plane that is perpendicular to the direction of flow of the partitions through the conduit. Numbered embodiment 110 comprises the system of numbered embodiments 104-109 wherein the detection element comprises an avalanche photodiode. Numbered embodiment 111 comprises the system of numbered embodiments 104-110 further comprising (iv) an optical restriction configured and positioned between the interrogation region and the detection element so that only a portion of the electromagnetic radiation, such as less than 10%, for example less than 1% of the electromagnetic radiation, from the interrogation region that can be detected by the detection element is actually detected. Numbered embodiment 112 comprises the system of numbered embodiments 104-111 further comprising a partitioner fluidly connected to the detector, wherein the partitioner is configured to generate partitions of dispersed phase in a continuous phase from a sample. Numbered embodiment 113 comprises the system of numbered embodiments 104-112 further comprising a reactor for initiating or modulating a reaction in the partitions. Numbered embodiment 114 comprises the system of numbered embodiments 104-113 wherein at least a portion of the partitions comprise a single nucleic acid molecule and the reactor comprises a thermal cycler for polymerase chain reaction (PCR) reactions. Numbered embodiment 115 comprises the system of numbered embodiments 104-114 wherein the partitioner is configured to produce partitions of an average volume of 0.05-50 nL. Numbered embodiment 116 comprises the system of numbered embodiments 104-115 further comprising a partition separation system configured to add a separation fluid to the flow of partitions prior to the interrogation region of the detector. Numbered embodiment 117 comprises the system of numbered embodiments 104-116 further comprising an intake system fluidly connected to a sample container and to an injector, wherein the injector can be repositioned to be fluidly connected to the partitioner, for supplying sample to the partitioner. Numbered embodiment 118 comprises the system of numbered embodiments 104-117 wherein the injector is configured to inject a fixed volume. Numbered embodiment 119 comprises a system for producing a serial flow emulsion comprising partitions of dispersed phase in a continuous phase comprising (i) a partitioner to generate partitions from a sample, wherein the partitioner comprises (a) an first inlet operably connected to a source of the sample, wherein the sample comprises a first dispersed phase comprising a first fluid, and a first force generator operably connected to the sample source to cause the sample to flow through the first inlet; (b) a second inlet operably connected to a source of continuous phase, and a second force generator operably connected to the continuous phase source to cause the continuous phase fluid to flow through the second inlet; and (c) an outlet; wherein the first and second inlets are positioned to intersect at an angle of no more than 30, 20, 15, 10, 5, 4, 3, 2, 1 degree from 180°, for example, an angle of no more than 5 degrees from 180 degrees such as an angle no more than 1 degree from 180 degrees and the outlet is positioned at the intersection of the two inlets and at an angle within 20, 15, 10, 5, 4, 3, 2, 1° of 90° from the inlets, for example an angle within 20 degrees of 90 degrees, for example, an angle within 10 degrees of 90 degrees. Numbered embodiment 120 comprises the system of numbered embodiment 119 further comprising (ii) an intake system to provide the sample from a sample source; fluidly connected to an injector, wherein the injector is configured to be fluidly connected to the intake system, or fluidly connected to the partitioner, but not both simultaneously. Numbered embodiment 121 comprises the system of numbered embodiments 119-120 wherein surfaces of the partitioner that come in contact with the sample have a higher affinity for continuous phase than for the first fluid. Numbered embodiment 122 comprises an apparatus comprising a partitioner for portioning a sample into a plurality of partitions comprising (i) first inlet channel that carries dispersed phase comprising the sample; (ii) a second inlet channel that carries a flow of a continuous phase, and (iii) a third outlet channel, wherein (a) the axes of first and second inlet channels are oriented within 30°, 25°, 20°, 18°, 15°, 13°, 10°, 8°, 5°, 2°, or 1°, such as within 30 degrees, of orthogonal to an ambient gravitational field, (b) the first and second inlet channels intersect at the third outlet channel, and (c) the axis of third outlet channel is oriented within 30°, 25°, 20°, 18°, 15°, 13°, 10°, 8°, 5°, 2°, 1°, such as within 30 degrees, of parallel with the ambient gravitational field, and the direction of flow in the third channel is opposed to the gravitational field; wherein surfaces of the first inlet channel and the outlet channel have greater affinity for the continuous phase than for the dispersed phase. Numbered embodiment 123 comprises the apparatus of numbered embodiment 122 further comprising (iv) an intake system to provide the sample from a sample source; fluidly connected to an injector, wherein the injector is configured to be fluidly connected to the intake system, or fluidly connected to the partitioner, but not both simultaneously. Numbered embodiment 124 comprises the apparatus of numbered embodiments 122-123 wherein surfaces of the partitioner that come in contact with the sample have a higher affinity for continuous phase than for the first fluid. Numbered embodiment 125 comprises a system for amplifying nucleic acids comprising (i) an intake system for sampling a sample comprising nucleic acids operably connected to a first inlet channel in a partitioner; (ii) the partitioner, wherein the partitioner comprises the first inlet channel, a second inlet channel that carries a flow of a continuous phase, and a third outlet channel, wherein (a) the axes of first and second inlet channels are oriented within 30°, 25°, 20°, 18°, 15°, 13°, 10°, 8°, 5°, 2°, or 1 degree, for example, within 30 degrees, of orthogonal to an ambient gravitational field, (b) the first and second inlet channels intersect at the third outlet channel, and (c) the axis of third outlet channel is oriented within 30°, 25°, 20°, 18°, 15°, 13°, 10°, 8°, 5°, 2°, or 1 degree, for example, within 30 degrees, of parallel with the ambient gravitational field, and the direction of flow in the third channel is opposed to the gravitational field; and (iii) a thermal cycler operably connected to the partitioner for thermally cycling the nucleic acids. Numbered embodiment 126 comprises the system of numbered embodiment 125 wherein the first and second inlet channels intersect at an angle between 150° and 180°. Numbered embodiment 127 comprises a system for conducting a serial flow emulsion process comprising components comprising (i) an intake system for supplying a sample to a process system, wherein the process system comprises a partitioner; (ii) a partitioner to divide the sample into partitions; (iii) a reactor; and (iv) a detector; wherein the intake system can be fluidly connected to an injector, wherein the injector is configured to be fluidly connected to the intake system, or fluidly connected to the partitioner, but not both simultaneously, and wherein the intake system is configured to provide a sample comprising a first fluid to the system and the system is configured to provide a second fluid to the system after the first fluid, and wherein at least 80, 90, 95, 99, 99.5, 99.9, 99.99%, for example at least 90%, such as at least 99%, of surfaces of all components of the system that come into contact with the sample have greater affinity for the second fluid than for the first fluid. Numbered embodiment 128 comprises the system of numbered embodiment 127 wherein the first fluid and the second fluid are immiscible. Numbered embodiment 129 comprises the system of numbered embodiments 127-128 wherein the partitioner is configured to produce an emulsion of sample comprising the first fluid in the second fluid. Numbered embodiment 130 comprises the system of numbered embodiments 127-129 wherein the partitioner is configured to produce partitions with an average volume between 0.05 and 50 nL. Numbered embodiment 131 comprises the system of numbered embodiments 127-130 wherein the first fluid comprise a dispersed phase and the second fluid comprises a continuous phase. Numbered embodiment 132 comprises a system for conduction of a serial flow emulsion reaction, comprising: a sampling device comprising: a first dispersed phase reservoir; a second dispersed phase reservoir; a third dispersed phase reservoir; optionally, a fourth dispersed phase reservoir; and a sampler intake, wherein the sampler intake comprises a first tube configured to puncture a seal of the first dispersed phase reservoir, and a second tube located within the first tube; an injector; a droplet generator; a reactor; and a detector, wherein the detector comprises an optical stage, and wherein the optical stage comprises an optical restriction. Numbered embodiment 133 comprises the system of numbered embodiment 132 wherein the first dispersed phase reservoir comprises a reaction sample. Numbered embodiment 134 comprises the system of numbered embodiments 132-133 wherein the reaction sample comprises a nucleic acid molecule, a buffer, a primer, a probe, mastermix, a dNTP, an enzyme, or any combination thereof. Numbered embodiment 135 comprises the system of numbered embodiments 132-134 wherein the nucleic acid molecule comprises RNA or DNA. Numbered embodiment 136 comprises the system of numbered embodiments 132-135 wherein the second dispersed phase reservoir comprises a decontamination fluid. Numbered embodiment 137 comprises the system of numbered embodiments 132-136 wherein the decontamination fluid comprises sodium hypochlorite, phosphoric acid, sodium hydroxide, RNAse, or DNAase. Numbered embodiment 138 comprises the system of numbered embodiments 132-137 wherein the third dispersed phase reservoir comprises a purge fluid. Numbered embodiment 139 comprises the system of numbered embodiments 132-138 wherein the purge fluid comprises water. Numbered embodiment 140 comprises the system of numbered embodiments 132-139 wherein the fourth dispersed phased reservoir comprises a separation fluid. Numbered embodiment 141 comprises the system of numbered embodiments 132-140 wherein the separation fluid comprises an oil. Numbered embodiment 142 comprises the system of numbered embodiments 132-141 wherein the sampling device further comprises a staging container. Numbered embodiment 143 comprises the system of numbered embodiments 132-142 wherein the staging container comprises a sample to be analyzed. Numbered embodiment 144 comprises the system of numbered embodiments 132-143 wherein the staging container is a microwell plate, a strip of PCR tubes, or a single PCR tube. Numbered embodiment 145 comprises the system of numbered embodiments 132-144 wherein the sampling device further comprises a pump. Numbered embodiment 146 comprises the system of numbered embodiments 132-145 wherein the pump is a peristaltic pump. Numbered embodiment 147 comprises the system of numbered embodiments 132-146 wherein the sampler intake further comprises a double spring configured to position the first tube and the second tube. Numbered embodiment 148 comprises the system of numbered embodiments 132-147 wherein the first tube of the sampler intake comprises a pointed end. Numbered embodiment 149 comprises the system of numbered embodiments 132-148 wherein the first tube of the sampler intake is a lance, knife, or needle. Numbered embodiment 150 comprises the system of numbered embodiments 132-149 wherein the second tube is configured to inject the sample. Numbered embodiment 151 comprises the system of numbered embodiments 132-150 wherein the sampler intake is a zero-dead volume injector. Numbered embodiment 152 comprises the system of numbered embodiments 132-151 wherein the sampler intake comprises one or more revolvers. Numbered embodiment 153 comprises the system of numbered embodiments 132-152 wherein the one or more revolvers inject fluid from the first dispersed phase, the second dispersed phase, the third dispersed phase, the fourth dispersed phase, or combinations thereof. Numbered embodiment 154 comprises the system of numbered embodiments 132-153 wherein the injector is a zero-dead volume injector. Numbered embodiment 155 comprises the system of numbered embodiments 132-154 wherein the reactor is a thermal cycler. Numbered embodiment 156 comprises the system of numbered embodiments 132-155 wherein the optical restriction is a pinhole or slit. Numbered embodiment 157 comprises the system of numbered embodiments 132-156 wherein the injector, the droplet generator, the reactor, or the detector comprises microfluidic channels or tubes. Numbered embodiment 158 comprises the system of numbered embodiments 132-157 wherein the microfluidic channels or the tubes comprise one or more connections. Numbered embodiment 159 comprises a method for conducting a serial flow emulsion reaction, comprising: injecting a first dispersed phase into a flow pathway, wherein the flow pathway is connected to a reactor and one or more detectors; sampling a second dispersed phase; injecting the second dispersed phase to a waste channel; injecting a third dispersed phase into the flow pathway; optionally, injecting a fourth dispersed phase into the flow pathway; generating droplets from the first dispersed phase, the third dispersed phase, and optionally the fourth dispersed phase; performing an amplification reaction in the reactor; and detecting a product of the amplification reaction in step (g) by the one or more detectors. Numbered embodiment 160 comprises the method of numbered embodiment 159 wherein a first dispersed phase comprises a reaction sample. Numbered embodiment 161 comprises the method of numbered embodiments 159-160 wherein the reaction sample comprises a nucleic acid molecule, a buffer, a primer, a probe, mastermix, a dNTP, an enzyme, or any combination thereof. Numbered embodiment 162 comprises the method of numbered embodiments 159-161 wherein the nucleic acid molecule comprises RNA or DNA. Numbered embodiment 163 comprises the method of numbered embodiments 159-162 wherein the second dispersed phase comprises a decontamination fluid. Numbered embodiment 164 comprises the method of numbered embodiments 159-163 wherein the decontamination fluid comprises sodium hypochlorite, phosphoric acid, sodium hydroxide, RNAse, or DNAase. Numbered embodiment 165 comprises the method of numbered embodiments 159-164 wherein the third dispersed phase comprises a purge fluid. Numbered embodiment 166 comprises the method of numbered embodiments 159-165 wherein the purge fluid comprises water. Numbered embodiment 167 comprises the method of numbered embodiments 159-166 wherein the fourth dispersed phased comprises a separation fluid. Numbered embodiment 168 comprises the method of numbered embodiments 159-167 wherein the separation fluid comprises an oil. Numbered embodiment 169 comprises the method of numbered embodiments 159-168 wherein the droplet generator comprises orifices, t-junctions, flow-focusing junctions, or v-junctions. Numbered embodiment 170 comprises the method of numbered embodiments 159-169 wherein the droplets comprise about 0.10 nL to about 1.0 nL. Numbered embodiment 171 comprises the method of numbered embodiments 159-170 the droplets comprise no more than about 0.75 nL. Numbered embodiment 172 comprises the method of numbered embodiments 159-171 wherein the reactor is a thermal cycler. Numbered embodiment 173 comprise the method of numbered embodiments 159-172 wherein the detector comprises an optical restriction. Numbered embodiment 174 comprises the method of numbered embodiments 159-173 wherein the optical restriction is a pinhole or slit. Numbered embodiment 175 comprises the method of numbered embodiments 159-174 wherein the one or more detector comprises one or more channels. Numbered embodiment 176 comprises the method of numbered embodiments 159-175 wherein the one or more channels are configured to detect one or more wavelengths. Numbered embodiment 177 comprises the method of numbered embodiments 159-176 wherein the one or more detectors are arranged spatially. Numbered embodiment 178 comprises the method of numbered embodiments 159-177 further comprising introducing a continuous phase following step (g). Numbered embodiment 179 comprises the method of numbered embodiments 159-178 wherein a channel is narrowed following introducing a continuous phase. Numbered embodiment 180 comprises the method of numbered embodiments 159-179 wherein a frequency of amplification in the droplets generated not comprising nucleic acids is at most 10%. Numbered embodiment 181 comprises the method of numbered embodiments 159-180 wherein a rate of false amplification is about 1:1000 droplets. Numbered embodiment 182 comprises the method of numbered embodiments 159-181 wherein a frequency of amplification in the droplets generated from the third dispersed phase and the fourth dispersed phase is at most 10%. Numbered embodiment 183 comprises an apparatus comprising a sampler intake comprising a first tube configured to puncture a seal; a second tube located within the first tube; and a double spring. Numbered embodiment 184 comprises the apparatus of numbered embodiment 183 wherein the first tube comprises a pointed end. Numbered embodiment 185 comprises the apparatus of numbered embodiments 183-184 wherein the first tube of the sampler intake is a lance, knife, or needle. Numbered embodiment 186 comprises the apparatus of numbered embodiments 183-185 wherein the sampler intake is a zero-dead volume injector. Numbered embodiment 187 comprises the apparatus of numbered embodiments 183-186 wherein the double spring comprises a first spring and a second spring. Numbered embodiment 188 comprises the apparatus of numbered embodiments 183-187 wherein the double spring provides movement in a x, y, or z direction.

The invention claimed is:

1. A system comprising a detector for detecting one or more characteristics of single partitions in a plurality of partitions, wherein the partitions comprise a first fluid and are dispersed in a second fluid, and flow through an interrogation region of a conduit, wherein the detector comprises:
(i) a conduit configured to flow the partitions within the conduit in single file, comprising the interrogation region wherein the one or more characteristics of the partitions is detected, wherein the interrogation region has a cross-sectional area in a plane substantially normal to the direction of flow of the partitions within the conduit that is less than 80% of an average spherical cross-sectional area of the partitions; and
(ii) a detection element for detecting electromagnetic radiation emitted by at least one component of the partitions in the interrogation region, if present; and
wherein the system further comprises a partitioner fluidly connected to the detector, wherein the partitioner is configured to generate the plurality of partitions of the first fluid in the second fluid, wherein the first fluid is substantially immiscible with the second fluid, and wherein the partitioner is electrically grounded.

2. The system of claim 1 wherein the interrogation region has a cross-sectional area in a plane substantially normal to the direction of flow of the partitions within the conduit of 10-100,000 $\mu m^2$.

3. The system of claim 1 further comprising
(iii) an optical restriction configured and positioned between the interrogation region and the detection element so that the amount of electromagnetic radiation incident on the detection element is reduced to less than 50% of electromagnetic radiation that would be incident on the detection element in the absence of the optical restriction.

4. The system of claim 1 further comprising an excitation source for supplying electromagnetic radiation to the interrogation region.

5. The system of claim 1 wherein the interrogation region comprises a wall wherein transmittance of electromagnetic radiation in a range of wavelengths emitted by at least one component of a partition in the interrogation region is the same or substantially the same around a circumference of the interrogation region.

6. The system of claim 1 wherein the conduit comprising the interrogation region is a tube.

7. The system of claim 1 wherein the interrogation region has a cross-section in a plane substantially normal to the direction of flow of the partitions within the conduit that is circular or substantially circular.

8. The system of claim 1 wherein the conduit comprises a fluoropolymer.

9. The system of claim 1 further comprising an intake system, wherein the intake system can be in a first configuration in which it is fluidly connected to a sample in a sample container, wherein the sample comprises the first fluid, or in a second configuration in which it is fluidly connected to the detector, but not both at the same time.

10. The system of claim 1 further comprising a first excitation source for supplying electromagnetic radiation in a first wavelength or range of wavelengths to the interrogation region and a second excitation source for supplying electromagnetic radiation in a second wavelength or range of wavelengths, different from the first wavelength or range of wavelengths, to the interrogation region, wherein the first and second excitation sources and the detection element are situated less than 10° away from a plane normal to the direction of flow of the partitions through the interrogation region.

11. The system of claim 1 wherein the detection element comprises a photodiode, charge-coupled device, silicon photomultiplier, or photomultiplier tube.

12. The system of claim 1 that is configured so that when a first partition is passing through the interrogation region, not more than 10% of electromagnetic radiation incident on the detection element due to one or more components in a partition is from one or more partitions other than the first partition.

13. The system of claim 1 further comprising a reactor for initiating or modulating a reaction in the partitions, wherein the reactor is fluidly connected to the detector and upstream from the detector.

14. The system of claim 13 wherein the reactor comprises a thermal cycler configured to provide a plurality of temperature zones.

15. The system of claim 14 wherein the reactor comprises at least two zones of different temperatures.

16. The system of claim 15 wherein the reactor comprises at least three zones of different temperatures.

17. The system of claim 16 wherein the reactor comprises at least four zones of different temperatures.

18. The system of claim 6 wherein the tube comprises glass.

19. The system of claim 18 wherein the tube comprises glass coated with a coating comprising a fluoropolymer.

20. The system of claim 3 that is configured so that when a first partition is passing through the interrogation region, not more than 10% of electromagnetic radiation incident on the detection element due to one or more components in a partition is from one or more partitions other than the first partition.

21. The system of claim 10 wherein a wall of the interrogation region transmits at least 20% of the first and second wavelength or range of wavelengths.

22. The system of claim 1 wherein the partitioner is configured to produce partitions of an average volume of 0.05-50 nL.

23. The system of claim 11 wherein the detection element comprises a silicon photomultiplier or photomultiplier tube.

24. The system of claim 9 further comprising a sampling device configured to hold the sample container.

25. The system of claim 9 wherein the sample container is a microwell plate.

26. The system of claim 25 wherein the microwell plate comprises at least 12 wells, at least 24 wells, at least 36 wells, at least 48 wells, at least 60 wells, at least 72 wells, at least 84 wells, at least 96 wells, at least 108 wells, at least 120 wells, at least 240 wells, at least 384 wells, at least 768 wells, or at least 1536 wells.

27. The system of claim 26 wherein the microwell plate comprises 96 wells.

28. The system of claim 24 wherein the sampling device further comprises a cooling element such that the temperature of the sample may be held at a temperature less than 21° C.

29. The system of claim 4 wherein the system is configured for lock-in amplification.

30. The system of claim 14 wherein the reactor comprises at least five zones of different temperatures.

* * * * *